(12) United States Patent
Boniface et al.

(10) Patent No.: US 10,961,584 B2
(45) Date of Patent: *Mar. 30, 2021

(54) BIOMARKER PAIRS FOR PREDICTING PRETERM BIRTH

(71) Applicant: Sera Prognostics, Inc., Salt Lake City, UT (US)

(72) Inventors: John Jay Boniface, Salt Lake City, UT (US); Andrew Gassman, Salt Lake City, UT (US); Jeff Flick, Salt Lake City, UT (US); Chad Bradford, Salt Lake City, UT (US); Ashoka Polpitiya, Salt Lake City, UT (US); Tracey Cristine Fleischer, Sandy, UT (US); Durlin Edward Hickok, Seattle, WA (US); Paul Kearney, Seattle, WA (US); Gregory Charles Critchfield, Holladay, UT (US)

(73) Assignee: SERA PROGNOSTICS, INC., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,938

(22) Filed: Apr. 10, 2019

(65) Prior Publication Data

US 2020/0071761 A1 Mar. 5, 2020

Related U.S. Application Data

(63) Continuation of application No. 15/186,322, filed on Jun. 17, 2016, now Pat. No. 10,392,665.

(60) Provisional application No. 62/290,796, filed on Feb. 3, 2016, provisional application No. 62/387,420, filed on Dec. 24, 2015, provisional application No. 62/182,349, filed on Jun. 19, 2015.

(51) Int. Cl.
| | | |
|---|---|---|
| *C12Q 1/6883* | (2018.01) | |
| *C07K 14/47* | (2006.01) | |
| *G01N 33/68* | (2006.01) | |

(52) U.S. Cl.
CPC .......... *C12Q 1/6883* (2013.01); *C07K 14/47* (2013.01); *G01N 33/689* (2013.01); *C12Q 2600/158* (2013.01); *G01N 2333/4713* (2013.01); *G01N 2333/4745* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,130,238 A | 7/1992 | Malek et al. | |
| 5,270,184 A | 12/1993 | Walker et al. | |
| 5,399,491 A | 3/1995 | Kacian et al. | |
| 5,455,166 A | 10/1995 | Walker | |
| 5,480,784 A | 1/1996 | Kacian et al. | |
| 7,091,316 B2 | 8/2006 | Uchida et al. | |
| 7,191,068 B2 | 3/2007 | Rosenfeld et al. | |
| 7,323,346 B2 | 1/2008 | Thadhani et al. | |
| 7,425,419 B2 | 9/2008 | Poston et al. | |
| 7,435,419 B2 | 10/2008 | Karumanchi et al. | |
| 7,790,463 B2 | 9/2010 | Mor et al. | |
| 2002/0137086 A1 | 9/2002 | Olek et al. | |
| 2003/0105731 A1 | 6/2003 | Lapointe et al. | |
| 2004/0197930 A1 | 10/2004 | Rosenfeld et al. | |
| 2004/0203023 A1 | 10/2004 | Chandrasiri-Herath | |
| 2005/0043640 A1 | 2/2005 | Chang | |
| 2005/0059013 A1 | 3/2005 | Kokudo | |
| 2005/0074746 A1 | 4/2005 | Mor et al. | |

(Continued)

FOREIGN PATENT DOCUMENTS

| | | |
|---|---|---|
| CA | 2629451 | 5/2007 |
| EA | 002520 | 6/2002 |

(Continued)

OTHER PUBLICATIONS

Alcaraz et al., "Tenascin-X promotes epithelial-to-mesenchymal transition by activating latent TGF-β," *J. Cell Biol.*, 205(3):409-428 (2014).

(Continued)

*Primary Examiner* — Christina M Borgeest
(74) *Attorney, Agent, or Firm* — Jones Day

(57) ABSTRACT

The disclosure provides a pair of isolated biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein the pair of biomarkers exhibits a change in reversal value between pregnant females at risk for pre-term birth and term controls. Also provided is a method of determining probability for preterm birth in a pregnant female, the method comprising measuring in a biological sample obtained from the pregnant female a reversal value for at least one pair of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1 to determine the probability for preterm birth in the pregnant female.

5 Claims, 113 Drawing Sheets
(65 of 113 Drawing Sheet(s) Filed in Color)
Specification includes a Sequence Listing.

(56) References Cited

U.S. PATENT DOCUMENTS

| | | |
|---|---|---|
| 2005/0148023 A1 | 7/2005 | Thadhani et al. |
| 2005/0148040 A1 | 7/2005 | Thadhani et al. |
| 2005/0233400 A1 | 10/2005 | Weiner et al. |
| 2006/0046265 A1 | 3/2006 | Becker et al. |
| 2006/0094039 A1 | 5/2006 | Rosenfeld et al. |
| 2006/0127962 A1 | 6/2006 | Buhimschi et al. |
| 2006/0166242 A1 | 7/2006 | Pennell et al. |
| 2006/0166280 A1 | 7/2006 | Strauss et al. |
| 2007/0054329 A1 | 3/2007 | Fung et al. |
| 2007/0111326 A1 | 5/2007 | Sogin et al. |
| 2007/0141055 A1 | 6/2007 | Kajander et al. |
| 2007/0161125 A1 | 7/2007 | Rosenfeld et al. |
| 2007/0178605 A1 | 8/2007 | Mor et al. |
| 2008/0090759 A1 | 4/2008 | Kokenyesi et al. |
| 2008/0187929 A1 | 8/2008 | Meiri et al. |
| 2008/0213794 A1 | 9/2008 | Thadhani et al. |
| 2008/0233583 A1 | 9/2008 | Fisher et al. |
| 2008/0274481 A1 | 11/2008 | Fung et al. |
| 2009/0018778 A1 | 1/2009 | Nation et al. |
| 2010/0016173 A1 | 1/2010 | Nagalla et al. |
| 2010/0017143 A1 | 1/2010 | Nagalla et al. |
| 2010/0035284 A1 | 2/2010 | Buhimschi et al. |
| 2010/0062471 A1 | 3/2010 | Kantor |
| 2010/0113286 A1 | 5/2010 | Lajoie et al. |
| 2010/0143949 A1 | 6/2010 | Petricoin |
| 2010/0163721 A1 | 7/2010 | Graves et al. |
| 2010/0167267 A1 | 7/2010 | Schulzknappe et al. |
| 2010/0173317 A1 | 7/2010 | Nakamura et al. |
| 2010/0173786 A1 | 7/2010 | Brun et al. |
| 2010/0216250 A1 | 8/2010 | Lopez et al. |
| 2010/0291612 A1 | 11/2010 | Luider et al. |
| 2010/0297679 A1 | 11/2010 | Graves et al. |
| 2011/0008805 A1 | 1/2011 | Urdea |
| 2011/0165554 A1 | 7/2011 | Levin et al. |
| 2011/0171645 A1 | 7/2011 | McManus et al. |
| 2011/0195478 A1 | 8/2011 | Chen et al. |
| 2011/0247404 A1 | 10/2011 | Graves et al. |
| 2011/0256560 A1 | 10/2011 | Diamandis |
| 2012/0046261 A1 | 2/2012 | Manuck et al. |
| 2012/0149041 A1 | 6/2012 | Graves et al. |
| 2012/0190561 A1 | 7/2012 | Wildt et al. |
| 2012/0315630 A1 | 12/2012 | Gong et al. |
| 2013/0040844 A1 | 2/2013 | Wyss-Coray |
| 2013/0130278 A1 | 5/2013 | Gruslin et al. |
| 2013/0137595 A1 | 5/2013 | Zangar et al. |
| 2013/0296198 A1 | 11/2013 | Gordon et al. |
| 2014/0287947 A1 | 9/2014 | Boniface et al. |
| 2014/0287948 A1 | 9/2014 | Boniface et al. |
| 2014/0287950 A1 | 9/2014 | Hickok et al. |
| 2014/0296108 A1 | 10/2014 | Hickok et al. |
| 2016/0003837 A1 | 1/2016 | Murtha et al. |
| 2016/0154003 A1 | 6/2016 | Boniface et al. |
| 2017/0022565 A1 | 1/2017 | Boniface et al. |
| 2017/0146548 A1 | 5/2017 | Hickok et al. |
| 2018/0143202 A1 | 5/2018 | Boniface et al. |
| 2018/0172696 A1 | 6/2018 | Boniface et al. |
| 2018/0172698 A1 | 6/2018 | Boniface et al. |
| 2019/0219588 A1 | 7/2019 | Boniface et al. |
| 2019/0317107 A1 | 10/2019 | Boniface et al. |

FOREIGN PATENT DOCUMENTS

| | | |
|---|---|---|
| EP | 0684315 | 6/2002 |
| EP | 1914548 | 4/2008 |
| EP | 1914552 | 4/2008 |
| EP | 1914553 | 4/2008 |
| WO | WO 1991/016633 A1 | 10/1991 |
| WO | WO 1993/009438 A1 | 5/1993 |
| WO | WO 2002/070742 A1 | 9/2002 |
| WO | WO 2004/088324 A2 | 10/2004 |
| WO | WO 2005/014635 A2 | 2/2005 |
| WO | WO 2005/031364 A1 | 4/2005 |
| WO | WO 2006/029838 A2 | 3/2006 |
| WO | WO 2006/034427 A2 | 3/2006 |
| WO | WO 2006/074360 A2 | 7/2006 |
| WO | WO 2007/022248 A2 | 2/2007 |
| WO | WO 2007/051069 A2 | 5/2007 |
| WO | WO 2007/092353 A2 | 8/2007 |
| WO | WO 2007/110625 A2 | 10/2007 |
| WO | WO 2008/046160 A1 | 4/2008 |
| WO | WO 2008/054764 A2 | 5/2008 |
| WO | WO 2008/063369 A2 | 5/2008 |
| WO | WO 2009/014987 A2 | 1/2009 |
| WO | WO 2009/158423 A1 | 12/2009 |
| WO | WO 2011/022526 A1 | 2/2011 |
| WO | WO 2011/077129 A1 | 6/2011 |
| WO | WO 2011/100792 A1 | 8/2011 |
| WO | WO 2012/017071 A1 | 2/2012 |
| WO | WO 2012/170711 A1 | 12/2012 |
| WO | WO 2014/066568 A1 | 5/2014 |
| WO | WO 2014/089124 A1 | 6/2014 |
| WO | WO 2014/143977 A2 | 9/2014 |
| WO | WO 2014/144129 A2 | 9/2014 |
| WO | WO 2016/205723 A2 | 12/2016 |
| WO | WO 2018/027160 A1 | 2/2018 |
| WO | WO 2018/027171 A1 | 2/2018 |
| WO | WO 2019/036032 A1 | 2/2019 |

OTHER PUBLICATIONS

Ananth et al., "Association of Temporal Changes in Gestational Age With Perinatal Mortality in the United States, 2007-2015," *JAMA Pediatr.*, 172(7):627-634 (2018).

Anderson et al., "Quantitative mass spectrometric multiple reaction monitoring assays for major plasma proteins," *Mol. Cell. Proteomics*, 5(4):573 (2006).

Anderson, "Sex-hormone-binding globulin," *Clin. Endocrinol (Oxf)*,3(1):69-96 (1974).

Bamber, "The area above the ordinal dominance graph and the area below the receiver operating characteristic graph," *J. Math. Psychol.*, 12(4):387-415 (1975).

Banaem et al., "Maternal serum C-reactive protein in early pregnancy and occurrence of preterm premature rupture of membranes and preterm birth," *J. Obstet. Gynaecol. Res.*, 38(5):780-786 (2012).

Behrman et al. eds., "Preterm Birth: Causes, Consequences, and Prevention," Institute of Medicine (US) Committee on Understanding Premature Birth and Assuring Healthy Outcomes, National Academies Press, Washington DC, 791 pages (2007).

Belfiore et al., "Insulin receptor and cancer," *Endocr. Relat. Cancer*, 18:R125—R147 (2011).

Berkley et al., "Multiple Marker Screen for Preeclampsia," *Am. J. Obstet. Gynecol.*, 197(6):S142 (2007).

Beta et al., Prediction of spontaneous preterm delivery from maternal factors, obstetric history and placental perfusion and function at 11-13 weeks, *Prenat. Diagn.*, 31(1):75-83 (2011).

Bezold et al., "The genomics of preterm birth: from animal models to human studies," *Genome Med.*, 5(4):34 (2013).

Biemann, "Sequencing of peptides by tandem mass spectrometry and high-energy collision-induced dissociation," *Methods Enzymol.*, 193:455-479 (1990).

Blencowe et al., "National, regional and worldwide estimates of preterm birth." *Lancet*, 9; 379(9832):2162-2172 (2012).

Box et al., "An analysis of transformations," *Royal Stat. Soc. Series B*, 26:211-246 (1964).

Breiman, "Random Forests," *Mach. Learn.*, 45:5-32 (2001).

Brody et al., "Life's simple measures: unlocking the proteome," *J Mol Biol.* 422(5):595-606 (2012).

Brown et al., "Interval estimation for a binomial proportion.," *Statistical Science*, 16(2):101-133 (2001).

Carty et al., "Novel Biomarkers for Predicting Preeclampsia," *Trends Cardiovasc. Med.*, 15(5):186-194 (2008).

Catov et al., "Activation of the Fibrinolytic Cascade Early in Pregnancy Among Women with Spontaneous Preterm Birth," *Obstet. Gynecol.*, 112(5):1116-1122 (2008).

Chen et al., "Lysophosphatidic acid up-regulates expression of growth-regulated oncogene-alpha, interleukin-8, and monocyte chemoattractant protein-1 in human first-trimester trophoblasts: possible roles in angiogenesis and immune regulation," *Endocrinology*, 151(1):369-379 (2010).

(56) References Cited

OTHER PUBLICATIONS

Chim et al., "Systematic identification of spontaneous preterm birth-associated RNA transcripts in maternal plasma," *PLoS One*, 7(4):e34328 (2012).
Cozens et al., "DNA sequences of two expressed nuclear genes for human mitochondrial ADP/ATP translocase," *J. Mol. Biol.*, 206(2):261-280 (1989).
Craig et al., "TANDEM: matching proteins with tandem mass Spectra," *Bioinformatics*, 20:1466-1467 (2004).
Crosley et al., "IGFBP-4 and -5 are expressed in first-trimester villi and differentially regulate the migration of HTR-8/SVneo cells," *Reprod. Biol. Endocrinol.*, 12(1):123 (2014).
Cunningham et al., "The complete amino acid sequence of beta 2-microglobulin," *Biochemistry*, 12(24):4811-4822 (1973).
Damsky et al., "Distribution patterns of extracellular matrix components and adhesion receptors are intricately modulated during first trimester cytotrophoblast differentiation along the invasive pathway, in vivo," *J. Clin. Invest.*, 89(1):210-222 (1992).
Dasari et al., "Comprehensive proteomic analysis of human cervical-vaginal fluid," *J. Proteome Res.*, 6(4):1258-1268 (2007).
De Groot et al., "Specific Peptides Identified by Mass Spectometry in Placental Tissue from Pregnancies Attained by Laser Capture Dissection," *Protemics Clin. Appl.*, 1(3):325-335 (2007).
Demetriou et al., "Paternally expressed, imprinted insulin-like growth factor-2 in chorionic villi correlates significantly with birth weight," *PLoS One*, 9(1):e85454 (2014).
Dmitrienko et al., "Key multiplicity issues in clinical drug development," *Stat Med.*, 32(7):1079-1111 (2012).
Domanski et al., "MRM-Based Multiplexed Quantification of 67 Putative Cardiovascular Disease Biomarkers in Human Plasma," *Proteomics*, 12:1222-1243 (2012).
Eastaugh et al., "Comparison of Neural Networks and Statistical Models to Predict Gestational Age at Birth," *Neural Comput. Applic.*, 6(3):158-164 (1997).
Efron et al., "Least angle regression," *Annals Statistics*, 32:407-451 (2004).
Endo et al., "Primary structure and gene localization of human prolidase," *J. Biol. Chem.*, 264(8):4476-4481 (1989).
Eng et al., "An Approach to Correlate Tandem Mass Spectral Data of Peptides with Amino Acid Sequences in a Protein Database," *J. Am. Soc. Mass Spectrom*, 5:976-989 (1994).
Enquobahrie et al., "Early pregnancy peripheral blood gene expression and risk of preterm delivery: a nested case control study," *BMC Pregnancy Childbirth*, 9(1):56 (2009).
Erez et al., "High Tissue Factor Activity and Low Tissue Factor Pathway Inhibitor Concentrations in Patients with Preterm Labor," *J. Matern. Fetal Neonatal Med.*, 23(1):23-33 (2010).
Esplin et al., "Proteomic identification of serum peptides predicting subsequent spontaneous preterm birth," *Am. J. Obstet. Gynecol.*, 204(5):391e1-8 (2010).
Flick et al., "Mechanistic insights from serum proteomic biomarkers predictive of spontaneous preterm birth," *Am. J. Obstet. Gynecol.*, Abstract No. 253, S148-S149 (2016).
Forbes et al., "Insulin-like growth factor I and II regulate the life cycle of trophoblast in the developing human placenta," *Am. J. Physiol. Cell Physiol.*, 294(6):C1313-1322 (2008).
Fullerton et al., "Sequence polymorphism at the human apolipoprotein AII gene (APOA2): unexpected deficit of variation in an African-American sample," *Hum. Genet.*, 111(1):75-87 (2002).
Fullerton et al., "The effects of scale: variation in the APOA1/C3/A4/A5 gene cluster," *Hum. Genet.*, 115(1):36-56 (2004).
Geisert et al., "Expression of an inter-alpha-trypsin inhibitor heavy chain-like protein in the pig endometrium during the oestrous cycle and early pregnancy," *J. Reprod. Fertility*, 114(1):35-43 (1998).
Geman et al., "Classifying gene expression profiles from pair wise mRNA comparisons," *Stat. Appl. Genet. Mol. Biol.*, 3(1):Article19 (2004).
Gershagen et al., "A cDNA coding for human sex hormone binding globulin," *FEBS Lett.*, 220(1):129-135 (1987).

Goldenberg et al., "Epidemiology and causes of preterm birth," *Lancet*, 371(9606):75-84 (2008).
Goldenberg et al., "The Preterm Prediction Study: Cervical lactoferrin concentration, other markers of lower genital tract infection, and preterm birth," *Am. J. Obstet. Gynecol.*, 182(3):631-635 (2000).
Goldenberg et al., "The preterm prediction study: the value of new vs standard risk factors in predicting early and all spontaneous preterm births," *Am. J. Public Health*, 88(2):233-238 (1998).
Gomez-Lopez et al., "Immune cells in term and preterm labor.," *Cell Mol. Immunol.*, 11(6):571-581 (2014).
Gravett et al., "Diagnosis of intra-amniotic infection by proteomic profiling and identification of novel biomarkers," *JAMA*, 292(4):462-469 (2004).
Gravett et al., "Proteomic analysis of cervical-vaginal fluid: identification of novel biomarkers for detection of intra-amniotic infection," *J. Proteome Res.*, 6(1):89-96 (2007).
Greene, "Choices in Managing Full-Term Pregnancy," *N. Engl. J. Med.*, 379(6):580-581 (2018).
Grobman et al., "Labor Induction versus Expectant Management in Low-Risk Nulliparous Women," *N. Engl. J. Med.*, 379(6):513-523 (2018).
Grobman, "A randomized trial of elective induction of labor at 39 weeks compared with expectant management of low-risk nulliparous women," *Am. J. Obst. Gyn.*, 218(1):S601 (2018).
Grundmann et al., "Complete cDNA sequence encoding the B subunit of human factor XIII," *Nucleic Acids Res.*, 18(9):2817-2818 (1990).
Guatelli et al., "Isothermal, in vitro amplification of nucleic acids by a multienzyme reaction modeled after retroviral replication," *Proc. Natl. Acad. Sci. USA*, 87:1874-1878 (1990).
Haataja et al., "Mapping a new spontaneous preterm birth susceptibility gene, IGF1R, using linkage, haplotype sharing, and association analysis," *PLoS Genet.*, 7(2):e1001293 (2011).
Haefliger et al., "Structural and Functional Characterization of Complement C8γ, A Member of the Lipocalin Protein Family," *Mol. Immunol.*, 28(1-2):123-131 (1991).
Hammond, "Diverse roles for sex hormone-binding globulin in reproduction," *Biol. Reprod.*, 85(3):431-441 (2011).
Hassan et al. "Vaginal progesterone reduces the rate of preterm birth in women with a sonographic short cervix: a multicenter, randomized, double-blind, placebo-controlled trial," *Ultrasound Obstet. Gynecol.*, 38(1):18-31 (2011).
Haviland et al., "Complete cDNA sequence of human complement pro-C5. Evidence of truncated transcripts derived from a single copy gene," *J. Immunol.*, 146(1):362-368 (1991).
Heitner et al., "Differneitiation of HELLP patients from healthy pregnant women by proteome analysis—On the way towards a clinical marker set," *J. Chromatog. B*, 840(1):10-19 (2006).
Hobel et al., "Maternal plasma corticotropin-releasing hormone associated with stress at 20 weeks gestation in pregnancies ending in preterm delivery," *Am. J. Obstet. Gynecol.*, 180(1):S257-S263 (1999).
Howard et al., "Complementary DNA and derived amino acid sequence of the beta subunit of human complement protein C8: identification of a close structural and ancestral relationship to the alpha subunit and C9," *Biochemistry*, 26(12):3565-3570 (1987).
Howson et al. eds., "Born too soon: The Global Action Report on Preterm Birth," World Health Organization, Geneva, 126 pages (2012).
Huang et al., "Tree-structured supervised learning and the genetics of hypertension," *Proc. Nat. Acad. Sci. U.S.A.*, 101:10529-10534 (2004).
Huynh et al., "Low pregnancy-associated plasma protein A level in the first trimester," *Can. Fam. Physician*, 60(10):899-903 (2014).
Iams et al., "The length of the cervix and the risk of spontaneous premature delivery," *N. Engl. J. Med.*, 334(9):567-572 (1996).
Katayama et al., "Application of serum proteomics to the Women's Health Initiative conjugated equine estrogens trial reveals a multitude of effects relevant to clinical findings," *Genome Med.*, 1:47 (2009).
Keller et al., "Empirical Stat istical Model to Estimate the Accuracy of Peptide Identificat ions Made by MS/MS and Database Search," *Anal. Chem*, 74:5383-5392 (2002).

(56) References Cited

OTHER PUBLICATIONS

Kenny et al., "Novel biomarkers for pre-eclampsia detected using metabolomics and machine learning," *Metabolomics*, 1(3):227-234 (2005).

Khan et al., "Delineation and synthesis of the membrane receptor-binding domain of sex hormone-binding globulin," *J Biolog. Chem.*, 265(30):18362-18365 (1990).

Kim et al., "ITI-H4, as a biomarker in the serum of recurrent pregnancy loss (RPL) patients," *Mol. Biosyst.*, 7(5):1430-1440 (2011).

Klee et al., "Strategy for the development of a mass spectrometry assay for measuring sex hormone binding globulin (SHBG) in human serum," *Clinical Chemistry*, Poster B-103, 58(S10):A1-A77 (2012).

Knott et al., "Complete protein sequence and identification of structural domains of human apolipoprotein B," *Nature*, 323:734-738 (1986).

Kuhn et al., "Quantification of C-reactive protein in the serum of patients with rheumatoid arthritis using multiple reaction monitoring mass spectrometry and 13C-labeled peptide standards," *Proteomics*, 4:1175-1186 (2004).

Kwoh et al., "Transcription-based amplification system and detection of amplified human immunodeficiency virus type 1 with a bead-based sandwich hybridization format," *Proc. Natl. Acad. Sci. USA*, 86:1173-1177 (1989).

Larrea et al. "Evidence that human placenta is a site of sex hormone-binding globulin gene expression," *J. Steroid Biochem. Mol. Biol.*, 46(4):497-505 (1993).

Li et al., "A blood-based proteomic classifier for the molecular characterization of pulmonary nodules," *Sci. Transl. Med.*, 5(207):ra142 (2013).

Li et al., "An integrated quantification method to increase the precision, robustness, and resolution of protein measurement in human plasma samples," *Clin. Proteomics*, 12(1):3 (2015).

Lin et al., "Simple and Rapid Sample Preparation Methods for Whole Blood and Blood Plasma," *Diagnostic Molecular Microbiology, Principles and Applications*, Persing et al., eds., Rochester, MN, pp. 605-616 (1993).

Lindström et al. "The role of nuclear factor kappa B in human labour," *Reproduction*, 130(5):569-581 (2005).

Ling et al. "Multiplexing molecular diagnostics and immunoassays using emerging microarray technologies" *Expert Rev. Mol. Diagn.*, 7:87-98 (2007).

Liu et al., "Recent developments in protein and cell-targeted aptamer selection and applications," *Curr. Med. Chem.*, 18(27):4117-4125 (2011).

Lizardi et al., "Exponential amplification of recombinant-RNA hybridization probes," *BioTechnol.*, 6:1197-1202 (1988).

Lukanova et al., "Body mass index, circulating levels of sex-steroid hormones, IGF-I and IGF-binding protein-3: a cross-sectional study in healthy women," *Eur. J. Endocrinol.*, 150(2):161-171 (2004).

Macdorman et al., "Fetal and Perinatal Mortality: United States, 2013," *Natl. Vital. Stat. Rep.*, 64(8):1-24 (2015).

Mackinnon et al., "Molecular cloning of cDNA for human complement component C1s. The complete amino acid sequence," *Eur. J. Biochem.*, 169(3):547-553 (1987).

Martin et al., "Births: Final Data for 2012," *Natl Vital Stat Rep.*, 64(1):1-65 (2015).

Martin et al., "Births: Final Data for 2016," *Natl. Vital Stat. Rep.*, 67(1):1-55 (2018).

Mason et al., "Areas beneath the relative operating characteristics (ROC) and relative operating levels (ROL) curves: Statistical significance and interpretation," *QJR Meteorol. Soc.*, 128(584):2145-2166 (2002).

Mayo Clinic, "Researchers Discover Link Between High Levels of HtrA1 Protein and Preeclampsia, a Complication of Pregnancy," URL: http://www.mayoclinic/org/news2006-rst/3234.html, Publication Date: Feb. 1, 2006.

McElroy et al., "Maternal coding variants in complement receptor 1 and spontaneous idiopathic preterm birth," *Hum. Genet.*, 132(8):935-942 (2013).

McLean et al., "Effect of Collision Energy Optimization on the Measurement of Peptides by Selected Reaction Monitoring (SRM) Mass Spectrometry," *Anal. Chem.*, 82(24):10116-10124 (2010).

McLean et al., "Skyline: an open source document editor for creating and analyzing targeted proteomics experiments," *Bioinformatics*, 26(7):966-968 (2010).

Mendelson, "Minireview: fetal-maternal hormonal signaling in pregnancy and labor," *Mol Endocrinol.*, 23(7):947-954 (2009).

Menon et al., "Amniotic fluid metabolomic analysis in spontaneous preterm birth," *Reprod. Sci.*, 21(6):791-803 (2014).

Menon et al., "Genetic regulation of amniotic fluid TNF-alpha and soluble TNF receptor concentrations affected by race and preterm birth," *Human Genet.*, 124(3):243-253 (2008).

Middleton et al., "Induction of labour for improving birth outcomes for women at or beyond term," *Cochrane Database Syst. Rev.*, 5:CD004945 (2018).

Moore et al., "Pregnancy-specific glycoproteins: complex gene families regulating maternal-fetal interactions," *Int. J. Dev. Biol.*, 58:273-280 (2014).

Morisaki et al., "Risk factors for spontaneous and provider-initiated preterm delivery in high and low Human Development Index countries: a secondary analysis of the World Health Organization Multicountry Survey on Maternal and Newborn Health," *BJOG*, 121(Supp. 1):101-109 (2014).

Moutquin, "Classification and heterogeneity of preterm birth," *BJOG*, 110 (Suppl 20):30-33 (2003).

Murata et al., "Molecular cloning and expression of the human interleukin 5 receptor," *J. Exp. Med.*, 175(2):341-351 (1992).

Murphy et al., "Deaths: Final Data for 2012," *Natl. Vital Stat. Rep.*, 63(9):1-118 (2015).

Nakajima et al., "Elevated vasoinhibin derived from prolactin and cathepsin D activities in sera of patients with preeclampsia," *Hypertens. Res.*, 38:899-901 (2015).

Nielsen et al., "Multiplexed sandwich assays in microarray format," *J. Immunol. Methods*, 290: 107-120 (2004).

O'Leary et al., "Longitudinal assessment of changes in reproductive hormones during normal pregnancy," *Clin. Chem.*, 37(5):667-672 (1991).

Oliveira et al., "Primary Structure of Human C-reactive Protein," *J. Biol. Chem.*, 254(2):489-502 (1979).

Pal et al., "Fetuin-A acts as an endogenous ligand of TLR4 to promote lipid-induced insulin resistance," *Nature Med.*, 18(8):1279-1285 (2012).

Pereira et al., "Identification of novel protein biomarkers of preterm birth in human cervical-vaginal fluid," *J. Proteome Res.*, 6(4):1269-1276 (2007).

Pereira et al., "Insights into the multifactorial nature of preterm birth: proteomic profiling of the maternal serum glycoproteome and maternal serum peptidome among women in preterm labor," *Am. J. Obstet. Gynecol.*, 202(6):555.e1-10 (2010).

Petersen et al., "Characterization of the gene for human plasminogen, a key proenzyme in the fibrinolytic system," *J. Biol. Chem.*, 265(11):6104-6111 (1990).

Petrini et al. "Estimated effect of 17 alpha-hydroxyprogesterone caproate on preterm birth in the United States," *Obstet. Gynecol.*, 105(2):267-272 (2005).

Poirier et al., "Obesity and cardiovascular disease: pathophysiology, evaluation, and effect of weight loss: an update of the 1997 American Heart Association Scientific Statement on Obesity and Heart Disease from the Obesity Committee of the Council on Nutrition, Physical Activity, and Metabolism," *Circulation*, 113:898-918 (2006).

Polpitiya et al., "DAnTE: a statistical tool for quantitative analysis of-omics data," *Bioinformatics*, 24:1556-1558 (2008).

Powe et al., "First Trimester Vitamin D, Vitamin D Binding Protein, and Subsequent Preeclampsia," *Hypertension*, 56(4):758-763 (2010).

Price et al., "Highly accurate two-gene classifier for differentiating gastrointestinal stromal tumors and leiomyosarcomas," *Proc. Natl. Acad. Sci. USA*, 104(9):3414-3419 (2007).

(56) References Cited

OTHER PUBLICATIONS

Qiu et al., "Significance of IGFBP-4 in the development of fetal growth restriction," *J. Clin. Endocrinol. Metab.*, 97(8):E1429-1439 (2012).
Rasanen et al., "First Trimester Maternal Serum Biomarkers for Prediction of Preeclampsia," *Am. J Obstet. Gynecol.*, 197(6):S10 (2007).
Rask et al., "Structural and functional studies of vitamin A-binding proteins," *Ann. N. Y. Acad. Sci.*, 359:79-90 (1981).
Red-Horse et al., "Trophoblast differentiation during embryo implantation and formation of the maternal-fetal interface," *J. Clin. Invest.*, 114:744-754 (2004).
Reid, "Complete Amino Acid Sequences of the Three Collagen-Like Regions present in Subcomponent Clq of the First Component of Human Complement," *Biochem. J.*, 179(2):367-371 (1979).
Romero et al., "Identification of fetal and maternal single nucleotide polymorphisms in candidate genes that predispose to spontaneous preterm labor with intact membranes," *Am. J. Obstet. Gynecol.*, 202(5):431.e1-34 (2010).
Ruczinski et al., "Logic Regression," *J. Comput. Graph. Stat.*, 12(3):475-511 (2003).
Saade et al., "Development and validation of a spontaneous preterm delivery predictor in asymptomatic women," *Am. J. Obstet. Gynecol.*, 214(5): 633.e1-633.e24 (2016).
Salier et al., "The inter-alpha-inhibitor family: from structure to regulation," *Biochem. J.*, 315:1-9 (1996).
Sambrook et al., "Analysis of RNA," *Molecular Cloning, A laboratory Manual*, Cold Spring Harbor Laboratory Press, Plainview, NY, pp. 7.37-7.57 (1989).
Scholl et al., "Anemia, Iron and Pregnancy Outcome," *J. Nutrition*, 130(2S):443S-447S (2000).
Schumann et al., "Structure and Function of Lipopolysaccharide Binding Protein," *Science*, 249(4975):1429-1431 (1990).
Seegar et al., "Tie1-Tie2 interactions mediate functional differences between angiopoietin ligands," *Mol. Cell.*, 37(5):643-655 (2010).
Selby et al., "Analysis of a Major Human Chorionic Somatomammotropin Gene," *J. Biol. Chem.*, 259(21):13131-13138 (1984).
Self et al., "Advances in immunoassay technology" *Curr. Opin. Biotechnol.*, 7:60-65 (1996).
Sera Prognostics, Inc., "Proteomic Assessment of Preterm Birth (PAPR)," ClinicalTrials.gov archive, pp. 1-6 (Apr. 18, 2019). Retrieved from the Internet: https://clinicaltrials.gov/ct2/show/NCT01371019, on Apr. 18, 2019.
Shi et al., "IgY14 and SuperMix immunoaffinity separations coupled with liquid chromatography—mass spectrometry for human plasma proteomics biomarker discovery," *Methods*, 56(2):246-253 (2012).
Sibai, "Preeclampsia and Hypertensive Disorders," *Obstetrics: Normal and Problem Pregnancies*, 7th ed., Gabbe et al. eds., Elsevier, Philadelphia, PA, pp. 661-705, 2017.
Simó et al. "Novel insights in SHBG regulation and clinical implications," *Trends Endocrinol. Metab.*, 26(7):376-383 (2015).
Sing et al., "ROCR: visualizing classifier performance in R," *Bioinformatics*, 21(20):3940-3941 (2005).
Smets et al., "Novel Biomarkers in Preeclampsia," *Clinica Chimica Acta*, 364:22-32 (2006).
Son et al., "Multiple FAS1 domains and the RGD motif of TGFBI act cooperatively to bind αvβ3 integrin, leading to anti-angiogenic and anti-tumor effects," *Biochim. Biophys. Acta*, 1833(10) 2378-2388 (2013).
Song et al., "Quantification of fragments of human serum inter-alpha-trypsin inhibitor heavy chain 4 by a surface-enhanced laser desorption/ionization-based immunoassay," *Clin. Chem.*, 52(6):1045-1053 (2006).
Spencer et al., "First trimester sex hormone-binding globulin and subsequent development of preeclampsia or other adverse pregnancy outcomes," *Hypertens. Pregnancy*, 24(3):303-311 (2005).
Stagnaro-Green et al., "Thyroid disorders in pregnancy," *Nat. Rev. Endocrinol.*, 8(11):650-658 (2012).
Stella et al., "Preterm labor biomarker discovery in serum using 3 proteomic profiling methodologies," *Am. J. Obstet. Gynecol.*, 387:e1-e13 (2009).
Swaggart et al., :Genomics of preterm birth, *Cold Spring Harb Perspect Med.*, 5(2):a023127 (2015).
Thompson et al., "Identification and confirmation of a module of coexpressed genes," *Genome Res.*, 12(10):1517-1522 (2002).
Tibshirani et al., "Diagnosis of multiple cancer types by shrunken centroids of gene expression," *Proc. Natl. Acad. Sci. USA*, 99:6567-6572 (2002).
Traboni et al., "Sequence of a full length cDNA coding for human protein HC (alpha 1 microglobulin)," *Nucleic Acids Res.*, 14(15):6340 (1986).
Tusher et al., "Significance analysis of microarrays applied to the ionizing radiation response," *Proc. Natl. Acad. Sci. USA*, 98:5116-5121 (2001).
Underwood et al., "The association of the angiotensinogen gene with insulin sensitivity in humans: a tagging single nucleotide polymorphism and haplotype approach," *Metabolism*, 60(8):1150-1157 (2011).
UniProt, P02753—RET4_Human, UniProtKB, 2002, 1.
Vascotto et al., "Oxidized Tmasthyretin in Amniotic Fluid as an Early Marker of Preeclampsia," *J. Proteome Res.*, 6:160-170 (2006).
Villanueva et al., "Automated serum peptide profiling," *Nat. Protoc.*, 1(2):880-891 (2006).
Walker et al., "Isothermal in vitro amplification of DNA by a restriction enzyme/DNA polymerase system," *Proc. Natl. Acad. Sci. USA*, 89:392-396 (1992).
Walker et al., "Randomized Trial of Labor Induction in Women 35 Years of Age or Older," *N. Engl. J. Med.*, 374(9):813-822 (2016).
Walz et al., "Amino acid sequence of human prothrombin fragments 1 and 2," *Proc. Natl. Acad. Sci. U.S.A.*, 74(5):1969-1972 (1977).
Wang et al., "LRG1 promotes angiogenesis by modulating endothelial TGF-β signaling," *Nature* 499:306-311 (2013).
Watanabe et al., "Proteome Analysis Reveals Elevated Serum Levels of Clusterin in Patients with Preeclampsia," 4:537-543 (2004).
Watt et al., "Amino Acid Sequence of the β Chain of Human Fibrinogen," *Biochemistry*, 18(1):68-76 (1979).
Weiner et al., "Human effector/initiator gene sets that regulate myometrial contractility during term and preterm labor," *Am. J. Obstet. Gynecol.*, 202(5):474.e1-20 (2010).
Weiss, "Hot prospect for new gene amplifier," *Science*, 254:1292-1293 (1991).
Xu et al., "ECE-1: a membrane-bound metalloprotease that catalyzes the proteolytic activation of big endothelin-1," *Cell*, 78(3):473-485 (1994).
Yocum et al., "Current affairs in quantitative targeted proteomics: multiple reaction monitoring-mass spectrometry," *Brief Funct. Genomic Proteomic.*, 8(2):145-157 (2009).
Pavcnik-Arnol et al., "Lipopolysaccharide-Binding Protein as Marker of Fetal Inflammatory Response Syndrome after Preterm Premature Rupture of Membranes," *Neonatol.*, 105:121-127 (2014).

weeks 19 - 21

FIG. 6

| Criteria | Comments |
|---|---|
| Analytical Robust | Analytes always detectable; stable instrument signal; immune to process factors such as run order; sample storage time; sample acquisition; etc. |
| Clinically Robust | Unaffected by co-morbidities (diabetes, hypertension, asthma, etc.); race; very early preterm; etc. |
| Performance | Robust Monte Carlo cross-validated performance in clinically relevant blood draw window. |

Candidate:    IBP4 / [SHBG CHL1 CLUS]

Perform 1000 trials and measure performance (AUC, ROC) for each.
Average over all trials is a conservative estimate of performance on a new sample set.

FIG. 9

Probability of successful validation (power analysis): > 90%

~.80 AUC

| Power | Cases | Controls | AUC0' | AUC1' |
|---|---|---|---|---|
| 0.90620 | 32 | 64 | 0.5000 | 0.7000 |
| 0.80569 | 24 | 48 | 0.5000 | 0.7000 |
| 0.91154 | 20 | 40 | 0.5000 | 0.7500 |
| 0.80907 | 15 | 30 | 0.5000 | 0.7500 |
| 0.90950 | 13 | 26 | 0.5000 | 0.8000 |
| 0.81058 | 10 | 20 | 0.5000 | 0.8000 |
| 0.91628 | 9 | 18 | 0.5000 | 0.8500 |
| 0.81623 | 7 | 14 | 0.5000 | 0.8500 |
| 0.90775 | 6 | 12 | 0.5000 | 0.9000 |
| 0.82436 | 5 | 10 | 0.5000 | 0.9000 |

134 proteins
216 clinical serum samples
GA 17-26 weeks

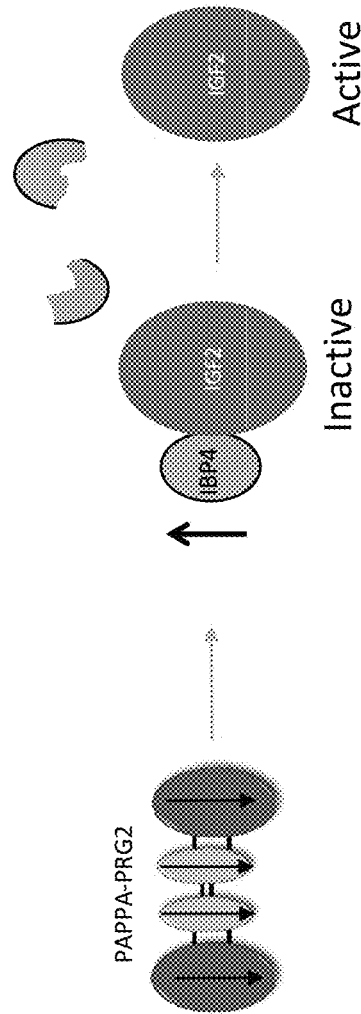
FIG. 18

FB = fetal blood vessel, CM = chorionic mesoderm, ST = syncytiotrophoblast.
Reproductive Biology and Endocrinology 12:123 (2014)

120 samples from GABD 119-180 with no BMI Restrictions

FIG. 41

```
IBP4_Isoform-1    MLPLCLVAALLLAAGPGPSLGDEAIHCPPCSEEKLARCRPPVGCEELVRE
IBP4_Isoform-1    PGCGCCATCALGLGMPCGVYTPRCGSGLRCYPPRGVEKPLHTLMHGQGVC IBP4_Isoform-1    MELAEIEAIQESLQPSDKDEGDHPMMSFPCSAHDRRCLQKHFAKIRDRS
IBP4_Isoform-2    MELAEIEAIQESLQPSDKDEGDHPNNSFPCSAHDRRCLQKHFAKIRDRS IBP4_Isoform-1    TSGGMKYNGAPREDARPVPQGSCQSELHRALERLAASQSRTHEDLYIIP
IBP4_Isoform-2    TSGGMKYNGAPREDARPVPQGSCQSELHRALERLAASQSRTHEDLYIIP IBP4_Isoform-1    IPNCDRNGNFHPKQCHPALDGQRGKCWCVDRKTGVKLPGGLEPKGELDCH
IBP4_Isoform-2    IPNCDRNGNFHPKQCHPALDGQRGKCWCVDRKTGVKLPGGLEPKGELDCH
QCHPALDGQR        QCHPALDGQR
                  **********

IBP4_Isoform-1    QLADSFRE
IBP4_Isoform-2    QLADSFRE
```

FIG. 43

```
Isoform-1  VEVKMEGDSVLLEVDGEEVLRLRQVSGPLTSKRHPIMRIALGGLLFPASNLRLP
Isoform-2  VEVKMEGDSVLLEVDGEEVLRLRQVSGPLTSKRHPIMRIALGGLLFPASNLRLP
Isoform-3  VEVKMEGDSVLLEVDGEEVLRLRQVSGPLTSKRHPIMRIALGGLLFPASNLRLP
Isoform-4  VEVKMEGDSVLLEVDGEEVLRLRQVSGPLTSKRHPIMRIALGGLLFPASNLRLP
Isoform-5  VEVKMEGDSVLLEVDGEEVLRLRQVSGPLTSKRHPIMRIALGGLLFPASNLRLP
Isoform-6  VEVKMEGDSVLLEVDGEEVLRLRQVSGPLTSKRHPIMRIALGGLLFPASNLRLP
Isoform-7  ------------------VLRLRQVSGPLTSKRHPIMRIALGGLLFPASNLR
IALGGLLFPASNLR                              IALGGLLFPASNLR
                                            **************
```

FIG. 51

| GA Boundary | Sens | Spec | AUC | OR (95% CI) |
|---|---|---|---|---|
| <37 vs >= 37 | 0.75 | 0.74 | 0.75 (p = 0.016) | 5.04 (1.4 - 18) |
| <37 vs >= 39 | 0.75 | 0.88 | 0.80 (p = 0.006) | 10.5 (1.6 - 68) |
| <35 vs >= 39 | 1.00 | 0.88 | 0.95 (p = 0.001) | 68.2 (2.8 - 1654) |
| <35 vs >= 37 | 1.00 | 0.83 | 0.93 (p = 0.001) | 37 (1.8 - 779) |
| <39 vs >= 39 | 0.72 | 0.88 | 0.76 (p = 0.008) | 9.38 (1.6 - 54) |
| <36 vs >= 36 | 0.83 | 0.83 | 0.79 (p = 0.027) | 17.33 (2.2 - 138) |
| <35 vs >= 35 | 1.00 | 0.83 | 0.93 (p = 0.001) | 34.47 (1.7 - 699) |

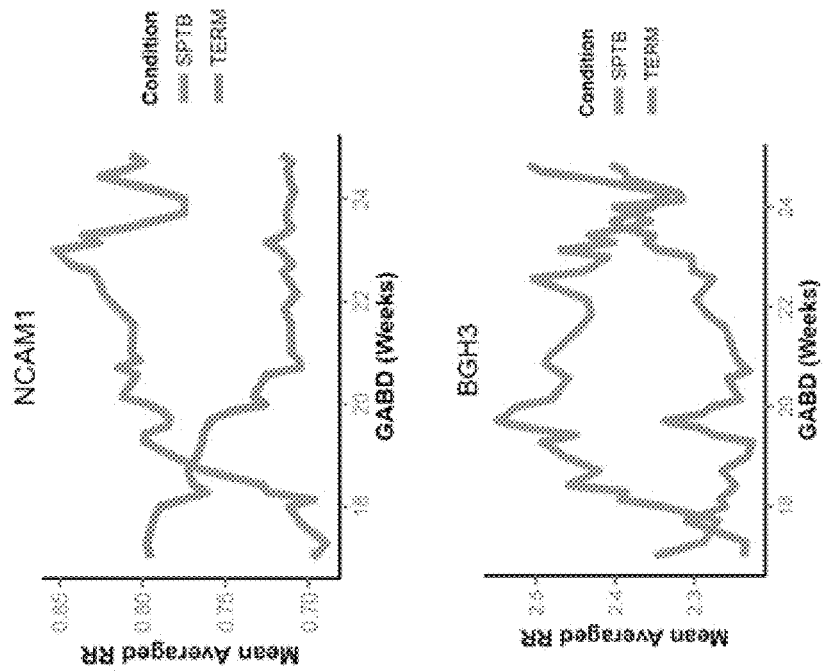
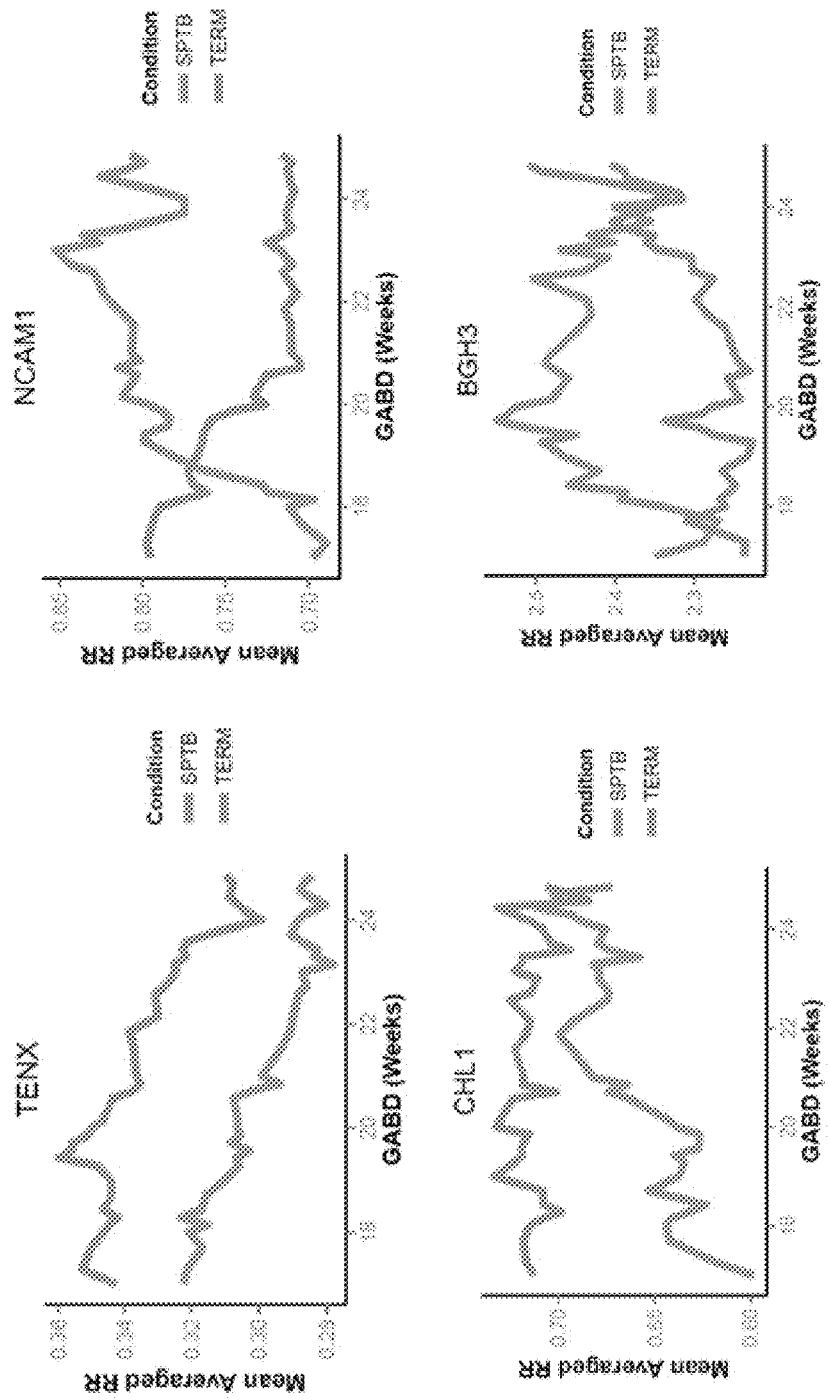
FIG. 54A  FIG. 54B  FIG. 54C  FIG. 54D

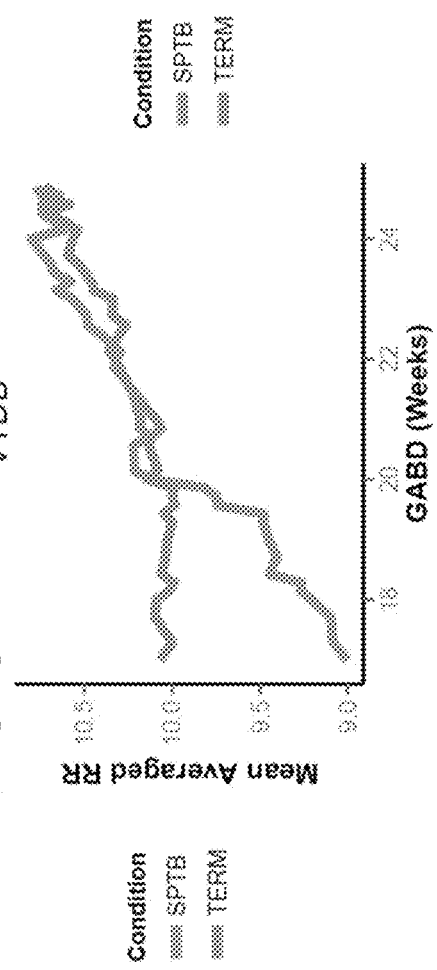
FIG. 67A
FIG. 67B
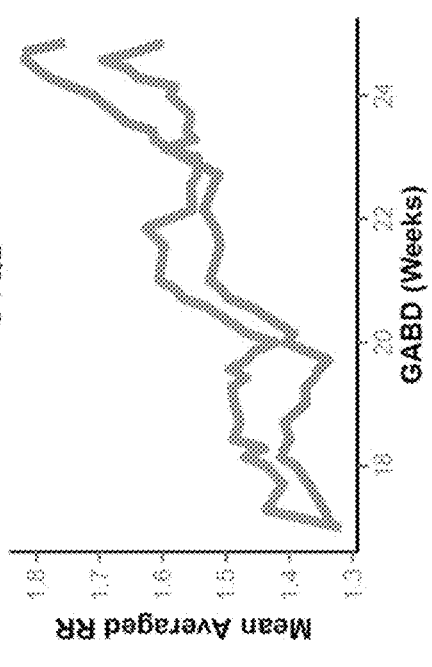
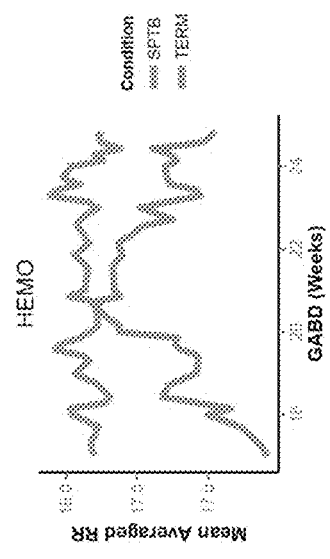
FIG. 67C
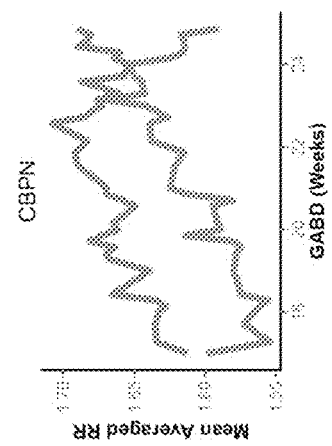
FIG. 67D
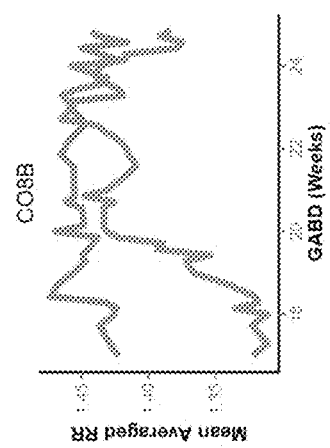
FIG. 67E

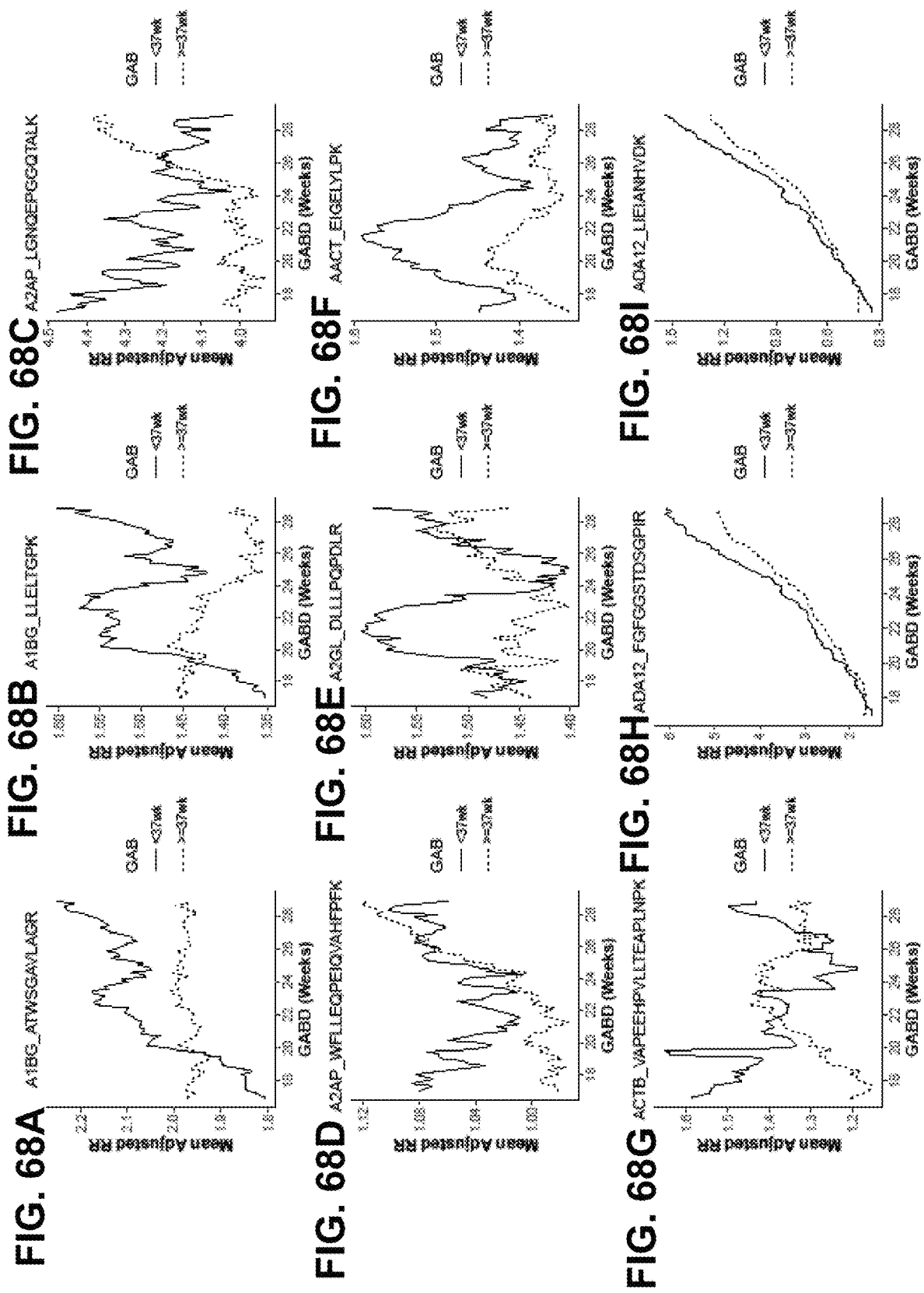

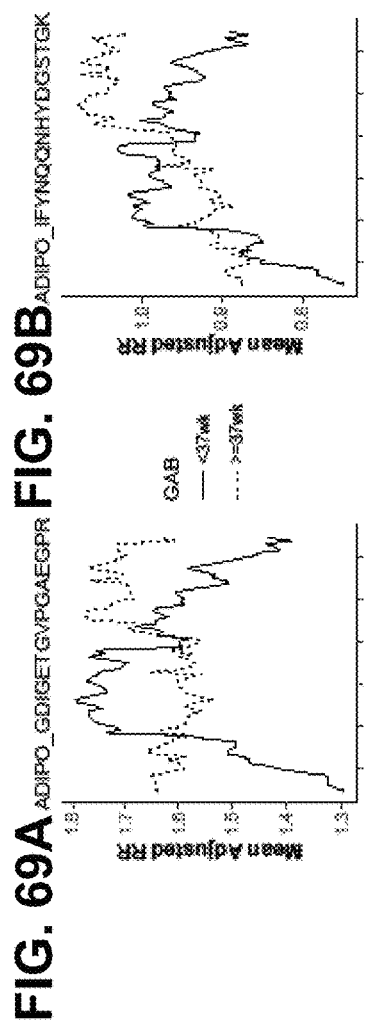
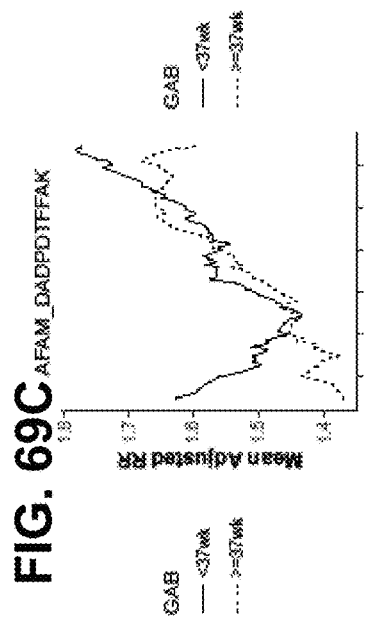
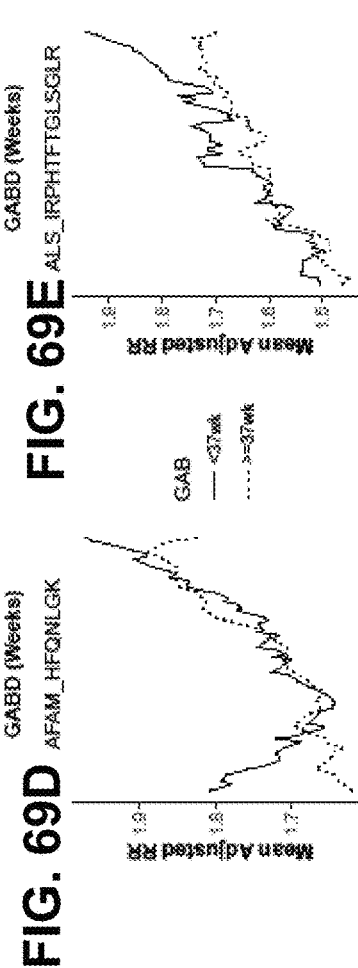
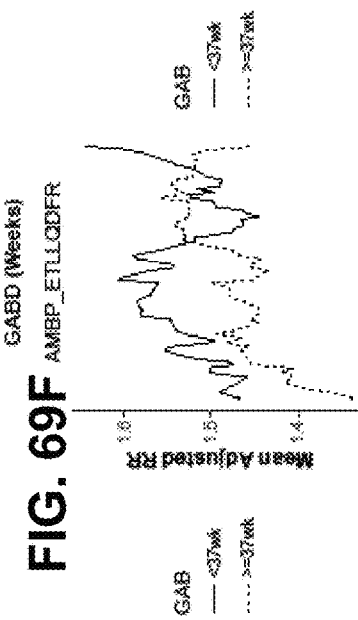
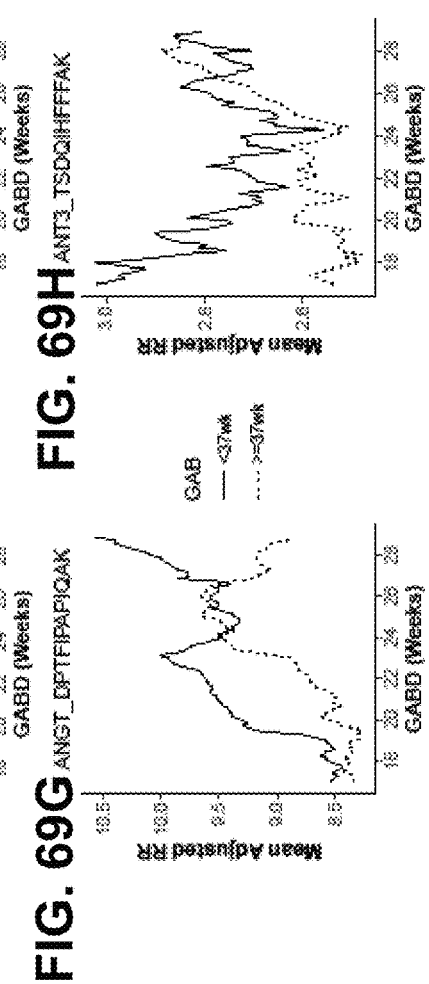
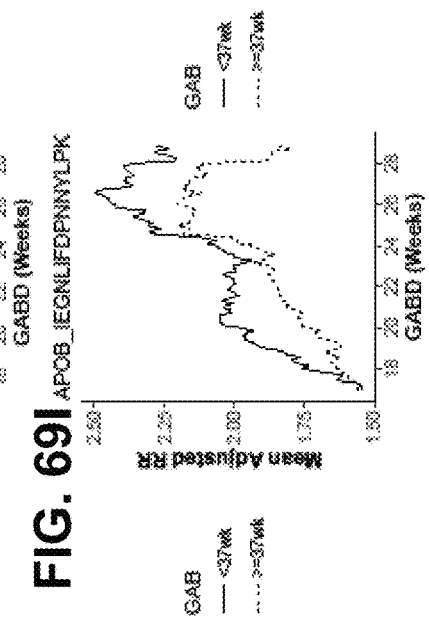

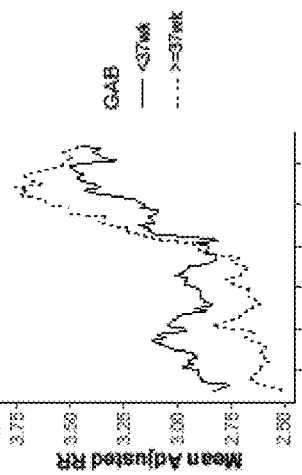
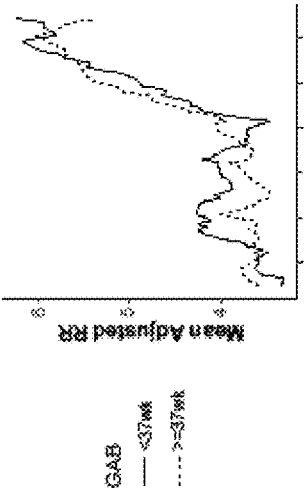
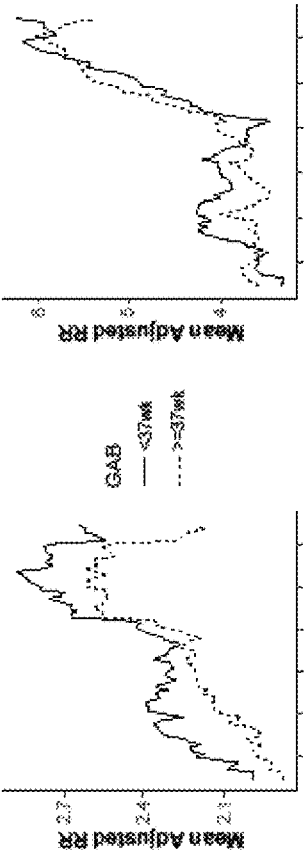
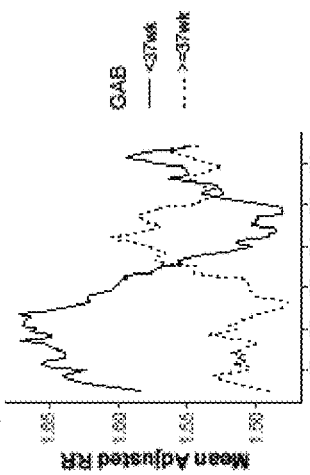
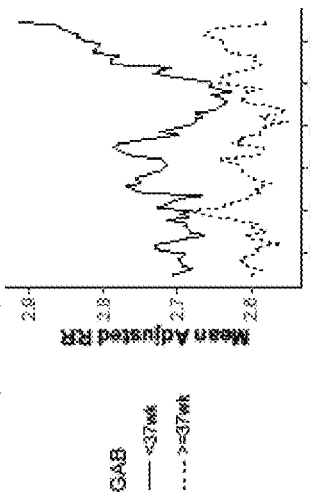
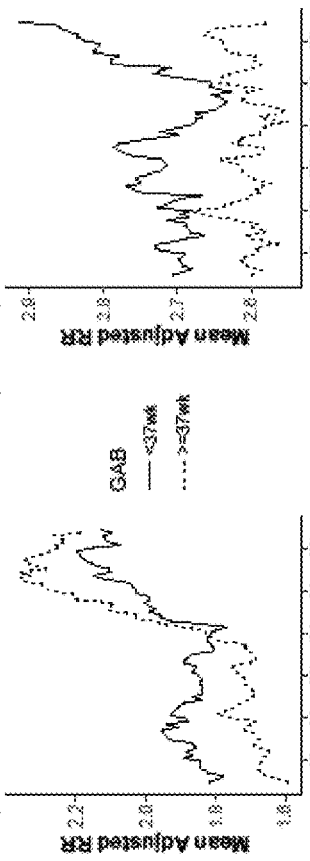
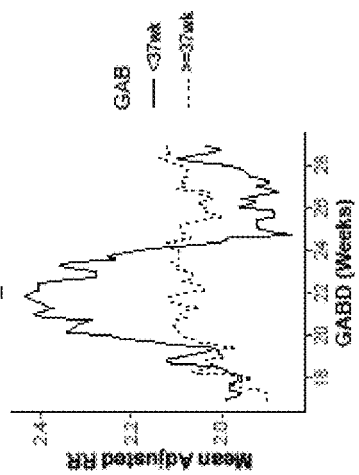
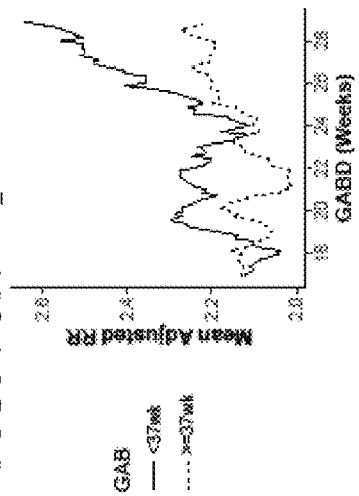
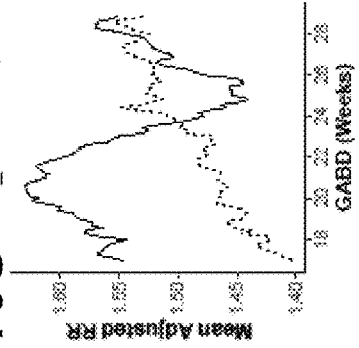

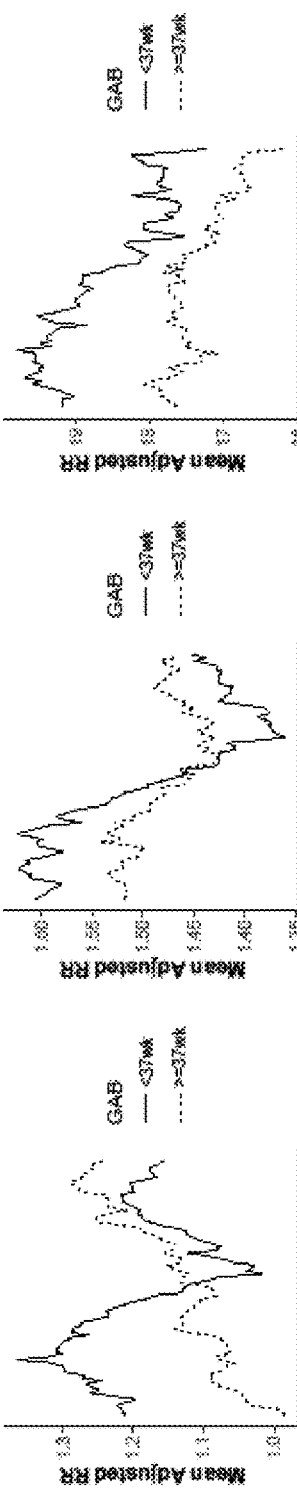
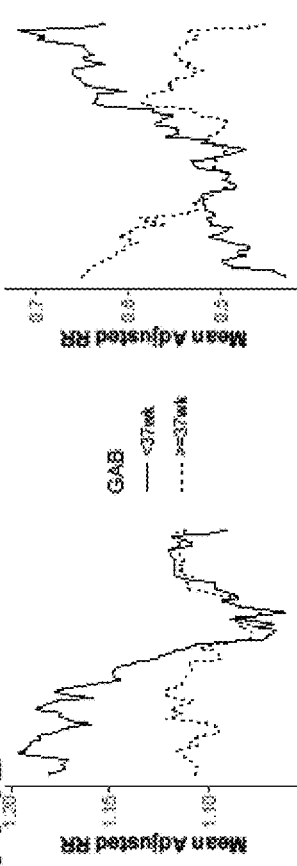
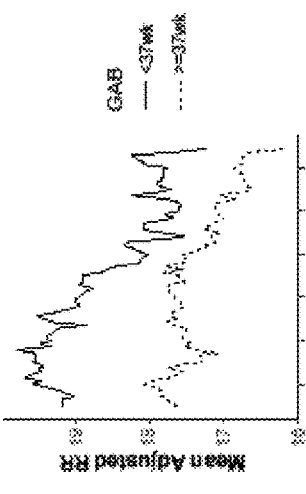
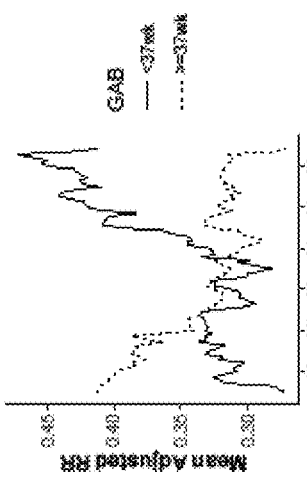
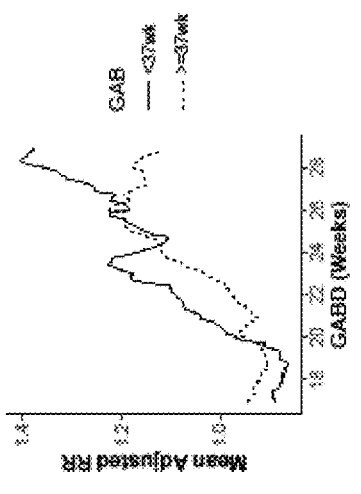
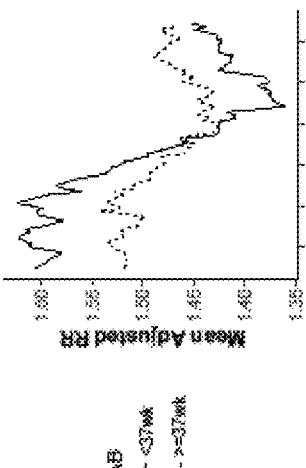
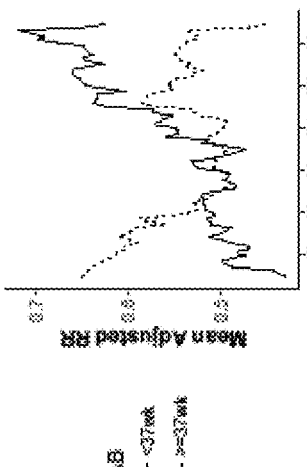
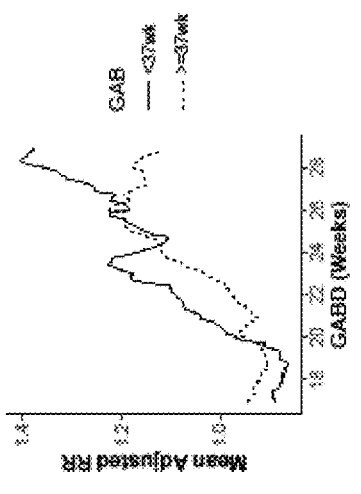
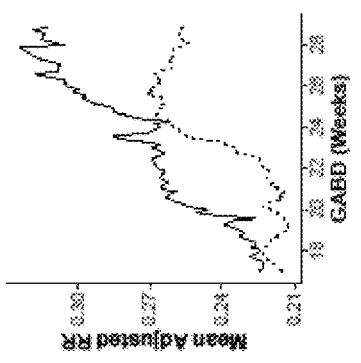

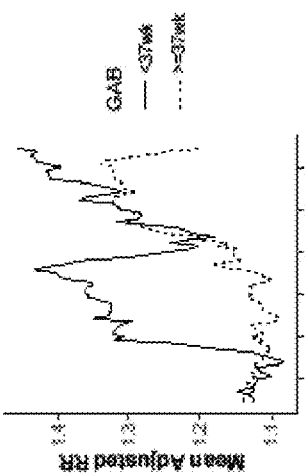
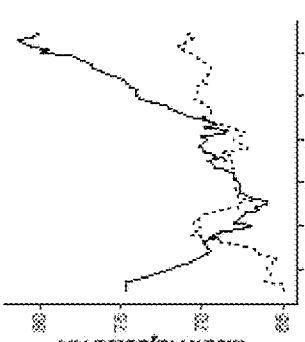
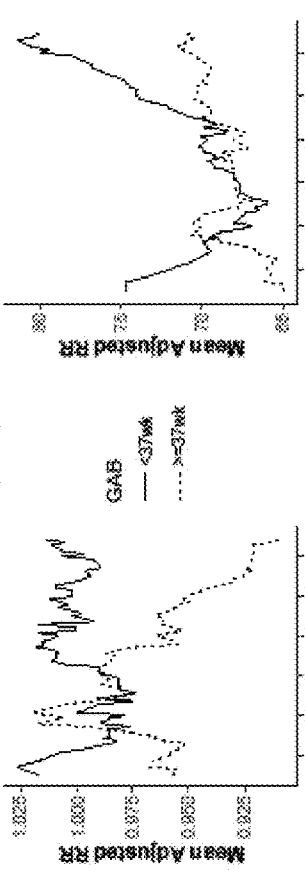
FIG. 72A CLUS_ASSIIDELFQDR
FIG. 72B CLUS_LFDSEPITVTVPVEVSR
FIG. 72C CNDP1_ALEQDLPVNIK
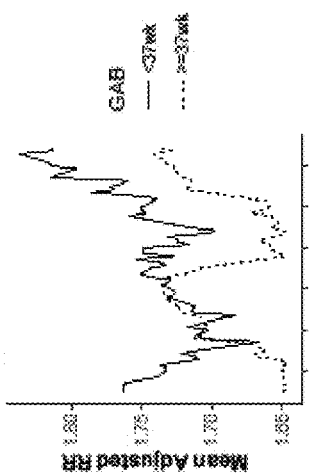
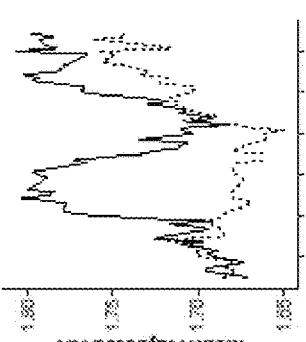
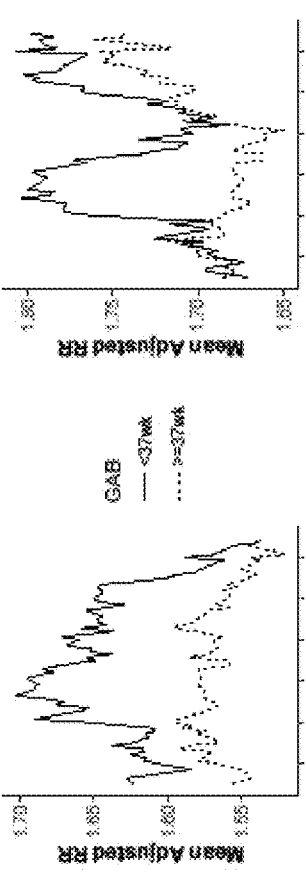
FIG. 72D CO5_TLLPVSKPEIR
FIG. 72E CO5_VFQFLEK
FIG. 72F CO6_ALMHLPLEYNSALYSR
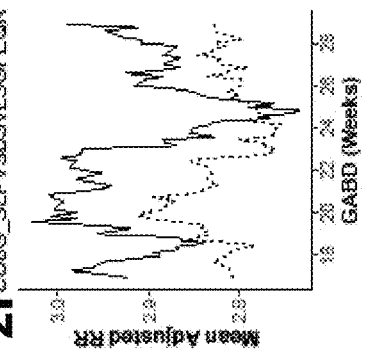
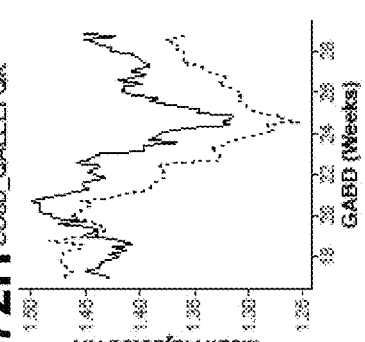
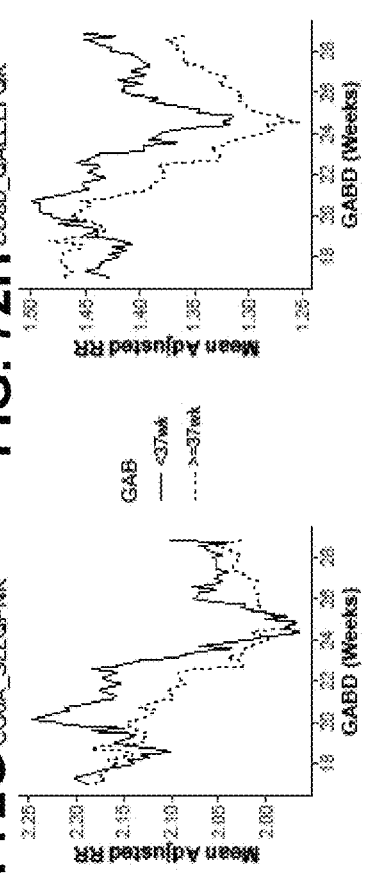
FIG. 72G CO6A_SLLQPNIK
FIG. 72H CO8B_QALEEFQK
FIG. 72I CO8G_SLPVSDSVLSGFEQR

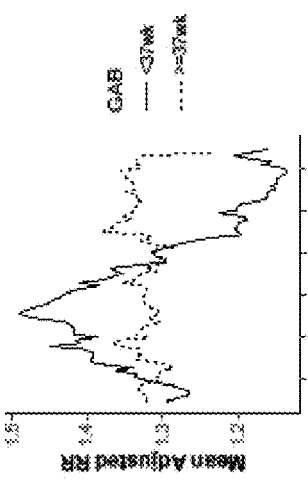
FIG. 73A CD8G_VQEAHLTEDQFYPK
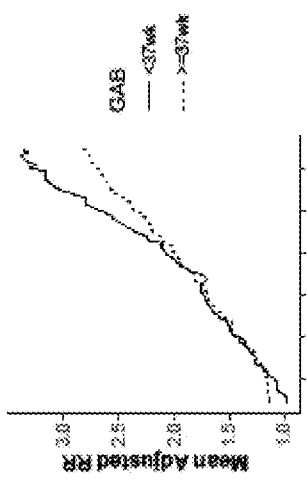
FIG. 73B CRIS3_AVSPPAR
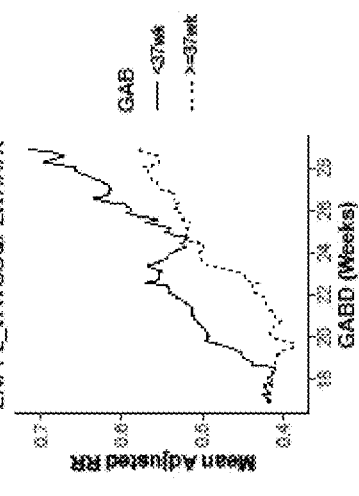
FIG. 73C CRIS3_YEDLYSNCK
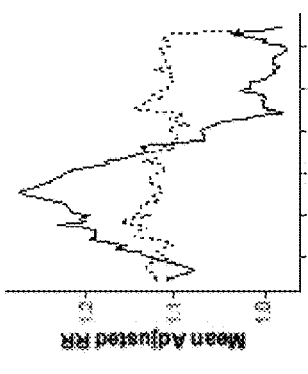
FIG. 73D CRP_ESDTSYVSLK
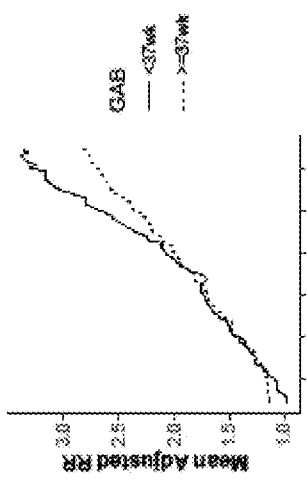
FIG. 73E CSH_AHQLAIDTYQEFEETYIPK
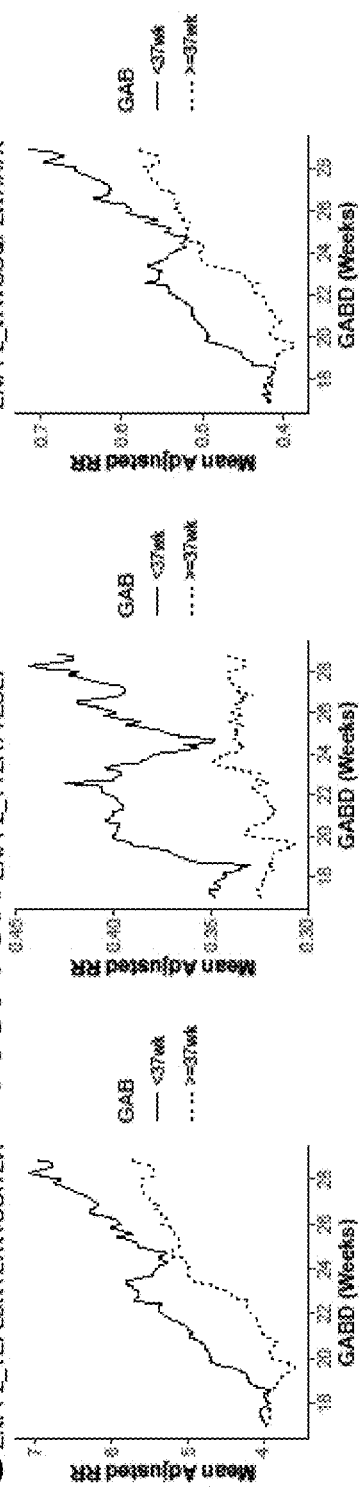
FIG. 73F CSH_ISLLLIESWLEPVR
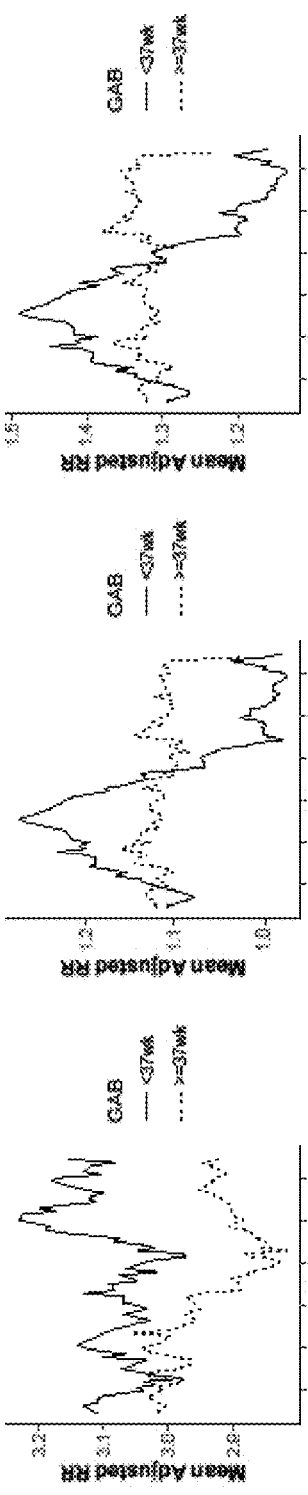
FIG. 73G ENPP2_TEFLSNYLTNVDDITLVP
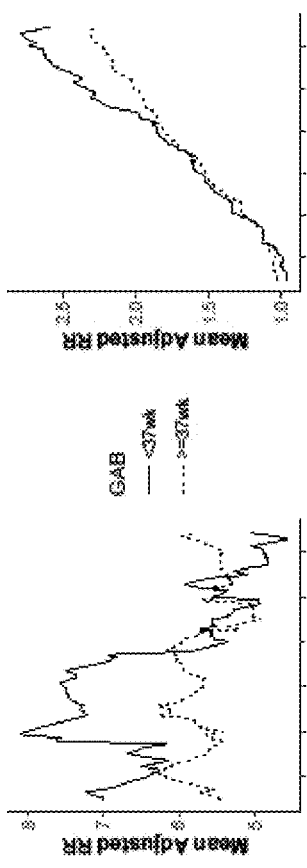
FIG. 73H ENPP2_TYLHTYESEI
FIG. 73I ENPP2_WWGGQPLWITATK

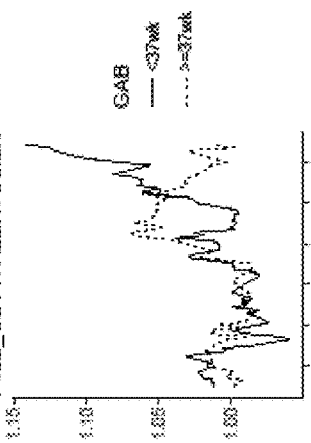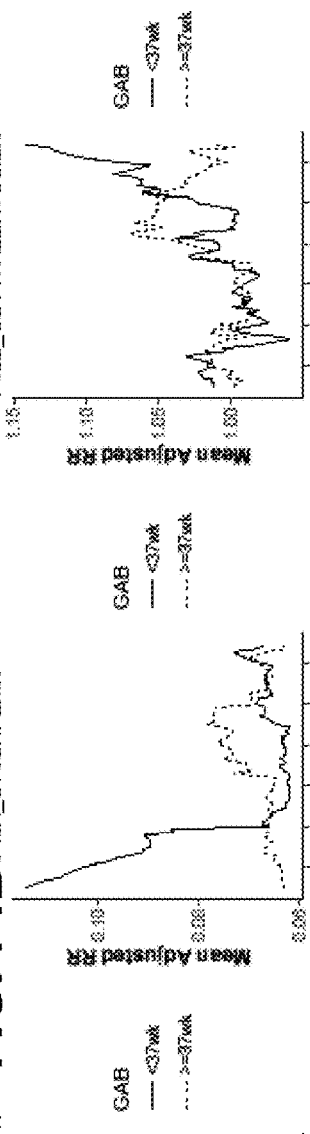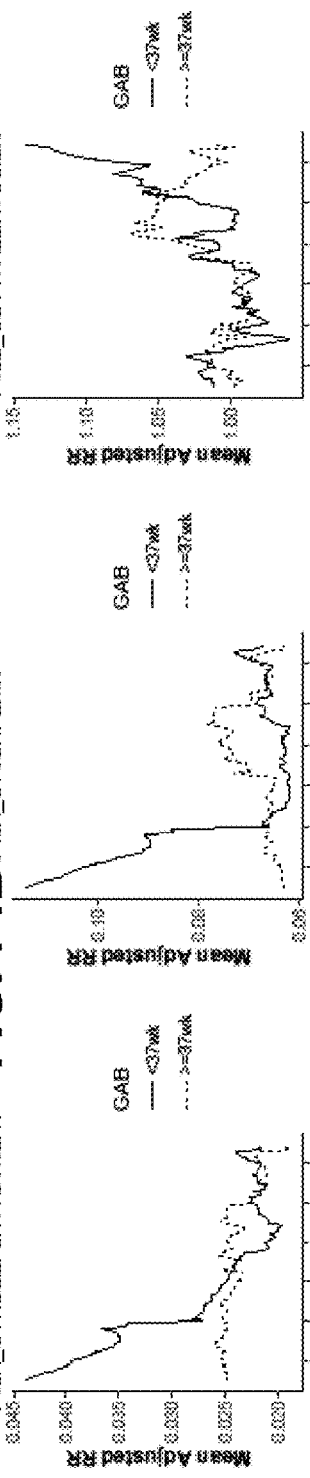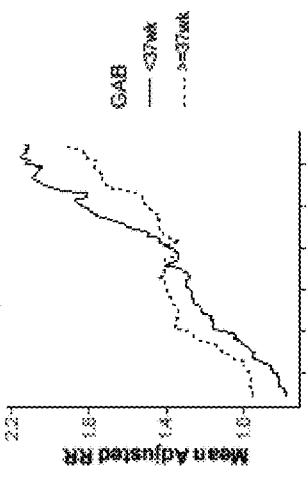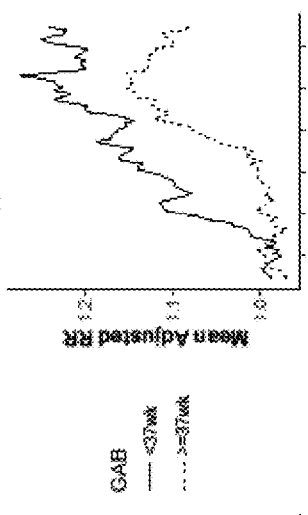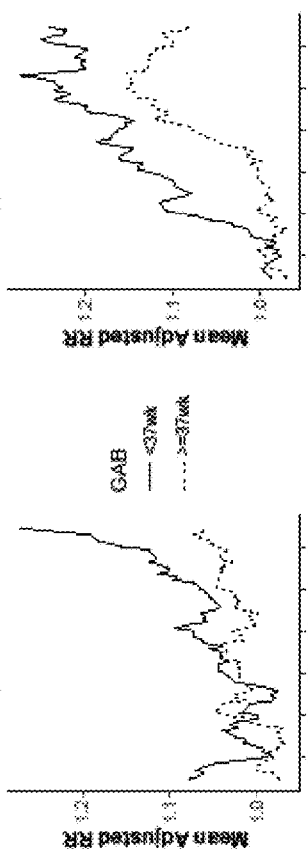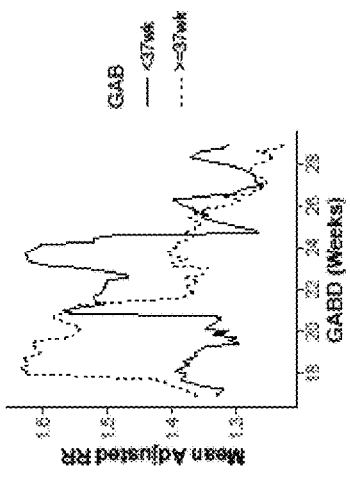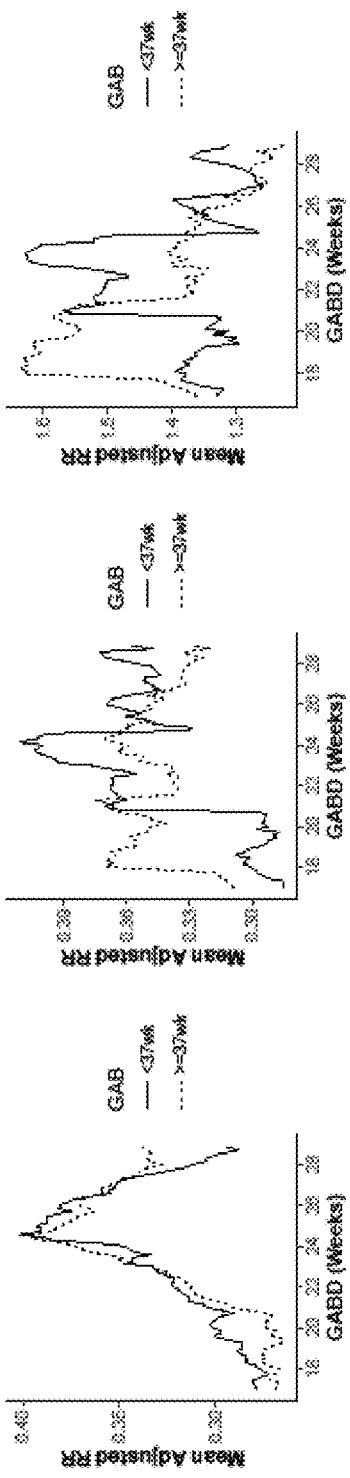
FIG. 74A FIG. 74B FIG. 74C FIG. 74D FIG. 74E FIG. 74F FIG. 74G FIG. 74H FIG. 74I

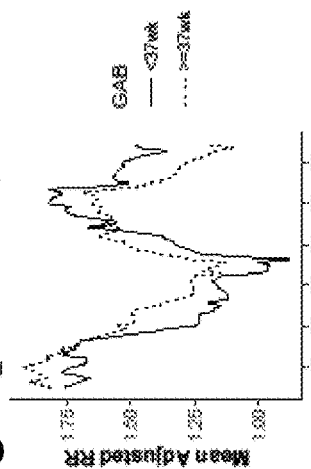
FIG. 75A FETUA_FSVVYAK
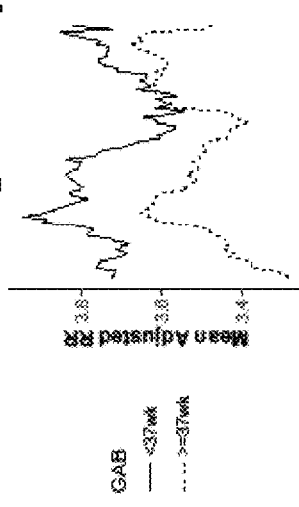
FIG. 75B FETUA_HTLNQIDEVK
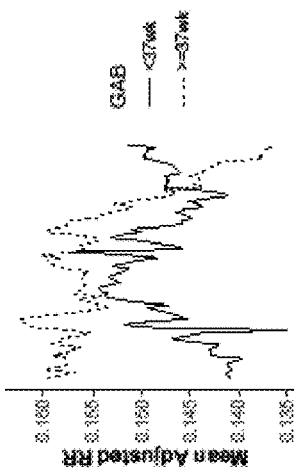
FIG. 75C FHR1_SIDTSCVNPPTVQNAIRLS
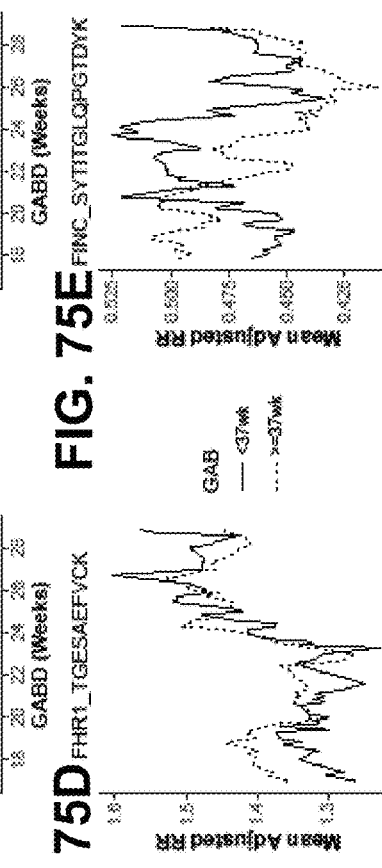
FIG. 75D FHR1_TGESAEFVCK
FIG. 75E FWC_SYTITGLQPGTDYK
FIG. 75F G6PE_LLDFEFSSGR
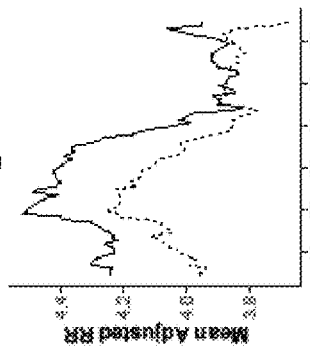
FIG. 75G GELS_AQPVQVAEGSEPDGFWEAL
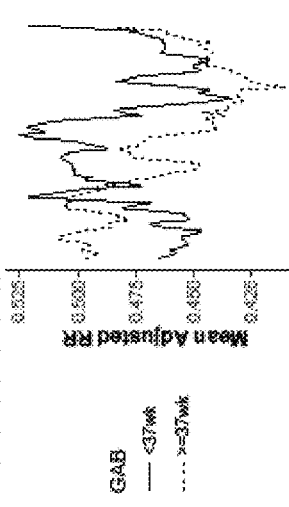
FIG. 75H GELS_TASDFITK
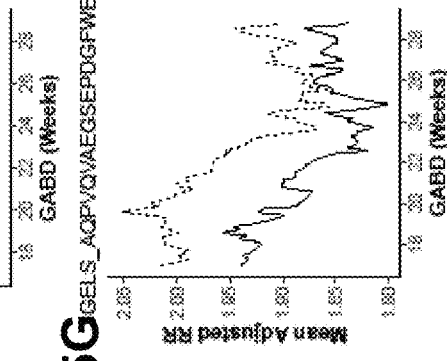
FIG. 75I GPX3_QEPGSENSEILPTLK

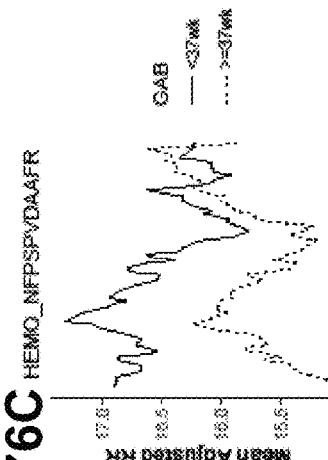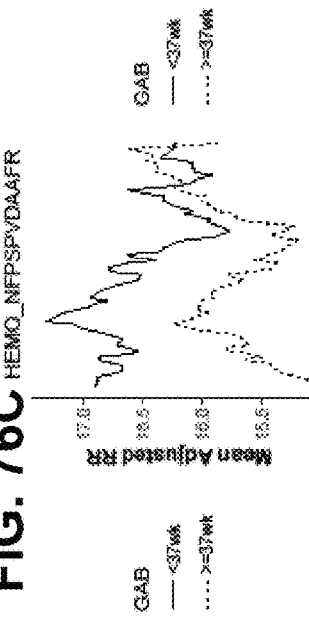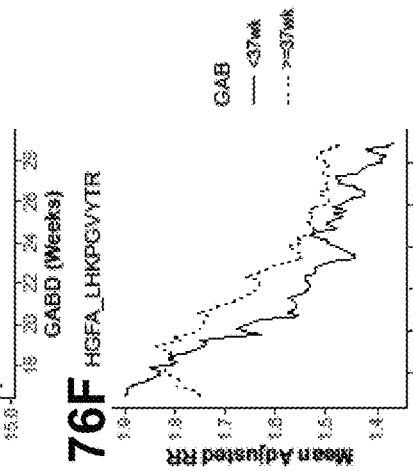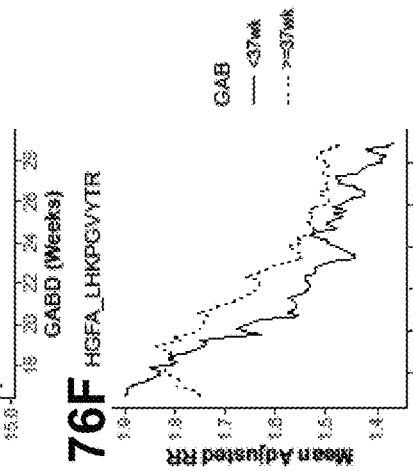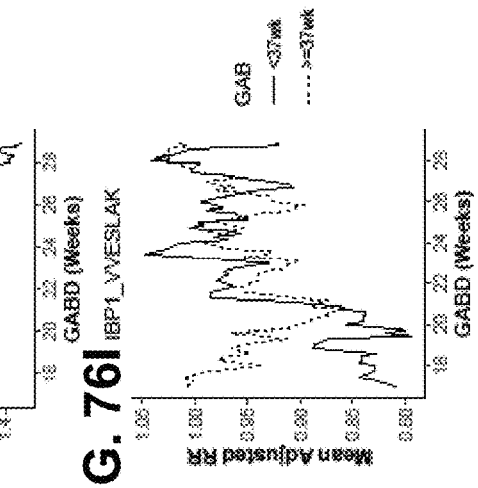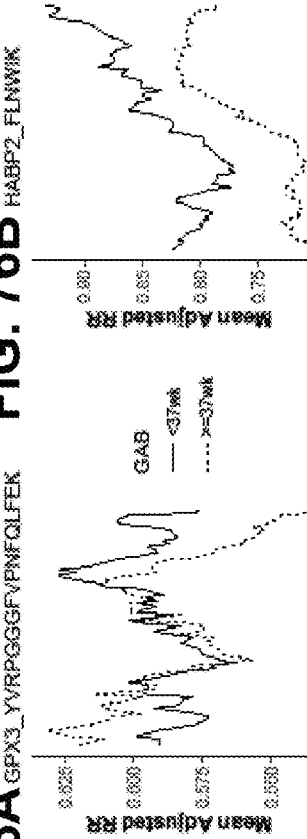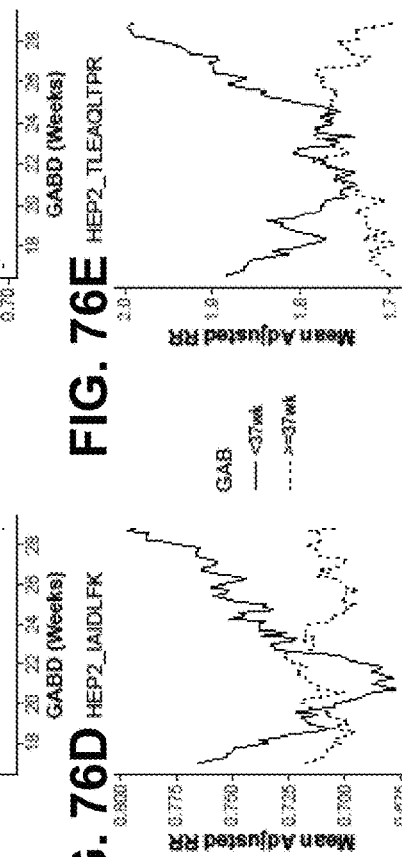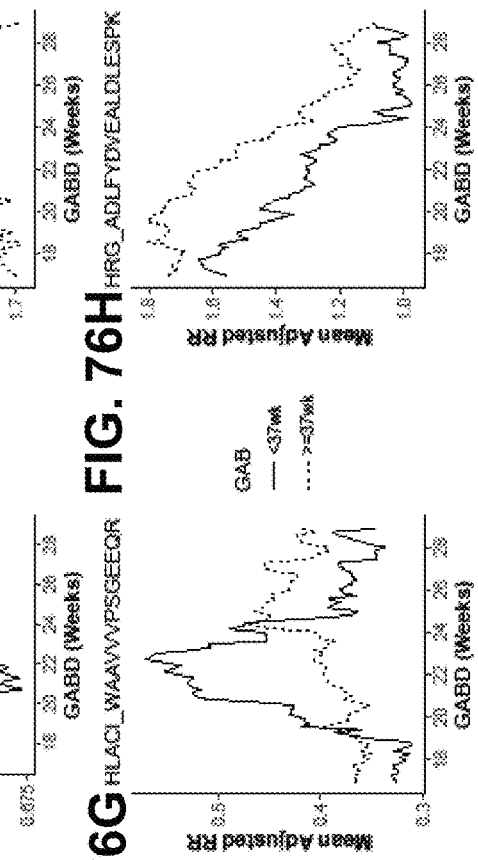

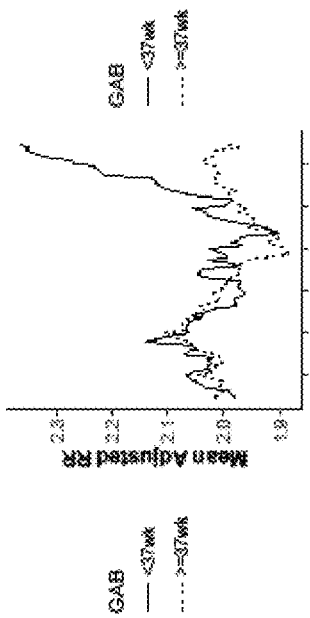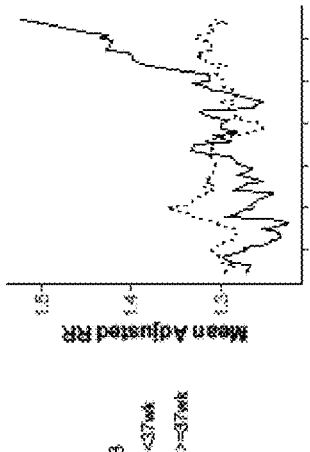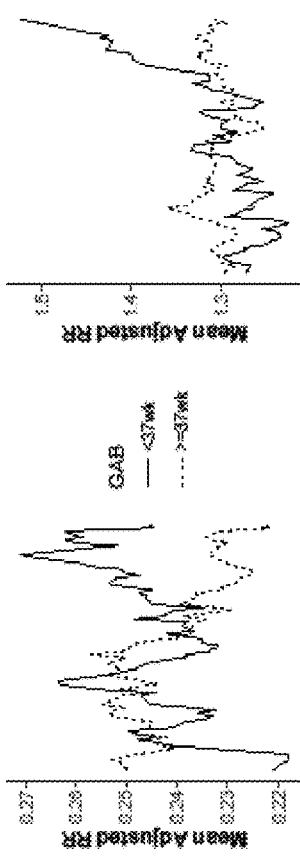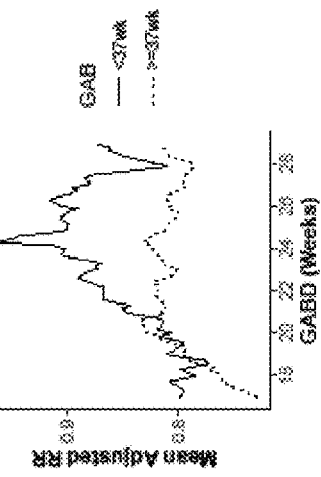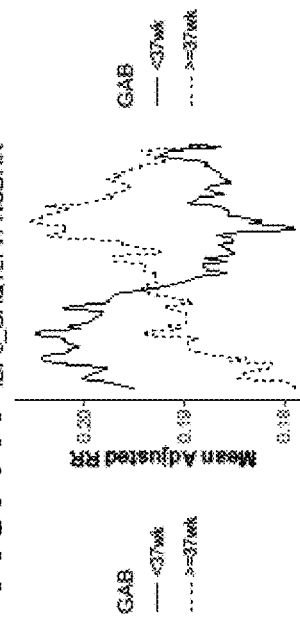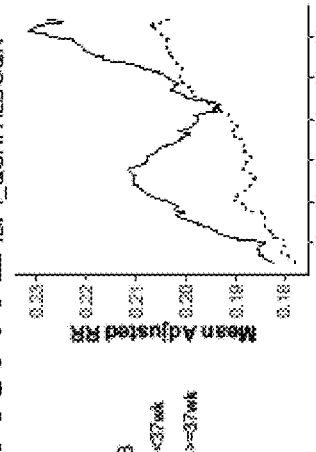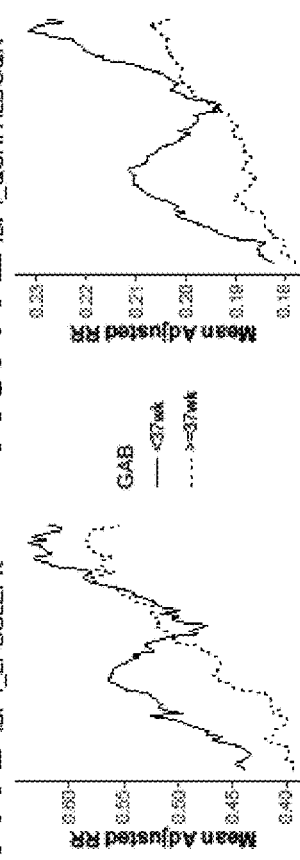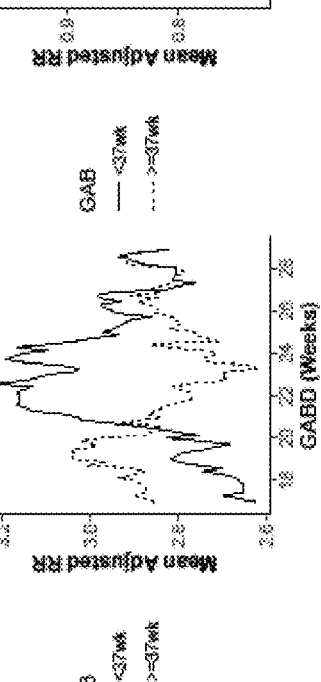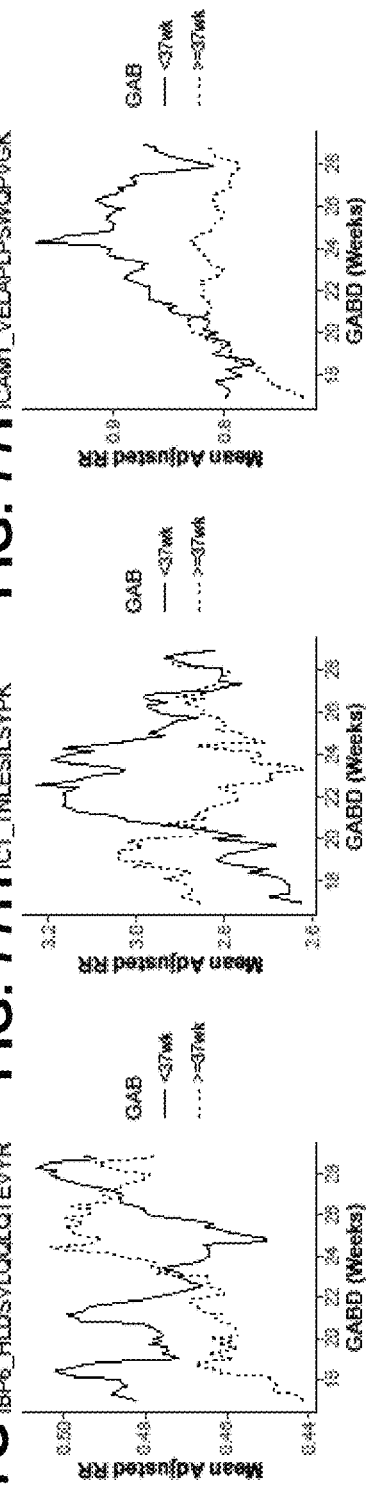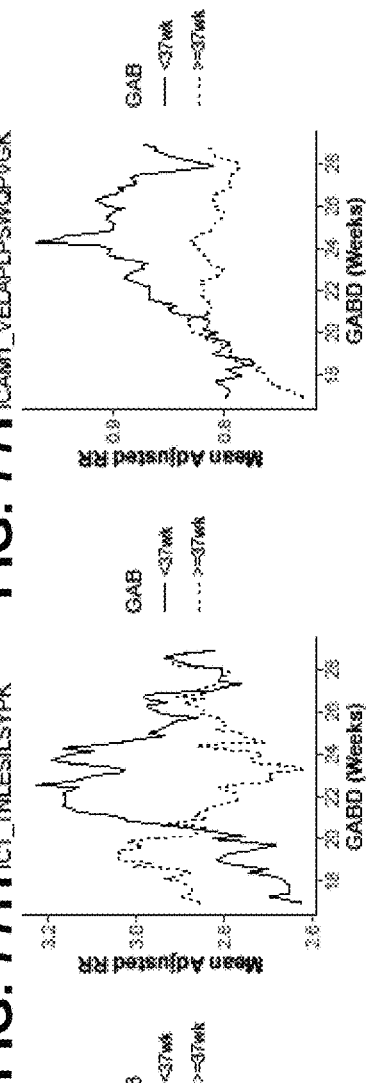
FIG. 77A – FIG. 77I

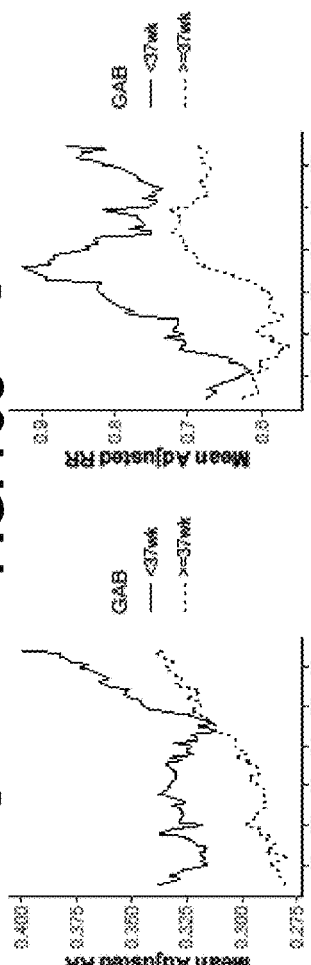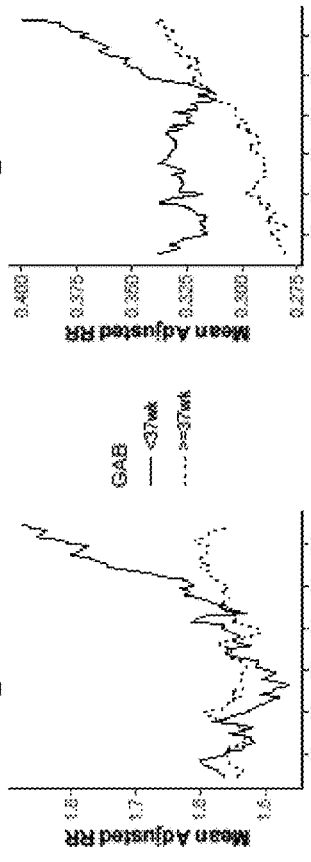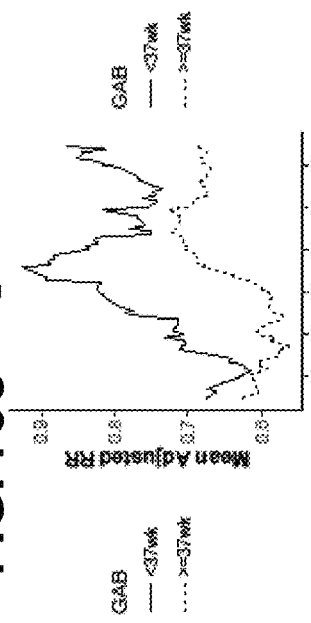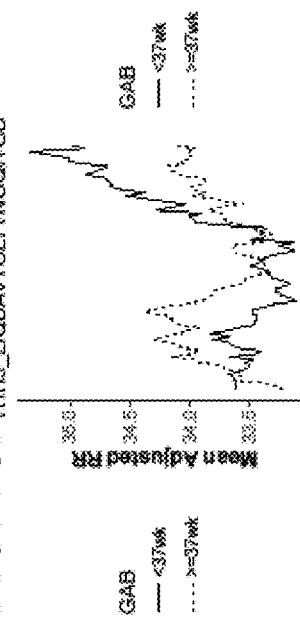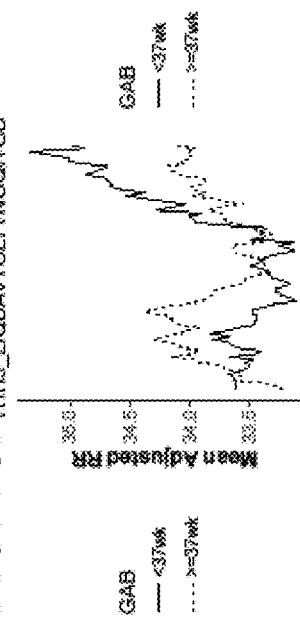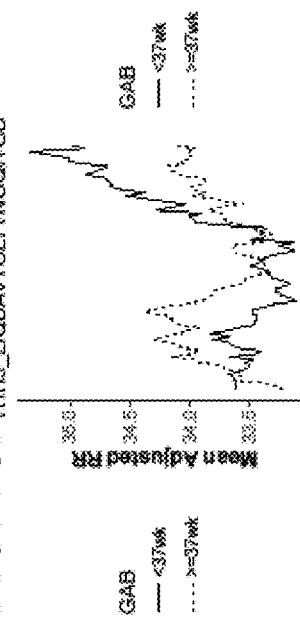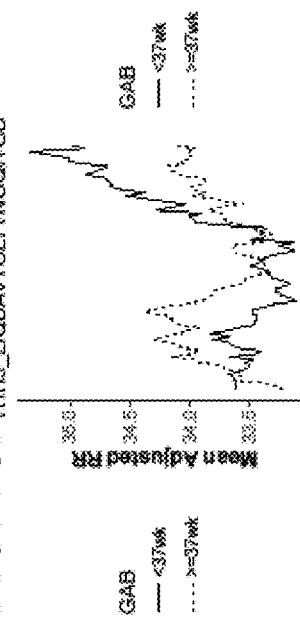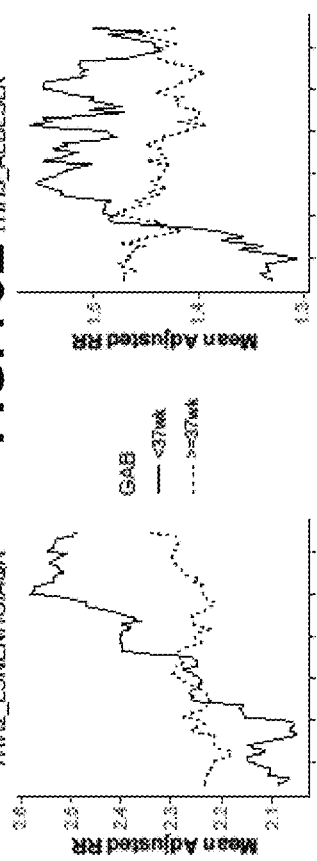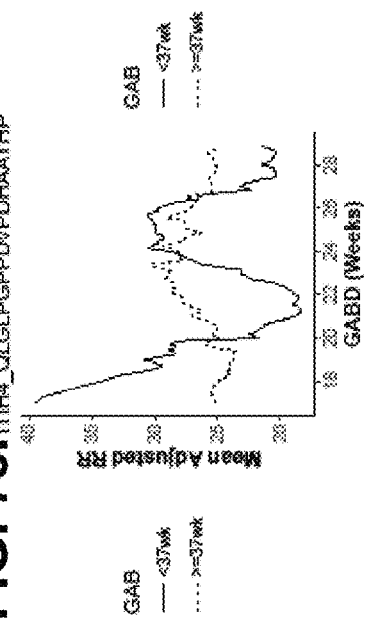

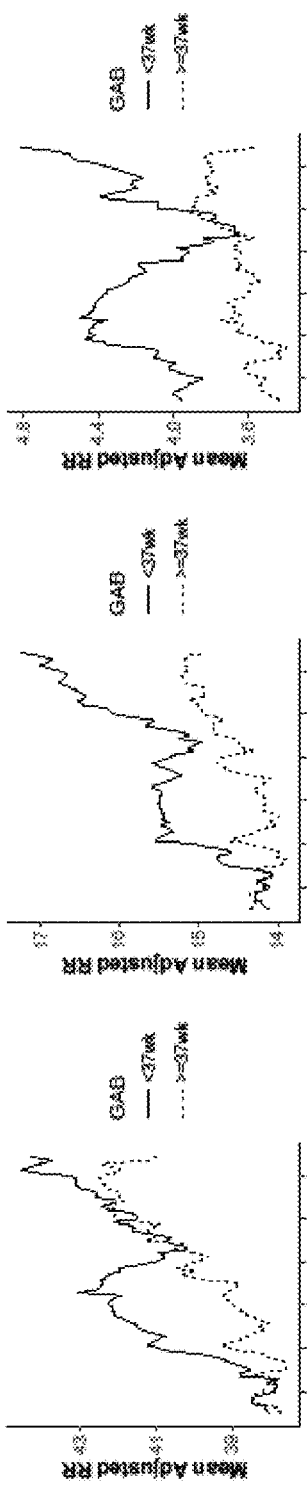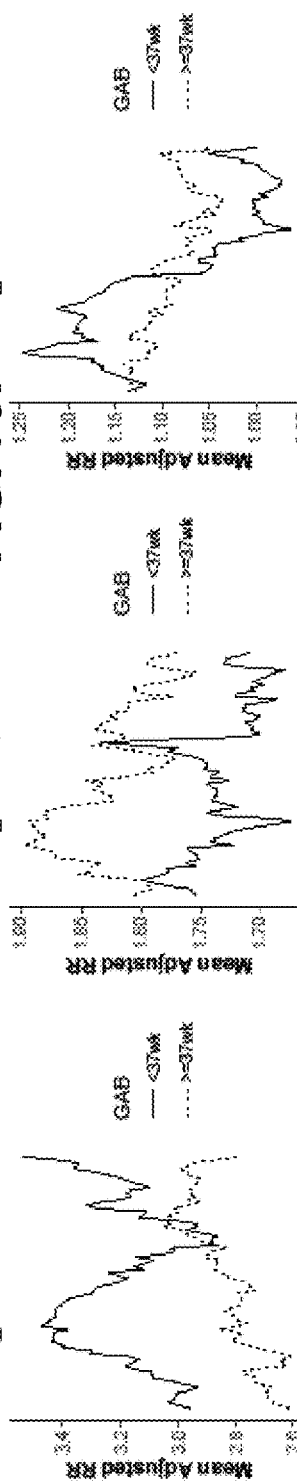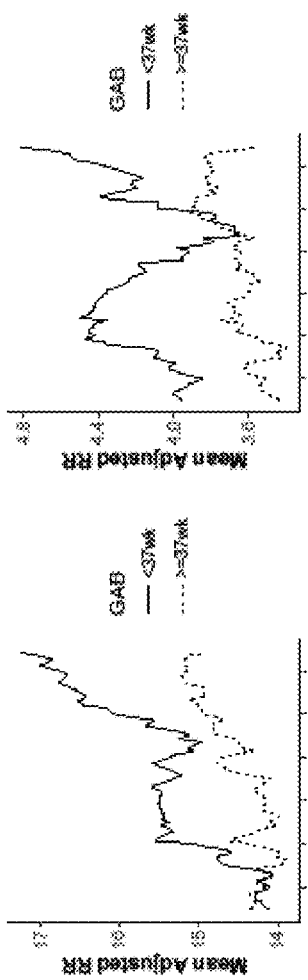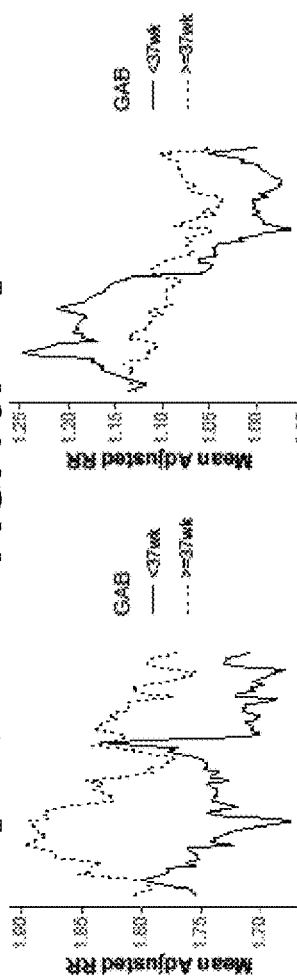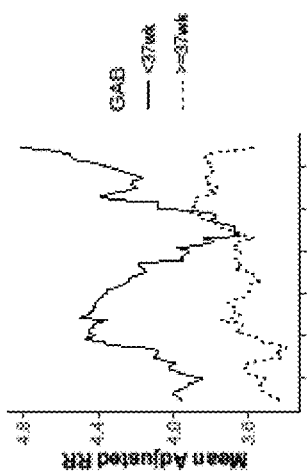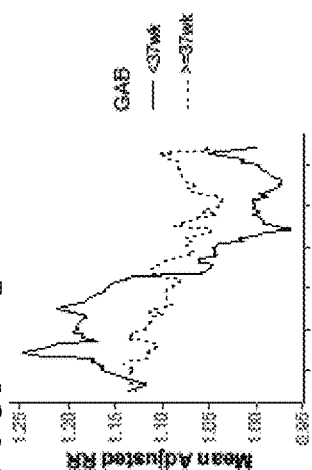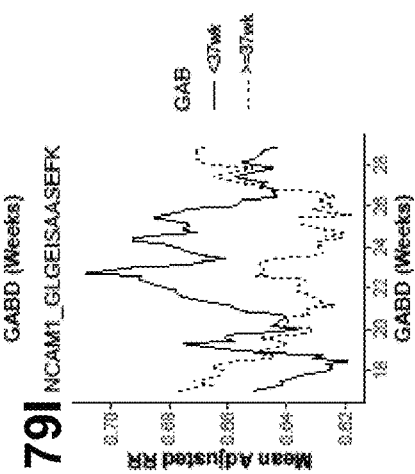

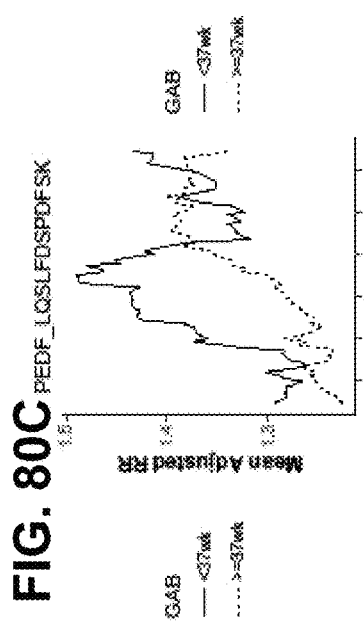
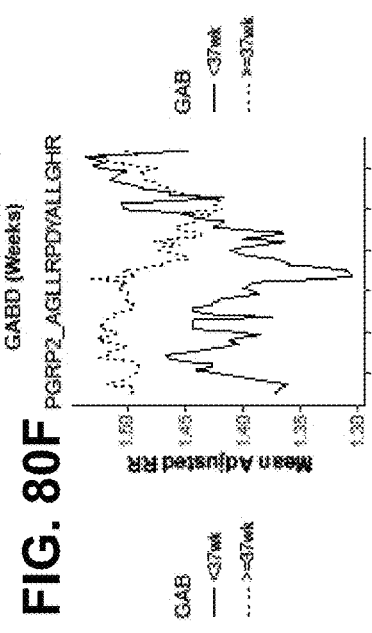
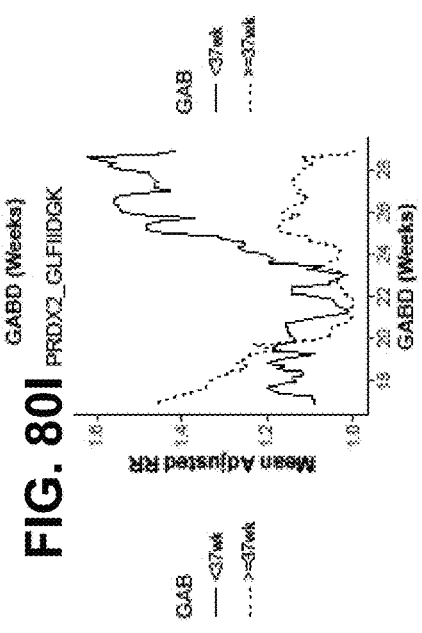
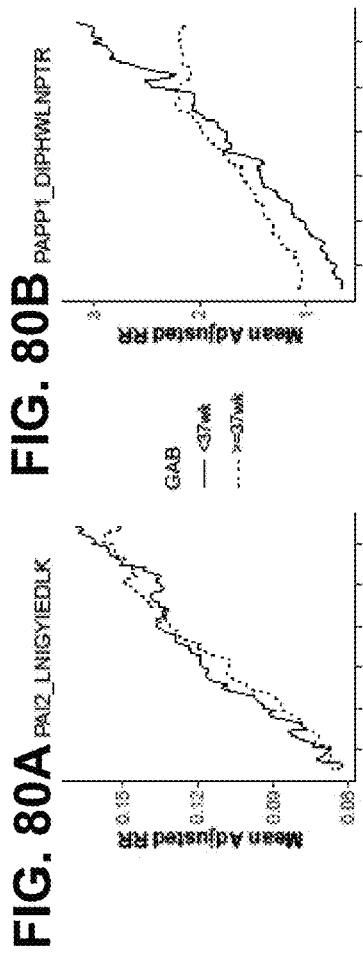
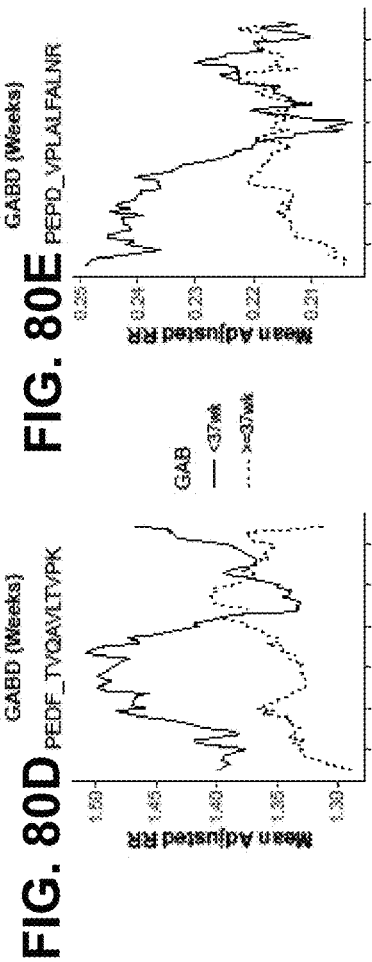
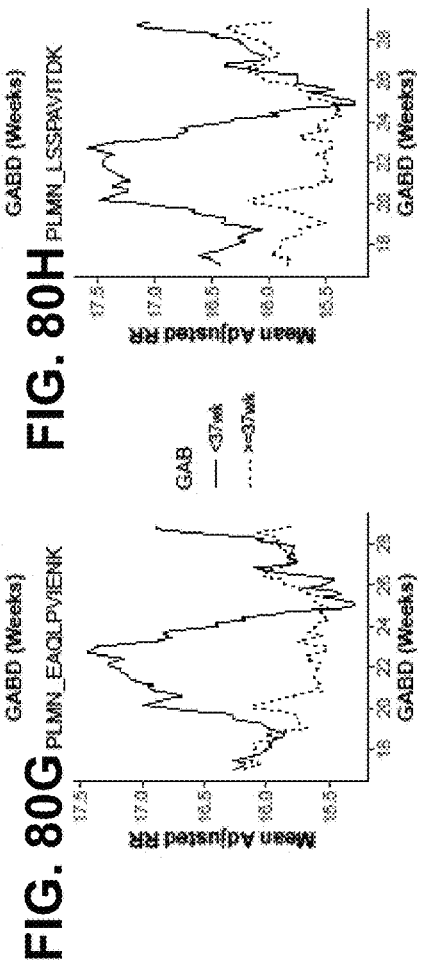

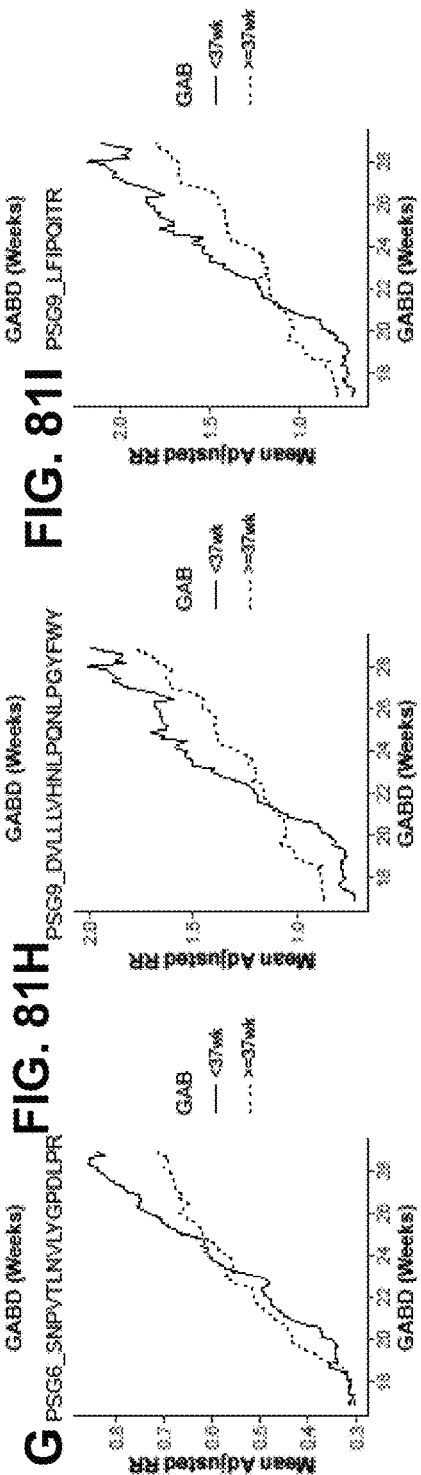
FIG. 81A PRG2_WNFAYWAAHQPWSR
FIG. 81B PSG1_FQLPGQK
FIG. 81C PSG11_LFIPQITPK
FIG. 81D PSG2_IHPSYTNYR
FIG. 81E PSG3_VSAPSGTGHLPGLNPL
FIG. 81F PSG4_TLFIFGVTK
FIG. 81G PSG6_SNPVTLNVLYGPDLPR
FIG. 81H PSG9_DVLLLVHNILPQNLPGYFWY
FIG. 81I PSG9_LFIPQITR

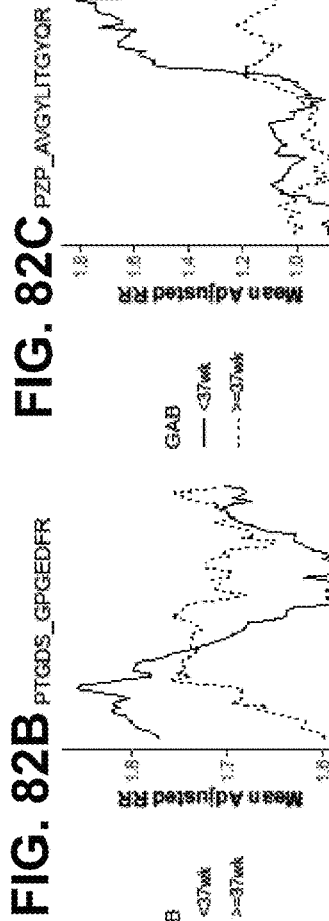
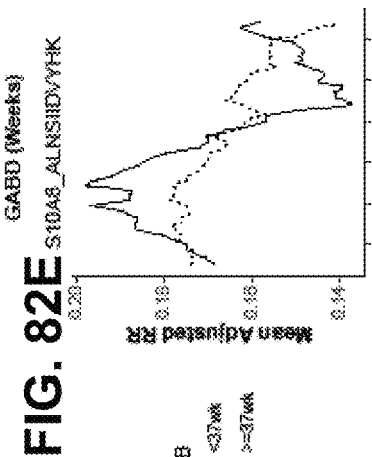
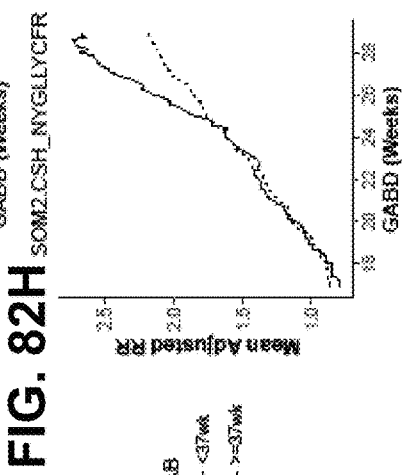
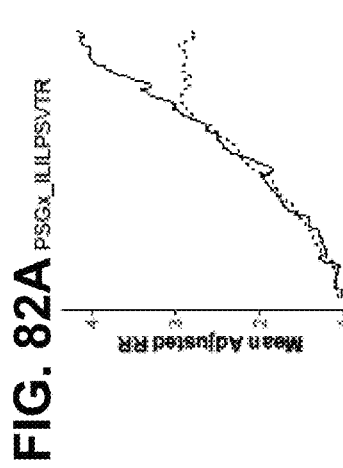
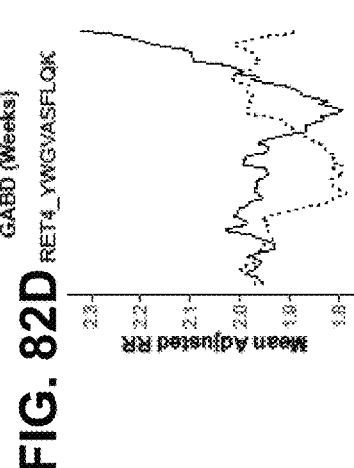
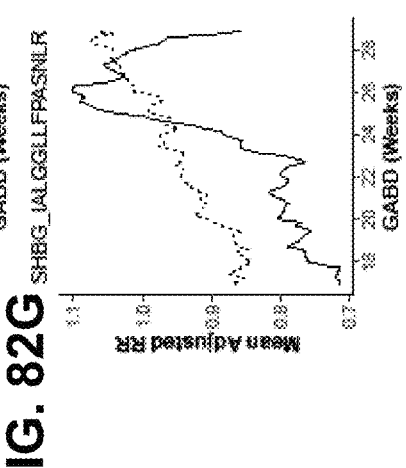

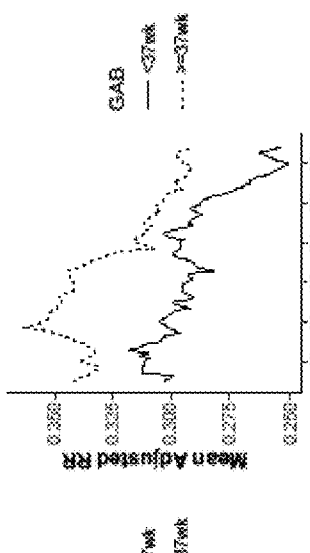
FIG. 83A SPRL1_SIPTCTDFEVIQPFLR
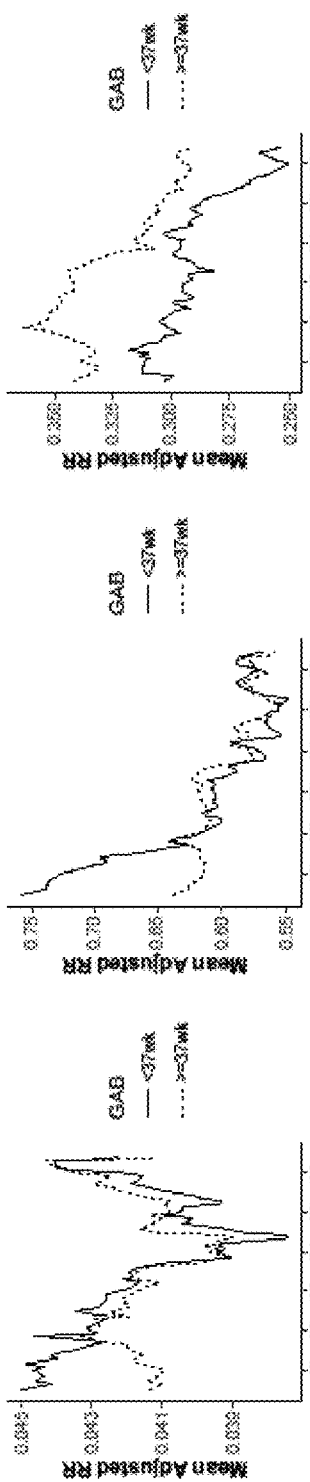
FIG. 83B SPRL1_VLTHSELAPLR
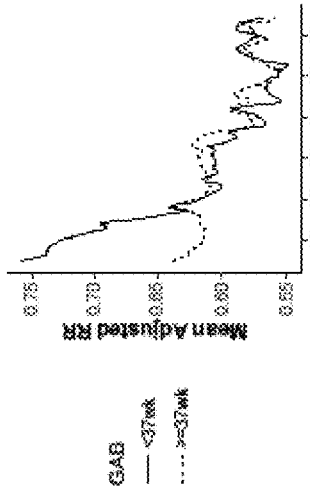
FIG. 83D TENX_LSQLSVTDVTTSSLR
FIG. 83C TENX_LRWEAPPGAFDSFLLR
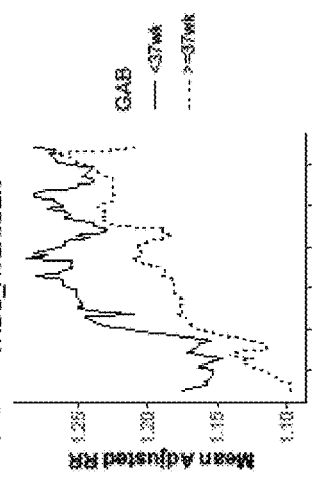
FIG. 83E TFR1_YNSQLLSFVR
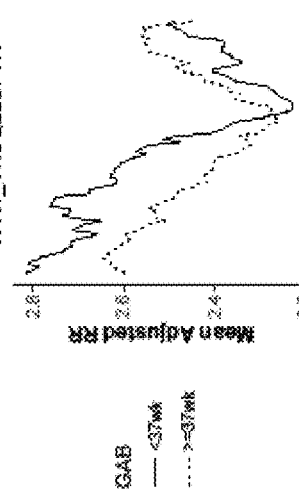
FIG. 83G THIO_VGEFSGANK
FIG. 83F THBG_AVLHGEK
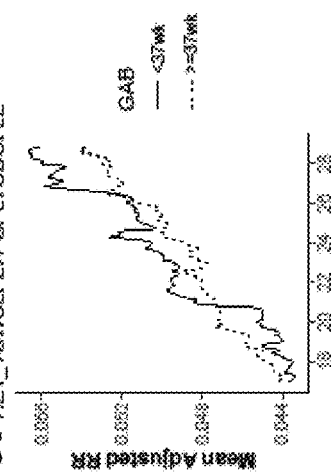
FIG. 83H THRB_ELLESYIDGR
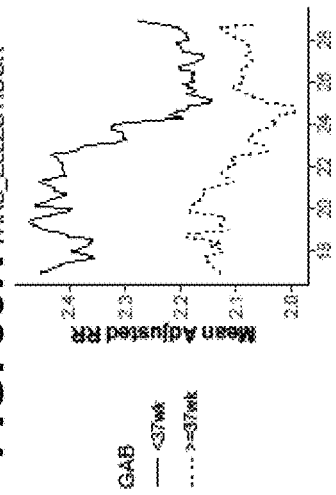
FIG. 83I TIE1_VSWSLPLVPGPLVGDGFLL
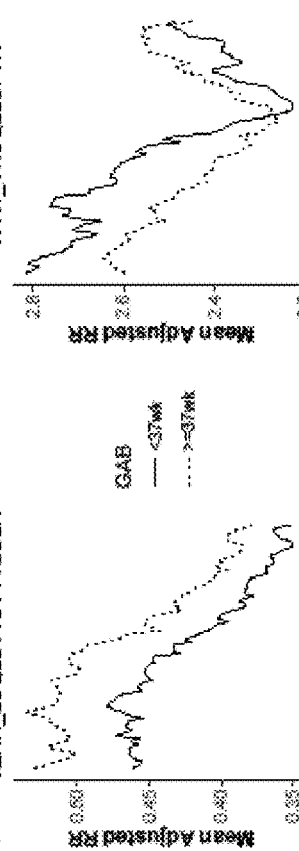
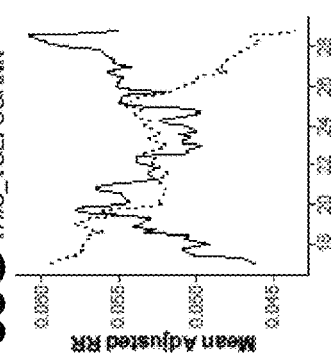

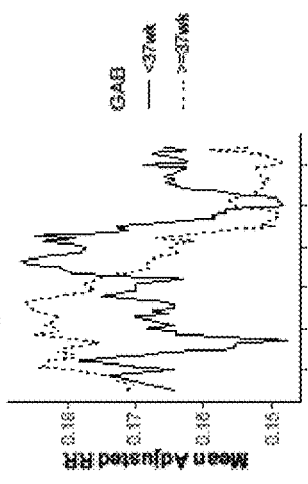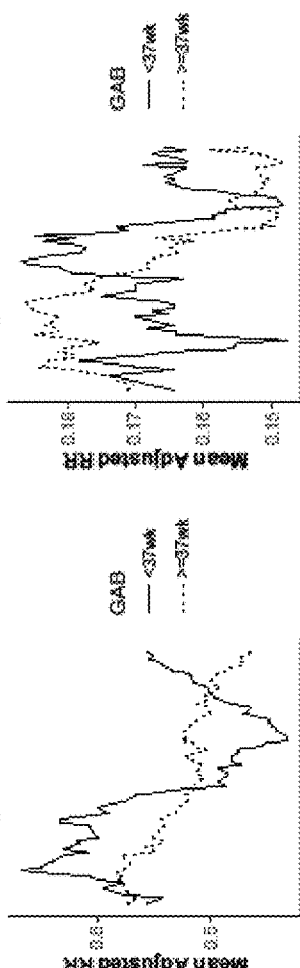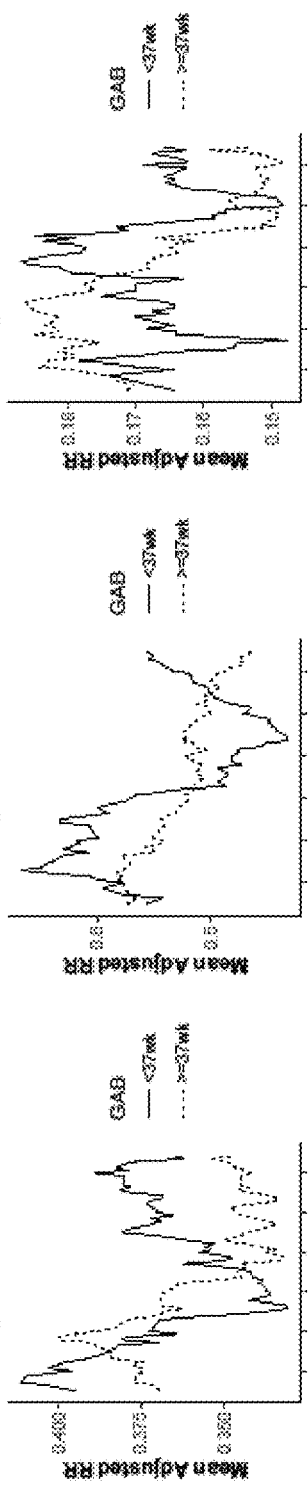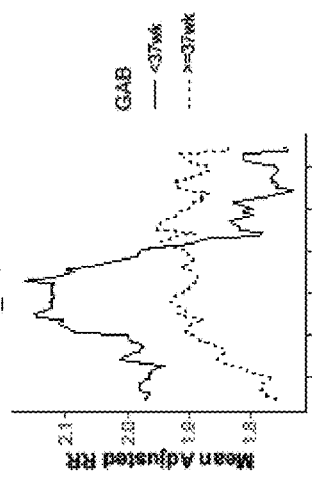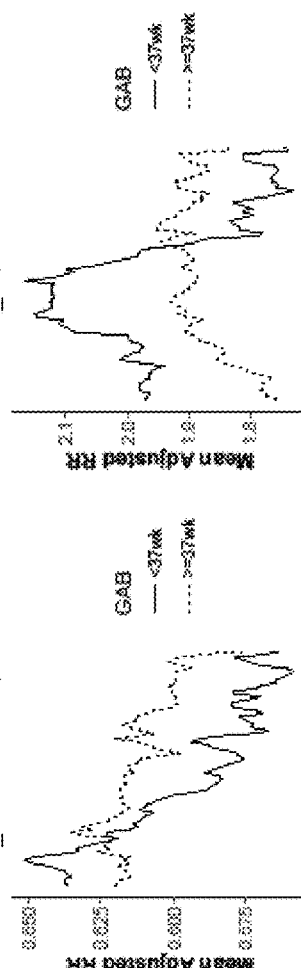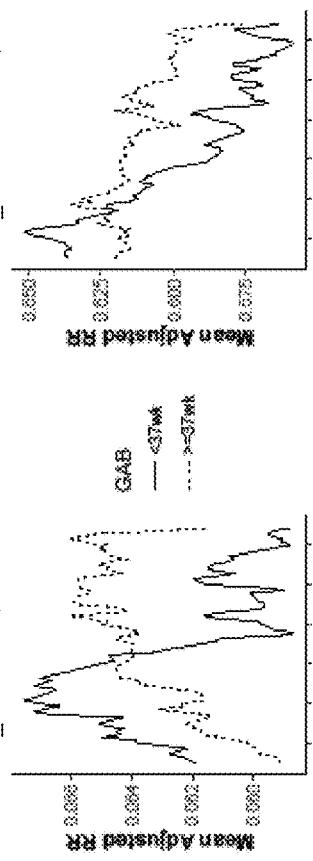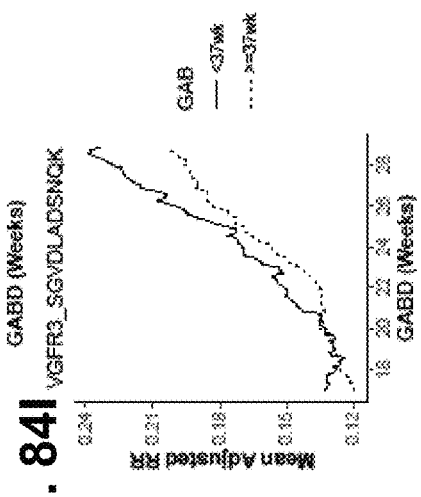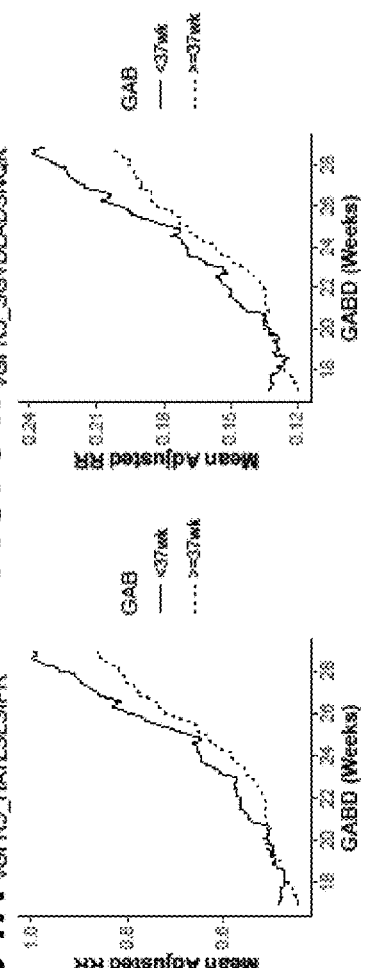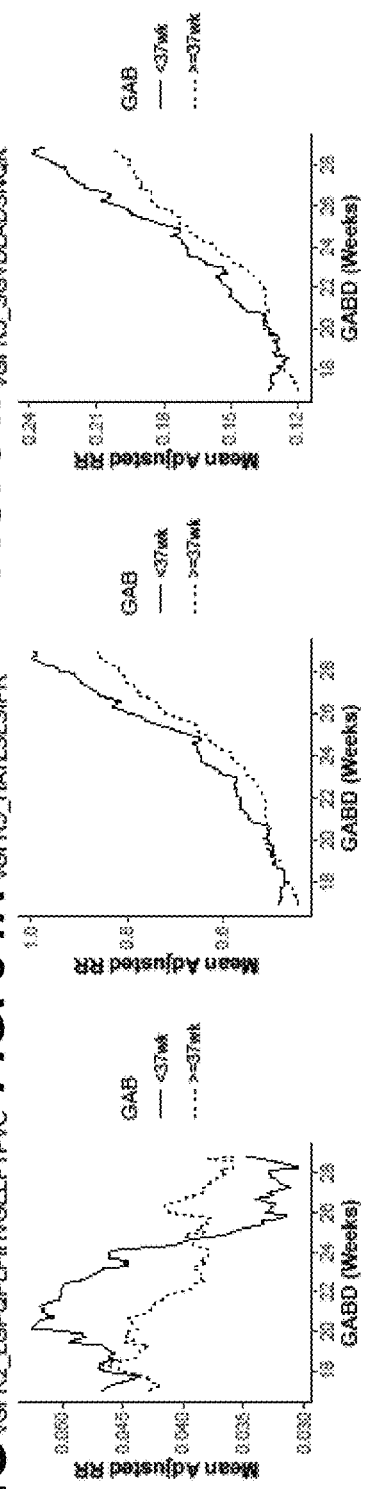
FIG. 84A TIMP1_GFQALGLOQLDEGLFSR
FIG. 84B TRFL_YYGYTGAFR
FIG. 84C TSP1_FYFGTTPEDILR
FIG. 84D VASN_LAGLGLQQLDEGLFSR
FIG. 84E VASN_NLHELDVSDNQLER
FIG. 84F VCAM1_TQIDSPLSGK
FIG. 84G VGFR2_LGPQPLPIHVGELPTPVC
FIG. 84H VGFR3_HATLSLSIPR
FIG. 84I VGFR3_SGVDLADSNQK

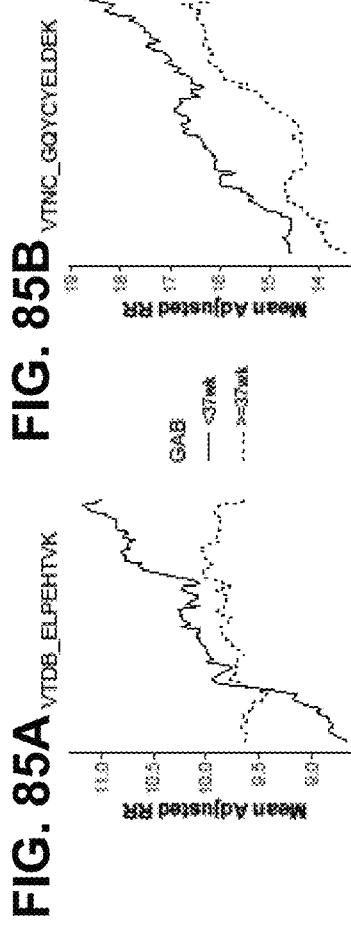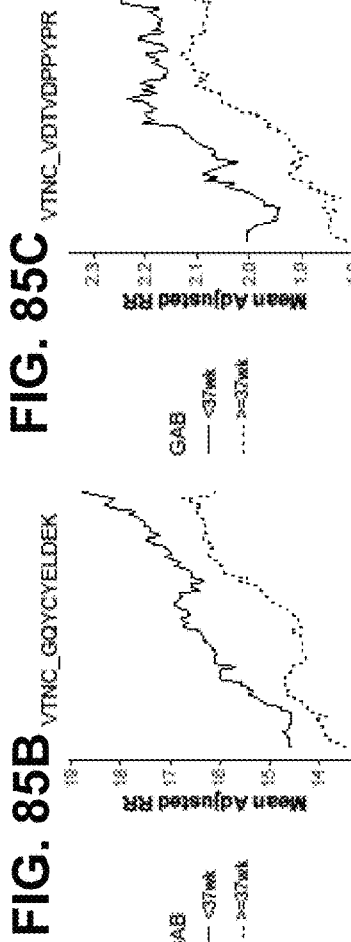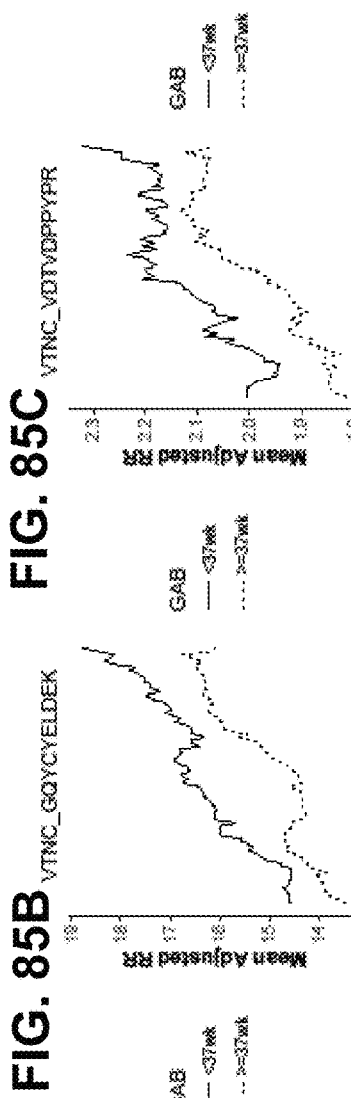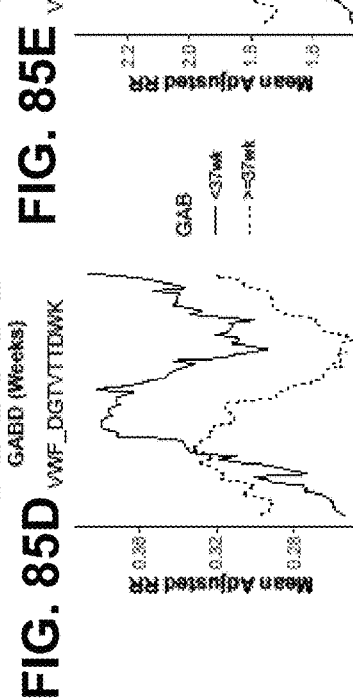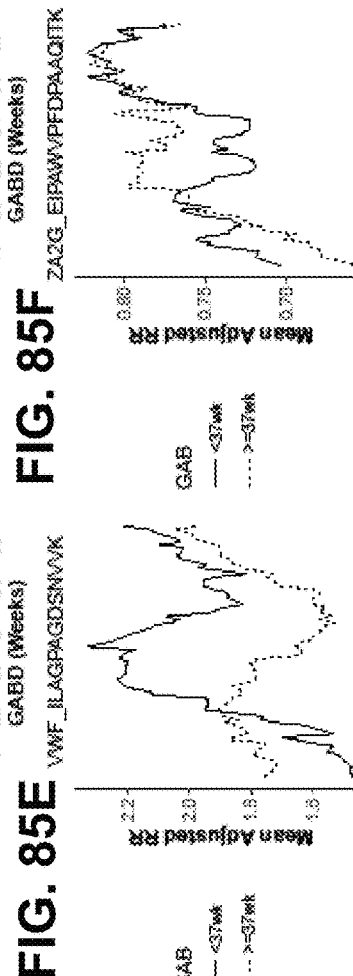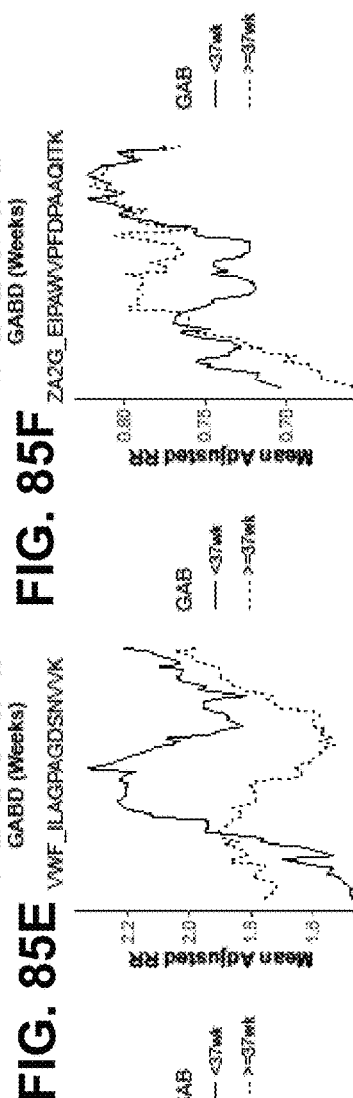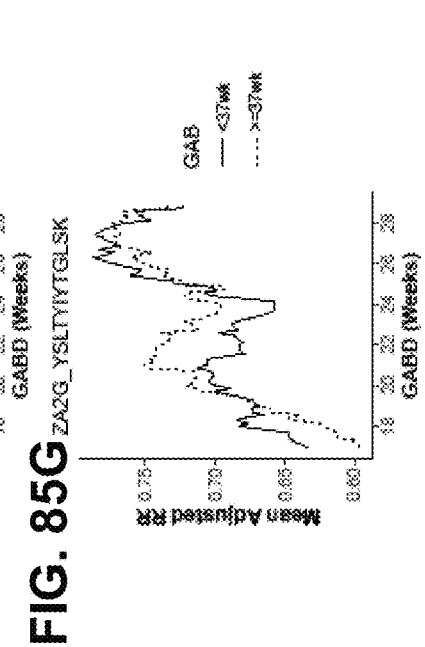
FIG. 85A VTDB_ELPEHTVK
FIG. 85B VTNC_GQYCYELDEK
FIG. 85C VTNC_VDTVDPPYPR
FIG. 85D VWF_DGTVTEDWK
FIG. 85E VWF_ILAGPAGDSNVVK
FIG. 85F ZA2G_EIPAWVPFDPAAQITK
FIG. 85G ZA2G_YSLTYIYTGLSK

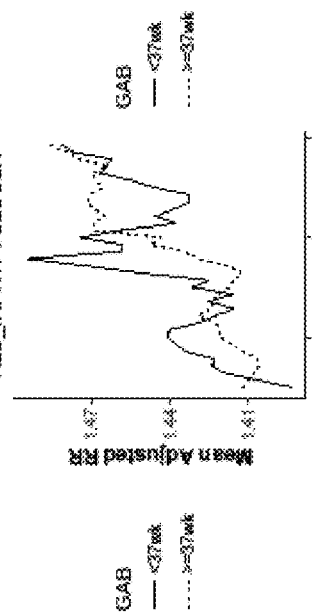
FIG. 86A
FIG. 86B
FIG. 86C
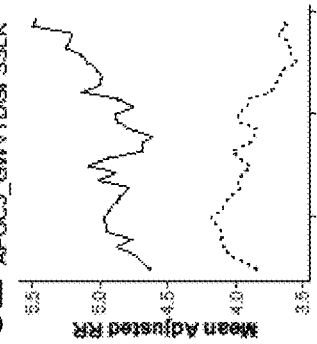
FIG. 86D
FIG. 86E
FIG. 86F
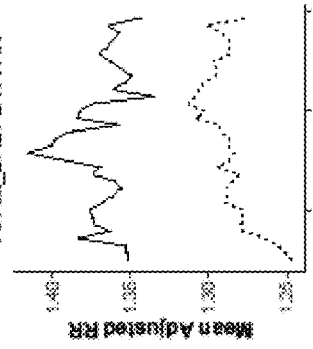
FIG. 86G
FIG. 86H
FIG. 86I

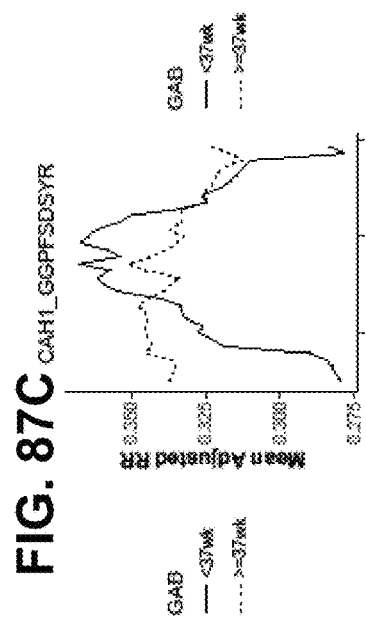
FIG. 87A C163A_INPASLDK
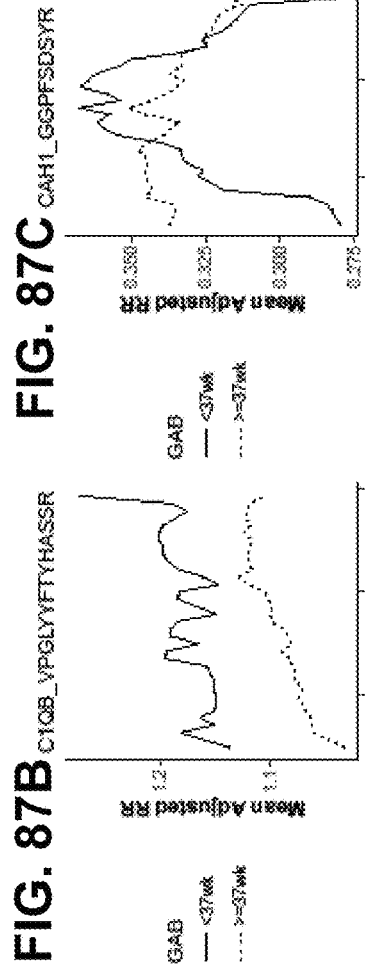
FIG. 87B C1QB_VPGLYYFTYHASSR
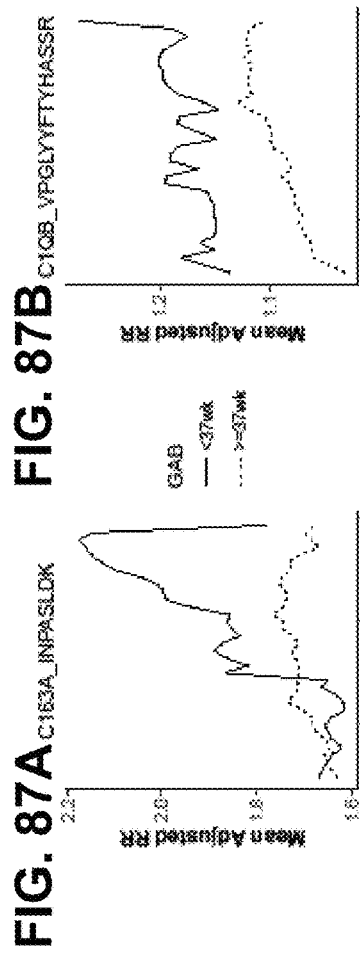
FIG. 87C CAH1_GGPFSDSYR
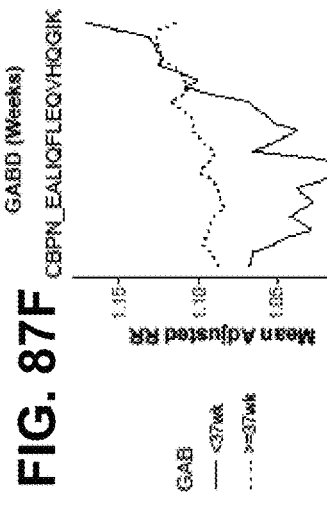
FIG. 87D CATD_VGFAEAAR
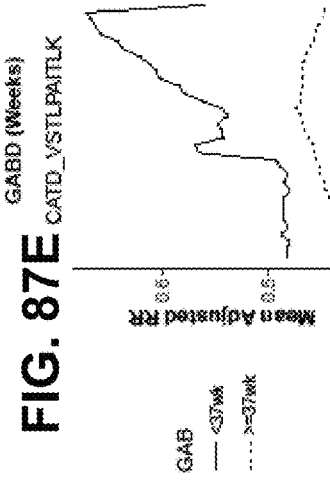
FIG. 87E CATD_YSTLPAITLK
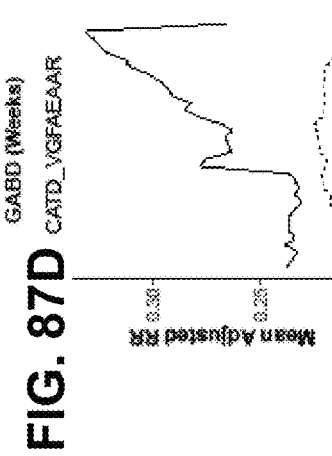
FIG. 87F CBPN_EALKQFLEQVHQGIK
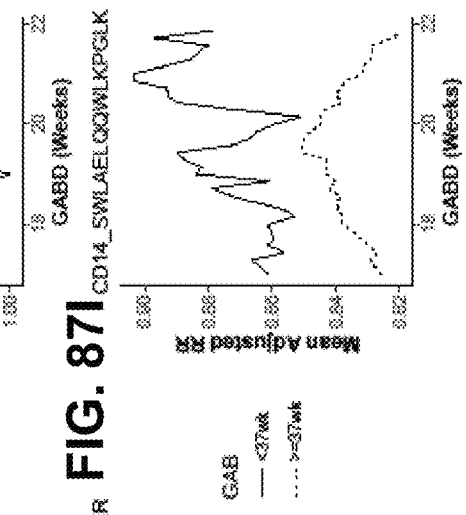
FIG. 87G CBPN_NNANGVDLNR
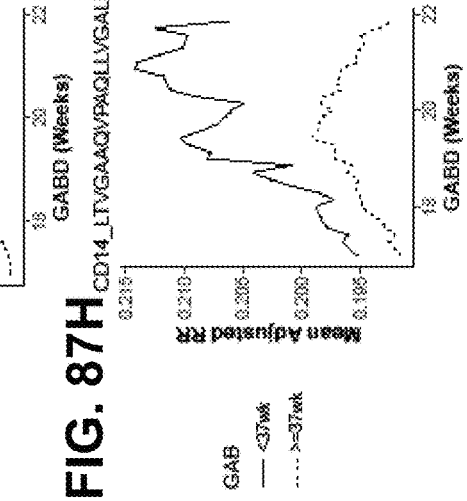
FIG. 87H CD14_LTVGAAQVPAQLLVGALR
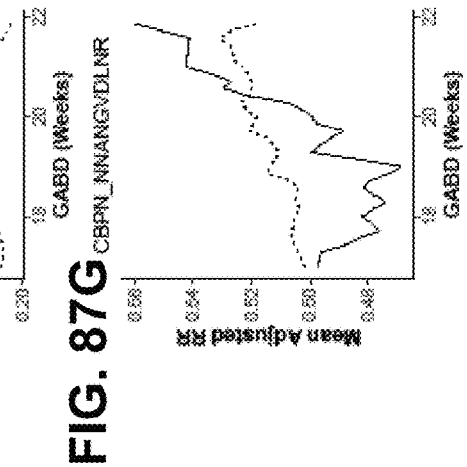
FIG. 87I CD14_SWLAELQQWLKPGLK

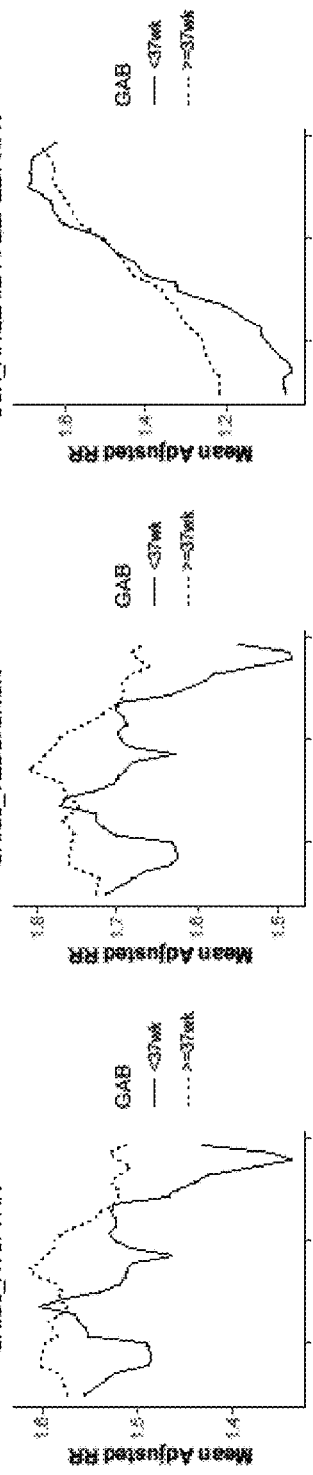
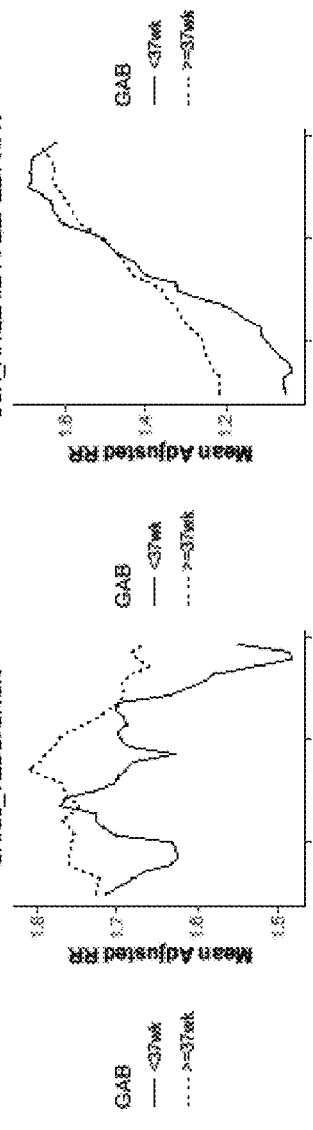
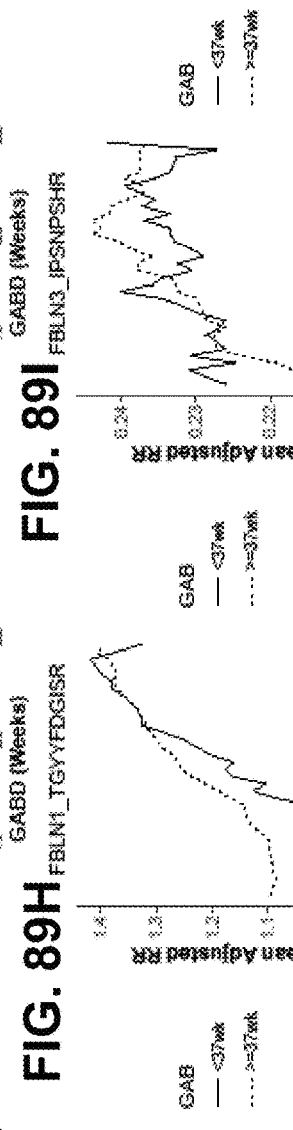
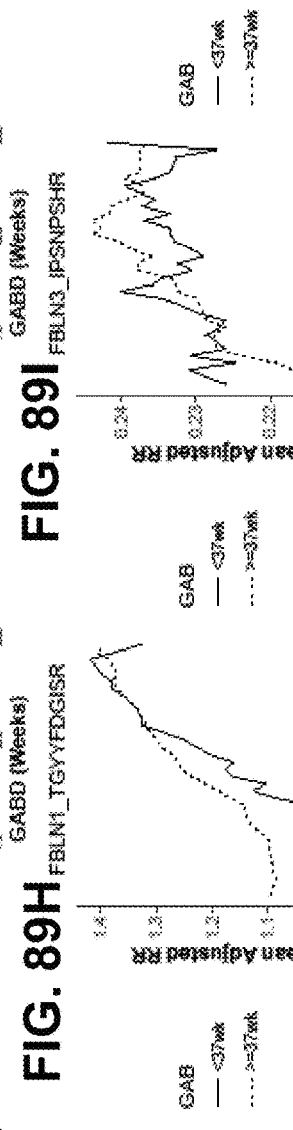
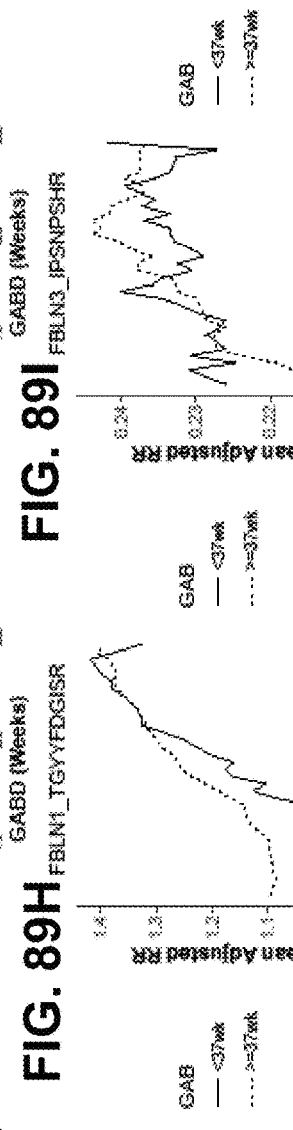

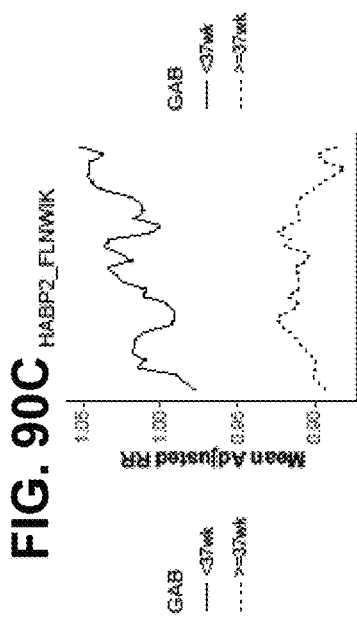
FIG. 90A FETUA_FSVVYAK
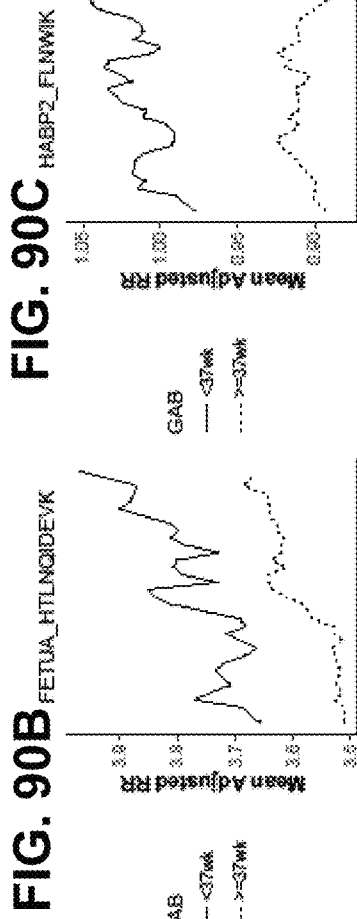
FIG. 90B FETUA_HTLNQIDEVK
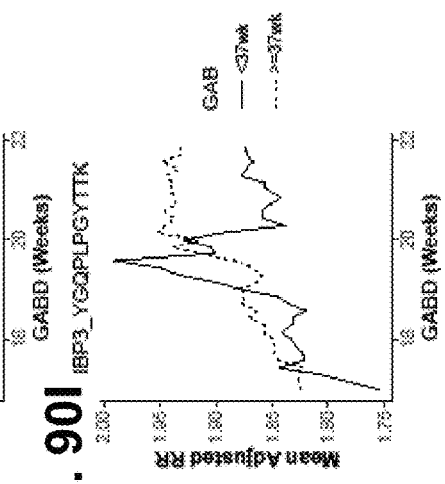
FIG. 90C HABP2_FLNWIK
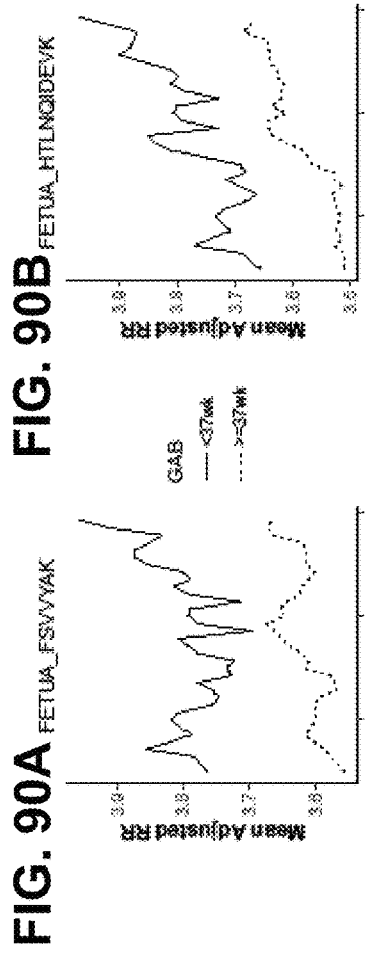
FIG. 90D HEMO_NFPSPVDAAFR
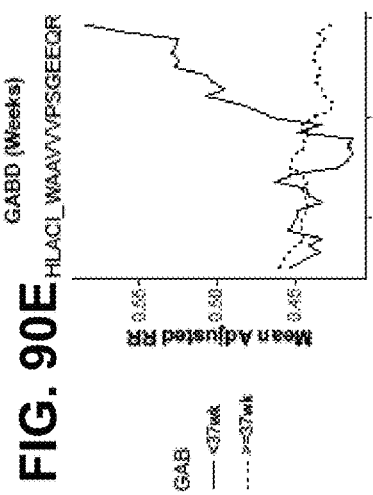
FIG. 90E HLAC1_WAAVVVPSGEEQR
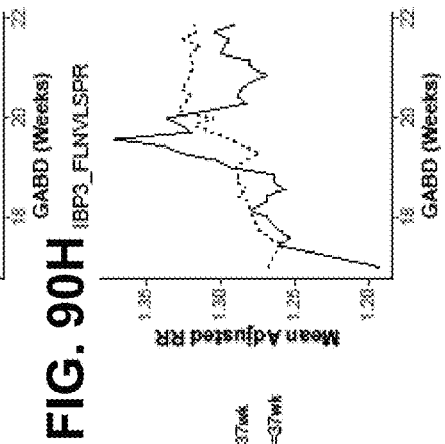
FIG. 90F IBP1_VVESLAK
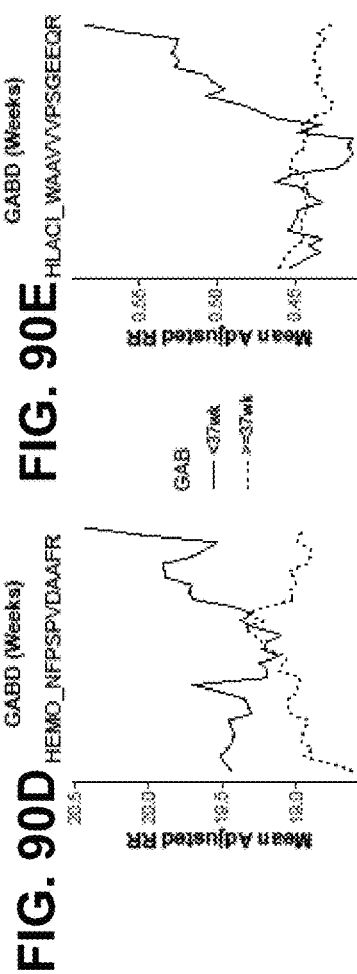
FIG. 90G IBP2_LIQGAPTIR
FIG. 90H IBP3_FLNVLSPR
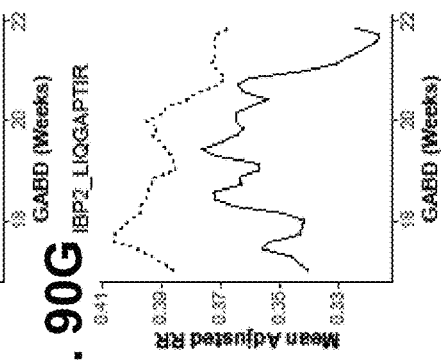
FIG. 90I IBP3_YGQPLPGYTTK

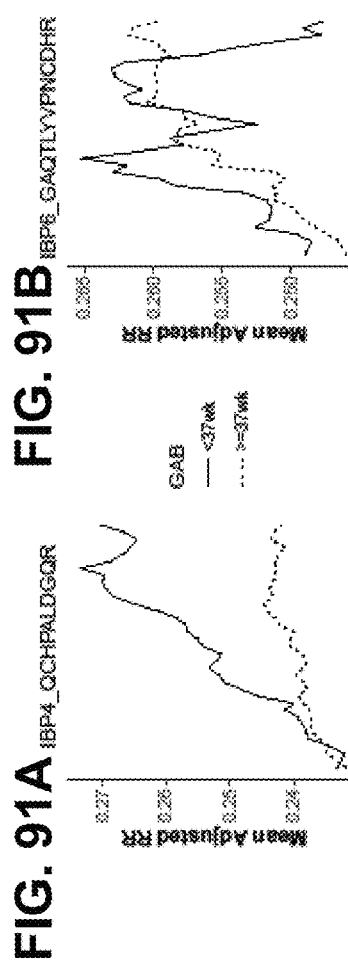
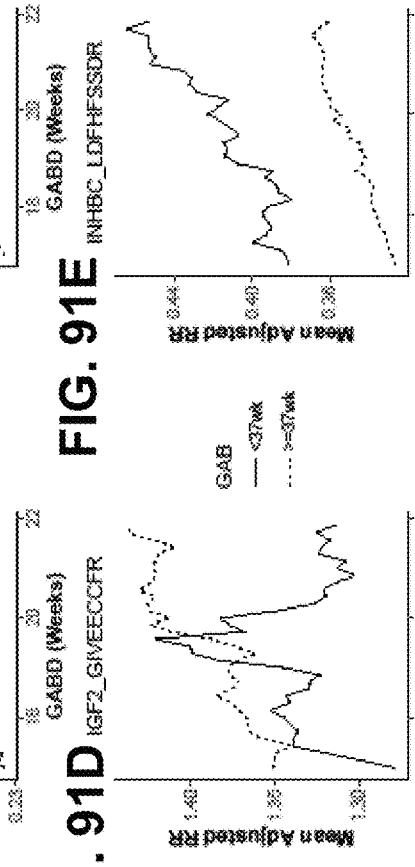
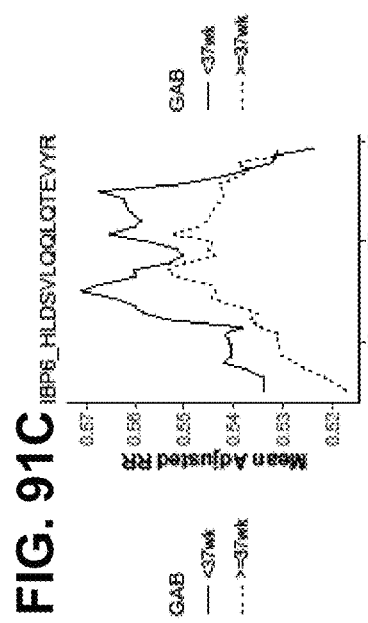
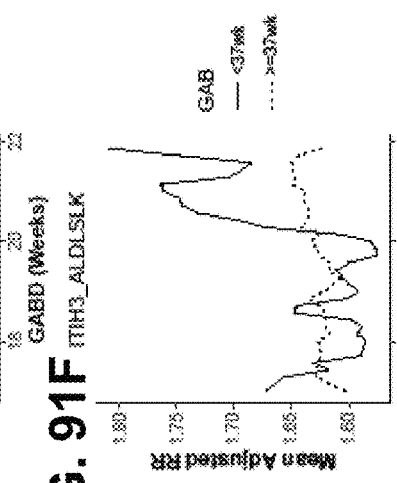
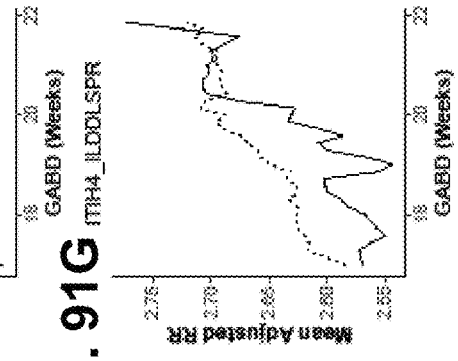
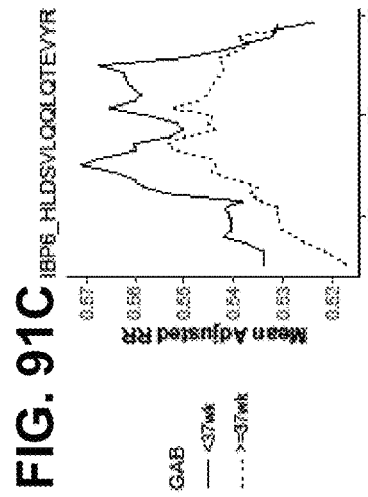
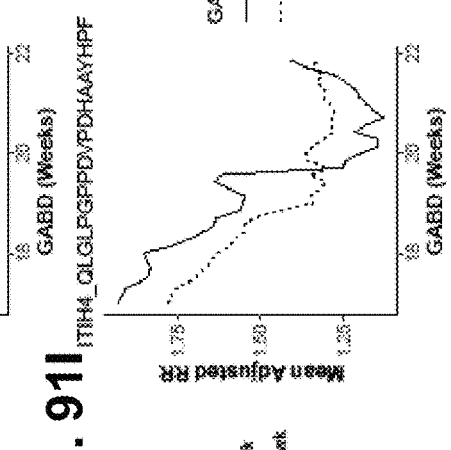

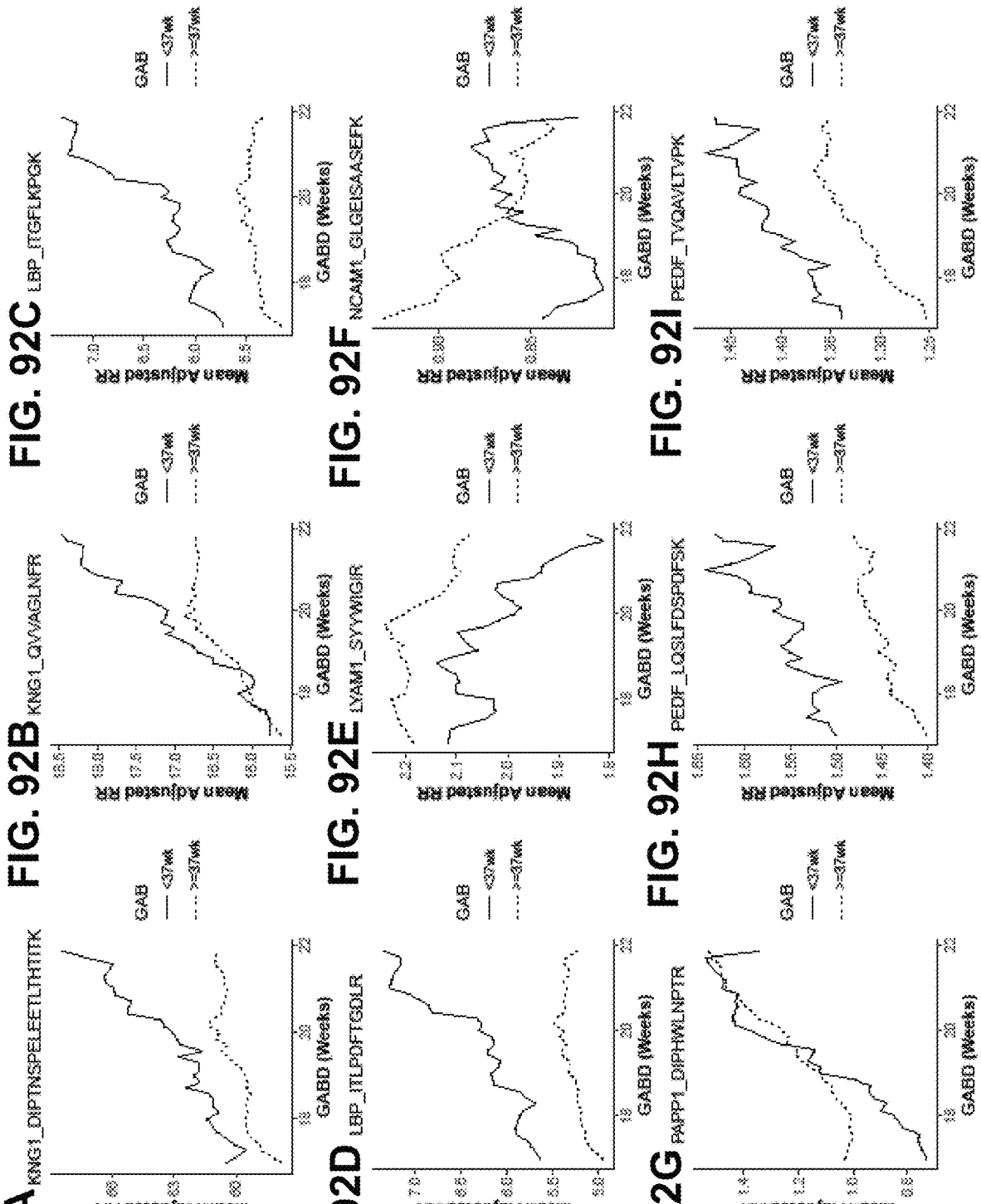

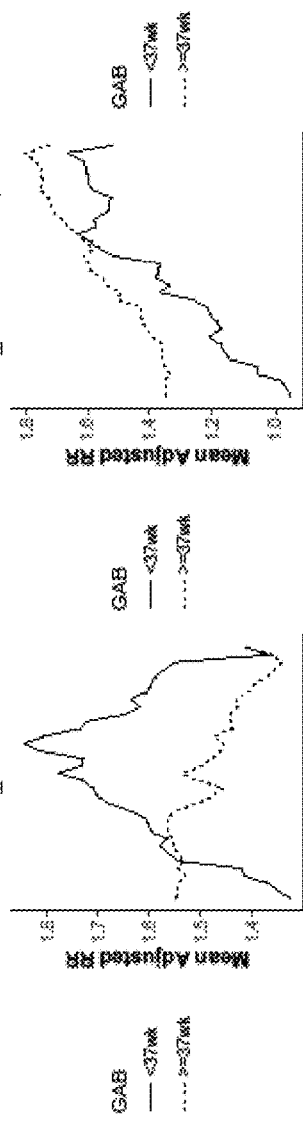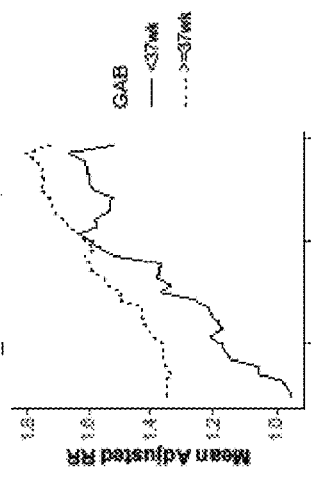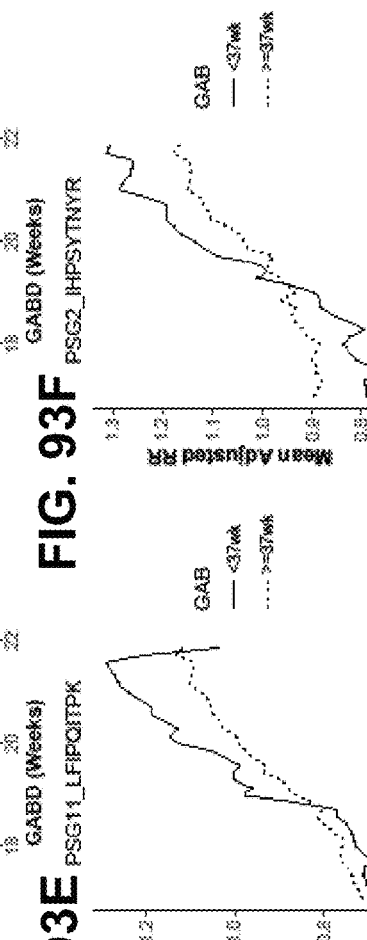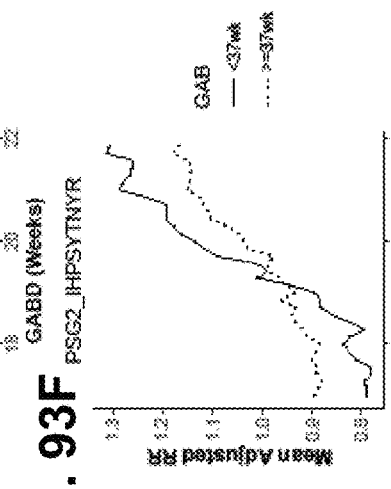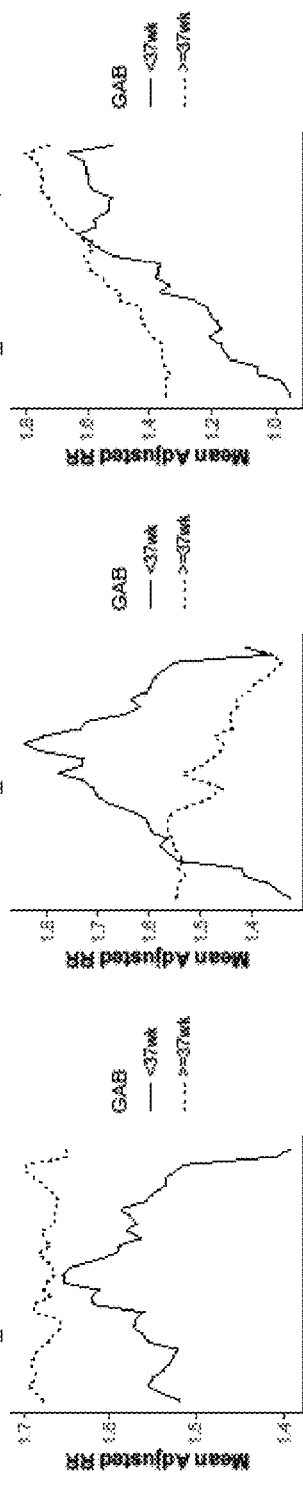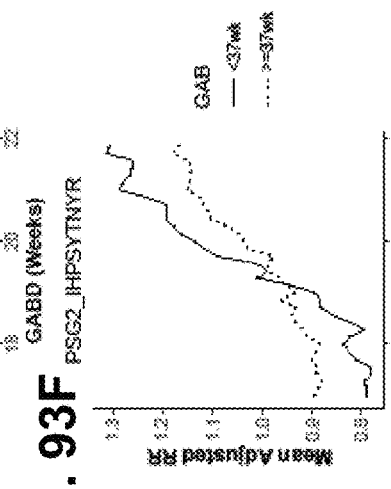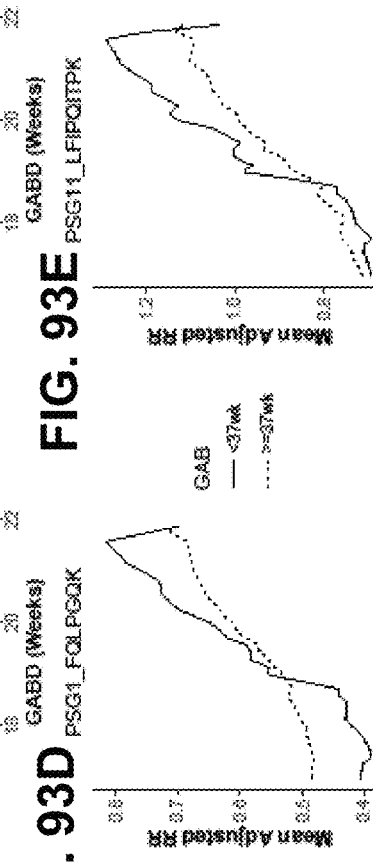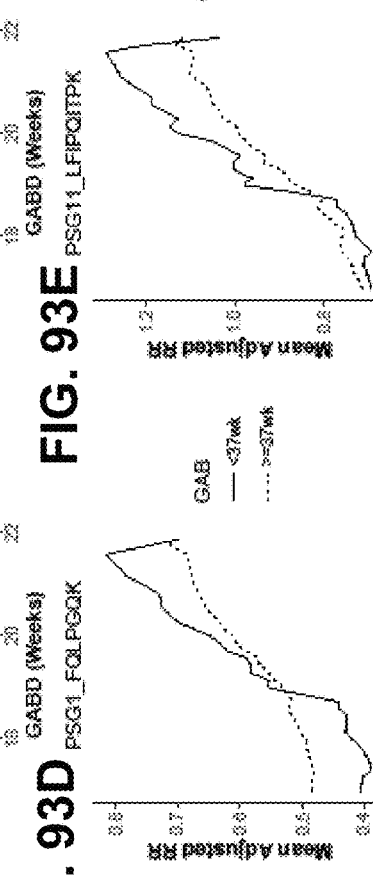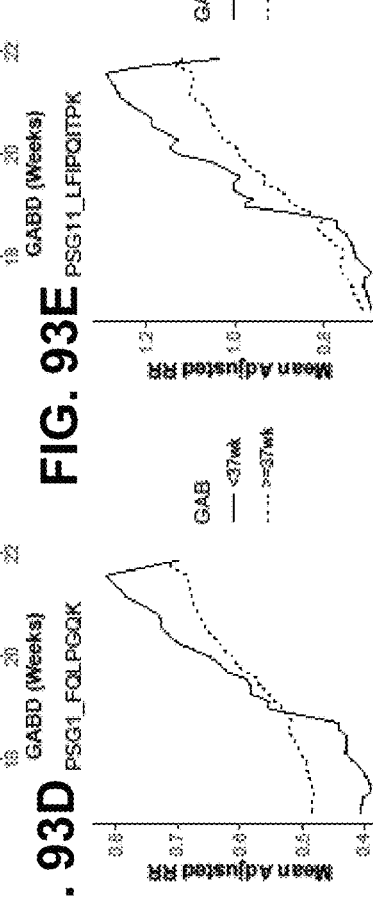
FIG. 93A PGRP2_AGLLRPDYALLGHR
FIG. 93B PRDX2_GLFIIDGK
FIG. 93C PRG2_WMFAYWAAHQPWSR
FIG. 93D PSG1_FQLPGGK
FIG. 93E PSG11_LFIPQITPK
FIG. 93F PSG2_IHPSYTNYR
FIG. 93G PSG3_VSAPSGTGHLPGLNPL
FIG. 93H PSG9_DVLLLVHNLPQNLPGYFWYK
FIG. 93I PSG9_LFIPQITR

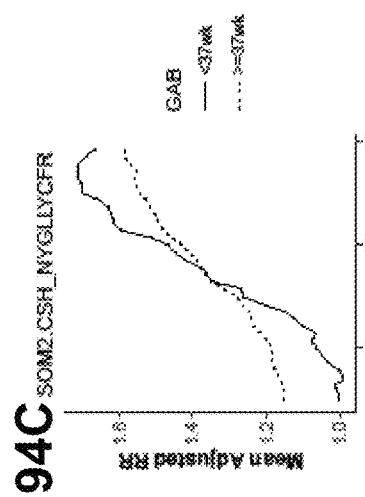
FIG. 94A PTGDS_GPGEDFR
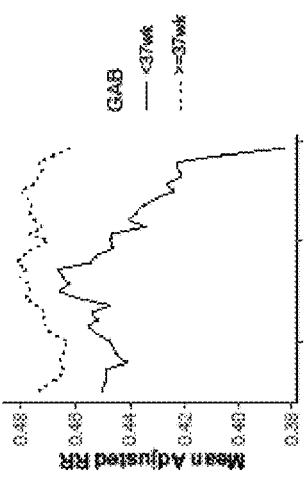
FIG. 94B SHBG_IALGGLLFPASNLR
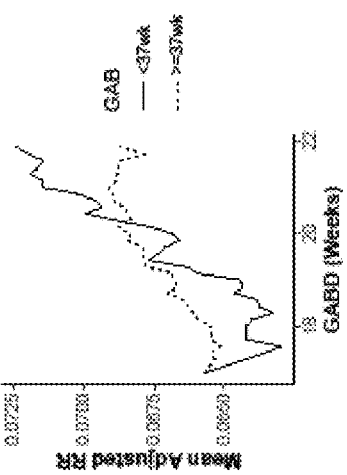
FIG. 94C SOM2_CSH_NYGLLYCFR
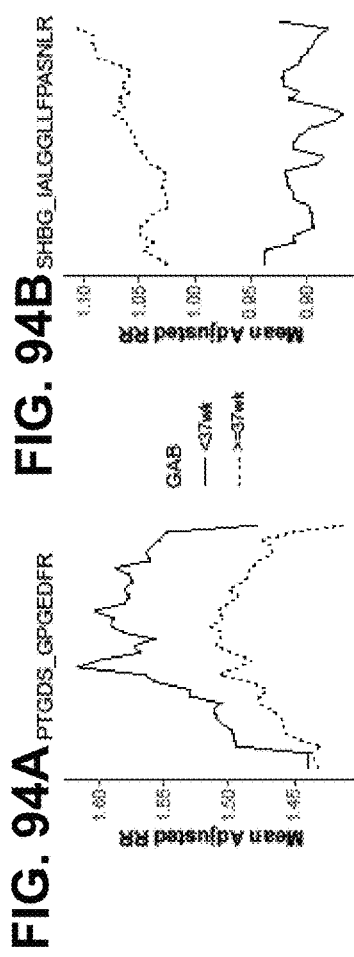
FIG. 94D SOM2_CSH_SVEGSCGF
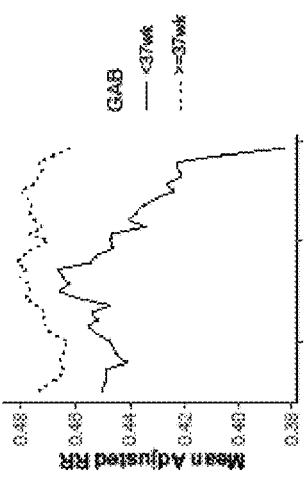
FIG. 94E SPRL1_VLTHSELAPLR
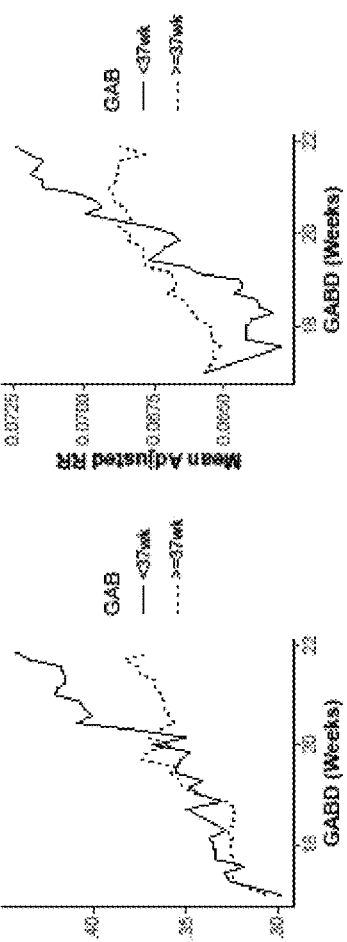
FIG. 94F TENX_LNWEAPPGAFDSFLLR
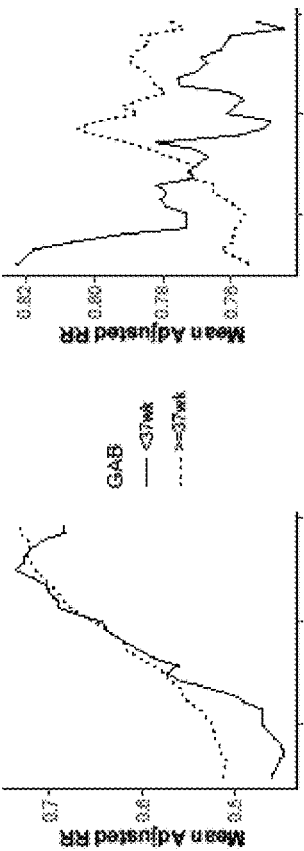
FIG. 94G TENX_LSQLSVTDVTTSSLR
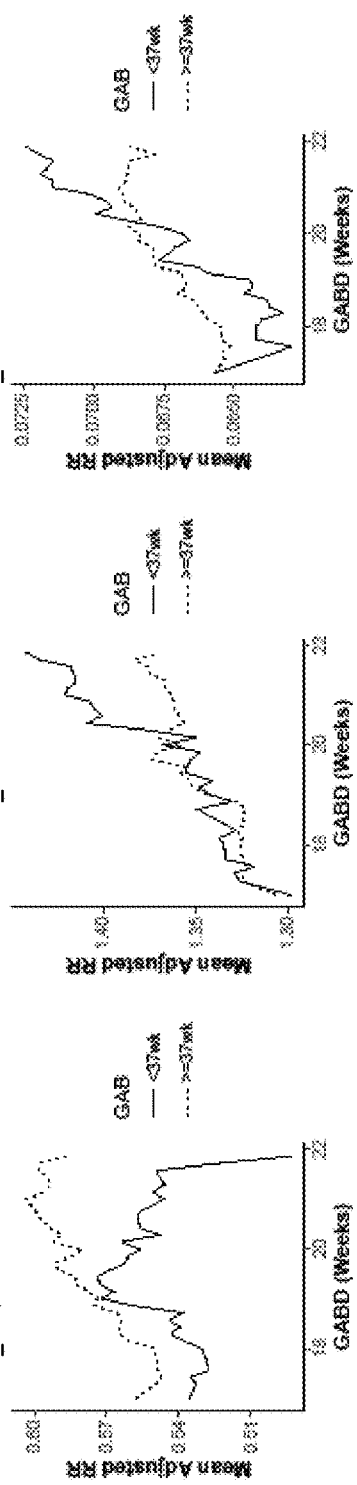
FIG. 94H THBG_AVLHIGEK
FIG. 94I TIE1_VSWSLPLVPGPLVGDGFLLR

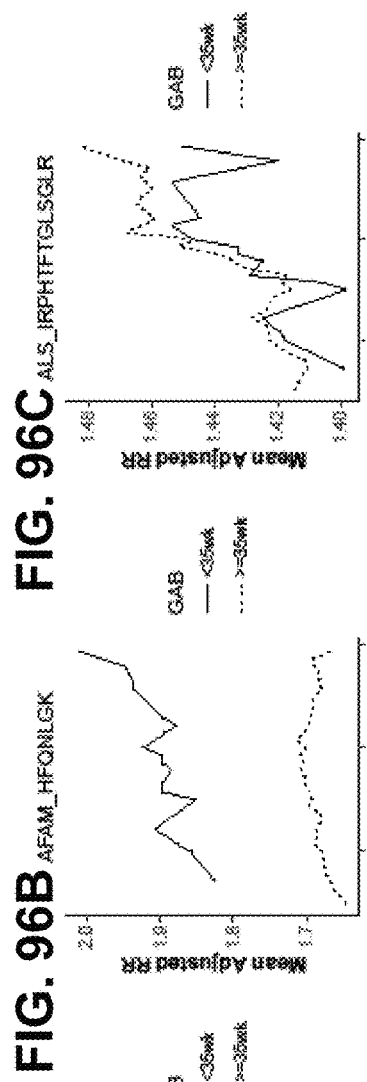
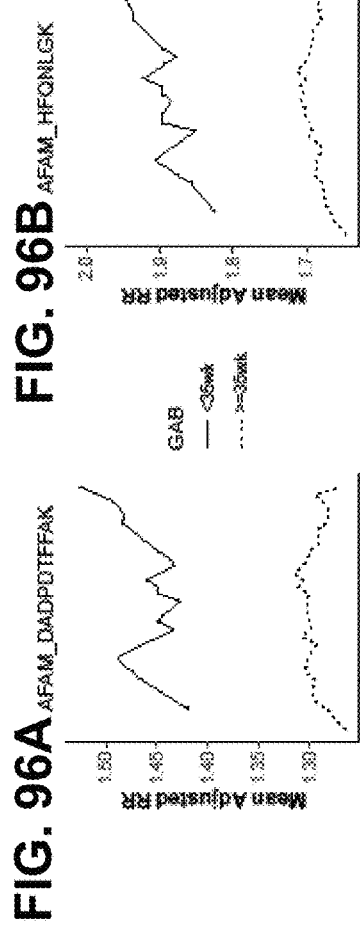
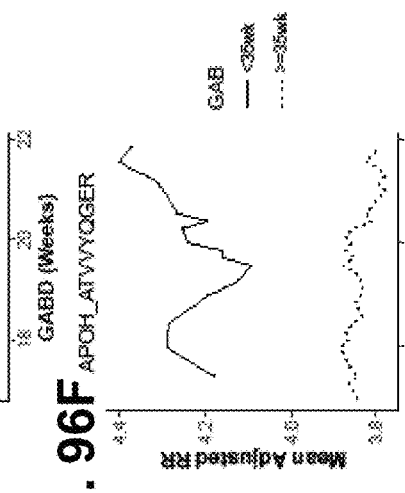
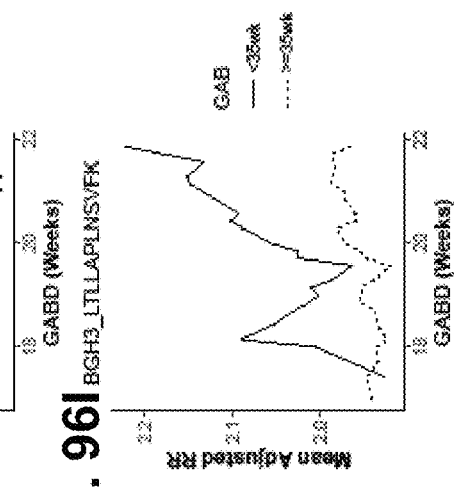
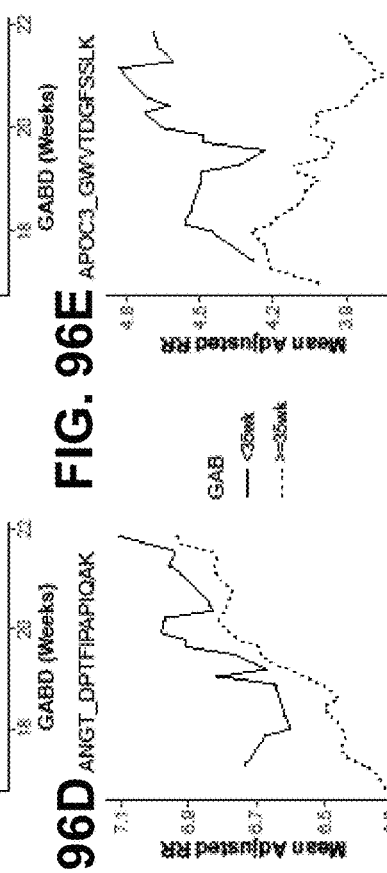
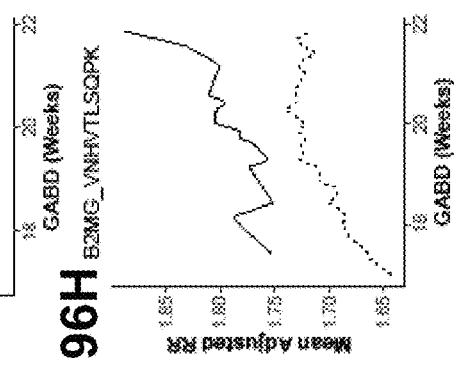
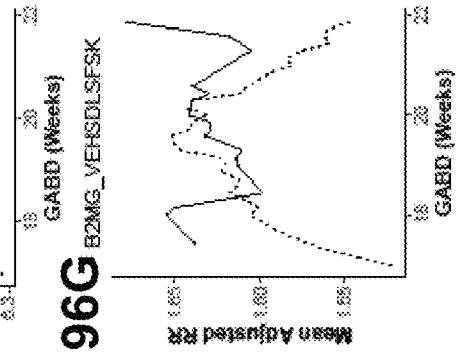

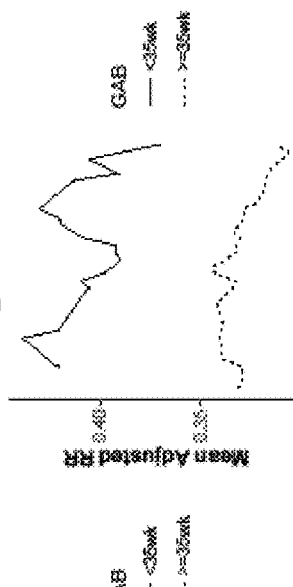
FIG. 97A C163A_RNPASLDK
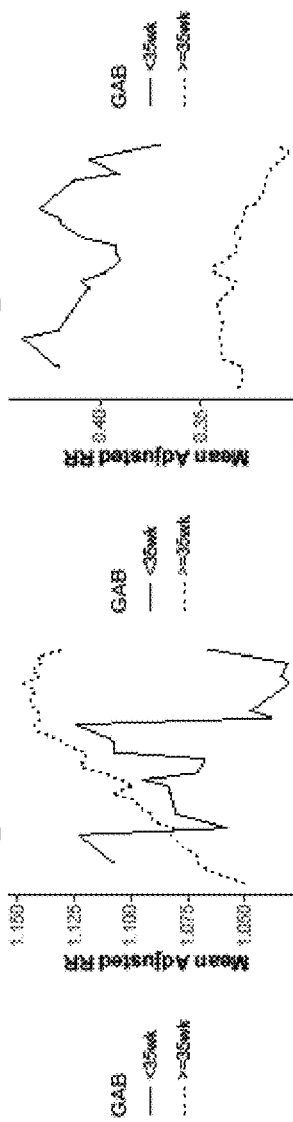
FIG. 97D CATD_VGFAEAAR
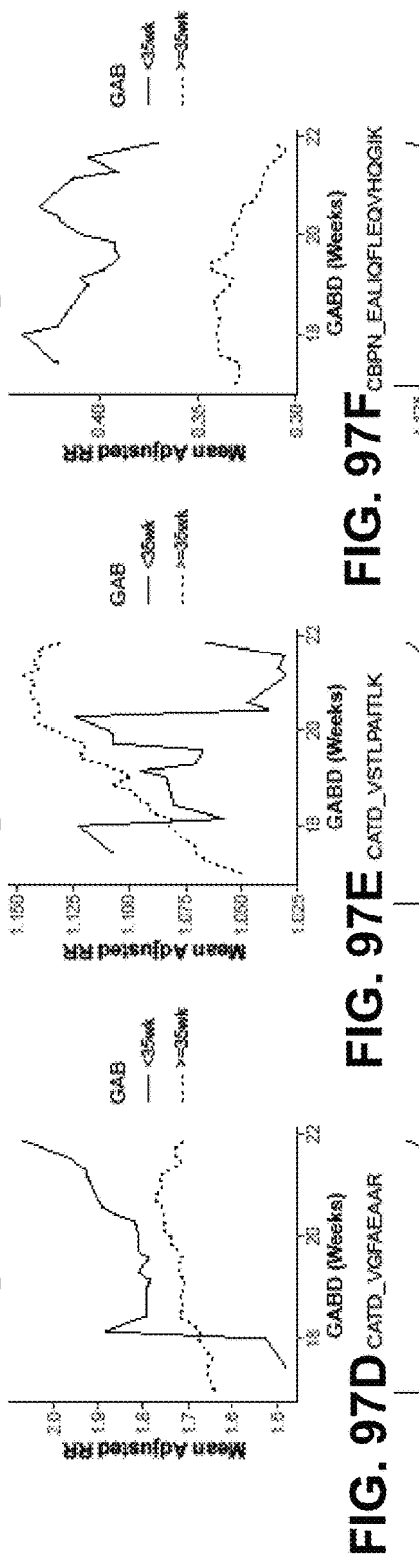
FIG. 97G CBPN_NNANGVDLNR
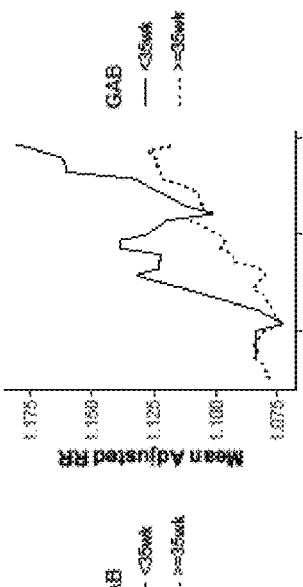
FIG. 97B C1QB_VPGLYYFTYHASSR
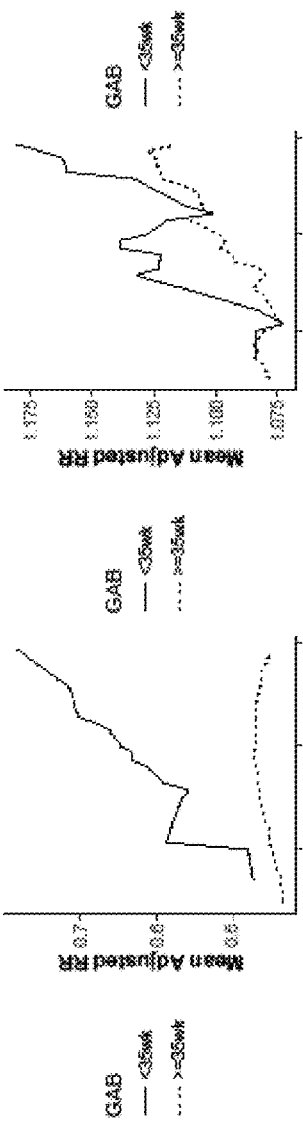
FIG. 97E CATD_VSTLPAITLK
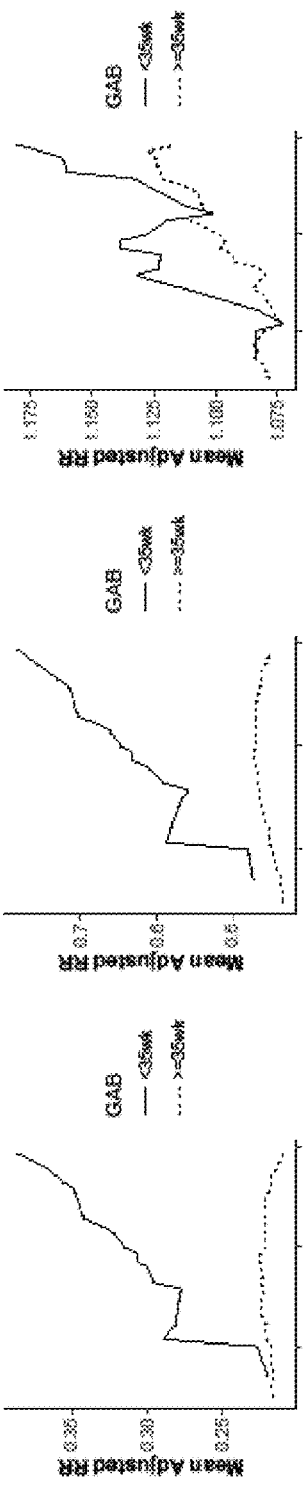
FIG. 97H CD14_LTVGAAQVPAQLLVGALR
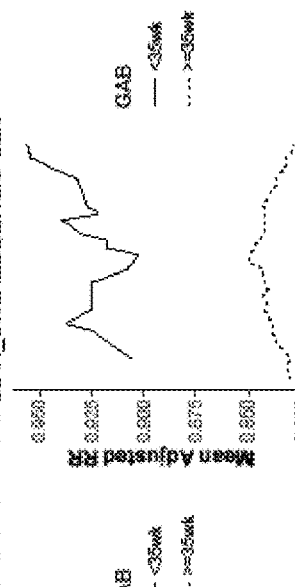
FIG. 97C CAH1_GGPFSDSYR
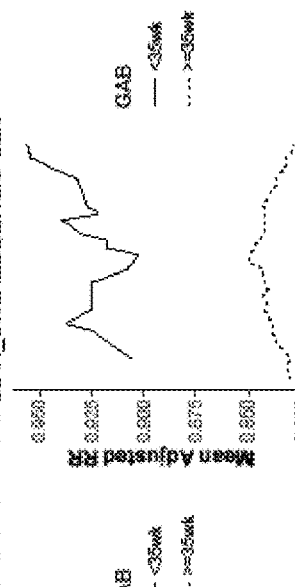
FIG. 97F CBPN_EALIQFLEQVHQGIK
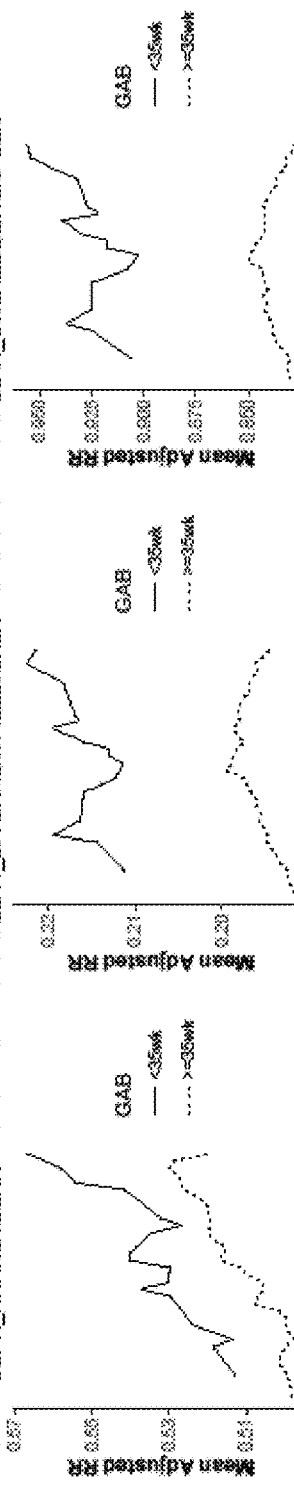
FIG. 97I CD14_SWLAELQQWLKPGLK

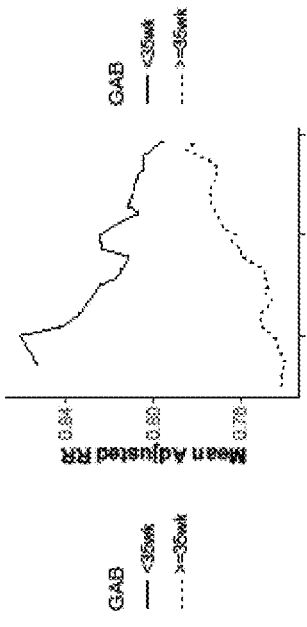 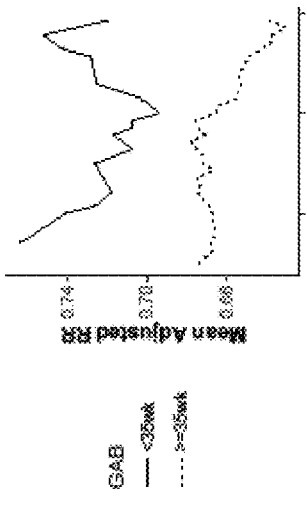 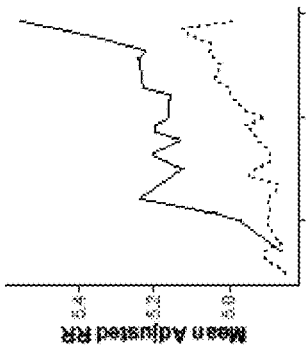
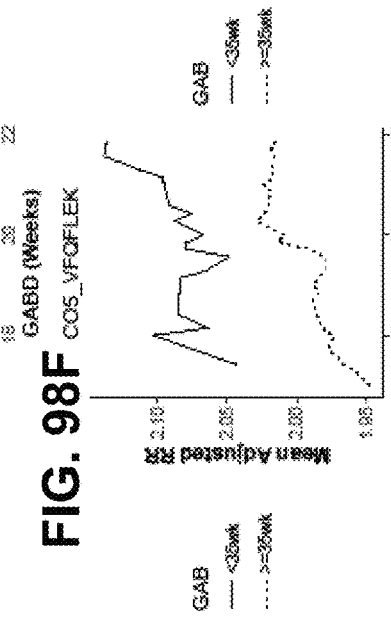 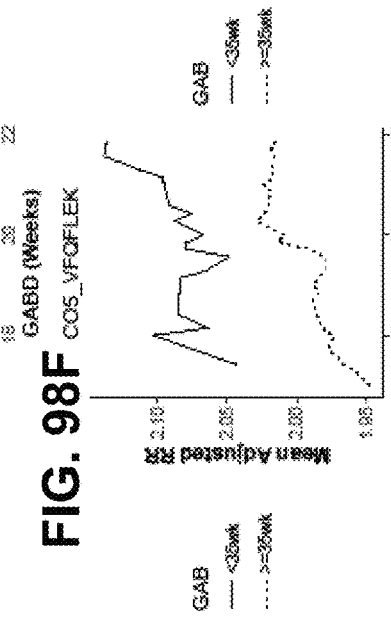 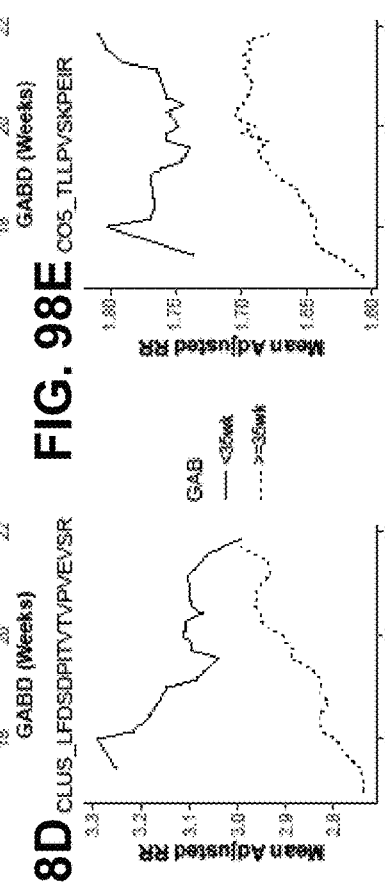
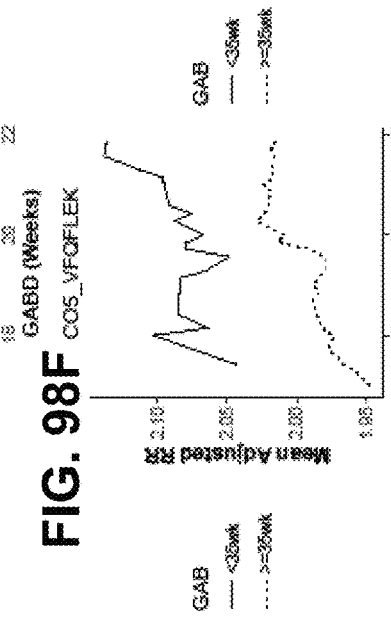 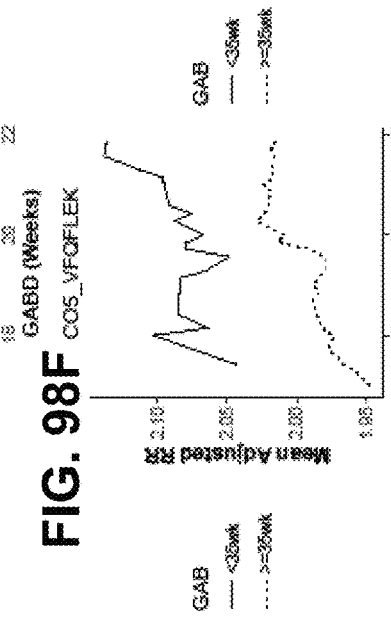 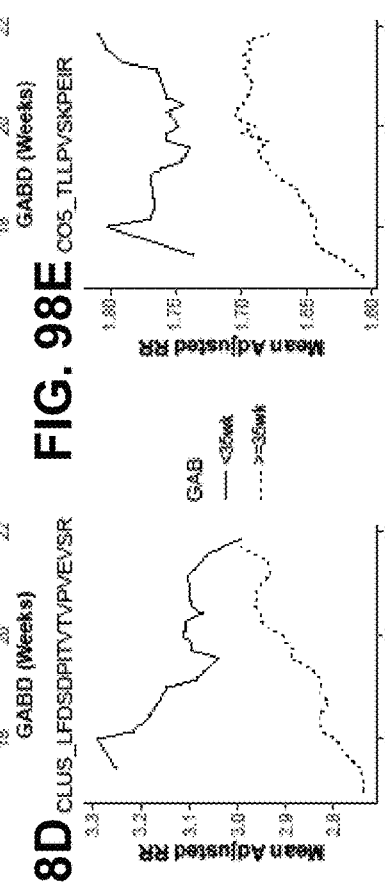

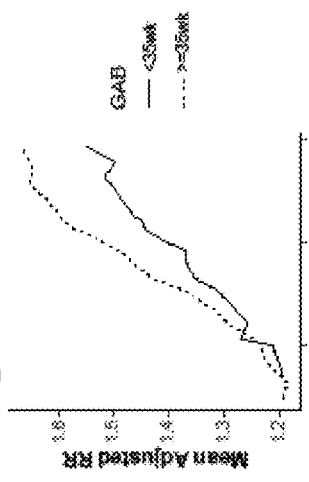
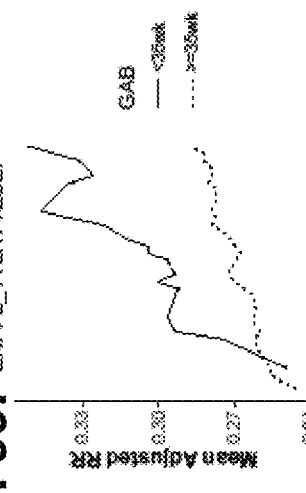
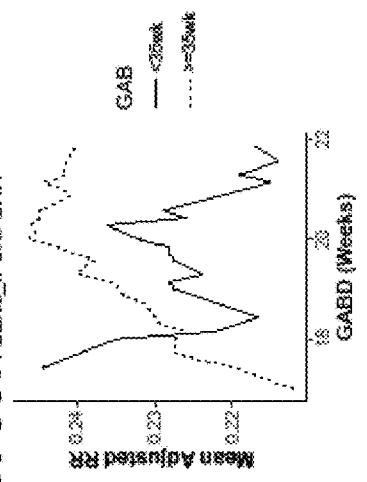
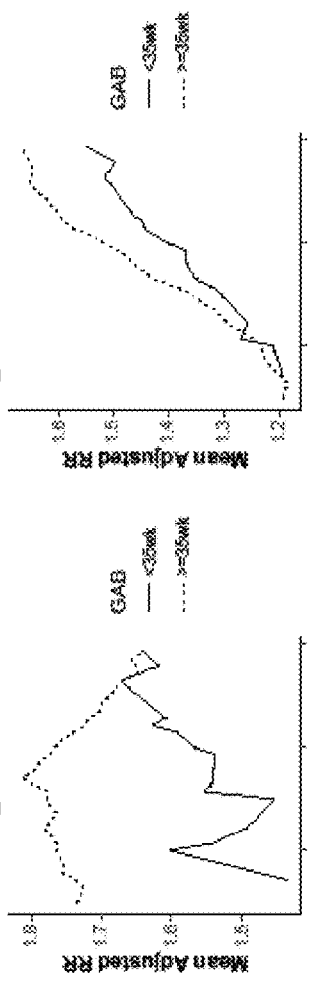
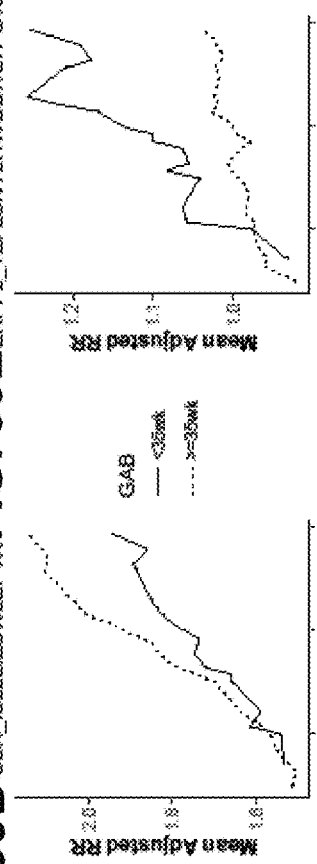
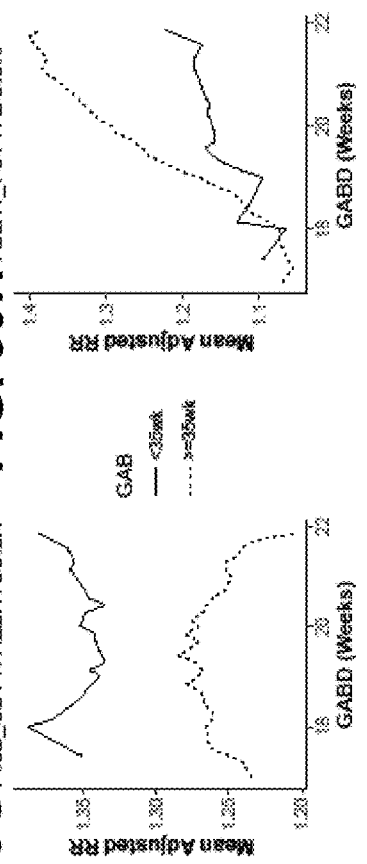
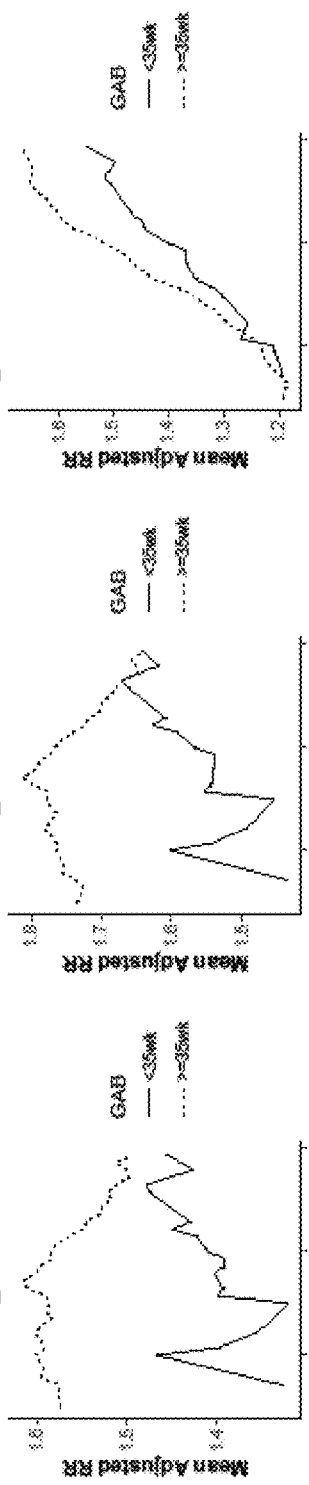
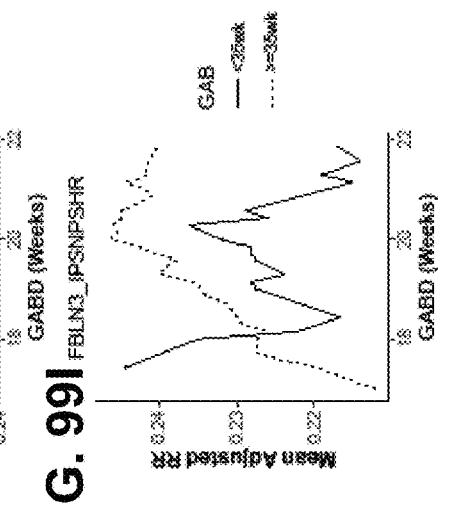
FIG. 99A CRIS3_AVSPPAR
FIG. 99B CRIS3_YEDLYSNCK
FIG. 99C CSH_AHQLAIDTYQEFEETYIPK
FIG. 99D CSH_ISLLLIESWLEPVR
FIG. 99E ENPP2_TEFLSNYLTNVDDITLVPGTLGR
FIG. 99F ENPP2_TYLHTYESEI
FIG. 99G F13B_GDTYPAELYTTGSILR
FIG. 99H FBLN1_TGYYFDGISR
FIG. 99I FBLN3_IPSNPSHR

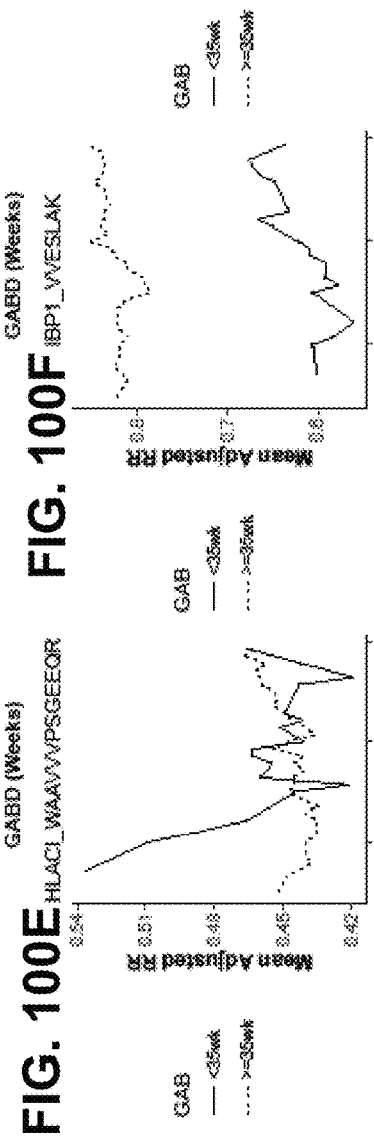
FIG. 100A FETUA_FSVVYAK
FIG. 100B FETUA_HTLNQIDEVK
FIG. 100C HABP2_FLNWIK
FIG. 100D HEMO_NFPSPVDAAFR
FIG. 100E HLAC1_WAAVVVPSGEEQR
FIG. 100F IBP1_VVESLAK
FIG. 100G IBP2_LIQGAPTIR
FIG. 100H IBP3_FLNVLSPR
FIG. 100I IBP3_YGQPLPGYTTK

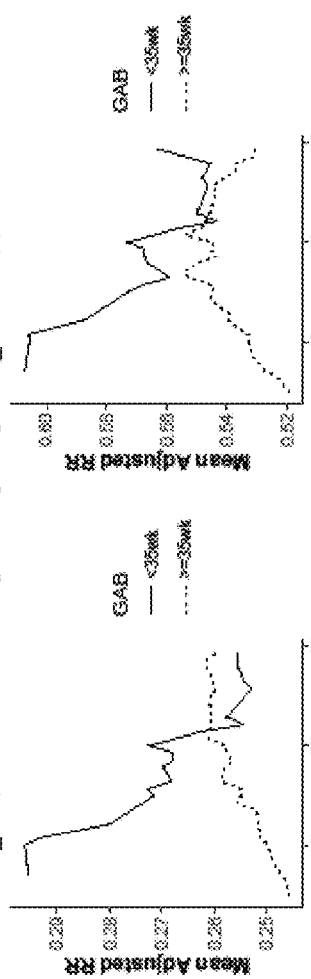
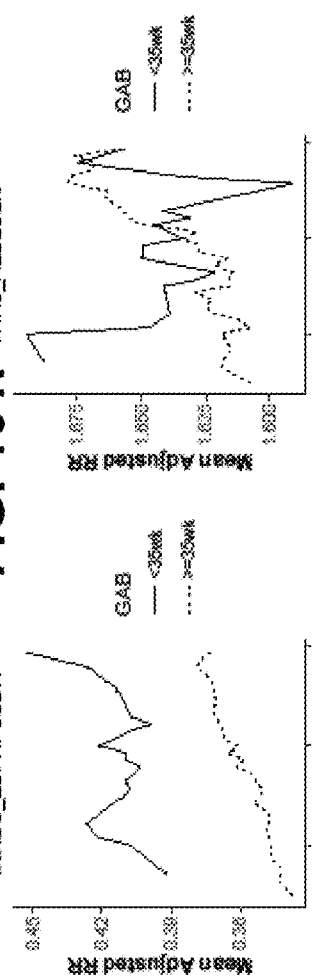
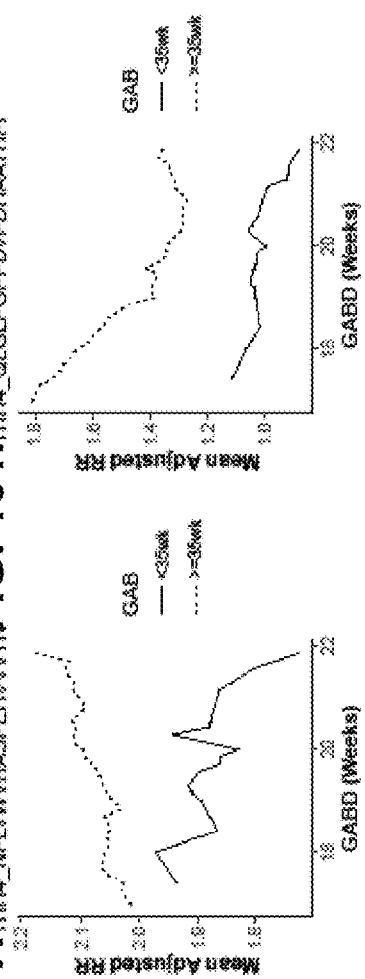
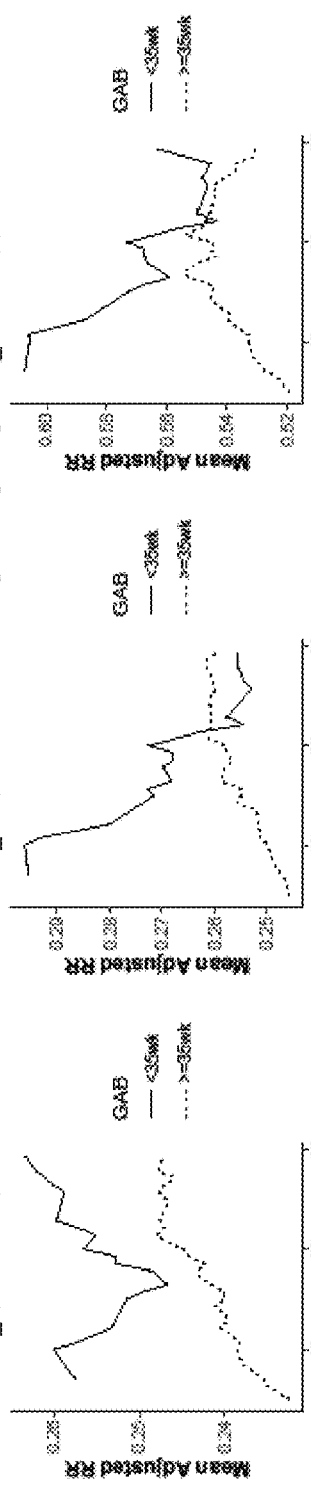
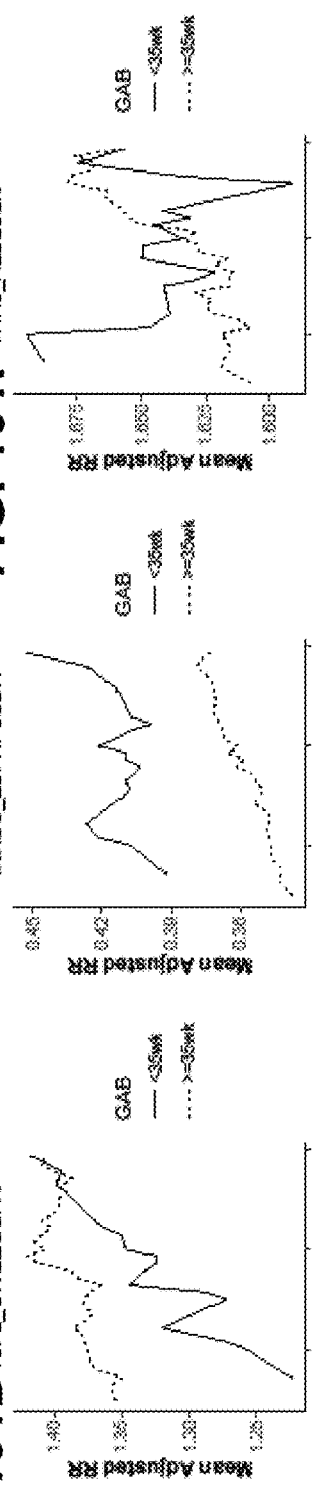
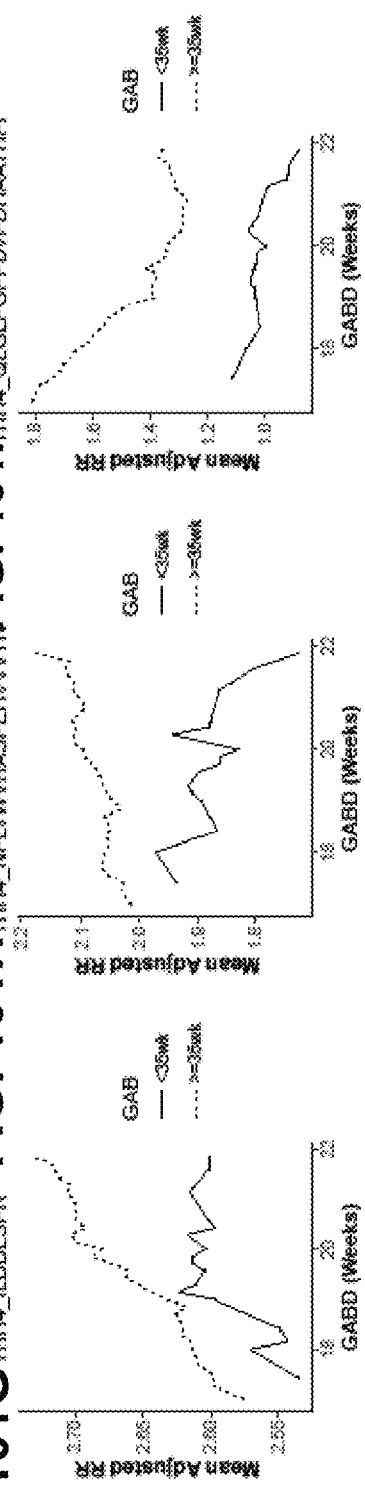
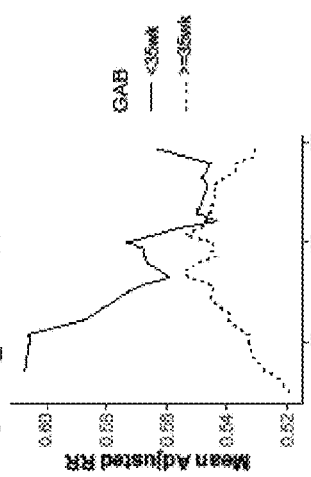
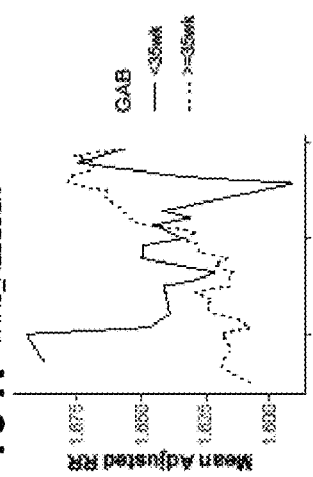

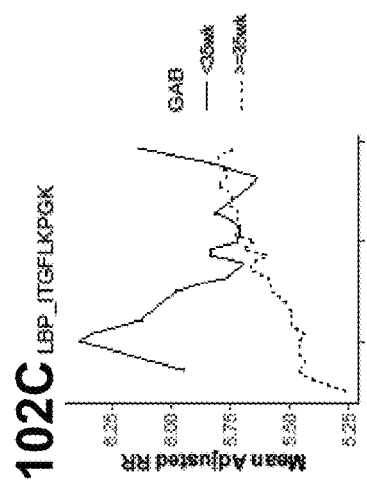
FIG. 102A KNG1_DIPTNSPELEETLTHTTTK
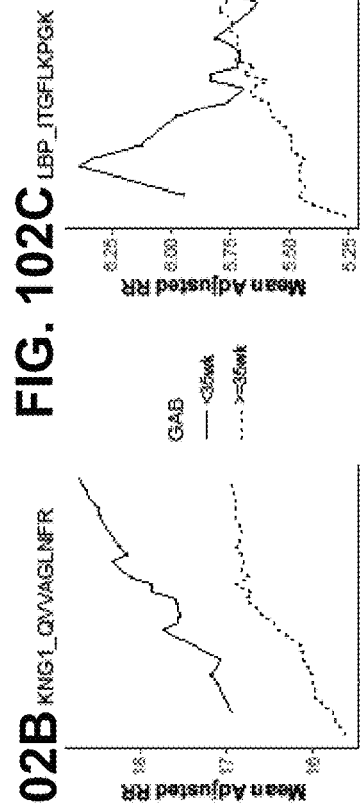
FIG. 102D LBP_ITLPDFTGDLR
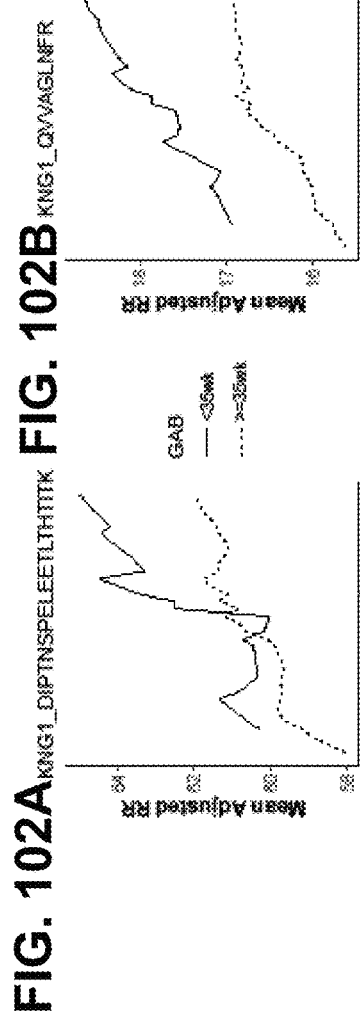
FIG. 102G PAPP3_DIPHWLNPTR
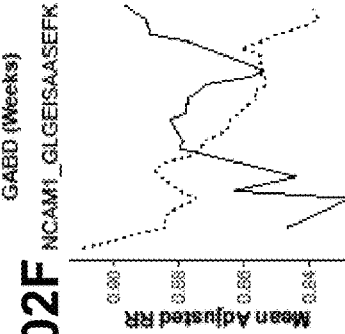
FIG. 102B KNG1_QVVAGLNFR
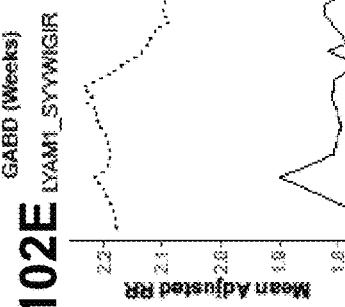
FIG. 102E LYAM1_SYYWIGIR
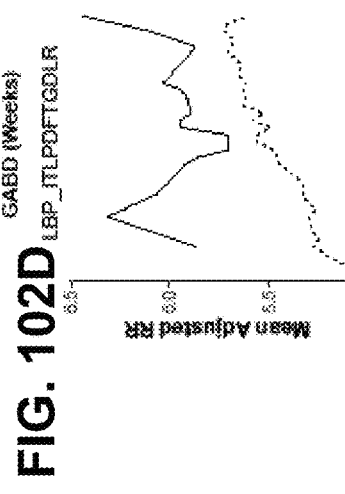
FIG. 102H PEDF_LQSLFDSPDFSK
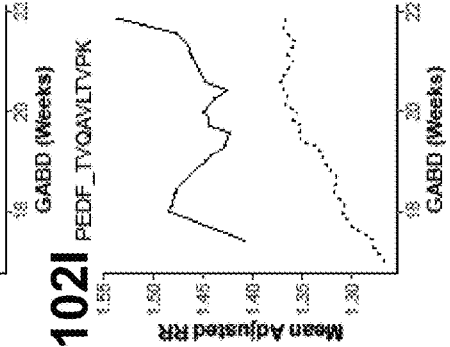
FIG. 102C LBP_ITGFLKPGK
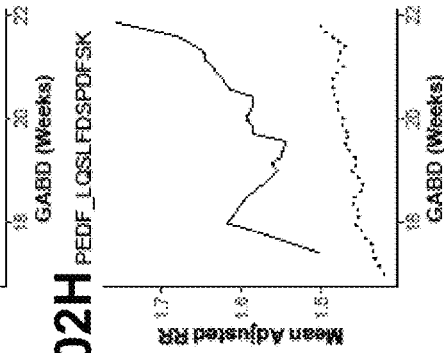
FIG. 102F NCAM1_GLGEISAASEFK
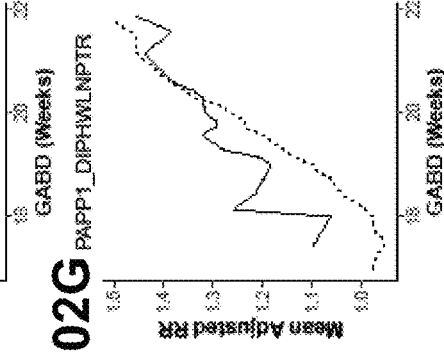
FIG. 102I PEDF_TVQAVLTVPK

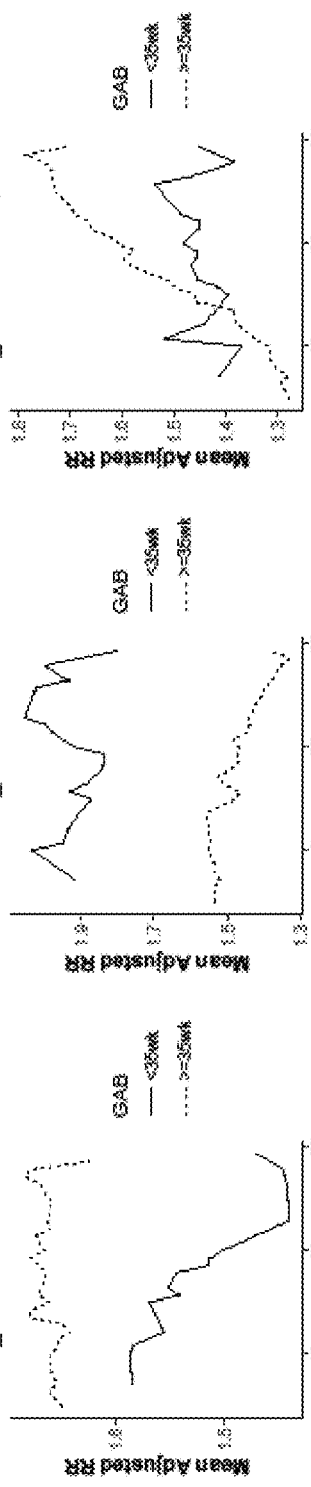
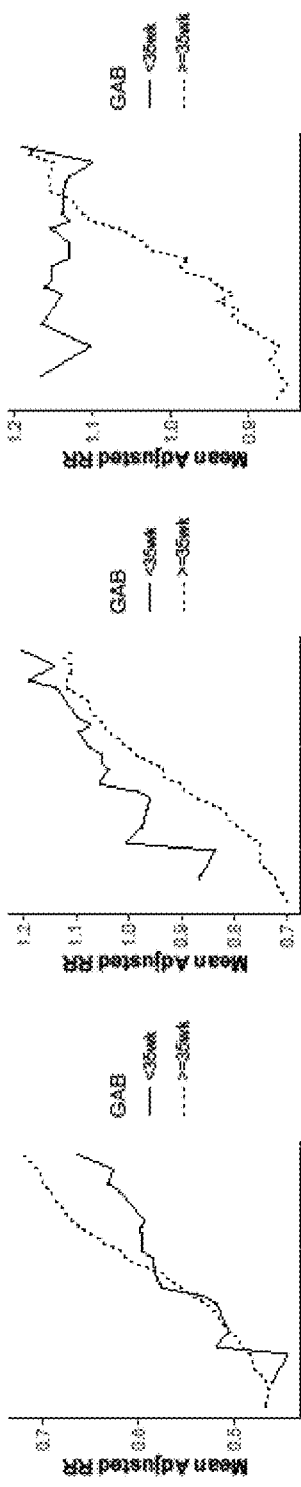
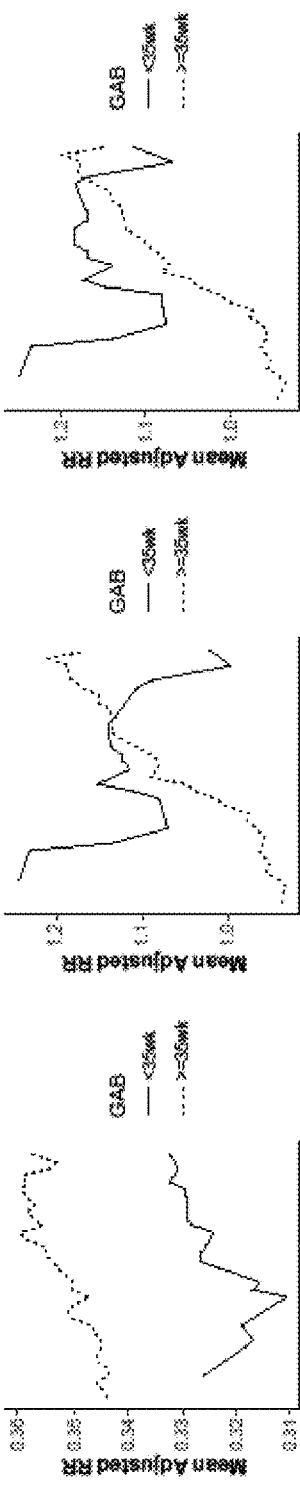
FIG. 103A PGRP2_AGLLRPDYALLGHR
FIG. 103B PROX2_GLFIIDGK
FIG. 103C PRG2_WNFAYWAAHQPWSR
FIG. 103D PSG1_FQLPGQK
FIG. 103E PSG11_LFIPQITPK
FIG. 103F PSG2_IHPSYTNYR
FIG. 103G PSG3_VSAPSGTGHLPGLNPL
FIG. 103H PSG9_DVLLVHNLPQNLPGYFWYK
FIG. 103I PSG9_LFIPQITR

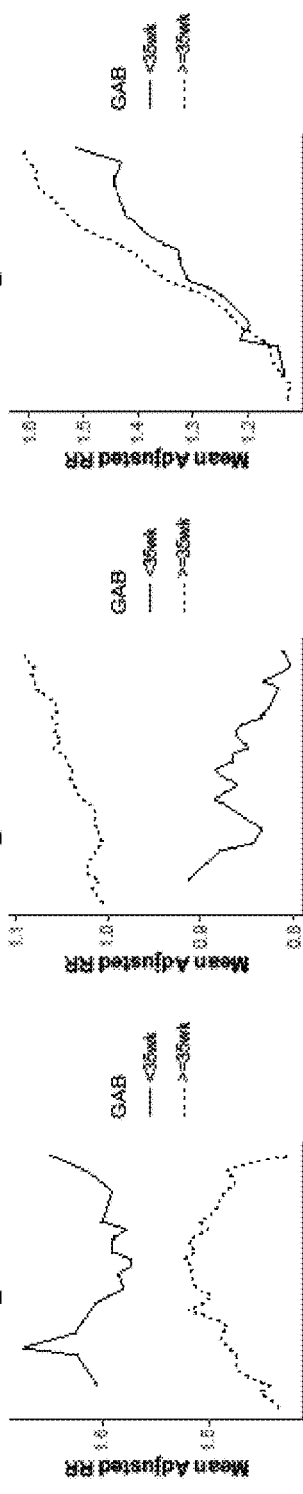
FIG. 104A PTGDS_GPGEDFR
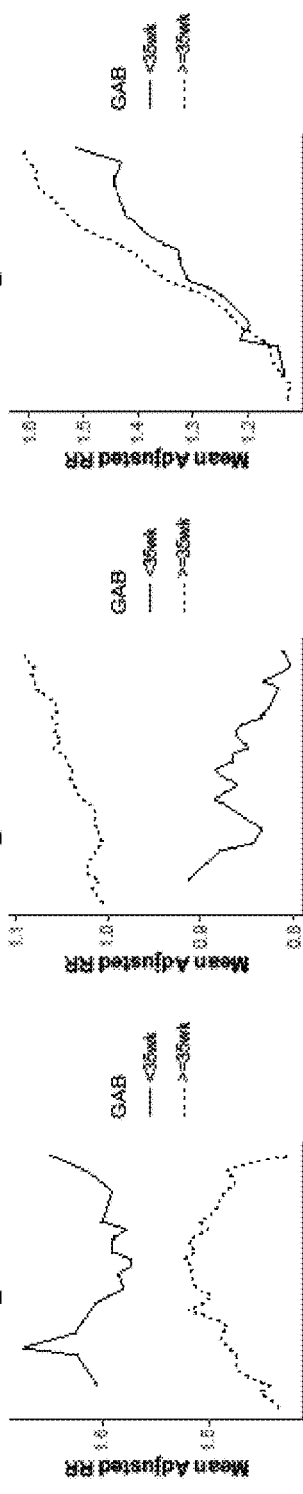
FIG. 104B SHBG_IALGGLLFPASNLR
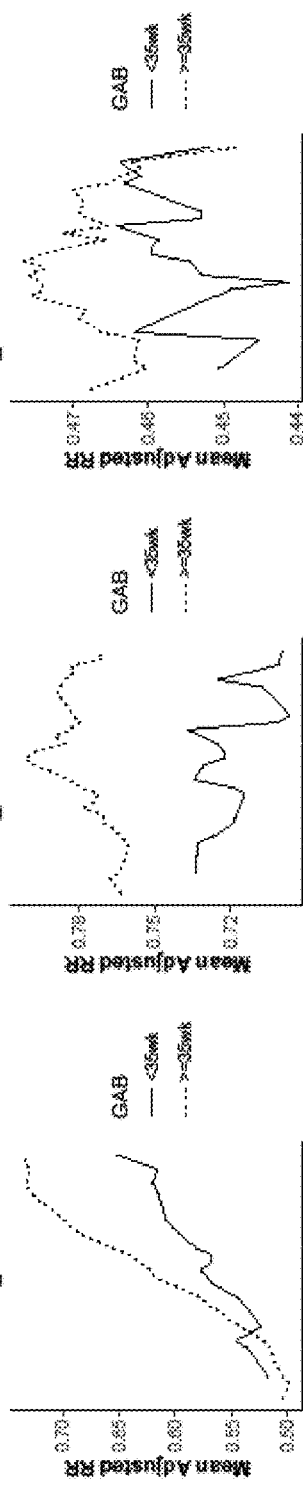
FIG. 104C SOM2.CSH_NYGLLYCFR
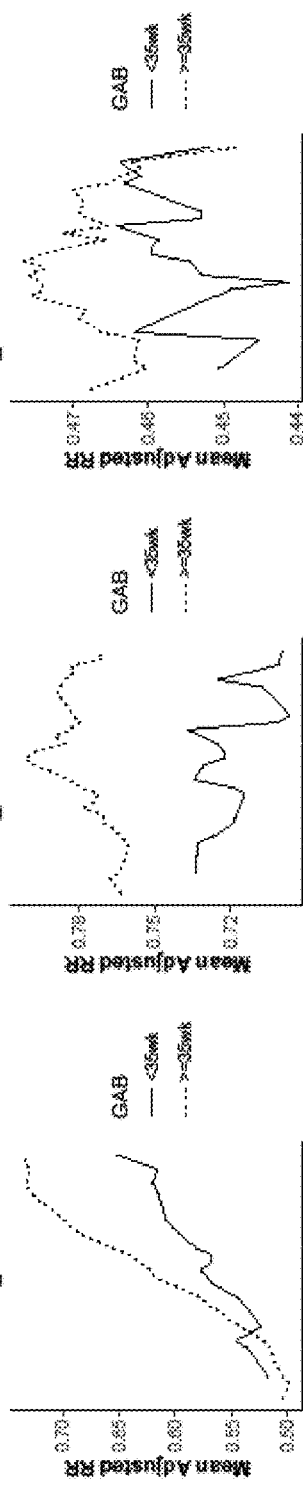
FIG. 104D SOM2.CSH_SVEGSCGF
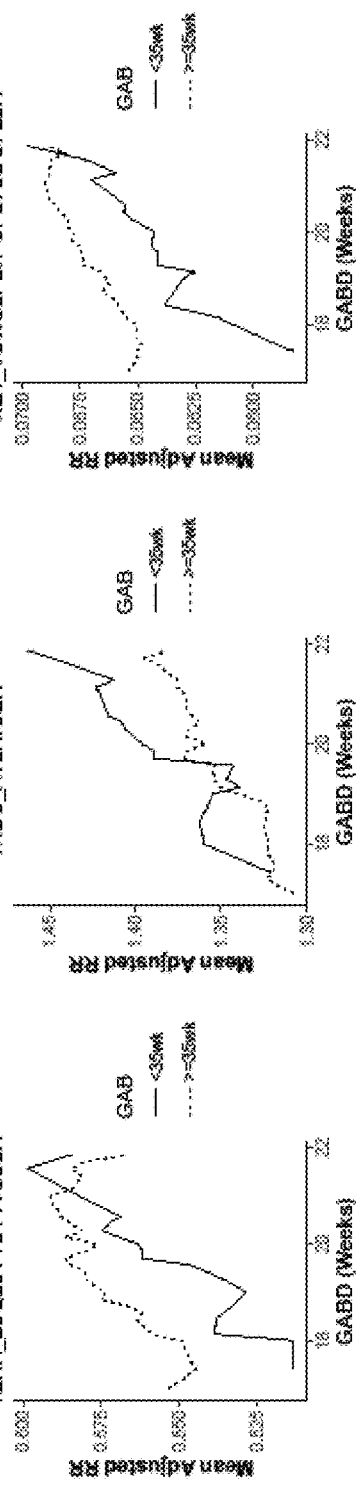
FIG. 104E SPRL1_VLTHSELAPLR
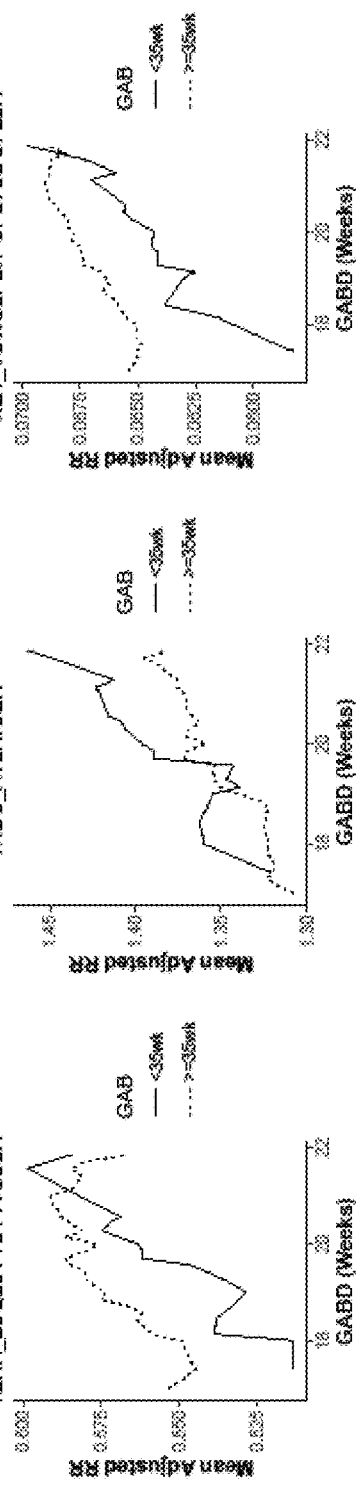
FIG. 104F TENX_LNWEAPPGAFDSFLLR
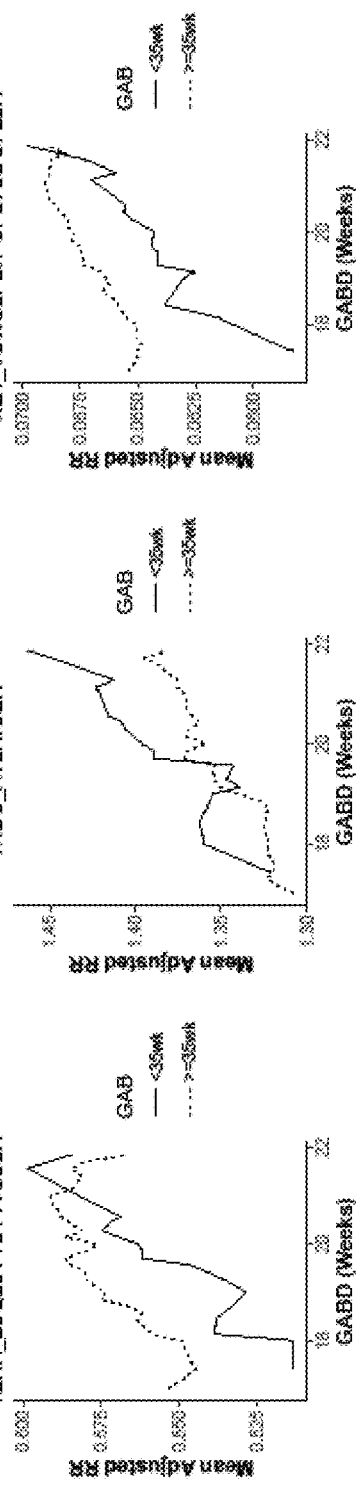
FIG. 104G TENX_LSQLSVTDVTTSSLR
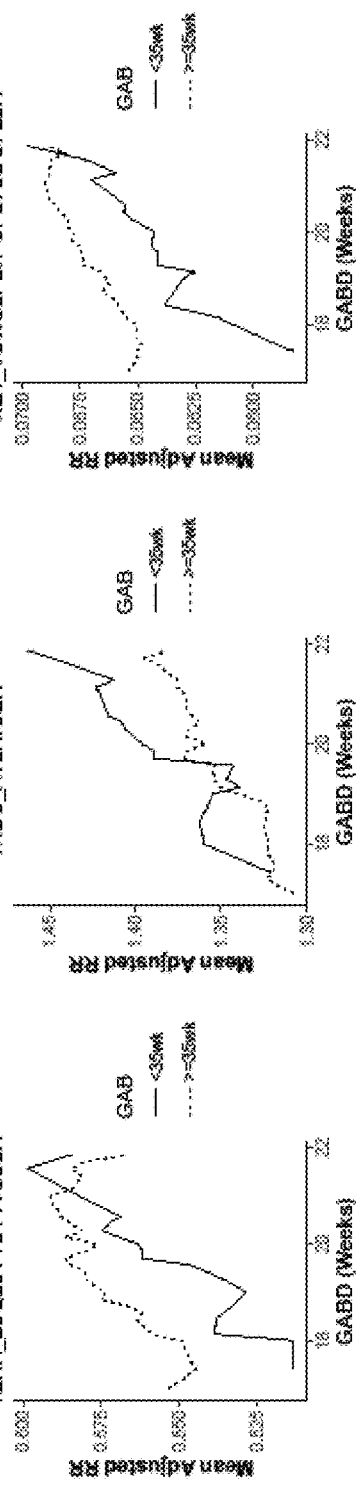
FIG. 104H THBG_AVLHIGEK
FIG. 104I TIE1_VSWSLPLVPGPLVGDGFLLR

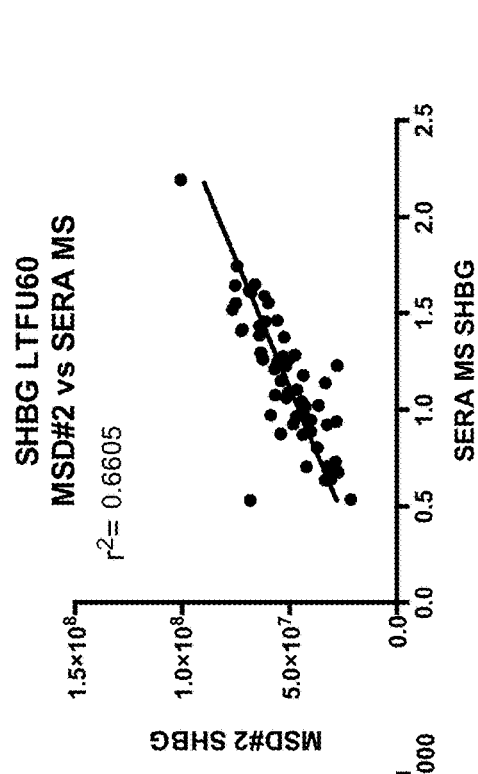
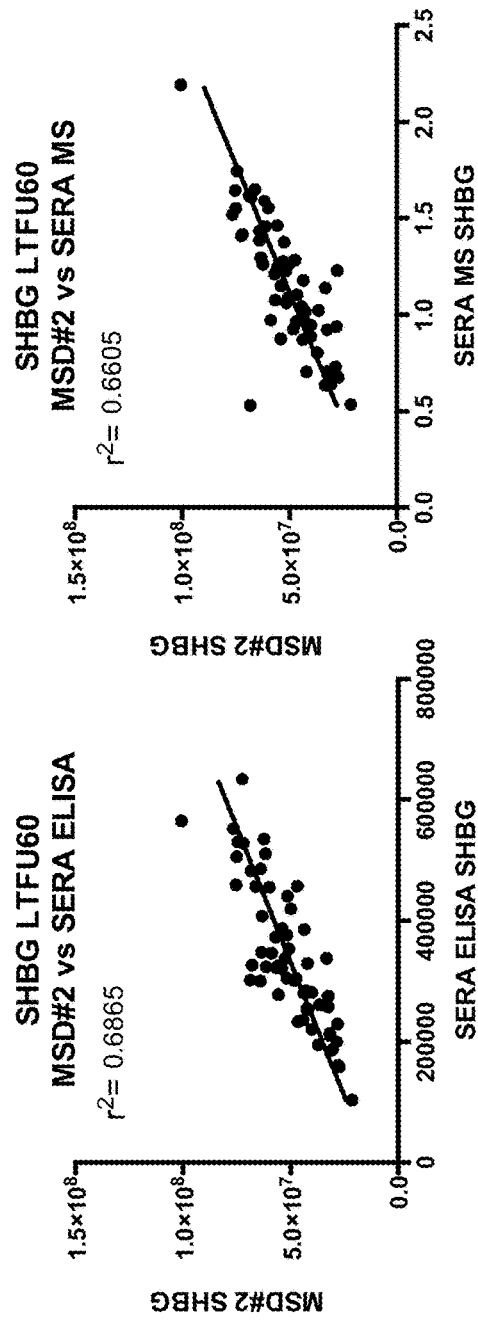
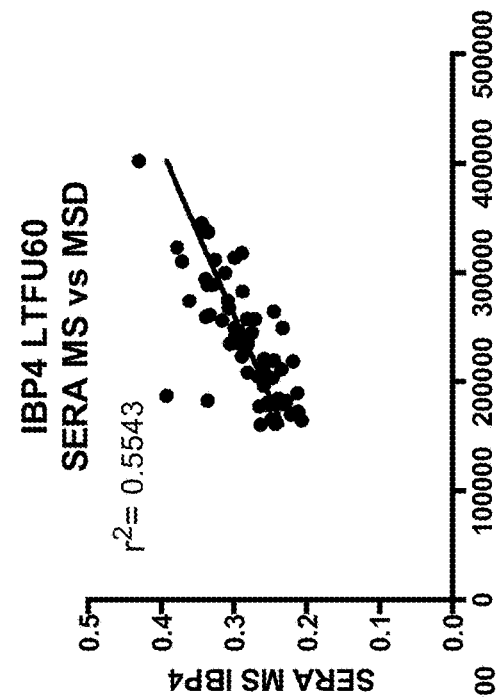
FIG. 107A  FIG. 107B  FIG. 107C  FIG. 107D

BIOMARKER PAIRS FOR PREDICTING PRETERM BIRTH

This application is a continuation of U.S. patent application Ser. No. 15/186,322, filed Jun. 17, 2016, which claims the benefit of U.S. Provisional Application No. 62/290,796, filed Feb. 3, 2016, U.S. Provisional Application No. 62/387,420, filed Dec. 24, 2015, and U.S. Provisional Application No. 62/182,349, filed Jun. 19, 2015, the entire contents of each of which are incorporated herein by reference.

This application incorporates by reference a Sequence Listing submitted as an ASCII text file entitled 13271-034-999_SL.TXT created on Nov. 6, 2020, and having a size of 44,453 bytes.

The invention relates generally to the field of precision medicine and, more specifically to compositions and methods for determining the probability for preterm birth in a pregnant female.

BACKGROUND

According to the World Health Organization, an estimated 15 million babies are born preterm (before 37 completed weeks of gestation) every year. In almost all countries with reliable data, preterm birth rates are increasing. See, World Health Organization; March of Dimes; The Partnership for Maternal, Newborn & Child Health; Save the Children, *Born too soon: the global action report on preterm birth*, ISBN 9789241503433(2012). An estimated 1 million babies die annually from preterm birth complications. Globally, preterm birth is the leading cause of newborn deaths (babies in the first four weeks of life) and the second leading cause of death after pneumonia in children under five years. Many survivors face a lifetime of disability, including learning disabilities and visual and hearing problems.

Across 184 countries with reliable data, the rate of preterm birth ranges from 5% to 18% of babies born. Blencowe et al., "National, regional and worldwide estimates of preterm birth." *The Lancet*, 9; 379(9832):2162-72 (2012). While over 60% of preterm births occur in Africa and south Asia, preterm birth is nevertheless a global problem. Countries with the highest numbers include Brazil, India, Nigeria and the United States of America. Of the 11 countries with preterm birth rates over 15%, all but two are in sub-Saharan Africa. In the poorest countries, on average, 12% of babies are born too soon compared with 9% in higher-income countries. Within countries, poorer families are at higher risk. More than three-quarters of premature babies can be saved with feasible, cost-effective care, for example, antenatal steroid injections given to pregnant women at risk of preterm labor to strengthen the babies' lungs.

Infants born preterm are at greater risk than infants born at term for mortality and a variety of health and developmental problems. Complications include acute respiratory, gastrointestinal, immunologic, central nervous system, hearing, and vision problems, as well as longer-term motor, cognitive, visual, hearing, behavioral, social-emotional, health, and growth problems. The birth of a preterm infant can also bring considerable emotional and economic costs to families and have implications for public-sector services, such as health insurance, educational, and other social support systems. The greatest risk of mortality and morbidity is for those infants born at the earliest gestational ages. However, those infants born nearer to term represent the greatest number of infants born preterm and also experience more complications than infants born at term.

To prevent preterm birth in women who are less than 24 weeks pregnant with an ultrasound showing cervical opening, a surgical procedure known as cervical cerclage can be employed in which the cervix is stitched closed with strong sutures. For women less than 34 weeks pregnant and in active preterm labor, hospitalization may be necessary as well as the administration of medications to temporarily halt preterm labor and/or promote the fetal lung development. If a pregnant women is determined to be at risk for preterm birth, health care providers can implement various clinical strategies that may include preventive medications, for example, 17-α hydroxyprogesterone caproate (Makena) injections and/or vaginal progesterone gel, cervical pessaries, restrictions on sexual activity and/or other physical activities, and alterations of treatments for chronic conditions, such as diabetes and high blood pressure, that increase the risk of preterm labor.

There is a great need to identify and provide women at risk for preterm birth with proper antenatal care. Women identified as high-risk can be scheduled for more intensive antenatal surveillance and prophylactic interventions. Current strategies for risk assessment are based on the obstetric and medical history and clinical examination, but these strategies are only able to identify a small percentage of women who are at risk for preterm delivery. Prior history of spontaneous PTB (sPTB) is currently the single strongest predictor of subsequent PTB. After one prior sPTB the probability of a second PTB is 30-50%. Other maternal risk factors include: black race, low maternal body-mass index, and short cervical length. Amniotic fluid, cervicovaginal fluid, and serum biomarker studies to predict sPTB suggest that multiple molecular pathways are aberrant in women who ultimately deliver preterm. Reliable early identification of risk for preterm birth would enable planning appropriate monitoring and clinical management to prevent preterm delivery. Such monitoring and management might include: more frequent prenatal care visits, serial cervical length measurements, enhanced education regarding signs and symptoms of early preterm labor, lifestyle interventions for modifiable risk behaviors such as smoking cessation, cervical pessaries and progesterone treatment. Finally, reliable antenatal identification of risk for preterm birth also is crucial to cost-effective allocation of monitoring resources.

Despite intense research to identify at-risk women, PTB prediction algorithms based solely on clinical and demographic factors or using measured serum or vaginal biomarkers have not resulted in clinically useful tests. More accurate methods to identify women at risk during their first pregnancy and sufficiently early in gestation are needed to allow for clinical intervention. The present invention addresses this need by providing compositions and methods for determining whether a pregnant woman is at risk for preterm birth. Related advantages are provided as well.

SUMMARY

The present invention provides compositions and methods for predicting the probability of preterm birth in a pregnant female.

The invention provides isolated biomarkers selected from the group set forth in Table 26. The biomarkers of the invention can predict risk for pre-term birth in a pregnant female. In some embodiments, the isolated biomarkers are selected from the group consisting of IBP4, SHBG, PSG3, LYAM1, IGF2, CLUS, IBP3, INHBC, PSG2, PEDF, CD14, and APOC3.

The invention provides surrogate peptides of the isolated biomarkers selected from the group set forth in Table 26. In some embodiments, the surrogate peptides of the isolated biomarkers are selected from the group of surrogate peptides set forth in Table 26. The biomarkers of the invention and their surrogate peptides can be used in methods to predict risk for pre-term birth in a pregnant female. In some embodiments, the surrogate peptides correspond to isolated biomarkers selected from the group consisting of IBP4, SHBG, PSG3, LYAM1, IGF2, CLUS, IBP3, INHBC, PSG2, PEDF, CD14, and APOC3.

The invention provides stable isotope labeled standard peptides (SIS peptides) corresponding to the surrogate peptides selected from the group set forth in Table 26. The biomarkers of the invention, their surrogate peptides and the SIS peptides can be used in methods to predict risk for pre-term birth in a pregnant female. In some embodiments, the SIS peptides correspond to surrogate peptides of the isolated biomarkers selected from the group consisting of IBP4, SHBG, PSG3, LYAM1, IGF2, CLUS, IBP3, INHBC, PSG2, PEDF, CD14, and APOC3.

The invention provides a pair of isolated biomarkers selected from the group consisting of the isolated biomarkers listed in Table 26, wherein the pair of biomarkers exhibits a change in ratio value between pregnant females at risk for pre-term birth and term controls.

The invention provides a pair of isolated biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein the pair of biomarkers exhibits a change in ratio value between pregnant females at risk for pre-term birth and term controls.

The invention provides a pair of isolated biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein the pair of biomarkers exhibits a change in ratio value between pregnant females at risk for pre-term birth and term controls.

In one embodiment, the invention provides a pair of isolated biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein the pair of biomarkers exhibits a change in reversal value between pregnant females at risk for pre-term birth and term controls.

In one embodiment, the invention provides a pair of isolated biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein the pair of biomarkers exhibits a change in reversal value between pregnant females at risk for pre-term birth and term controls.

In one embodiment, the invention provides a composition comprising a pair of surrogate peptides corresponding to a pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein the pair of biomarkers exhibits a change in reversal value between pregnant females at risk for pre-term birth and term controls. In one embodiment, the composition comprises stable isotope labeled standard peptides (SIS peptides) for each of the surrogate peptides.

In one embodiment, the invention provides a composition comprising a pair of surrogate peptides corresponding to a pair of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein the pair of biomarkers exhibits a change in reversal value between pregnant females at risk for pre-term birth and term controls. In one embodiment, the composition comprises stable isotope labeled standard peptides (SIS peptides) for each of the surrogate peptides.

In a particular embodiment, the invention provides a pair of isolated biomarkers IBP4/SHBG, wherein the pair of biomarkers exhibits a change in reversal value between pregnant females at risk for pre-term birth compared to term controls. In a further embodiment, the invention provides a pair of isolated biomarkers IBP4/SHBG, wherein the pair of biomarkers exhibits a higher ratio in pregnant females at risk for pre-term birth compared to term controls.

In one embodiment, the invention provides a composition comprising a pair of surrogate peptides corresponding to a pair of biomarkers IBP4/SHBG, wherein the pair of biomarkers exhibits a higher ratio in pregnant females at risk for pre-term birth compared to term controls. In one embodiment, the composition comprises stable isotope labeled standard peptides (SIS peptides) for each of the surrogate peptides.

In a further embodiment, the invention provides a panel of at least two pairs of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein each of the pairs exhibits a change in reversal value between pregnant females at risk for pre-term birth and term controls. In one embodiment, the panel comprises stable isotope labeled standard peptides (SIS peptides) for surrogate peptides derived from each of said biomarkers.

In a further embodiment, the invention provides a panel of at least two pairs of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein each of the pairs exhibits a change in reversal value between pregnant females at risk for pre-term birth and term controls. In one embodiment, the panel comprises stable isotope labeled standard peptides (SIS peptides) for surrogate peptides derived from each of said biomarkers.

In an additional embodiment, the invention provides a panel of at least two pairs of surrogate peptides, each pair of the of surrogate peptides corresponding to a pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein each of the pairs exhibits a change in reversal value between pregnant females at risk for pre-term birth and term controls. In one embodiment, the panel comprises stable isotope labeled standard peptides (SIS peptides) for each of the surrogate peptides.

In an additional embodiment, the invention provides a panel of at least two pairs of surrogate peptides, each pair of the of surrogate peptides corresponding to a pair of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein each of the pairs exhibits a change in reversal value between pregnant females at risk for pre-term birth and term controls. In one embodiment, the panel comprises stable isotope labeled standard peptides (SIS peptides) for each of the surrogate peptides.

In a further embodiment, the invention provides a panel of at least two pairs of surrogate peptides, each pair of the of surrogate peptides corresponding to a pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein at least one of the pairs exhibits a change in reversal value between pregnant females at risk for pre-term birth and term controls. In one embodiment, the composition comprises stable isotope labeled standard peptides (SIS peptides) for each of the surrogate peptides.

In a further embodiment, the invention provides a panel of at least two pairs of surrogate peptides, each pair of the of surrogate peptides corresponding to a pair of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein at least one of the pairs exhibits a change in reversal value between pregnant females at risk for pre-term birth and term controls. In one embodiment, the composition comprises stable isotope labeled standard peptides (SIS peptides) for each of the surrogate peptides.

In an additional embodiment, the invention provides a panel of at least two pairs of surrogate peptides, each pair of the of surrogate peptides corresponding to a pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein a calculated score, derived from the panel of at least two pairs of biomarkers exhibits a change in value between pregnant females and term controls. In one embodiment, the composition comprises stable isotope labeled standard peptides (SIS peptides) for each of the surrogate peptides.

In an additional embodiment, the invention provides a panel of at least two pairs of surrogate peptides, each pair of the of surrogate peptides corresponding to a pair of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1, wherein a calculated score, derived from the panel of at least two pairs of biomarkers exhibits a change in value between pregnant females and term controls. In one embodiment, the composition comprises stable isotope labeled standard peptides (SIS peptides) for each of the surrogate peptides.

In one embodiment, the invention provides a method of determining probability for preterm birth in a pregnant female, the method comprising measuring in a biological sample obtained from the pregnant female a ratio for at least one pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS to determine the probability for preterm birth in the pregnant female. In some embodiments, the pregnant female has a body mass index (BMI) of greater than 22 and less or equal to 37 kg/m$^2$.

In one embodiment, the invention provides a method of determining probability for preterm birth in a pregnant female, the method comprising measuring in a biological sample obtained from the pregnant female a ratio for at least one pair of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1 to determine the probability for preterm birth in the pregnant female. In some embodiments, the pregnant female has a body mass index (BMI) of greater than 22 and less or equal to 37 kg/m$^2$. In some embodiments, the method comprises an initial step of obtaining a biological sample. In some embodiments, the method comprises detecting, measuring or quantifying an SIS surrogate peptide of each of the biomarkers.

In some embodiments, determining the probability for preterm birth in a pregnant female encompasses an initial step that includes formation of a probability/risk index by measuring the ratio of isolated biomarkers selected from the group in a cohort of preterm pregnancies and term pregnancies with known gestational age at birth. In further embodiments, the preterm risk index is formed by measuring the ratio of IBP4/SHBG in a cohort of preterm and term pregnancies where the gestational age at birth is recorded. In some embodiments, determining the probability for preterm birth in a pregnant female comprises measuring the ratio of IBP4/SHBG and comparing the value to the index to derive the preterm risk using the same isolation and measurement technologies to derive IBP4/SHBG as in the index group.

In one embodiment, the invention provides a method of determining probability for preterm birth in a pregnant female, the method comprising measuring in a biological sample obtained from the pregnant female a reversal value for at least one pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS to determine the probability for preterm birth in the pregnant female. In some embodiments, the pregnant female has a body mass index (BMI) of greater than 22 and less or equal to 37 kg/m$^2$. In some embodiments, the method comprises an initial step of obtaining a biological sample. In some embodiments, the method comprises detecting, measuring or quantifying an SIS surrogate peptide of each of the biomarkers.

In one embodiment, the invention provides a method of determining probability for preterm birth in a pregnant female, the method comprising measuring in a biological sample obtained from the pregnant female a reversal value for at least one pair of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1 to determine the probability for preterm birth in the pregnant female. In some embodiments, the pregnant female has a body mass index (BMI) of greater than 22 and less or equal to 37 kg/m$^2$. In some embodiments, the method comprises an initial step of obtaining a biological sample. In some embodiments, the method comprises detecting, measuring or quantifying an SIS surrogate peptide of each of the biomarkers.

In another embodiment, the invention provides a method of determining probability for preterm birth in a pregnant female, the method comprising measuring in a biological sample obtained from the pregnant female a change in reversal value for a panel of at least two pairs of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS to determine the probability for preterm birth in the pregnant female. In another embodiment, the invention provides a method of determining probability for preterm birth in a pregnant female, the method comprising measuring in a biological sample obtained from the pregnant female a change in reversal value for a panel of at least two pairs of biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1 to determine the probability for preterm birth in the pregnant female. In some embodiments, the reversal value reveals the existence of a change in the relative intensities of the individual biomarkers between the pregnant female and a term control and indicates the probability for preterm birth in the pregnant female. In additional embodiments, the measuring step comprises measuring surrogate peptides of the biomarkers in the biological sample obtained from the pregnant female. In some embodiments, the pregnant female has a body mass index (BMI) of greater than 22 and less or equal to 37 kg/m$^2$. In some embodiments, the method comprises an initial step of obtaining a biological sample. In some embodiments, the method comprises detecting, measuring or quantifying an SIS surrogate peptide of each of the biomarkers.

In one embodiment, the invention provides a method of determining probability for preterm birth in a pregnant female, the method comprising measuring in a biological sample obtained from the pregnant female a reversal value for a pair of biomarkers consisting of IBP4 and SHBG to determine the probability for preterm birth in the pregnant female. In some embodiments, the pregnant female has a body mass index (BMI) of greater than 22 and less or equal to 37 kg/m$^2$. In some embodiments, the method comprises an initial step of obtaining a biological sample. In some embodiments, the method comprises detecting, measuring or quantifying an SIS surrogate peptide of each of the biomarkers.

In one embodiment, the invention provides a method of determining probability for preterm birth in a pregnant female, the method comprising measuring in a biological sample obtained from the pregnant female a reversal value for a pair of biomarkers consisting of a ratio of IBP4 over SHBG (IBP4/SHBG) to determine the probability for preterm birth in the pregnant female, wherein a higher ratio in pregnant female compared to term controls indicates an increased risk for pre-term birth. In further embodiments, the pregnant female has a body mass index (BMI) of greater than 22 and less or equal to 37 kg/m$^2$. In some embodiments, the method comprises an initial step of obtaining a biological sample. In some embodiments, the method comprises detecting, measuring or quantifying an SIS surrogate peptide of each of the biomarkers.

In one embodiment, the invention provides a method of determining probability for preterm birth in a pregnant female, the method comprising measuring in a biological sample obtained from the pregnant female a reversal value for a pair of biomarkers IBP4 and SHBG to determine the probability for preterm birth in the pregnant female. In some embodiments, the pregnant female has a body mass index (BMI) of greater than 22 and less or equal to 37 kg/m$^2$. In some embodiments, the method comprises an initial step of obtaining a biological sample. In some embodiments, the method comprises detecting, measuring or quantifying an SIS surrogate peptide of each of the biomarkers.

The invention also provides a method of detecting a pair of isolated biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1 in a pregnant female, said method comprising the steps of a. obtaining a biological sample from the pregnant female; b. detecting whether the pair of isolated biomarkers is present in the biological sample by contacting the biological sample with a first capture agent that specifically binds a first member of said pair and a second capture agent that specifically binds a second member of said pair; and detecting binding between the first biomarker of said pair and the first capture agent and between the second member of said pair and the second capture agent.

In one embodiment the invention provides a method of detecting IBP4 and SHBG in a pregnant female, said method comprising the steps of a. obtaining a biological sample from the pregnant female; b. detecting whether IBP4 and SHBG are present in the biological sample by contacting the biological sample with a capture agent that specifically binds IBP4 and a capture agent that specifically binds SHBG; and c. detecting binding between IBP4 and the capture agent and between SHBG and the capture agent. In one embodiment, the method comprises measuring a reversal value for the pair of biomarkers. In a further embodiment, the existence of a change in reversal value between the pregnant female and a term control indicates the probability for preterm birth in the pregnant female. In one embodiment, the sample is obtained between 19 and 21 weeks of gestational age. In a further embodiment, the capture agent is selected from the group consisting of and antibody, antibody fragment, nucleic acid-based protein binding reagent, small molecule or variant thereof. In an additional embodiment, the method is performed by an assay selected from the group consisting of enzyme immunoassay (EIA), enzyme-linked immunosorbent assay (ELISA), and radioimmunoassay (IA).

The invention also provides a method of detecting a pair of isolated biomarkers selected from the group consisting of IBP4/SHBG, IBP4/PSG3, IBP4/LYAM1, IBP4/IGF2, CLUS/IBP3, CLUS/IGF2, CLUS/LYAM1, INHBC/PSG3, INHBC/IGF2, PSG2/LYAM1, PSG2/IGF2, PSG2/LYAM1, PEDF/PSG3, PEDF/SHBG, PEDF/LYAM1, CD14/LYAM1, and APOC3/LYAM1 in a pregnant female, said method comprising the steps of a. obtaining a biological sample from the pregnant female; and b. detecting whether the pair of isolated biomarkers is present in the biological sample comprising subjecting the sample to a proteomics work-flow comprised of mass spectrometry quantification.

In one embodiment the invention provides a method of detecting IBP4 and SHBG in a pregnant female, said method comprising the steps of a. obtaining a biological sample from the pregnant female; and b. detecting whether the pair of isolated biomarkers is present in the biological sample comprising subjecting the sample to a proteomics work-flow comprised of mass spectrometry quantification.

In some embodiments, the reversal value reveals the existence of a change in the relative intensities of the individual biomarkers between the pregnant female and a term control and indicates the probability for preterm birth in the pregnant female. In additional embodiments, the measuring step comprises measuring surrogate peptides of the biomarkers in the biological sample obtained from the pregnant female. In one embodiment a preterm risk index is formed by measuring the ratio of IBP4/SHBG in a cohort of preterm and term pregnancies where the gestational age at birth is recorded. Then, in clinical practice the measured ratio of IBP4/SHBG in an individual pregnancy is compared in the index to derive the preterm risk using the same isolation and measurement technologies to derive IBP4/SHBG as in the index group.

Other features and advantages of the invention will be apparent from the detailed description, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3C show expression of pregnancy-related proteins during gestation. These proteins and their networks are unaffected by preterm pathology in the gestational age shown.

FIG. 4 shows an enlarged version of the graph shown in FIG. 3 relating to placenta-specific growth hormone.

FIG. 6. Verification selection criteria. FIG. 6 describes criteria for performing a clinically and analytically robust preterm test of high performance.

FIG. 9. Power and sample size analysis. Power and sample size analysis predicts the likelihood that a study is powered sufficiently to reject the null hypothesis (AUC=0.5) at thresholds of sample number and performance estimates.

FIG. 11 shows criteria for developing classifiers.

FIG. 12 shows the distribution of proteins by pathway.

FIG. 18. Interactions of IBP4, IGF2, PAPP-A and PRG2. IBP4 is a negative regulator of IGF2. IBP4 is freed from IGF2 by PAPPA mediated proteolysis. Low levels of PAPPA have been implicated in IUGR and PE. Elevated levels of IBP4 are indicative of suppressed activity of IGF2. PTB cases have suppressed levels of PAPPA, PRG2 and elevated levels of IBP4.

FIG. 41 highlights the position of the QCHPALDGQR peptide (SEQ ID NO: 2) in the two IBP4 isoforms (SEQ ID NOS 158 and 159, respectively, in order of appearance).

FIG. 43 highlights the position of the IALGGLL-FPASNLR peptide (SEQ ID NO: 18) in exon 4 within the seven isoforms of SHBG (SEQ ID NOS 160, 160, 160, 160, 160, 160, and 161, respectively, in order of appearance).

FIG. 51 shows a table of metrics of IBP4/SHBG predictor performance in the validation sample set (BMI>22<=37). Using different boundaries to define cases (below the cut-off) from controls (above the cut-off) the predictor sensitivity, specificity, area under the ROC curve (AUC) and odds ratio were determined.

FIGS. 54A-54D show differentially expressed proteins that function in extracellular matrix interactions.

FIGS. 67A-67E show kinetic plots of differentially expressed complement/acute phase proteins-4.

FIGS. 68A-68I show kinetic plots for analytes specified in FIGS. 68A through 68I with data from gestational age at blood draw (GABD) of 17 weeks 0 days, through 28 weeks, 6 days. Figures disclose SEQ ID NOS:162, 163, 164, 165, 34, 166, 167, 151, and 152, respectively, in order of appearance.

FIGS. 69A-69I show kinetic plots for analytes specified in FIGS. 69A through 69I with data from GABD of 17 weeks 0 days, through 28 weeks, 6 days. Figures disclose SEQ ID NOS:168, 169, 37, 38, 40, 170, 42, 171 and 172, respectively, in order of appearance.

FIGS. 70A-70I show kinetic plots for analytes specified in FIGS. 70A through 70I with data from GABD of 17 weeks 0 days, through 28 weeks, 6 days. Figures disclose SEQ ID NOS:173, 47, 174, 175, 48, 50, 51, 52 and 54, respectively, in order of appearance FIGS. 71A-71I show kinetic plots for analytes specified in FIGS. 71A through 71I with data from GABD of 17 weeks 0 days, through 28 weeks, 6 days. Figures disclose SEQ ID NOS:55, 176, 177, 178, 179, 56, 57, 58 and 180, respectively, in order of appearance.

FIGS. 72A-72I show kinetic plots for analytes specified in FIGS. 72A through 72I with data from GABD of 17 weeks 0 days, through 28 weeks, 6 days. Figures disclose SEQ ID NOS:67, 68, 181, 70, 71, 72, 74, 76 and 182, respectively, in order of appearance.

FIGS. 73A-73I show kinetic plots for analytes specified in FIGS. 73A through 73I with data from GABD of 17 weeks 0 days, through 28 weeks, 6 days. Figures disclose SEQ ID NOS:183, 78, 79, 184, 80, 81, 185, 83 and 186, respectively, in order of appearance.

FIGS. 74A-74I show kinetic plots for analytes specified in FIGS. 74A through 74I with data from GABD of 17 weeks 0 days, through 28 weeks, 6 days. Figures disclose SEQ ID NOS:187, 188, 84, 189, 190, 86, 87, 191 and 192, respectively, in order of appearance.

FIGS. 75A-75I show kinetic plots for analytes specified in FIGS. 75A through 75I with data from GABD of 17 weeks 0 days, through 28 weeks, 6 days. Figures disclose SEQ ID NOS:88, 89, 193, 194, 195, 196, 197, 198 and 199, respectively, in order of appearance.

FIGS. 76A-76I shows kinetic plots for analytes specified in FIGS. 76A through 76I with data from GABD of 17 weeks 0 days, through 28 weeks, 6 days. Figures disclose SEQ ID NOS:200, 92, 93, 201, 202, 203, 95, 204 and 97, respectively, in order of appearance.

FIGS. 77A-77I show kinetic plots for analytes specified in FIGS. 77A through 77I with data from GABD of 17 weeks 0 days, through 28 weeks, 6 days. Figures disclose SEQ ID NOS:98, 99, 100, 1, 2, 101, 102, 205 and 206, respectively, in order of appearance.

FIGS. 78A-78I shows kinetic plots for analytes specified in FIGS. 78A through 78I with data from GABD of 17 weeks 0 days, through 28 weeks, 6 days. Figures disclose SEQ ID NOS:103, 107, 207, 208, 111, 209, 112, 113 and 210, respectively, in order of appearance.

FIGS. 79A-79I show kinetic plots for analytes specified in FIGS. 79A through 79I with data from GABD of 17 weeks 0 days, through 28 weeks, 6 days. Figures disclose SEQ ID NOS:116, 117, 118, 119, 211, 212, 120, 213 and 121, respectively, in order of appearance.

FIGS. 80A-80I show kinetic plots for analytes specified in FIGS. 80A through 80I with data from GABD of 17 weeks 0 days, through 28 weeks, 6 days. Figures disclose SEQ ID NOS:153, 122, 124, 125, 214, 126, 215, 216 and 128, respectively, in order of appearance.

FIGS. 81A-81I show kinetic plots for analytes specified in FIGS. 81A through 81I with data from GABD of 17 weeks 0 days, through 28 weeks, 6 days. Figures disclose SEQ ID NOS:129, 131, 132, 133, 134, 217, 154, 218 and 136, respectively, in order of appearance.

FIGS. 82A-82I show kinetic plots for analytes specified in FIGS. 82A through 82I with data from 17 weeks 0 days, through 28 weeks, 6 days. Figures disclose SEQ ID NOS: 219, 137, 220, 221, 222, 223, 18, 138 and 139, respectively, in order of appearance.

FIGS. 83A-83I show kinetic plots for analytes specified in FIGS. 83A through 83I with data from GABD of 17 weeks 0 days, through 28 weeks, 6 days. Figures disclose SEQ ID NOS:224, 140, 141, 142, 225, 143, 226, 227 and 228, respectively, in order of appearance.

FIGS. 84A-84I show kinetic plots for analytes specified in FIGS. 84A through 84I with data from GABD of 17 weeks 0 days, through 28 weeks, 6 days. Figures disclose SEQ ID NOS:229, 230, 231, 232, 233, 234, 235, 156 and 155, respectively, in order of appearance.

FIGS. 85A-85G shows kinetic plots for peptide transitions specified in FIGS. 85A through 85G with data from GABD of 17 weeks 0 days, through 28 weeks, 6 days. Figures disclose SEQ ID NOS:147, 149, 150, 236, 237, 238 and 239, respectively, in order of appearance.

FIGS. 86A-86I show kinetic plots for peptide transitions specified in FIGS. 86A through 86I using gestational age at birth cutoff of <37 0/7 versus >=37 0/7 weeks. Figures disclose SEQ ID NOS:37, 38, 40, 42, 47, 48, 50, 51 and 52, respectively, in order of appearance.

FIGS. 87A-87I show kinetic plots for peptide transitions specified in FIGS. 87A through 87I using gestational age at birth cutoff of <37 0/7 versus >=37 0/7 weeks. Figures disclose SEQ ID NOS:54, 55, 56, 57, 58, 59, 60, 61 and 62, respectively, in order of appearance.

FIGS. 89A-89I show kinetic plots for peptide transitions specified in FIGS. 89A through 89I using gestational age at birth cutoff of <37 0/7 versus >=37 0/7 weeks. Figures disclose SEQ ID NOS:78, 79, 80, 81, 82, 83, 84, 86 and 87, respectively, in order of appearance.

FIGS. 90A-90I show kinetic plots for peptide transitions specified in FIGS. 90A through 90I using gestational age at birth cutoff of <37 0/7 versus >=37 0/7 weeks. Figures disclose SEQ ID NOS:88, 89, 92, 93, 95, 97, 98, 99 and 100, respectively, in order of appearance.

FIGS. 91A-91I show kinetic plots for peptide transitions specified in FIGS. 91A through 91I using gestational age at birth cutoff of <37 0/7 versus >=37 0/7 weeks. Figures disclose SEQ ID NOS:2, 101, 102, 103, 107, 111, 112, 113 and 114, respectively, in order of appearance.

FIGS. 92A-92I show kinetic plots for peptide transitions specified in FIGS. 92A through 92I using gestational age at birth cutoff of <37 0/7 versus >=37 0/7 weeks. Figures disclose SEQ ID NOS:116, 117, 118, 119, 120, 121, 122, 124 and 125, respectively, in order of appearance.

FIGS. 93A-93I show kinetic plots for peptide transitions specified in FIGS. 93A through 93I using gestational age at birth cutoff of <37 0/7 versus >=37 0/7 weeks. Figures disclose SEQ ID NOS:126, 128, 129, 131, 132, 133, 134, 135 and 136, respectively, in order of appearance.

FIGS. 94A-94I show kinetic plots for peptide transitions specified in FIGS. 94A through 94I using gestational age at birth cutoff of <37 0/7 versus >=37 0/7 weeks. Figures disclose SEQ ID NOS:137, 18, 138, 139, 140, 141, 142, 143 and 144, respectively, in order of appearance.

FIGS. 96A-96I show kinetic plots for peptide transitions specified in FIGS. 96A through 96I using gestational age at birth cutoff of <35 0/7 vs >=35 0/7 weeks. Figures disclose SEQ ID NOS:37, 38, 40, 42, 47, 48, 50, 51 and 52, respectively, in order of appearance.

FIGS. 97A-97I show kinetic plots for peptide transitions specified in FIGS. 97A through 97I using gestational age at birth cutoff of <35 0/7 vs >=35 0/7 weeks. Figures disclose SEQ ID NOS:54, 55, 56, 57, 58, 59, 60, 61 and 62, respectively, in order of appearance.

FIGS. 98A-98I show kinetic plots for peptide transitions specified in FIGS. 98A through 98I using gestational age at birth cutoff of <35 0/7 vs >=35 0/7 weeks. Figures disclose SEQ ID NOS:64, 66, 67, 68, 70, 71, 72, 74 and 76, respectively, in order of appearance.

FIGS. 99A-99I show kinetic plots for peptide transitions specified in FIGS. 99A through 99I using gestational age at birth cutoff of <35 0/7 vs >=35 0/7 weeks. Figures disclose SEQ ID NOS:78, 79, 80, 81, 82, 83, 84, 86 and 87, respectively, in order of appearance.

FIGS. 100A-100I show kinetic plots for peptide transitions specified in FIGS. 100A through 100I using gestational age at birth cutoff of <35 0/7 vs >=35 0/7 weeks. Figures disclose SEQ ID NOS:88, 89, 92, 93, 95, 97, 98, 99 and 100, respectively, in order of appearance.

FIGS. 101A-101I show kinetic plots for peptide transitions specified in FIGS. 101A through 101I using gestational age at birth cutoff of <35 0/7 vs >=35 0/7 weeks. Figures disclose SEQ ID NOS:2, 101, 102, 103, 107, 111, 112, 113 and 114, respectively, in order of appearance.

FIGS. 102A-102I show kinetic plots for peptide transitions specified in FIGS. 102A through 102I using gestational age at birth cutoff of <35 0/7 vs >=35 0/7 weeks. Figures disclose SEQ ID NOS:116, 117, 118, 119, 120, 121, 122, 124 and 125, respectively, in order of appearance.

FIGS. 103A-103I show kinetic plots for peptide transitions specified in FIGS. 103A through 103I using gestational age at birth cutoff of <35 0/7 vs >=35 0/7 weeks. Figures disclose SEQ ID NOS:126, 128, 129, 131, 132, 133, 134, 135 and 136, respectively, in order of appearance.

FIGS. 104A-104I show kinetic plots for peptide transitions specified in FIGS. 104A through 104I using gestational age at birth cutoff of <35 0/7 vs >=35 0/7 weeks. Figures disclose SEQ ID NOS:137, 18, 138, 139, 140, 141, 142, 143 and 144, respectively, in order of appearance.

FIGS. 107A-107D show the correlation of MSD results with commercial ELISA kits and MS-MRM.

DETAILED DESCRIPTION

Figure 1:
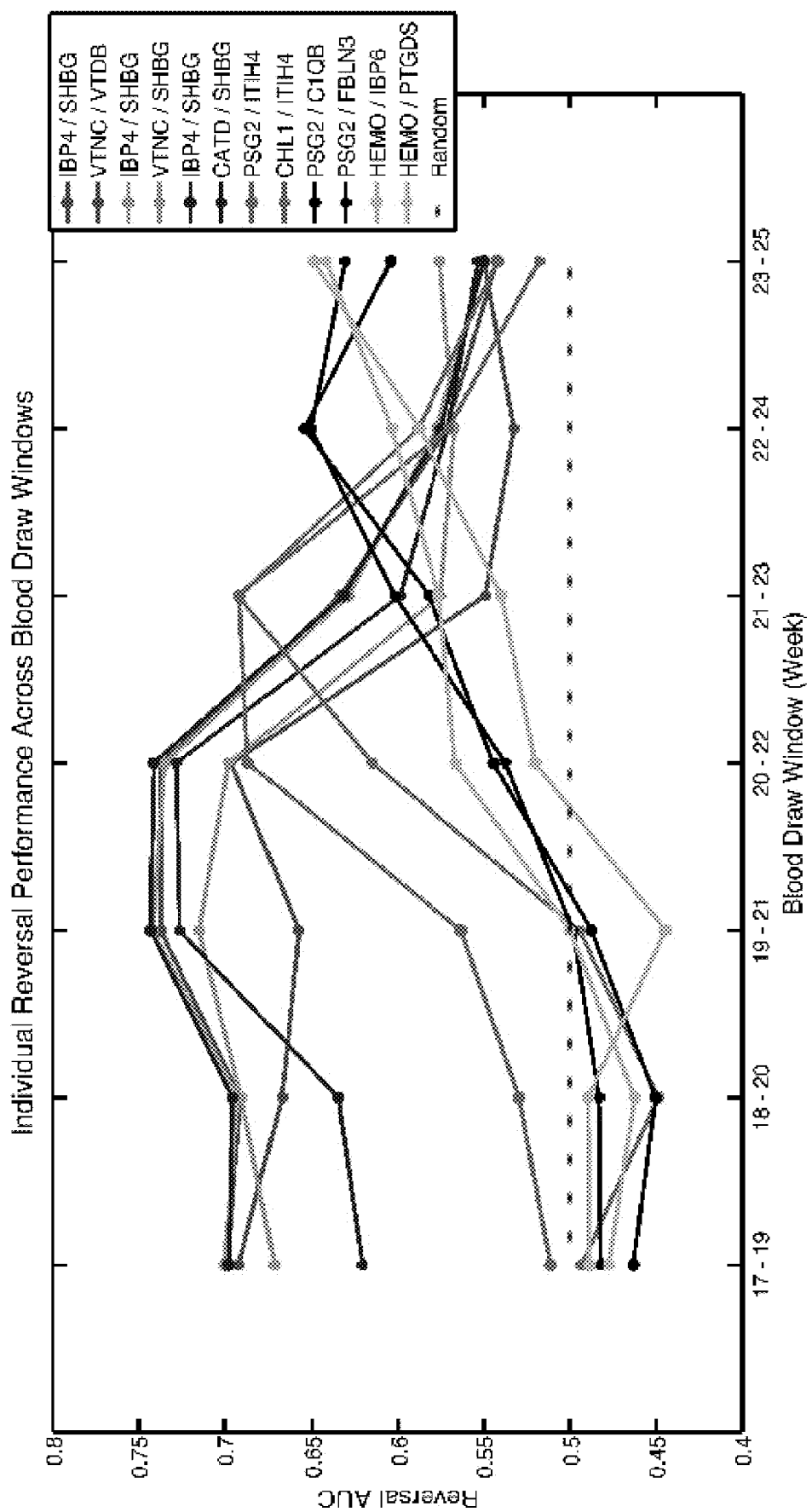
FIG. 1. Blood draw windows. Individual reversal performance is shown across blood draw windows. Reversals shown: IBP4/SHBG; VTNC/VTDB; IBP4/SHBG; VTNC/SHBG; IBP4/SHBG; CATD/SHBG; PSG2/ITIH4; CHL1/ITIH4; PSG2/C1QB; PSG2/FBLN3; HEMO/IBP6; HEMO/PTGDS.
Figure 2:
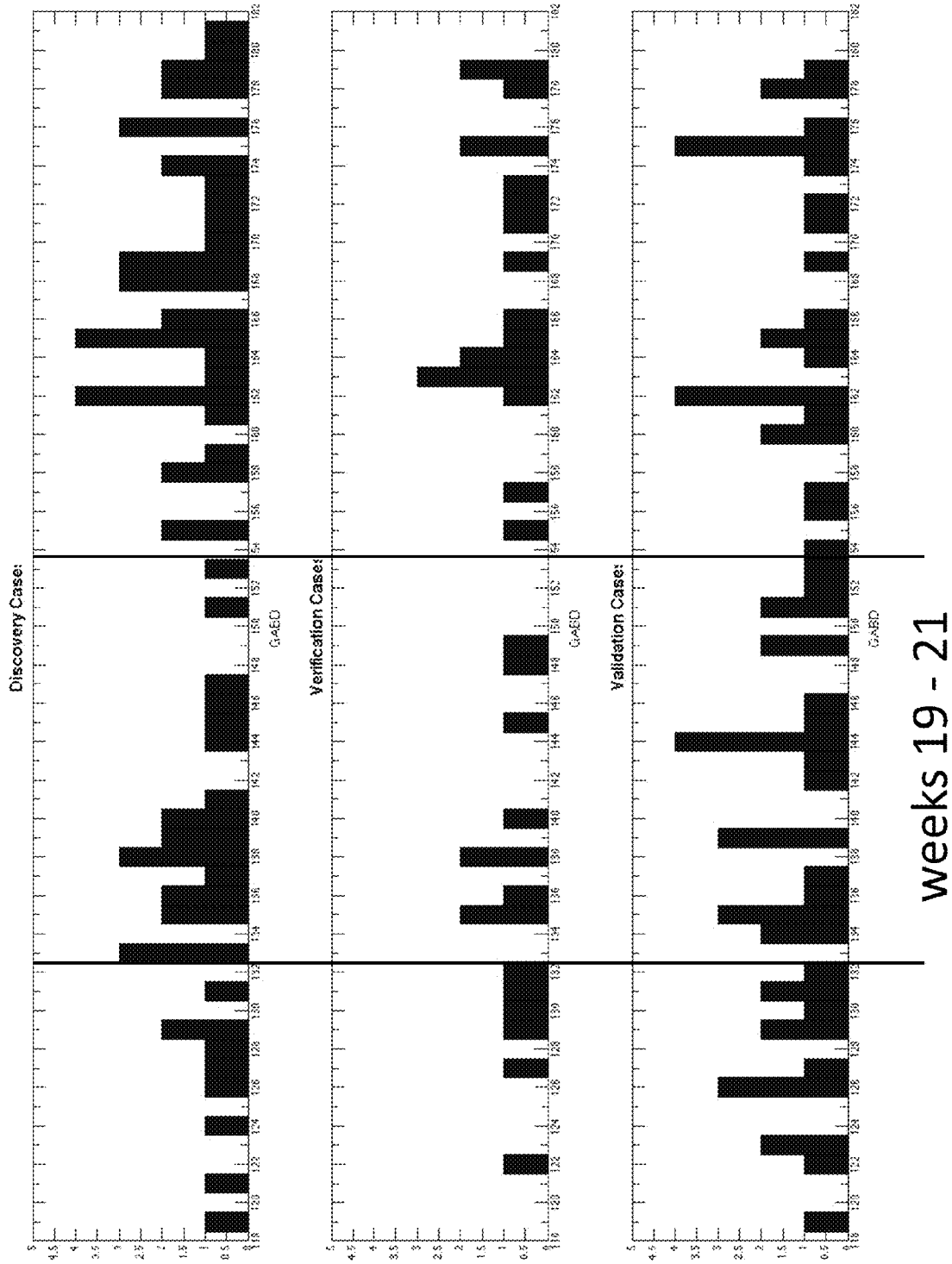
FIG. 2. Discovery case, verification case and validation case for GABD.

The present disclosure is based, generally, on the discovery that certain proteins and peptides in biological samples obtained from a pregnant female are differentially expressed in pregnant females that have an increased risk of preterm birth relative to controls. The present disclosure is further specifically based, in part, on the unexpected discovery that reversal values of pairs of biomarkers disclosed herein can be utilized in methods of determining the probability for preterm birth in a pregnant female with high sensitivity and specificity. The proteins and peptides disclosed herein as components of ratios and/or reversal pairs serve as biomarkers for classifying test samples, predicting probability of preterm birth, predicting probability of term birth, predicting gestational age at birth (GAB), predicting time to birth (TTB) and/or monitoring of progress of preventative therapy in a pregnant female at risk for PTB, either individually, in ratios, reversal pairs or in panels of biomarkers/reversal pairs. A reversal value is the ratio of the relative peak area of an up regulated biomarker over the relative peak area of a down regulated biomarker and serves to both normalize variability and amplify diagnostic signal. The invention lies, in part, in the selection of particular biomarkers that, when paired together, can predict the probability of pre-term birth based on reversal values. Accordingly, it is human ingenuity in selecting the specific biomarkers that are informative upon being paired in novel reversals that underlies the present invention.

The term "reversal value" refers to the ratio of the relative peak area of an up regulated analyte over the relative peak area of a down regulated analyte and serves to both normalize variability and amplify diagnostic signal. Out of all the possible reversals within a narrow window, a subset can selected based on individual univariate performance. As disclosed herein, the ratio of the relative peak area of an up regulated biomarker over the relative peak area of a down regulated biomarker, referred herein as a reversal value, can be used to identify robust and accurate classifiers and predict probability of preterm birth, predicting probability of term birth, predicting gestational age at birth (GAB), predicting time to birth and/or monitoring of progress of preventative therapy in a pregnant female. The present invention is thus based, in part, on the identification of biomarker pairs where the relative expression of a biomarker pair is reversed that exhibit a change in reversal value between PTB and non-PTB. Use of a ratio of biomarkers in the methods disclosed herein corrects for variability that is the result of human manipulation after the removal of the biological sample from the pregnant female. Such variability can be introduced, for example, during sample collection, processing, depletion, digestion or any other step of the methods used to measure the biomarkers present in a sample and is independent of how the biomarkers behave in nature. Accordingly, the invention generally encompasses the use of a reversal pair in a method of diagnosis or prognosis to reduce variability and/or amplify, normalize or clarify diagnostic signal.

While the term reversal value refers to the ratio of the relative peak area of an up regulated analyte over the relative peak area of a down regulated analyte and serves to both normalize variability and amplify diagnostic signal, it is also contemplated that a pair of biomarkers of the invention could be measured by any other means, for example, by subtraction, addition or multiplication of relative peak areas. The methods disclosed herein encompass the measurement of biomarker pairs by such other means.

This method is advantageous because it provides the simplest possible classifier that is independent of data normalization, helps to avoid overfitting, and results in a very simple experimental test that is easy to implement in the clinic. The use of marker pairs based on changes in reversal values that are independent of data normalization enabled the development of the clinically relevant biomarkers disclosed herein. Because quantification of any single protein is subject to uncertainties caused by measurement variability, normal fluctuations, and individual related variation in baseline expression, identification of pairs of markers that may be under coordinated, systematic regulation enables robust methods for individualized diagnosis and prognosis.

The disclosure provides biomarker reversal pairs and associated panels of reversal pairs, methods and kits for determining the probability for preterm birth in a pregnant female. One major advantage of the present disclosure is that risk of developing preterm birth can be assessed early during pregnancy so that appropriate monitoring and clinical management to prevent preterm delivery can be initiated in a timely fashion. The present invention is of particular benefit to females lacking any risk factors for preterm birth and who would not otherwise be identified and treated.

By way of example, the present disclosure includes methods for generating a result useful in determining probability for preterm birth in a pregnant female by obtaining a dataset associated with a sample, where the dataset at least includes quantitative data about the relative expression of biomarker pairs that have been identified as exhibiting changes in reversal value predictive of preterm birth, and inputting the dataset into an analytic process that uses the dataset to generate a result useful in determining probability for preterm birth in a pregnant female. As described further below, quantitative data can include amino acids, peptides, polypeptides, proteins, nucleotides, nucleic acids, nucleosides, sugars, fatty acids, steroids, metabolites, carbohydrates, lipids, hormones, antibodies, regions of interest that serve as surrogates for biological macromolecules and combinations thereof.

In addition to the specific biomarkers identified in this disclosure, for example, by accession number in a public database, sequence, or reference, the invention also contemplates use of biomarker variants that are at least 90% or at least 95% or at least 97% identical to the exemplified sequences and that are now known or later discovered and that have utility for the methods of the invention. These variants may represent polymorphisms, splice variants, mutations, and the like. In this regard, the instant specification discloses multiple art-known proteins in the context of the invention and provides exemplary accession numbers associated with one or more public databases as well as exemplary references to published journal articles relating to these art-known proteins. However, those skilled in the art appreciate that additional accession numbers and journal articles can easily be identified that can provide additional characteristics of the disclosed biomarkers and that the exemplified references are in no way limiting with regard to the disclosed biomarkers. As described herein, various techniques and reagents find use in the methods of the present invention. Suitable samples in the context of the present invention include, for example, blood, plasma, serum, amniotic fluid, vaginal secretions, saliva, and urine. In some embodiments, the biological sample is selected from the group consisting of whole blood, plasma, and serum. In a particular embodiment, the biological sample is serum. As described herein, biomarkers can be detected through a variety of assays and techniques known in the art. As further described herein, such assays include, without limitation, mass spectrometry (MS)-based assays, antibody-based assays as well as assays that combine aspects of the two.

Protein biomarkers that are components of reversal pairs described herein include, for example, Insulin-Like Growth Factor Binding Protein 4 (IBP4), Sex Hormone Binding Globulin (SHBG), Vitronectin (VTNC), Group-Specific Component (Vitamin D Binding Protein)(VTDB), cathepsin D (lysosomal aspartyl protease) (CATD), pregnancy specific beta-1-glycoprotein 2 (PSG2), Inter-Alpha-Trypsin Inhibitor Heavy Chain Family, Member 4 (ITIH4), cell adhesion molecule L1-like (CHL1), Complement Component 1, Q Subcomponent, B Chain (C1QB), Fibulin 3 (FBLN3), Hemopexin (HEMO or HPX), Insulin-Like Growth Factor Binding Protein 6 (IBP6), prostaglandin D2 synthase 21 kDa (PTGDS)

In some embodiments, the invention provides a method of determining probability for preterm birth in a pregnant female, the method comprising measuring in a biological sample obtained from the pregnant female a reversal value for at least one pair of biomarkers selected from the group comprising those pairs listed in any of the accompanying figures and tables, including FIG. 1.

In some embodiments, the invention provides a method of determining probability for preterm birth in a pregnant female, the method comprising measuring in a biological sample obtained from the pregnant female a reversal value for at least one pair of biomarkers selected from the group consisting of IBP4/SHBG, VTNC/VTDB, VTNC/SHBG, CATD/SHBG, PSG2/ITIH4, CHL1/ITIH4, PSG2/ITIH4, CHL1/ITIH4, PSG2/C1QB, PSG2/FBLN3, HPX/IBP4, HPX/PTGDS to determine the probability for preterm birth in said pregnant female.

The invention provides isolated biomarkers selected from the group set forth in Table 26. The biomarkers of the invention can predict risk for pre-term birth in a pregnant female. In some embodiments, the isolated biomarkers are selected from the group consisting of IBP4, SHBG, VTNC, VTDB, CATD, PSG2, ITIH4, CHL1, C1QB, FBLN3, HPX, and PTGDS. In some embodiments, the isolated biomarkers are selected from the group consisting of IBP4, SHBG, PSG3, LYAM1, IGF2, CLUS, IBP3, INHBC, PSG2, PEDF, CD14, and APOC3.

The invention provides surrogate peptides of the isolated biomarkers selected from the group set forth in Table 26. In some embodiments, the surrogate peptides of the isolated biomarkers are selected from the group of surrogate peptides set forth in Table 26. The biomarkers of the invention and their surrogate peptides can be used in methods to predict risk for pre-term birth in a pregnant female. In some embodiments, the surrogate peptides correspond to isolated biomarkers selected from the group consisting of IBP4, SHBG, VTNC, VTDB, CATD, PSG2, ITIH4, CHL1, C1QB, FBLN3, HPX, and PTGDS. In some embodiments, the surrogate peptides correspond to isolated biomarkers selected from the group consisting of IBP4, SHBG, PSG3, LYAM1, IGF2, CLUS, IBP3, INHBC, PSG2, PEDF, CD14, and APOC3.

The invention provides stable isotope labeled standard peptides (SIS peptides) corresponding to the surrogate peptides selected from the group set forth in Table 26. The biomarkers of the invention, their surrogate peptides and the SIS peptides can be used in methods to predict risk for pre-term birth in a pregnant female. In some embodiments, the SIS peptides correspond to surrogate peptides of the isolated biomarkers selected from the group consisting of IBP4, SHBG, VTNC, VTDB, CATD, PSG2, ITIH4, CHL1, C1QB, FBLN3, HPX, and PTGDS. In some embodiments, the SIS peptides correspond to surrogate peptides of the isolated biomarkers selected from the group consisting of IBP4, SHBG, PSG3, LYAM1, IGF2, CLUS, IBP3, INHBC, PSG2, PEDF, CD14, and APOC3.

In some embodiments, the invention provides a pair of isolated biomarkers IBP4/SHBG, wherein the pair of biomarkers exhibits a change in reversal value between pregnant females at risk for pre-term birth compared to term controls. In a further embodiment, the invention provides a pair of isolated biomarkers IBP4/SHBG, wherein the pair of biomarkers exhibits a higher ratio in pregnant females at risk for pre-term birth compared to term controls.

In some embodiments, the invention provides a method of determining probability for preterm birth in a pregnant female, the method comprising measuring in a biological sample obtained from the pregnant female a reversal value for at least one pair of biomarkers selected from the group consisting of IBP4/SHBG, VTNC/VTDB, VTNC/SHBG, and CATD/SHBG to determine the probability for preterm birth in said pregnant female. In additional embodiments the sample is obtained between 19 and 21 weeks of GABD. In further embodiments the sample is obtained between 19 and 22 weeks of GABD.

In some embodiments, the invention provides a method of determining probability for preterm birth in a pregnant female, the method comprising measuring in a biological sample obtained from the pregnant female a reversal value for IBP4/SHBG to determine the probability for preterm birth in said pregnant female. In additional embodiments the sample is obtained between 19 and 21 weeks of GABD. In further embodiments the sample is obtained between 19 and 22 weeks of GABD.

In some embodiments, the invention provides a method of determining probability for preterm birth in a pregnant female, the method comprising measuring in a biological sample obtained from the pregnant female a reversal value for at least one pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, HPX/PTGDS to determine the probability for preterm birth in said pregnant female, wherein the existence of a change in reversal value between the pregnant female and a term control determines the probability for preterm birth in the pregnant female. In additional embodiments the sample is obtained between 19 and 21 weeks of GABD. In further embodiments the sample is obtained between 19 and 22 weeks of GABD.

Included within the embodiments of the invention, are iterative methods of determining probability for preterm birth in a pregnant female, the method comprising measuring in a biological sample obtained from the pregnant female a reversal value for at least one pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, HPX/PTGDS and any other pair of biomarkers selected from the proteins described and/or exemplified herein to determine the probability for preterm birth in said pregnant female, wherein the existence of a change in reversal value between the pregnant female and a term control determines the probability for preterm birth in the pregnant female. Iterative performance of the methods described herein includes subsequent measurements obtained from a single sample as well as obtaining subsequent samples for measurement. For example, if it is determined that the probability for preterm birth in a pregnant female, which can be expressed as a risk score, is above a specified value, the method can be repeated using a distinct reversal pair from the same sample or the same or a distinct reversal pair from a subsequent sample to further stratify the risk for sPTB.

In addition to the specific biomarkers, the disclosure further includes biomarker variants that are about 90%, about 95%, or about 97% identical to the exemplified sequences. Variants, as used herein, include polymorphisms, splice variants, mutations, and the like. Although described with reference to protein biomarkers, changes in reversal value can be identified in protein or gene expression levels for pairs of biomarkers.

Additional markers can be selected from one or more risk indicia, including but not limited to, maternal characteristics, medical history, past pregnancy history, and obstetrical history. Such additional markers can include, for example, previous low birth weight or preterm delivery, multiple 2nd trimester spontaneous abortions, prior first trimester induced abortion, familial and intergenerational factors, history of infertility, nulliparity, placental abnormalities, cervical and uterine anomalies, short cervical length measurements, gestational bleeding, intrauterine growth restriction, in utero diethylstilbestrol exposure, multiple gestations, infant sex, short stature, low prepregnancy weight, low or high body mass index, diabetes, hypertension, urogenital infections (i.e. urinary tract infection), asthma, anxiety and depression, asthma, hypertension, hypothyroidism. Demographic risk indicia for preterm birth can include, for example, maternal age, race/ethnicity, single marital status, low socioeconomic status, maternal age, employment-related physical activity, occupational exposures and environment exposures and stress. Further risk indicia can include, inadequate prenatal care, cigarette smoking, use of marijuana and other illicit drugs, cocaine use, alcohol consumption, caffeine intake, maternal weight gain, dietary intake, sexual activity during late pregnancy and leisure-time physical activities. (Preterm Birth: Causes, Consequences, and Prevention, Institute of Medicine (US) Committee on Understanding Premature Birth and Assuring Healthy Outcomes; Behrman R E, Butler A S, editors. Washington (DC): National Academies Press (US); 2007). Additional risk indicia useful for as markers can be identified using learning algorithms known in the art, such as linear discriminant analysis, support vector machine classification, recursive feature elimination, prediction analysis of microarray, logistic regression, CART, FlexTree, LART, random forest, MART, and/or survival analysis regression, which are known to those of skill in the art and are further described herein.

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, the term "panel" refers to a composition, such as an array or a collection, comprising one or more biomarkers. The term can also refer to a profile or index of expression patterns of one or more biomarkers described herein. The number of biomarkers useful for a biomarker panel is based on the sensitivity and specificity value for the particular combination of biomarker values.

As used herein, and unless otherwise specified, the terms "isolated" and "purified" generally describes a composition of matter that has been removed from its native environment (e.g., the natural environment if it is naturally occurring), and thus is altered by the hand of man from its natural state so as to possess markedly different characteristics with regard to at least one of structure, function and properties. An isolated protein or nucleic acid is distinct from the way it exists in nature and includes synthetic peptides and proteins.

The term "biomarker" refers to a biological molecule, or a fragment of a biological molecule, the change and/or the detection of which can be correlated with a particular physical condition or state. The terms "marker" and "biomarker" are used interchangeably throughout the disclosure. For example, the biomarkers of the present invention are correlated with an increased likelihood of preterm birth. Such biomarkers include any suitable analyte, but are not limited to, biological molecules comprising nucleotides, nucleic acids, nucleosides, amino acids, sugars, fatty acids, steroids, metabolites, peptides, polypeptides, proteins, carbohydrates, lipids, hormones, antibodies, regions of interest that serve as surrogates for biological macromolecules and combinations thereof (e.g., glycoproteins, ribonucleoproteins, lipoproteins). The term also encompasses portions or fragments of a biological molecule, for example, peptide fragment of a protein or polypeptide that comprises at least 5 consecutive amino acid residues, at least 6 consecutive amino acid residues, at least 7 consecutive amino acid residues, at least 8 consecutive amino acid residues, at least 9 consecutive amino acid residues, at least 10 consecutive amino acid residues, at least 11 consecutive amino acid residues, at least 12 consecutive amino acid residues, at least 13 consecutive amino acid residues, at least 14 consecutive amino acid residues, at least 15 consecutive amino acid residues, at least 5 consecutive amino acid residues, at least 16 consecutive amino acid residues, at least 17 consecutive amino acid residues, at least 18 consecutive amino acid residues, at least 19 consecutive amino acid residues, at least 20 consecutive amino acid residues, at least 21 consecutive amino acid residues, at least 22 consecutive amino acid residues, at least 23 consecutive amino acid residues, at least 24 consecutive amino acid residues, at least 25 consecutive amino acid residues, or more consecutive amino acid residues.

As used herein, the term "surrogate peptide" refers to a peptide that is selected to serve as a surrogate for quantification of a biomarker of interest in an MRM assay configuration. Quantification of surrogate peptides is best achieved using stable isotope labeled standard surrogate peptides ("SIS surrogate peptides" or "SIS peptides") in conjunction with the MRM detection technique. A surrogate peptide can be synthetic. An SIS surrogate peptide can be synthesized with heavy labeled for example, with an Arginine or Lysine, or any other amino acid at the C-terminus of the peptide to serve as an internal standard in the MRM assay. An SIS surrogate peptide is not a naturally occurring peptide and has markedly different structure and properties compared to its naturally occurring counterpart.

In some embodiments, the invention provides a method of determining probability for preterm birth in a pregnant female, the method comprising measuring in a biological sample obtained from the pregnant female a ratio for at least one pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, HPX/PTGDS to determine the probability for preterm birth in said pregnant female, wherein the existence of a change in the ratio between the pregnant female and a term control determines the probability for preterm birth in the pregnant female. In some embodiments, the ratio may include an up-regulated protein in the numerator, a down-regulated protein in the denominator or both. For example, as exemplified herein, IBP4/SHBG is a ratio of an up-regulated protein in the numerator and a down-regulated protein in the denominator, which is defined herein as a "reversal". In the instances where the ratio includes an up-regulated protein in the numerator, or a down-regulated protein in the denominator, the un-regulated protein would serve to normalize (e.g. decrease pre-analytical or analytical variability). In the particular case of a ratio that is a "reversal" both amplification and normalization are possible. It is understood, that the methods of the invention are not limited to the subset of reversals, but also encompass ratios of biomarkers.

As used herein, the term "reversal" refers to the ratio of the measured value of an upregulated analyte over that of a down-regulated analyte. In some embodiments, the analyte value is itself a ratio of the peak area of the endogenous analyte over that of the peak area of the corresponding stable isotopic standard analyte, referred to herein as: response ratio or relative ratio.

As used herein, the term "reversal pair" refers to biomarkers in pairs that exhibit a change in value between the classes being compared. The detection of reversals in protein concentrations or gene expression levels eliminates the need for data normalization or the establishment of population-wide thresholds. In some embodiments, the reversal pair is a pair of isolated biomarkers IBP4/SHBG, wherein the reversal pair exhibits a change in reversal value between pregnant females at risk for pre-term birth compared to term controls. In a further embodiment, the reversal pair IBP4/SHBG exhibits a higher ratio in pregnant females at risk for pre-term birth compared to term controls. Encompassed within the definition of any reversal pair is the corresponding reversal pair wherein individual biomarkers are switched between the numerator and denominator. One skilled in the art will appreciate that such a corresponding reversal pair is equally informative with regard to its predictive power.

The term "reversal value" refers to the ratio of the relative peak area of an up regulated analyte over the relative peak area of a down regulated analyte and serves to both normalize variability and amplify diagnostic signal. Out of all the possible reversals within a narrow window, a subset can selected based on individual univariate performance. As disclosed herein, the ratio of the relative peak area of an up regulated biomarker over the relative peak area of a down regulated biomarker, referred herein as a reversal value, can be used to identify robust and accurate classifiers and predict probability of preterm birth, predicting probability of term birth, predicting gestational age at birth (GAB), predicting time to birth and/or monitoring of progress of preventative therapy in a pregnant female.

This reversal method is advantageous because it provides the simplest possible classifier that is independent of data normalization, helps to avoid overfitting, and results in a very simple experimental test that is easy to implement in the clinic. The use of biomarker pairs based on reversals that are independent of data normalization as described herein has tremendous power as a method for the identification of clinically relevant PTB biomarkers. Because quantification of any single protein is subject to uncertainties caused by measurement variability, normal fluctuations, and individual related variation in baseline expression, identification of pairs of markers that can be under coordinated, systematic regulation should prove to be more robust for individualized diagnosis and prognosis.

The invention provides a composition comprising a pair of isolated biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein the pair of biomarkers exhibits a change in reversal value between pregnant females at risk for pre-term birth and term controls. In one embodiment, the compositions comprises stable isotope labeled standard peptides (SIS peptides) for surrogate peptides derived from each of said biomarkers.

In particular embodiments, the invention provides a pair of isolated biomarkers consisting of IBP4 and SHBG, wherein the pair exhibits a change in reversal value between pregnant females at risk for pre-term birth and term controls.

IBP4 is a member of a family of insulin-like growth factor binding proteins (IBP) that negatively regulate the insulin-like growth factors IGF1 and IGF2. (Forbes et al. Insulin-like growth factor I and II regulate the life cycle of trophoblast in the developing human placenta. Am J Physiol, Cell Physiol. 2008; 294(6):C1313-22). IBP4 is expressed by syncytiotrophoblasts (Crosley et al., IGFBP-4 and -5 are expressed in first-trimester villi and differentially regulate the migration of HTR-8/SVneo cells. Reprod Biol Endocrinol. 2014; 12(1):123) and is the dominant IBP expressed by extravillous trophoblasts (Qiu et al. Significance of IGFBP-4 in the development of fetal growth restriction. J Clin Endocrinol Metab. 2012; 97(8):E1429-39). Compared to term pregnancies, maternal IBP4 levels in early pregnancy are higher in pregnancies complicated by fetal growth restriction and preeclampsia. (Qiu et al., supra, 2012)

SHBG regulates the availability of biologically active unbound steroid hormones. Hammond G L. Diverse roles for sex hormone-binding globulin in reproduction. Biol Reprod. 2011; 85(3):431-41. Plasma SHBG levels increase 5-10 fold during pregnancy (Anderson D C. Sex-hormone-binding globulin. Clin Endocrinol (Oxf). 1974; 3(1):69-96) and evidence exists for extra-hepatic expression, including placental trophoblastic cells. (Larrea et al. Evidence that human placenta is a site of sex hormone-binding globulin gene expression. *J Steroid Biochem Mol Biol.* 1993; 46(4): 497-505) Physiologically, SHBG levels negatively correlate with triglycerides, insulin levels and BMI. (Simó et al. Novel insights in SHBG regulation and clinical implications. Trends Endocrinol Metab. 2015; 26(7):376-83) BMI's effect on SHBG levels may explain, in part, the improved predictive performance with BMI stratification.

Intra-amniotic infection and inflammation have been associated with PTB, as has increased levels of proinflammatory cytokines including TNF-α and IL1-β (Mendelson C R. Minireview: fetal-maternal hormonal signaling in pregnancy and labor. Mol Endocrinol. 2009; 23(7):947-54; Gomez-Lopez et al. Immune cells in term and preterm labor. Cell Mol Immunol. 2014; 11(6):571-81). SHBG transcription in liver is suppressed by IL1-β and NF-kB mediated TNF-α signaling (Simó et al. Novel insights in SHBG regulation and clinical implications. Trends Endocrinol Metab. 2015; 26(7):376-83), a pathway implicated in initiation of normal and abnormal labor (Lindstrom T M, Bennett P R. The role of nuclear factor kappa B in human labour. Reproduction. 2005; 130(5):569-81). Lower levels of SHBG in women destined for sPTB may be a result of infection and/or inflammation. Hence, SHBG may be critical for control of androgen and estrogen action in the placental-fetal unit in response to upstream inflammatory signals.

In one embodiment, the invention provides a composition comprising a pair of surrogate peptides corresponding to a pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein the pair of biomarkers exhibits a change in reversal value between pregnant females at risk for pre-term birth and term controls.

In a further embodiment, the invention provides a panel of at least two pairs of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein each of the pairs exhibits a change in reversal value between pregnant females at risk for pre-term birth and term controls.

In an additional embodiment, the invention provides a panel of at least two pairs of surrogate peptides, each pair of the of surrogate peptides corresponding to a pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS, wherein each of the pairs exhibits a change in reversal value between pregnant females at risk for pre-term birth and term controls.

In one embodiment, the invention provides a method of determining probability for preterm birth in a pregnant female, the method comprising measuring in a biological sample obtained from the pregnant female a reversal value for at least one pair of biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS to determine the probability for preterm birth in the pregnant female.

In another embodiment, the invention provides a method of determining probability for preterm birth in a pregnant female, the method comprising measuring in a biological sample obtained from the pregnant female a change in reversal value for a panel of at least two pairs of biomarkers selected from the group consisting of IBP4/SHBG, VTNC/VTDB, VTNC/SHBG, CATD/SHBG, PSG2/ITIH4, CHL1/ ITIH4, PSG2/C1QB, PSG2/FBLN3, HPX/IBP4, and HPX/PTGDS to determine the probability for preterm birth in the pregnant female. In some embodiments, the reversal value reveals the existence of a change in reversal value between the pregnant female and a term control and indicates the probability for preterm birth in the pregnant female. In some embodiments, the measuring step comprises measuring surrogate peptides of the biomarkers in the biological sample obtained from the pregnant female.

Figure 111:
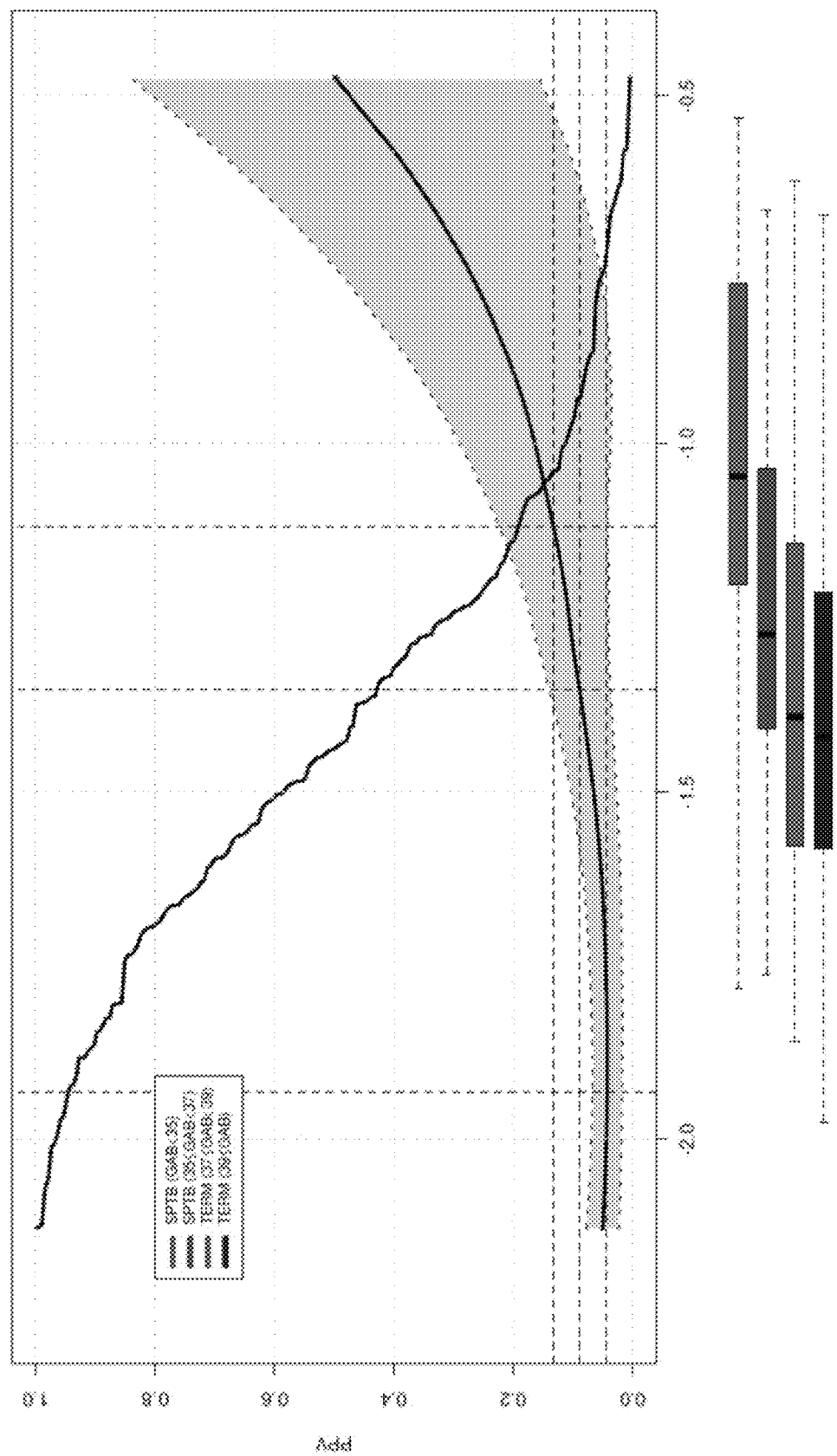
FIG. 111 is a risk curve showing relationships between the Predictor Score (ln IBP4/SHBG) and the prevalence adjusted relative risk of sPTB (Positive Predictive Value), using a cut-off of <35 0/7 weeks vs >=35 0/7 weeks gestation. Top (purple) line underneath risk curve graph corresponds to sPTB (GAB<35 weeks); second line (red) from top corresponds to sPTB (35≤GAB<37 weeks); third line (green) from corresponds to TERM (37≤GAB<39 weeks); fourth line (blue) from top corresponds to TERM (39 weeks≤GAB).

In one embodiment, the invention provides a method of determining probability for preterm birth in a pregnant female, the method comprising measuring in a biological sample obtained from the pregnant female a reversal value for at least one pair of biomarkers selected from the group consisting of the biomarkers listed in any of Tables 1 through 77 and FIGS. 1 through 111 in a pregnant female to determine the probability for preterm birth in the pregnant female.

In an additional embodiment, the invention provides a method of determining probability for preterm birth in a pregnant female, the method comprising measuring in a biological sample obtained from the pregnant female a reversal value for at least one pair of biomarkers selected from the group consisting of the biomarker pairs specified in Tables 27 through 59, 61 through 72, 76 and 77 in a pregnant female to determine the probability for preterm birth in the pregnant female.

In an further embodiment, the invention provides a method of determining probability for preterm birth in a pregnant female, the method comprising measuring in a biological sample obtained from the pregnant female a reversal value for at least one pair of biomarkers selected from the group consisting of the biomarkers listed in Table 26 in a pregnant female to determine the probability for preterm birth in the pregnant female.

In another embodiment, the invention provides a method of determining probability for preterm birth in a pregnant female, the method comprising measuring in a biological sample obtained from the pregnant female a change in reversal value for a panel of at least two pairs of biomarkers selected from the group consisting of the biomarker pairs specified in any of Tables 1 through 77 and FIGS. 1 through 111 in a pregnant female to determine the probability for preterm birth in the pregnant female. In some embodiments, the reversal value reveals the existence of a change in reversal value between the pregnant female and a term control and indicates the probability for preterm birth in the pregnant female. In some embodiments, the measuring step comprises measuring surrogate peptides of the biomarkers in the biological sample obtained from the pregnant female.

In another embodiment, the invention provides a method of determining probability for preterm birth in a pregnant female, the method comprising measuring in a biological sample obtained from the pregnant female a change in reversal value for a panel of at least two pairs of biomarkers selected from the group consisting of the biomarker pairs specified in Tables 27 through 59, 61 through 72, 76 and 77 in a pregnant female to determine the probability for preterm birth in the pregnant female. In some embodiments, the reversal value reveals the existence of a change in reversal value between the pregnant female and a term control and indicates the probability for preterm birth in the pregnant female. In some embodiments, the measuring step comprises measuring surrogate peptides of the biomarkers in the biological sample obtained from the pregnant female.

In another embodiment, the invention provides a method of determining probability for preterm birth in a pregnant female, the method comprising measuring in a biological sample obtained from the pregnant female a change in reversal value for a panel of at least two pairs of biomarkers selected from the group consisting of the biomarkers specified in Table 26 in a pregnant female to determine the probability for preterm birth in the pregnant female. In some embodiments, the reversal value reveals the existence of a change in reversal value between the pregnant female and a term control and indicates the probability for preterm birth in the pregnant female. In some embodiments, the measuring step comprises measuring surrogate peptides of the biomarkers in the biological sample obtained from the pregnant female.

For methods directed to predicating time to birth, it is understood that "birth" means birth following spontaneous onset of labor, with or without rupture of membranes.

Although described and exemplified with reference to methods of determining probability for preterm birth in a pregnant female, the present disclosure is similarly applicable to methods of predicting gestational age at birth (GAB), methods for predicting term birth, methods for determining the probability of term birth in a pregnant female as well methods of predicating time to birth (TTB) in a pregnant female. It will be apparent to one skilled in the art that each of the aforementioned methods has specific and substantial utilities and benefits with regard maternal-fetal health considerations.

Furthermore, although described and exemplified with reference to methods of determining probability for preterm birth in a pregnant female, the present disclosure is similarly applicable to methods of predicting an abnormal glucola test, gestational diabetes, hypertension, preeclampsia, intrauterine growth restriction, stillbirth, fetal growth restriction, HELLP syndrome, oligohyramnios, chorioamnionitis, chorioamnionitis, placental previa, placental acreta, abruption, abruptio placenta, placental hemorrhage, preterm premature rupture of membranes, preterm labor, unfavorable cervix, postterm pregnancy, cholelithiasis, uterine over distention, stress. As described in more detail below, the classifier described herein is sensitive to a component of medically indicated PTB based on conditions such as, for example, preeclampsia or gestational diabetes.

Figure 10:
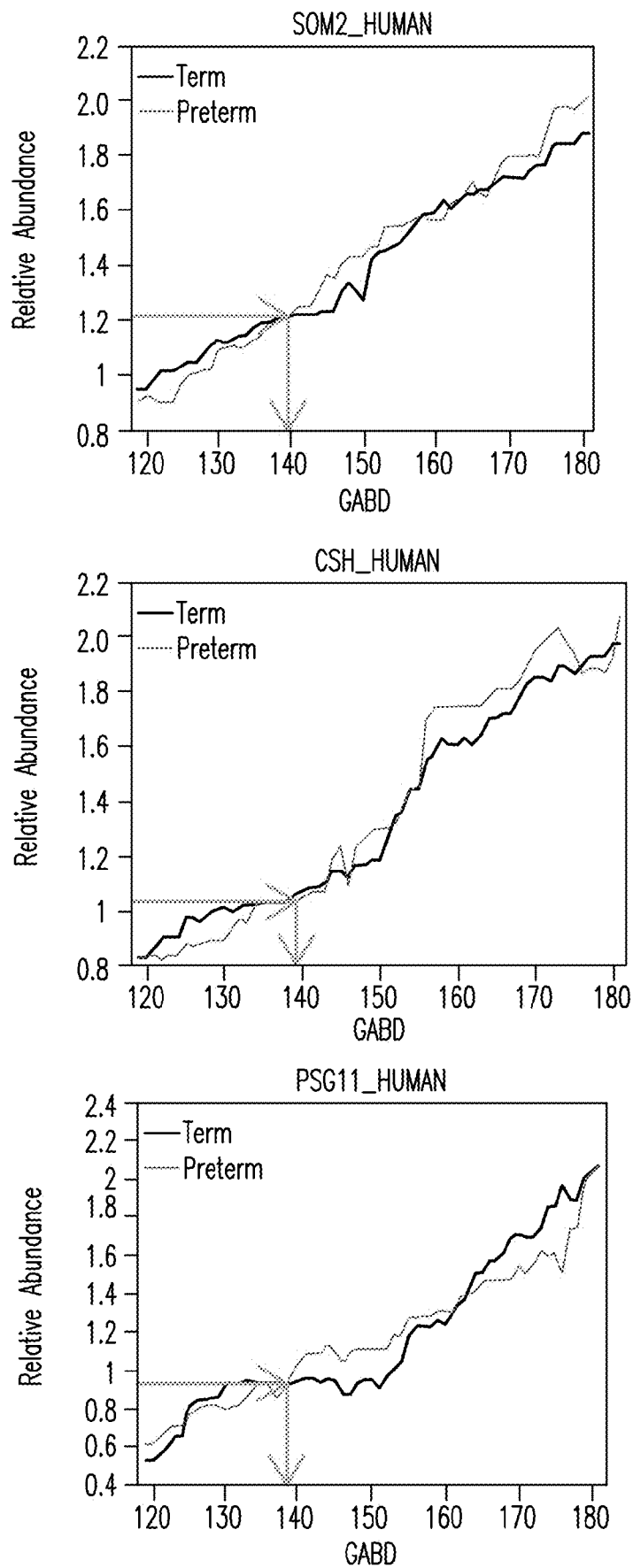
FIG. 10. Pregnancy clock and time to birth. Multiple analytes that increase in pregnancy but are not different in PTB cases and controls can be used to date pregnancy biochemically. Biochemical dating could be useful for confirmation of dating by date of last menstrual period or ultrasound dating, or prior to subsequent determinations of sPTB risk, TTB or GAB prediction.
Figure 10:
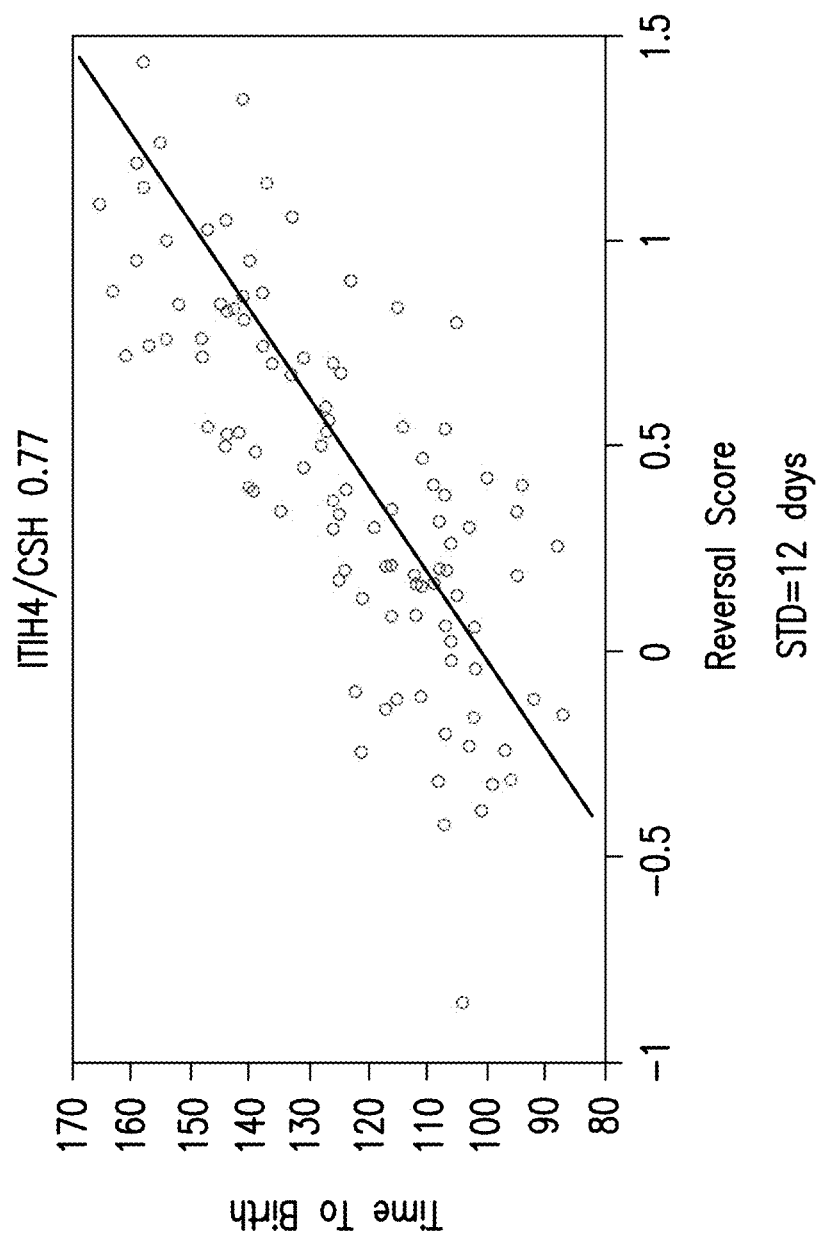
Figure 11:
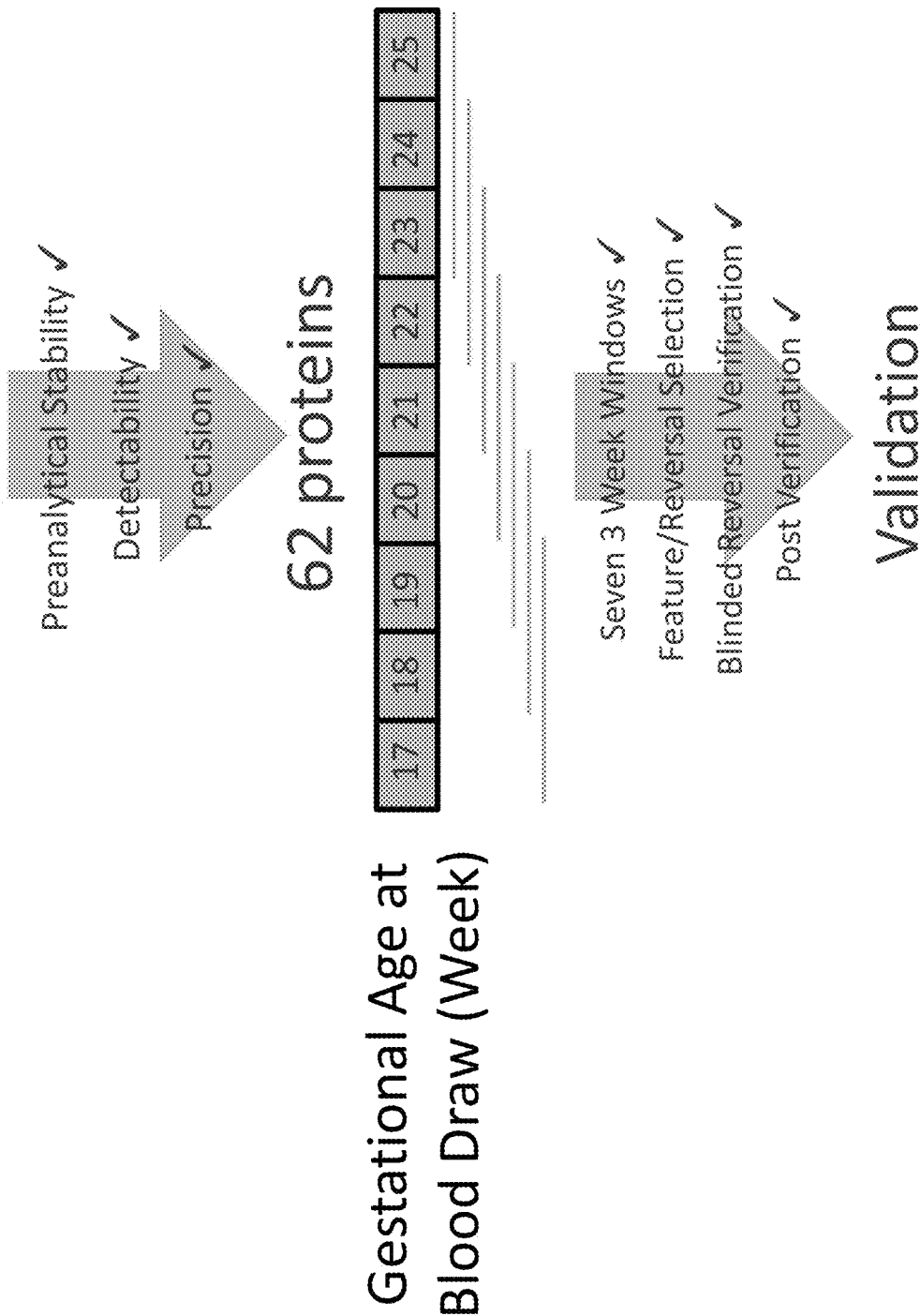
FIG. 11. Classifier development.
Figure 12:
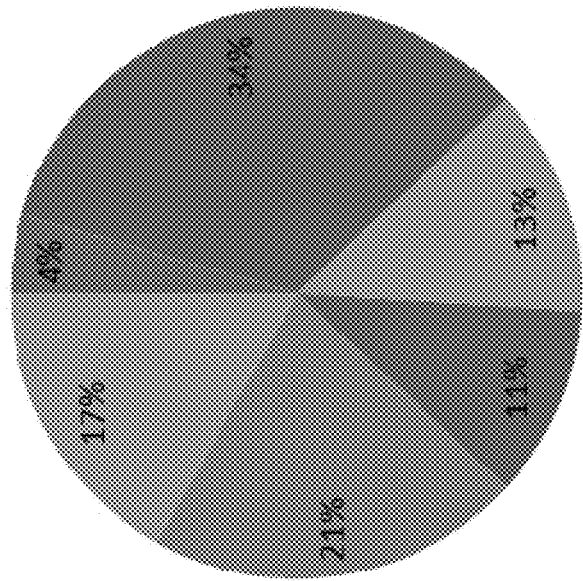
FIG. 12. Pathway coverage in discovery assay.
Figure 13:
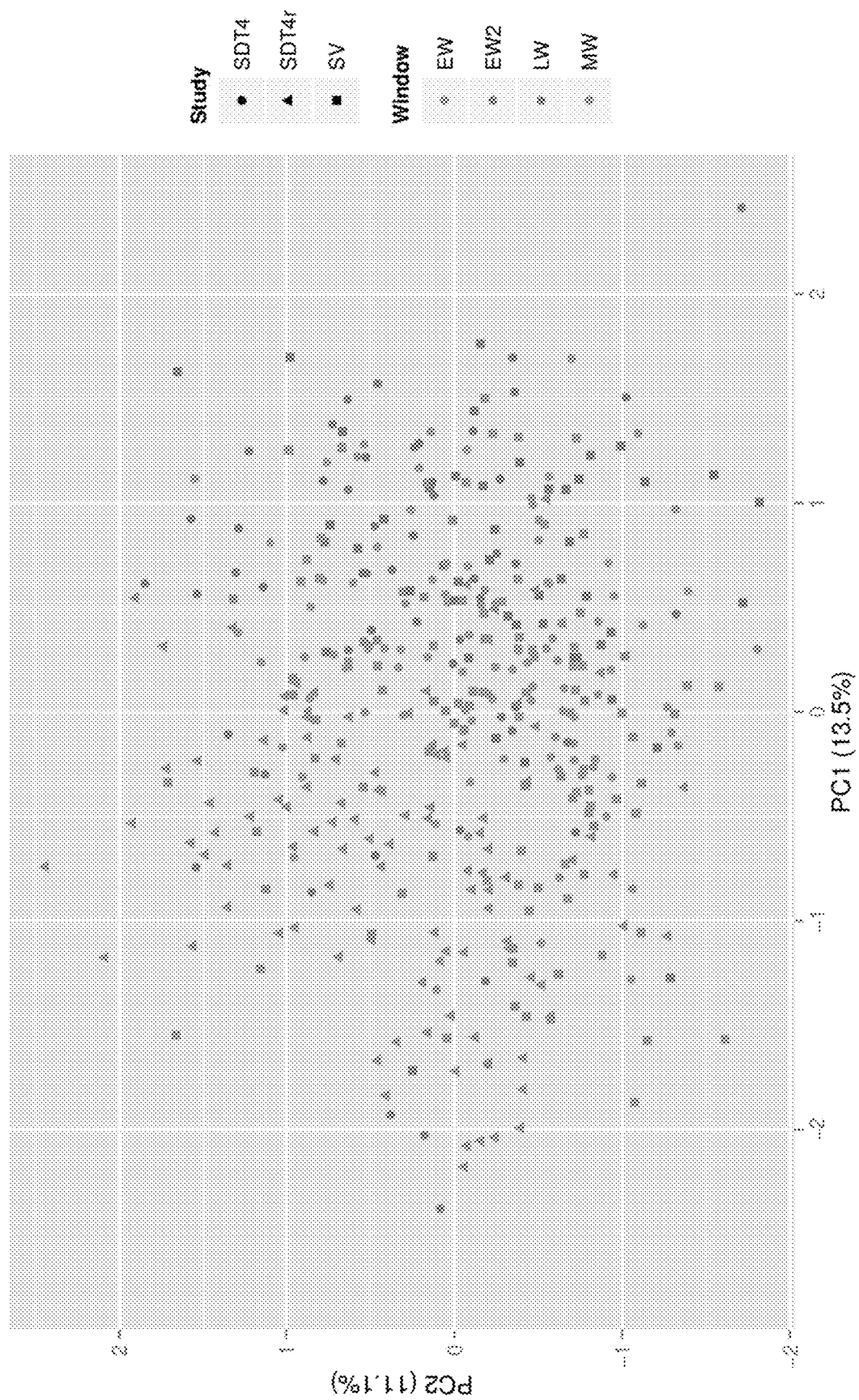
FIG. 13. PCA of discovery data detects changes across the blood draw windows and therefore indicates that the highly multiplexed assay is sensitive to gestational age.
Figure 14:
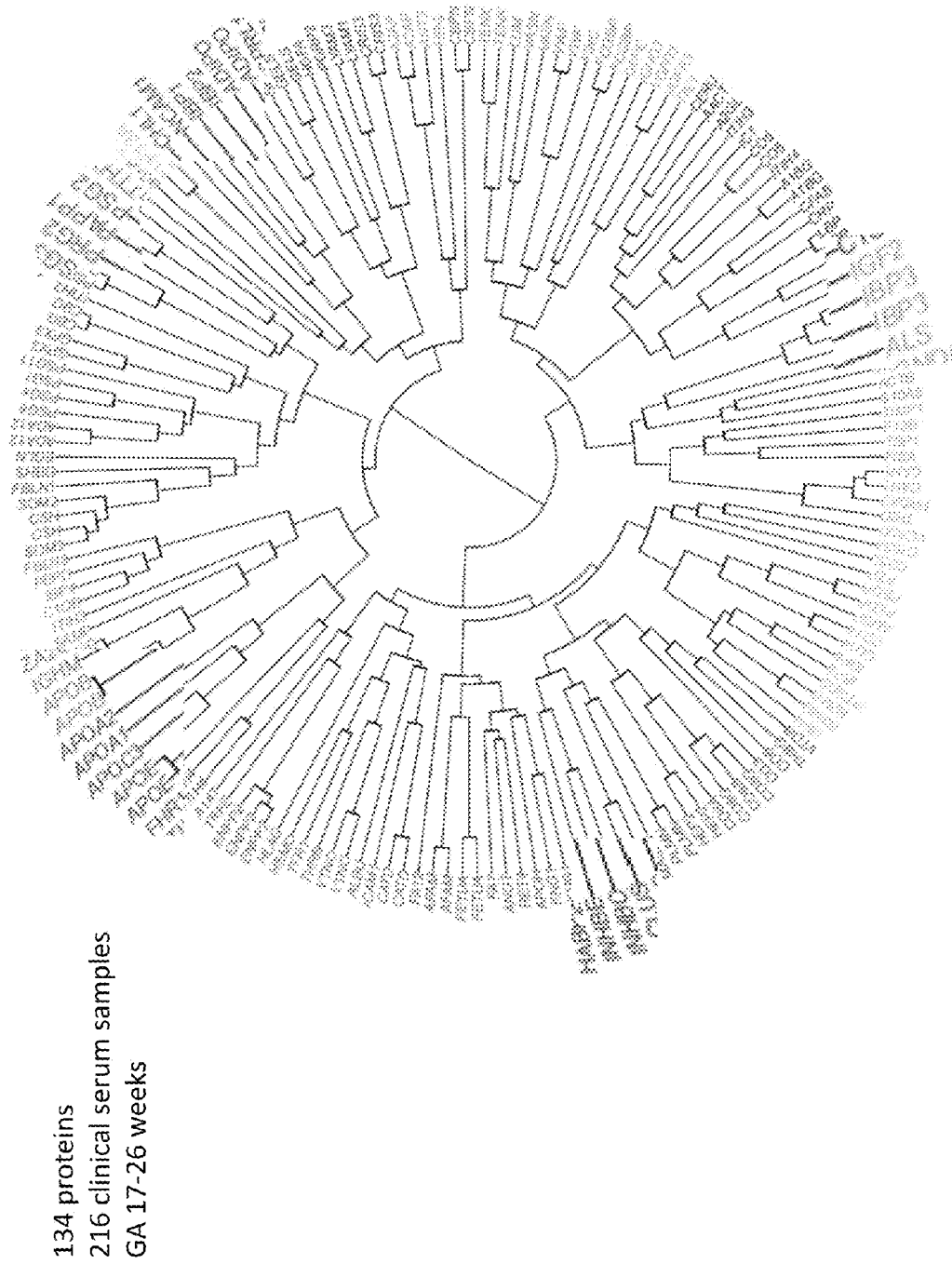
FIG. 14. Hierarchical clustering of proteins measured in discovery samples.
Figure 15:
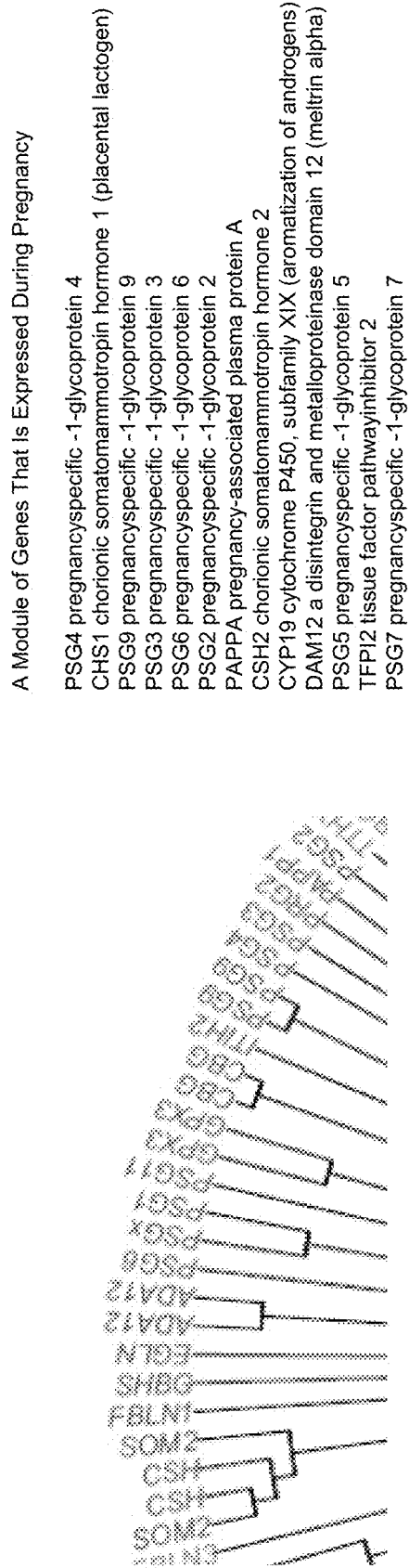
FIG. 15. Placenta specific protein branch within larger cluster. The right panel lists a module of genes that is expressed during pregnancy identified by Thompson and the left panel demonstrates that the discovery serum-proteomics assay reproduces the correlated expression of this module. (Thompson et al., *Genome Res.* 12(10):1517-1522 (2002).
Figure 16:
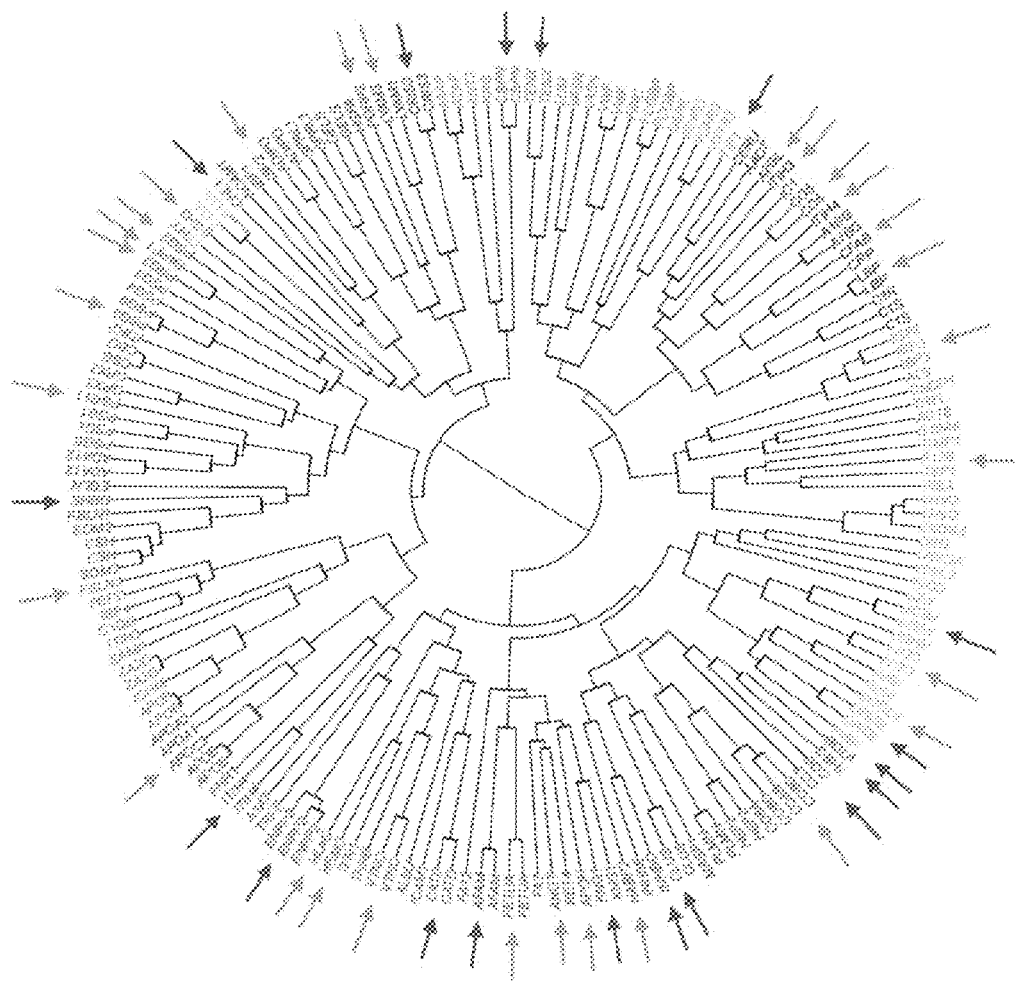
FIG. 16. Dysregulated proteins PreTRM™ samples.
Figure 17:
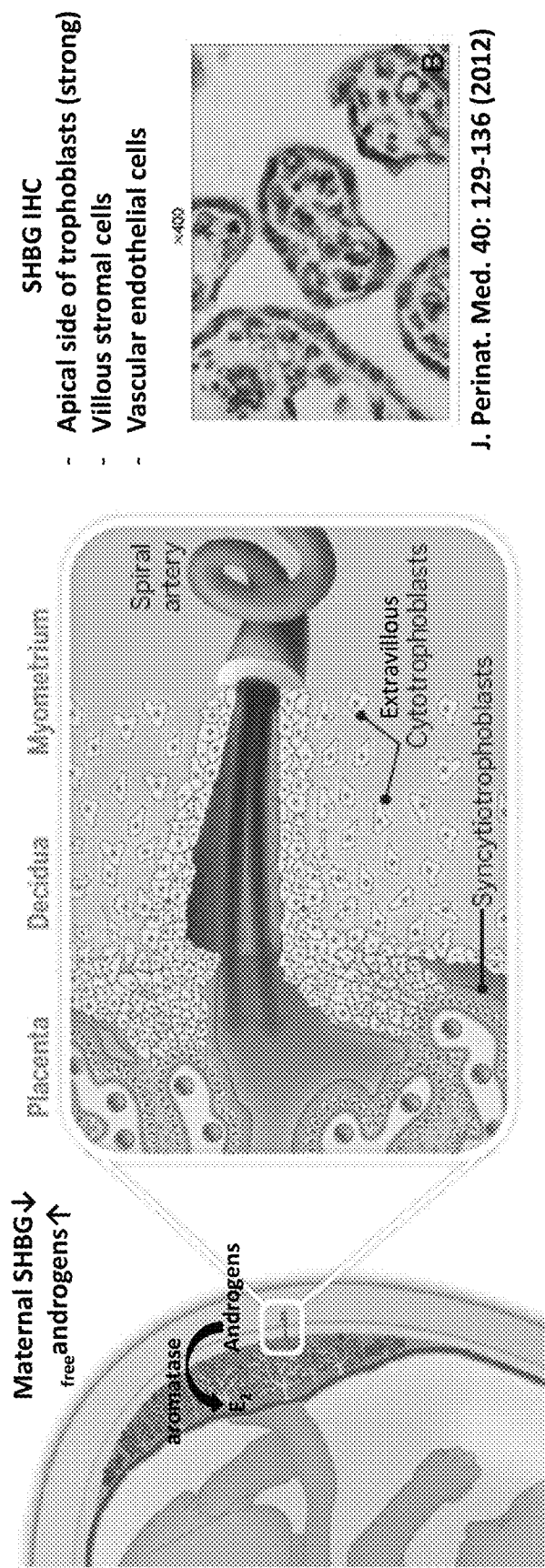
FIG. 17. Highlighted Sex hormone binding globulin (SHGB) biology. SHBG is expressed in placental cells (right). SHBG may be responsible for controlling the levels of free testosterone and estrogen levels in the placental fetal compartment (left).
Figure 19:
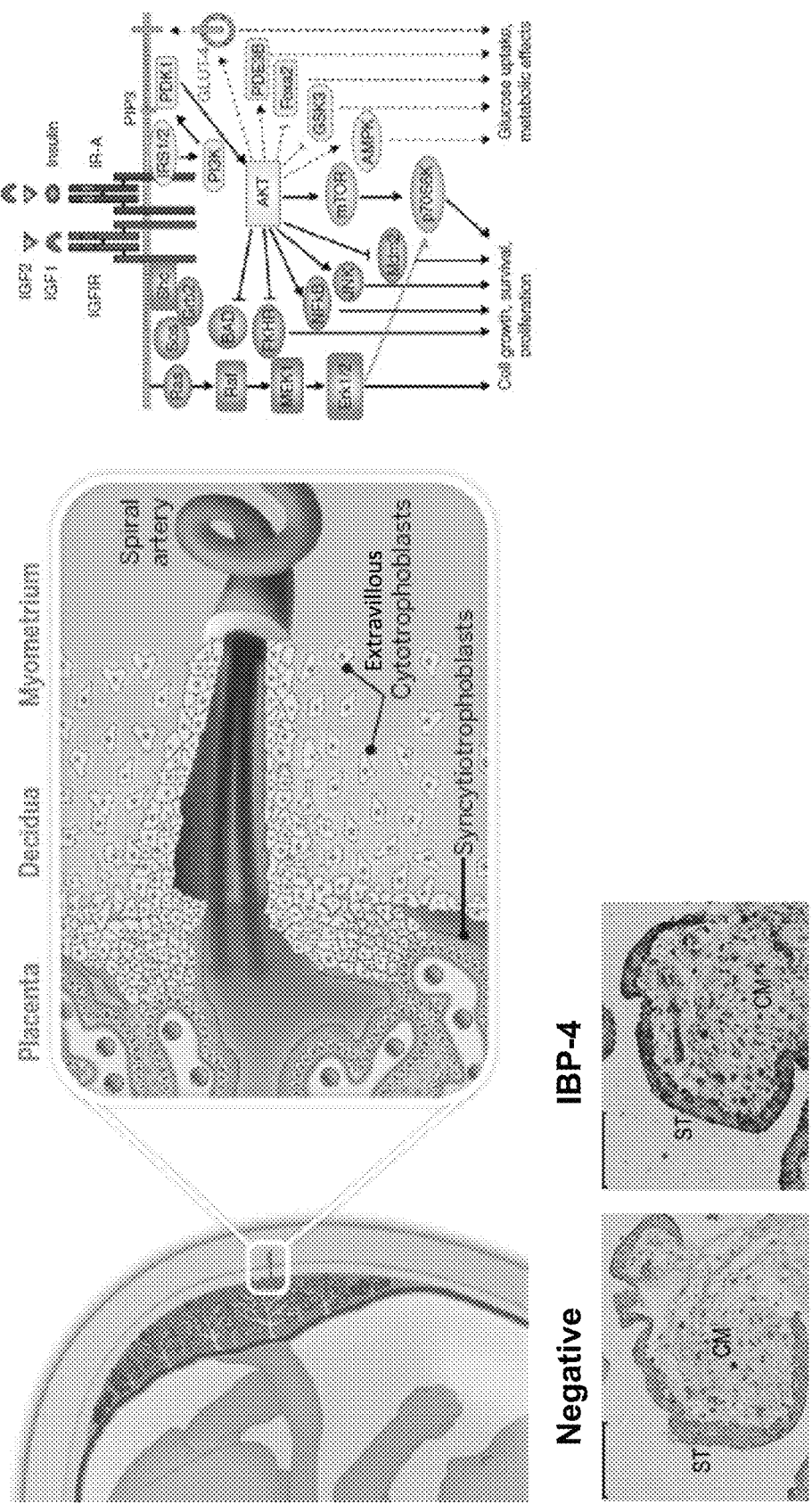
FIG. 19. Insulin-like growth factor binding protein 4 (IBP4). IBP4 is up-regulated in PTB cases. IGF2 stimulates proliferation, differentiation and invasion of EVT in early pregnancy. IGF activity is essential for normal placentation and fetal growth. IBP4 mediates autocrine and paracrine control of IGF2 activity at the maternal-fetal interface. Activity of IGF2 expressed by cytotrophoblasts is balanced by IBP produced by decidual cells. Elevated IBP4 and reduced IGF2 in 1st trimester correlated with placental dysfunction (e.g. IUGR/SGA).
Figure 20C:
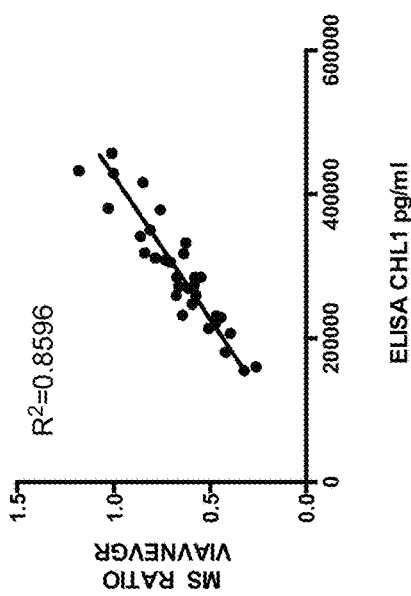
FIGS. 20A-20C. MS vs ELISA correlation for IBP4, SHBG and CHL1. Mass spectrometry and ELISA are in good agreement for key analytes. Agreement in two orthogonal platforms asserts analyte measurement reliability.
Figure 20B:
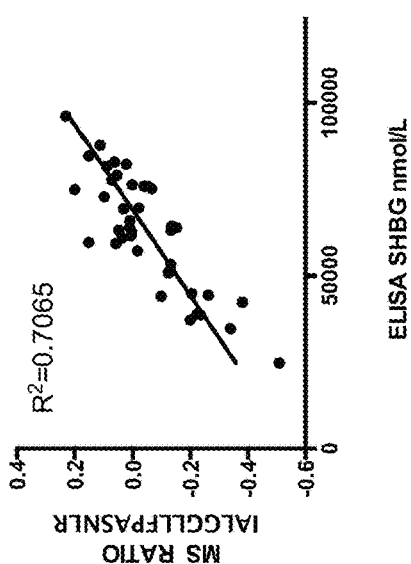
Figure 20A:
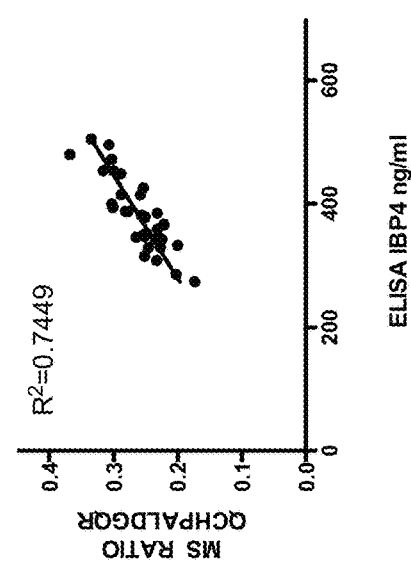

In some embodiments, the present disclosure provides biomarkers, biomarker pairs and/or reversals, exemplified here by using ITIH4/CSH, that are strong predictors of time to birth (TTB) (FIG. 10). TTB is defined as the difference between the GABD and the gestational age at birth (GAB). This discovery enables prediction, either individually or in mathematical combination of such analytes of TTB or GAB. Analytes that lack a case versus control difference, but demonstrate changes in analyte intensity across pregnancy, are useful in a pregnancy clock according to the methods of the invention. Calibration of multiple analytes that may not be diagnostic of preterm birth of other disorders, could be used to date pregnancy. Such a pregnancy clock is of value to confirm dating by another measure (e.g. date of last menstrual period and/or ultrasound dating), or useful alone to subsequently and more accurately predict sPTB, GAB or TTB, for example. These analytes, also referred to herein as "clock proteins", can be used to date a pregnancy in the absence of or in conjunction with other dating methods. Table 60 provides a list of clock proteins useful in a pregnancy clock of the invention to predict TTB and GAB.

In additional embodiments, the methods of determining probability for preterm birth in a pregnant female further encompass detecting a measurable feature for one or more risk indicia associated with preterm birth. In additional embodiments the risk indicia are selected form the group consisting of previous low birth weight or preterm delivery, multiple 2nd trimester spontaneous abortions, prior first trimester induced abortion, familial and intergenerational factors, history of infertility, nulliparity, gravidity, primigravida, multigravida, placental abnormalities, cervical and uterine anomalies, gestational bleeding, intrauterine growth restriction, in utero diethylstilbestrol exposure, multiple gestations, infant sex, short stature, low prepregnancy weight, low or high body mass index, diabetes, hypertension, and urogenital infections.

A "measurable feature" is any property, characteristic or aspect that can be determined and correlated with the probability for preterm birth in a subject. The term further encompasses any property, characteristic or aspect that can be determined and correlated in connection with a prediction of GAB, a prediction of term birth, or a prediction of time to birth in a pregnant female. For a biomarker, such a measurable feature can include, for example, the presence, absence, or concentration of the biomarker, or a fragment thereof, in the biological sample, an altered structure, such as, for example, the presence or amount of a post-translational modification, such as oxidation at one or more positions on the amino acid sequence of the biomarker or, for example, the presence of an altered conformation in comparison to the conformation of the biomarker in term control subjects, and/or the presence, amount, or altered structure of the biomarker as a part of a profile of more than one biomarker.

In addition to biomarkers, measurable features can further include risk indicia including, for example, maternal characteristics, age, race, ethnicity, medical history, past pregnancy history, obstetrical history. For a risk indicium, a measurable feature can include, for example, previous low birth weight or preterm delivery, multiple 2nd trimester spontaneous abortions, prior first trimester induced abortion, familial and intergenerational factors, history of infertility, nulliparity, placental abnormalities, cervical and uterine anomalies, short cervical length measurements, gestational bleeding, intrauterine growth restriction, in utero diethylstilbestrol exposure, multiple gestations, infant sex, short stature, low prepregnancy weight/low body mass index, diabetes, hypertension, urogenital infections, hypothyroidism, asthma, low educational attainment, cigarette smoking, drug use and alcohol consumption.

In some embodiments, the methods of the invention comprise calculation of body mass index (BMI).

In some embodiments, the disclosed methods for determining the probability of preterm birth encompass detecting and/or quantifying one or more biomarkers using mass spectrometry, a capture agent or a combination thereof.

In additional embodiments, the disclosed methods of determining probability for preterm birth in a pregnant female encompass an initial step of providing a biological sample from the pregnant female.

In some embodiments, the disclosed methods of determining probability for preterm birth in a pregnant female encompass communicating the probability to a health care provider. The disclosed of predicting GAB, the methods for predicting term birth, methods for determining the probability of term birth in a pregnant female as well methods of predicating time to birth in a pregnant female similarly encompass communicating the probability to a health care provider. As stated above, although described and exemplified with reference to determining probability for preterm birth in a pregnant female, all embodiments described throughout this disclosure are similarly applicable to the methods of predicting GAB, the methods for predicting term birth, methods for determining the probability of term birth in a pregnant female as well methods of predicating time to birth in a pregnant female. Specifically, the biomarkers and panels recited throughout this application with express reference to methods for preterm birth can also be used in methods for predicting GAB, the methods for predicting term birth, methods for determining the probability of term birth in a pregnant female as well methods of predicating time to birth in a pregnant female. It will be apparent to one skilled in the art that each of the aforementioned methods has specific and substantial utilities and benefits with regard maternal-fetal health considerations.

In additional embodiments, the communication informs a subsequent treatment decision for the pregnant female. In some embodiments, the method of determining probability for preterm birth in a pregnant female encompasses the additional feature of expressing the probability as a risk score.

In the methods disclosed herein, determining the probability for preterm birth in a pregnant female encompasses an initial step that includes formation of a probability/risk index by measuring the ratio of isolated biomarkers selected from the group in a cohort of preterm pregnancies and term pregnancies with known gestational age at birth. For an individual pregnancy, determining the probability of for preterm birth in a pregnant female encompasses measuring the ratio of the isolated biomarker using the same measurement method as used in the initial step of creating the probability/risk index, and comparing the measured ratio to the risk index to derive the personalized risk for the individual pregnancy. In one embodiment, a preterm risk index is formed by measuring the ratio of IBP4/SHBG in a cohort of preterm and term pregnancies where the gestational age at birth is recorded. Then, in clinical practice the measured ratio of IBP4/SHBG in an individual pregnancy is compared in the index to derive the preterm risk using the same isolation and measurement technologies to derive IBP4/SHBG as in the index group.

As used herein, the term "risk score" refers to a score that can be assigned based on comparing the amount of one or more biomarkers or reversal values in a biological sample obtained from a pregnant female to a standard or reference score that represents an average amount of the one or more biomarkers calculated from biological samples obtained from a random pool of pregnant females. In some embodiments, the risk score is expressed as the log of the reversal value, i.e. the ratio of the relative intensities of the individual biomarkers. One skilled in the art will appreciate that a risk score can be expressed based on a various data transformations as well as being expressed as the ratio itself. Furthermore, with particular regard to reversal pairs, one skilled in the art will appreciate the any ratio is equally informative if the biomarkers in the numerator and denominator are switched or that related data transformations (e.g. subtraction) are applied. Because the level of a biomarker may not be static throughout pregnancy, a standard or reference score has to have been obtained for the gestational time point that corresponds to that of the pregnant female at the time the sample was taken. The standard or reference score can be predetermined and built into a predictor model such that the comparison is indirect rather than actually performed every time the probability is determined for a subject. A risk score can be a standard (e.g., a number) or a threshold (e.g., a line on a graph). The value of the risk score correlates to the deviation, upwards or downwards, from the average amount of the one or more biomarkers calculated from biological samples obtained from a random pool of pregnant females. In certain embodiments, if a risk score is greater than a standard or reference risk score, the pregnant female can have an increased likelihood of preterm birth. In some embodiments, the magnitude of a pregnant female's risk score, or the amount by which it exceeds a reference risk score, can be indicative of or correlated to that pregnant female's level of risk.

Figure 25:
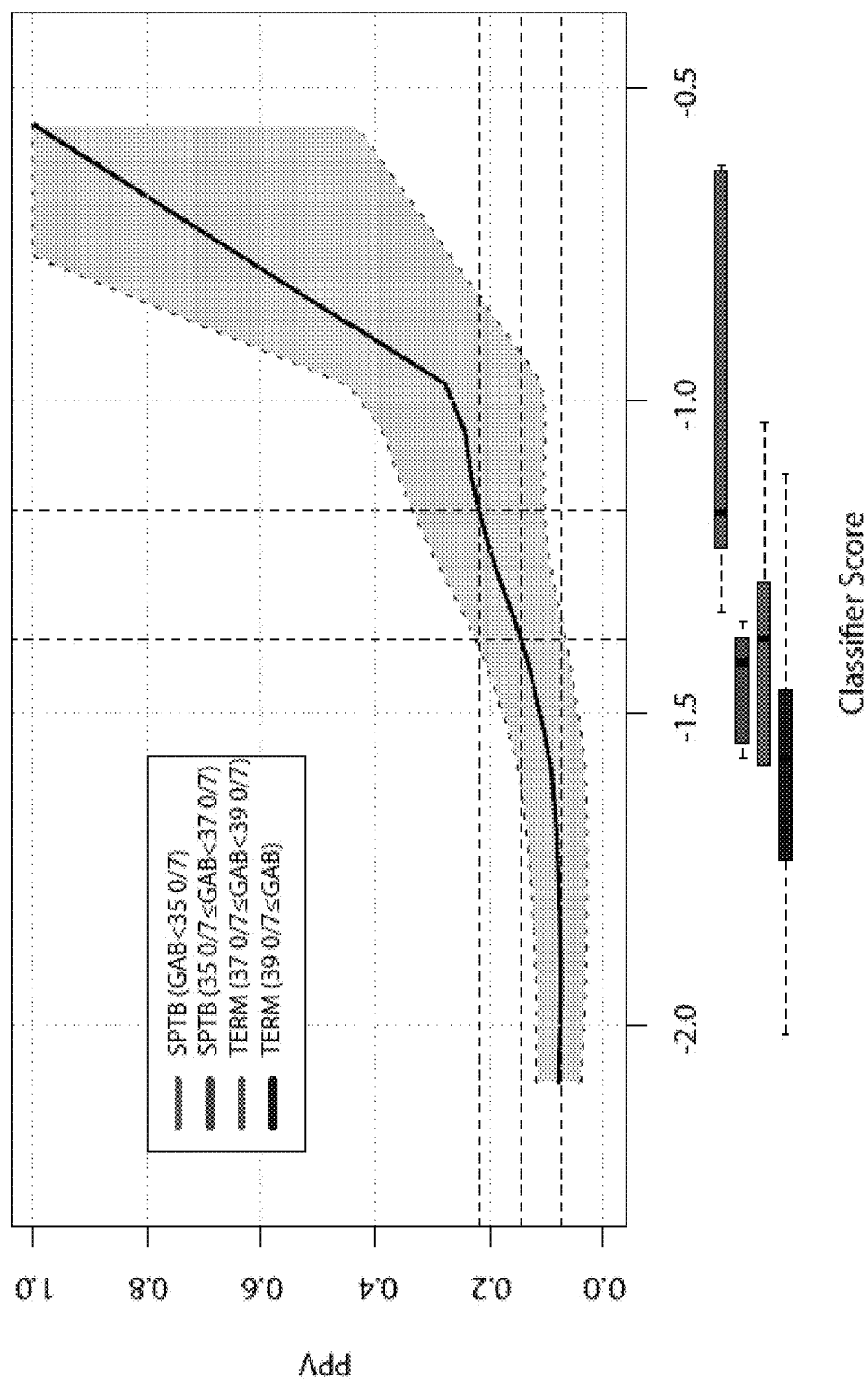
FIG. 25 shows prevalence adjusted positive predictive value (PPV), a measure of clinical risk, as a function of predictor score. The calculated association of predictor score and PPV, allows the determination of probability of sPTB risk for any unknown subject. Top (purple) line underneath risk curve graph corresponds to GAB<35 0/7 weeks; second line (red) from top corresponds to GAB between 35 0/7 and 37 0/7/weeks; third line (green) from corresponds to GAB between 37 0/7 and 39 0/7/weeks; fourth line (blue) from top corresponds to GAB 39 0/7 weeks ≤GAB.

As exemplified herein, the PreTRM™ Classifier is defined as the natural log of the SIS normalized intensities of the IBP4 peptide transition (QCHPALDGQR_394.5_475.2 (SEQ ID NO: 2)) and the SHBG peptide transition (IALGGLLFPASNLR_481.3_657.4 (SEQ ID NO: 18)). Score=ln($P^1_n/P^2_n$), where $P^1_n$ and $P^2_n$ denote the SIS normalized peak area values for the IBP4 and SHBG transitions, respectively. SIS normalization is defined as the relative ratio of the endogenous peak area divided by the corresponding SIS peak area: e.g. $P^1_n = P^1_e/P^1_{SIS}$, where $P^1_e$=the peak area for the IBP4 endogenous transition and $P^1_{SIS}$=the peak area for IBP4 SIS transition. From the identified association between the distribution of PreTRM™ scores and the corresponding prevalence adjusted positive predictive value a probability of sPTB can be assigned to an unknown subject based on the determination of their score". This relationship or association is shown in FIG. 25, and connects a laboratory measurement with a clinical prediction.

While the PreTRM™ Classifier is defined as the natural log of the SIS normalized intensities of the IBP4 peptide transition (QCHPALDGQR_394.5_475.2 (SEQ ID NO: 2)) and the SHBG peptide transition (IALGGLLFPASNLR_481.3_657.4 (SEQ ID NO: 18)), the invention also comprises classifiers that include multiple reversals. Improved performance can be achieved by constructing predictors formed from more than one reversal. In additional embodiments, the invention methods therefore comprise multiple reversals that have a strong predictive performance for example, for separate GABD windows, preterm premature rupture of membranes (PPROM) versus preterm labor in the absence of PPROM (PTL), fetal gender, primigravida versus multigravida. This embodiment is exemplified in Example 10, and Table 61, for either reversals that produced strong predictive performance either early (e.g. weeks 17-19) or later (e.g. weeks 19-21) in the gestational age range. As exemplified, performance of predictors formed from combinations (SumLog) of multiple reversals were evaluated for the entire blood draw range and a predictor score was derived from summing the Log values of the individual reversal (SumLog). One skilled in the art can select other models (e.g. logistic regression) to construct a predictor formed from more than one reversal.

The methods of the invention further include classifiers that contain an indicator variable that selects one or a subset of reversals based on known clinical factors, for example, blood draw period, fetal gender, gravidity as well as any other knowable patient features and/or risk factors described throughout this application. This embodiment is exemplified in Example 10, Tables 61 through 64, which exemplify reversal performance (weeks 17-21) independently for two different phenotypes of sPTB, PPROM and PTL. This embodiment is similarly exemplified in Example 10, Tables 76 and 77 and FIGS. 108 and 109, which exemplify reversal performance (weeks 19-21) independently for two different phenotypes of sPTB, preterm premature rupture of membranes (PPROM) and preterm labor in the absence of PPROM (PTL). The methods of the invention thus include selection of reversals to build independent predictors of PPROM and PTL, or to maximize performance overall with the combination of more than one reversal in a single predictor as described above. This embodiment is further exemplified in Example 10, Tables 65-68, which exemplify reversal performance (weeks 17-21) independently for two different types of sPTB, primigravida and multigravida. This embodiment is further exemplified in Example 10, Tables 69-72 and FIG. 106, which exemplify reversal performance (weeks 17-21) independently for two different types of sPTB based on fetal gender. While exemplified with regard to PPROM and PTL, gravidity and fetal gender, the methods of the invention include classifiers that contain an indicator variable that selects one or a subset of reversals based on GABD or any known clinical factors/risk factors described herein or otherwise known to those of skill in the art. As an alternative to having a classifier that includes an indicator variable, the invention further provides separate classifiers that are tailored to subsets of pregnant women based on GABD or any known clinical factors/risk factors described herein or otherwise known to those of skill in the art. For example, this embodiment encompasses separate classifiers for consecutive and/or overlapping time windows for GABD that are based on the best performing reversals for each time window.

As exemplified herein, the predictive performance of the claimed methods can be improved with a BMI stratification of greater than 22 and equal or less than 37 kg/m'. Accordingly, in some embodiments, the methods of the invention can be practiced with samples obtained from pregnant females with a specified BMI. Briefly, BMI is an individual's weight in kilograms divided by the square of height in meters. BMI does not measure body fat directly, but research has shown that BMI is correlated with more direct measures of body fat obtained from skinfold thickness measurements, bioelectrical impedance, densitometry (underwater weighing), dual energy x-ray absorptiometry (DXA) and other methods. Furthermore, BMI appears to be as strongly correlated with various metabolic and disease outcome as are these more direct measures of body fatness. Generally, an individual with a BMI below 18.5 is considered underweight, an individual with a BMI of equal or greater than 18.5 to 24.9 normal weight, while an individual with a BMI of equal or greater than 25.0 to 29.9 is considered overweight and an individual with a BMI of equal or greater than 30.0 is considered obese. In some embodiments, the predictive performance of the claimed methods can be improved with a BMI stratification of equal or greater than 18, equal or greater than 19, equal or greater than 20, equal or greater than 21, equal or greater than 22, equal or greater than 23, equal or greater than 24, equal or greater than 25, equal or greater than 26, equal or greater than 27, equal or greater than 28, equal or greater than 29 or equal or greater than 30. In other embodiments, the predictive performance of the claimed methods can be improved with a BMI stratification of equal or less than 18, equal or less than 19, equal or less than 20, equal or less than 21, equal or less than 22, equal or less than 23, equal or less than 24, equal or less than 25, equal or less than 26, equal or less than 27, equal or less than 28, equal or less than 29 or equal or less than 30.

In the context of the present invention, the term "biological sample," encompasses any sample that is taken from pregnant female and contains one or more of the biomarkers disclosed herein. Suitable samples in the context of the present invention include, for example, blood, plasma, serum, amniotic fluid, vaginal secretions, saliva, and urine. In some embodiments, the biological sample is selected from the group consisting of whole blood, plasma, and serum. In a particular embodiment, the biological sample is serum. As will be appreciated by those skilled in the art, a biological sample can include any fraction or component of blood, without limitation, T cells, monocytes, neutrophils, erythrocytes, platelets and microvesicles such as exosomes and exosome-like vesicles. In a particular embodiment, the biological sample is serum.

As used herein, the term "preterm birth" refers to delivery or birth at a gestational age less than 37 completed weeks. Other commonly used subcategories of preterm birth have been established and delineate moderately preterm (birth at 33 to 36 weeks of gestation), very preterm (birth at <33 weeks of gestation), and extremely preterm (birth at ≤28 weeks of gestation). With regard to the methods disclosed herein, those skilled in the art understand that the cut-offs that delineate preterm birth and term birth as well as the cut-offs that delineate subcategories of preterm birth can be adjusted in practicing the methods disclosed herein, for example, to maximize a particular health benefit. In various embodiments of the invention, cut-off that delineate preterm birth include, for example, birth at ≤37 weeks of gestation, ≤36 weeks of gestation, ≤35 weeks of gestation, ≤34 weeks of gestation, ≤33 weeks of gestation, ≤32 weeks of gestation, ≤30 weeks of gestation, ≤29 weeks of gestation, ≤28 weeks of gestation, ≤27 weeks of gestation, ≤26 weeks of gestation, ≤25 weeks of gestation, ≤24 weeks of gestation, ≤23 weeks of gestation or ≤22 weeks of gestation. In some embodiments, the cut-off delineating preterm birth is ≤35 weeks of gestation. It is further understood that such adjustments are well within the skill set of individuals considered skilled in the art and encompassed within the scope of the inventions disclosed herein. Gestational age is a proxy for the extent of fetal development and the fetus's readiness for birth. Gestational age has typically been defined as the length of time from the date of the last normal menses to the date of birth. However, obstetric measures and ultrasound estimates also can aid in estimating gestational age. Preterm births have generally been classified into two separate subgroups. One, spontaneous preterm births are those occurring subsequent to spontaneous onset of preterm labor or preterm premature rupture of membranes regardless of subsequent labor augmentation or cesarean delivery. Two, medically indicated preterm births are those occurring following induction or cesarean section for one or more conditions that the woman's caregiver determines to threaten the health or life of the mother and/or fetus. In some embodiments, the methods disclosed herein are directed to determining the probability for spontaneous preterm birth or medically indicated preterm birth. In some embodiments, the methods disclosed herein are directed to determining the probability for spontaneous preterm birth. In additional embodiments, the methods disclosed herein are directed to medically indicated preterm birth. In additional embodiments, the methods disclosed herein are directed to predicting gestational age at birth.

As used herein, the term "estimated gestational age" or "estimated GA" refers to the GA determined based on the date of the last normal menses and additional obstetric measures, ultrasound estimates or other clinical parameters including, without limitation, those described in the preceding paragraph. In contrast the term "predicted gestational age at birth" or "predicted GAB" refers to the GAB determined based on the methods of the invention as disclosed herein. As used herein, "term birth" refers to birth at a gestational age equal or more than 37 completed weeks.

In some embodiments, the pregnant female is between 17 and 28 weeks of gestation at the time the biological sample is collected, also referred to as GABD (Gestational Age at Blood Draw). In other embodiments, the pregnant female is between 16 and 29 weeks, between 17 and 28 weeks, between 18 and 27 weeks, between 19 and 26 weeks, between 20 and 25 weeks, between 21 and 24 weeks, or between 22 and 23 weeks of gestation at the time the biological sample is collected. In further embodiments, the pregnant female is between about 17 and 22 weeks, between about 16 and 22 weeks between about 22 and 25 weeks, between about 13 and 25 weeks, between about 26 and 28, or between about 26 and 29 weeks of gestation at the time the biological sample is collected. Accordingly, the gestational age of a pregnant female at the time the biological sample is collected can be 15, 16, 17, 18, 19, 20, 21, 22, 23, 24, 25, 26, 27, 28, 29 or 30 weeks. In particular embodiments, the biological sample is collected between 19 and 21 weeks of gestational age. In particular embodiments, the biological sample is collected between 19 and 22 weeks of gestational age. In particular embodiments, the biological sample is collected between 19 and 21 weeks of gestational age. In particular embodiments, the biological sample is collected between 19 and 22 weeks of gestational age. In particular embodiments, the biological sample is collected at 18 weeks of gestational age. In further embodiments, the highest performing reversals for consecutive or overlapping time windows can be combined in a single classifier to predict the probability of sPTB over a wider window of gestational age at blood draw.

The term "amount" or "level" as used herein refers to a quantity of a biomarker that is detectable or measurable in a biological sample and/or control. The quantity of a biomarker can be, for example, a quantity of polypeptide, the quantity of nucleic acid, or the quantity of a fragment or surrogate. The term can alternatively include combinations thereof. The term "amount" or "level" of a biomarker is a measurable feature of that biomarker.

The invention also provides a method of detecting a pair of isolated biomarkers selected from the group consisting of the biomarker pairs specified in any of Tables 1 through 77 and FIGS. 1 through 111 in a pregnant female, said method comprising the steps of a. obtaining a biological sample from the pregnant female; b. detecting whether the pair of isolated biomarkers is present in the biological sample by contacting the biological sample with a first capture agent that specifically binds a first member of said pair and a second capture agent that specifically binds a second member of said pair; and detecting binding between the first biomarker of said pair and the first capture agent and between the second member of said pair and the second capture agent.

The invention also provides a method of detecting a pair of isolated biomarkers selected from the group consisting of the biomarker pairs specified in Tables 27 through 59, 61 through 72, 76 and 77 in a pregnant female, said method comprising the steps of a. obtaining a biological sample from the pregnant female; b. detecting whether the pair of isolated biomarkers is present in the biological sample by contacting the biological sample with a first capture agent that specifically binds a first member of said pair and a second capture agent that specifically binds a second member of said pair; and detecting binding between the first biomarker of said pair and the first capture agent and between the second member of said pair and the second capture agent.

The invention also provides a method of detecting a pair of isolated biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS in a pregnant female, said method comprising the steps of a. obtaining a biological sample from the pregnant female; b. detecting whether the pair of isolated biomarkers is present in the biological sample by contacting the biological sample with a first capture agent that specifically binds a first member of said pair and a second capture agent that specifically binds a second member of said pair; and detecting binding between the first biomarker of said pair and the first capture agent and between the second member of said pair and the second capture agent. In one embodiment the invention provides a method of detecting IBP4 and SHBG in a pregnant female, said method comprising the steps of a. obtaining a biological sample from the pregnant female; b. detecting whether IBP4 and SHBG are present in the biological sample by contacting the biological sample with a capture agent that specifically binds IBP4 and a capture agent that specifically binds SHBG; and c. detecting binding between IBP4 and the capture agent and between SHBG and the capture agent. In one embodiment, the method comprises measuring a reversal value for the pair of biomarkers. In a further embodiment, the existence of a change in reversal value between the pregnant female and a term control indicates the probability for preterm birth in the pregnant female. In one embodiment, the sample is obtained between 19 and 21 weeks of gestational age. In a further embodiment, the capture agent is selected from the group consisting of and antibody, antibody fragment, nucleic acid-based protein binding reagent, small molecule or variant thereof. In an additional embodiment, the method is performed by an assay selected from the group consisting of enzyme immunoassay (EIA), enzyme-linked immunosorbent assay (ELISA), and radioimmunoassay (MA).

The invention also provides a method of detecting a pair of isolated biomarkers selected from the group consisting of IBP4/SHBG, VTNC/VTDB, VTNC/SHBG, CATD/SHBG, PSG2/ITIH4, CHL1/ITIH4, PSG2/C1QB, PSG2/FBLN3, HPX/IBP4, and HPX/PTGDS in a pregnant female, said method comprising the steps of a. obtaining a biological sample from the pregnant female; and b. detecting whether the pair of isolated biomarkers is present in the biological sample comprising subjecting the sample to a proteomics work-flow comprised of mass spectrometry quantification.

In one embodiment the invention provides a method of detecting IBP4 and SHBG in a pregnant female, said method comprising the steps of a. obtaining a biological sample from the pregnant female; and b. detecting whether the pair of isolated biomarkers is present in the biological sample comprising subjecting the sample to a proteomics work-flow comprised of mass spectrometry quantification.

A "proteomics work-flow" generally encompasses one or more of the following steps: Serum samples are thawed and depleted of the 14 highest abundance proteins by immune-affinity chromatography. Depleted serum is digested with a protease, for example, trypsin, to yield peptides. The digest is subsequently fortified with a mixture of SIS peptides and then desalted and subjected to LC-MS/MS with a triple quadrupole instrument operated in MRM mode. Response ratios are formed from the area ratios of endogenous peptide peaks and the corresponding SIS peptide counterpart peaks. Those skilled in the art appreciate that other types of MS such as, for example, MALDI-TOF, or ESI-TOF, can be used in the methods of the invention. In addition, one skilled in the art can modify a proteomics work-flow, for example, by selecting particular reagents (such as proteases) or omitting or changing the order of certain steps, for example, it may not be necessary to immunodeplete, the SIS peptide could be added earlier or later and stable isotope labeled proteins could be used as standards instead of peptides.

Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of biomarkers, peptides, polypeptides, proteins and/or fragments thereof and optionally of the one or more other biomarkers or fragments thereof in samples. In some embodiments, detection and/or quantification of one or more biomarkers comprises an assay that utilizes a capture agent. In further embodiments, the capture agent is an antibody, antibody fragment, nucleic acid-based protein binding reagent, small molecule or variant thereof. In additional embodiments, the assay is an enzyme immunoassay (EIA), enzyme-linked immunosorbent assay (ELISA), and radio-immunoassay (MA). In some embodiments, detection and/or quantification of one or more biomarkers further comprises mass spectrometry (MS). In yet further embodiments, the mass spectrometry is co-immunoprecipitation-mass spectrometry (co-IP MS), where coimmunoprecipitation, a technique suitable for the isolation of whole protein complexes is followed by mass spectrometric analysis.

As used herein, the term "mass spectrometer" refers to a device able to volatilize/ionize analytes to form gas-phase ions and determine their absolute or relative molecular masses. Suitable methods of volatilization/ionization are matrix-assisted laser desorption ionization (MALDI), electrospray, laser/light, thermal, electrical, atomized/sprayed and the like, or combinations thereof. Suitable forms of mass spectrometry include, but are not limited to, ion trap instruments, quadrupole instruments, electrostatic and magnetic sector instruments, time of flight instruments, time of flight tandem mass spectrometer (TOF MS/MS), Fourier-transform mass spectrometers, Orbitraps and hybrid instruments composed of various combinations of these types of mass analyzers. These instruments can, in turn, be interfaced with a variety of other instruments that fractionate the samples (for example, liquid chromatography or solid-phase adsorption techniques based on chemical, or biological properties) and that ionize the samples for introduction into the mass spectrometer, including matrix-assisted laser desorption (MALDI), electrospray, or nanospray ionization (ESI) or combinations thereof.

Generally, any mass spectrometric (MS) technique that can provide precise information on the mass of peptides, and preferably also on fragmentation and/or (partial) amino acid sequence of selected peptides (e.g., in tandem mass spectrometry, MS/MS; or in post source decay, TOF MS), can be used in the methods disclosed herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000; Biemann 1990. Methods Enzymol 193: 455-79; or Methods in Enzymology, vol. 402: "Biological Mass Spectrometry", by Burlingame, ed., Academic Press 2005) and can be used in practicing the methods disclosed herein. Accordingly, in some embodiments, the disclosed methods comprise performing quantitative MS to measure one or more biomarkers. Such quantitative methods can be performed in an automated (Villanueva, et al., Nature Protocols (2006) 1(2):880-891) or semi-automated format. In particular embodiments, MS can be operably linked to a liquid chromatography device (LC-MS/MS or LC-MS) or gas chromatography device (GC-MS or GC-MS/MS). Other methods useful in this context include isotope-coded affinity tag (ICAT), tandem mass tags (TMT), or stable isotope labeling by amino acids in cell culture (SILAC), followed by chromatography and MS/MS.

As used herein, the terms "multiple reaction monitoring (MRM)" or "selected reaction monitoring (SRM)" refer to an MS-based quantification method that is particularly useful for quantifying analytes that are in low abundance. In an SRM experiment, a predefined precursor ion and one or more of its fragments are selected by the two mass filters of a triple quadrupole instrument and monitored over time for precise quantification. Multiple SRM precursor and fragment ion pairs can be measured within the same experiment on the chromatographic time scale by rapidly toggling between the different precursor/fragment pairs to perform an MRM experiment. A series of transitions (precursor/fragment ion pairs) in combination with the retention time of the targeted analyte (e.g., peptide or small molecule such as chemical entity, steroid, hormone) can constitute a definitive assay. A large number of analytes can be quantified during a single LC-MS experiment. The term "scheduled," or "dynamic" in reference to MRM or SRM, refers to a variation of the assay wherein the transitions for a particular analyte are only acquired in a time window around the expected retention time, significantly increasing the number of analytes that can be detected and quantified in a single LC-MS experiment and contributing to the selectivity of the test, as retention time is a property dependent on the physical nature of the analyte. A single analyte can also be monitored with more than one transition. Finally, included in the assay can be standards that correspond to the analytes of interest (e.g., same amino acid sequence), but differ by the inclusion of stable isotopes. Stable isotopic standards (SIS) can be incorporated into the assay at precise levels and used to quantify the corresponding unknown analyte. An additional level of specificity is contributed by the co-elution of the unknown analyte and its corresponding SIS and properties of their transitions (e.g., the similarity in the ratio of the level of two transitions of the unknown and the ratio of the two transitions of its corresponding SIS).

Mass spectrometry assays, instruments and systems suitable for biomarker peptide analysis can include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$_n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$_n$; ion mobility spectrometry (IMS); inductively coupled plasma mass spectrometry (ICP-MS) atmospheric pressure photoionization mass spectrometry (APPI-MS); APPI-MS/MS; and APPI-(MS)$_n$. Peptide ion fragmentation in tandem MS (MS/MS) arrangements can be achieved using manners established in the art, such as, e.g., collision induced dissociation (CID). As described herein, detection and quantification of biomarkers by mass spectrometry can involve multiple reaction monitoring (MRM), such as described among others by Kuhn et al. *Proteomics* 4: 1175-86 (2004). Scheduled multiple-reaction-monitoring (Scheduled MRM) mode acquisition during LC-MS/MS analysis enhances the sensitivity and accuracy of peptide quantitation. Anderson and Hunter, *Molecular and Cellular Proteomics* 5(4):573 (2006). As described herein, mass spectrometry-based assays can be advantageously combined with upstream peptide or protein separation or fractionation methods, such as for example with the chromatographic and other methods described herein below. As further described herein, shotgun quantitative proteomics can be combined with SRM/MRM-based assays for high-throughput identification and verification of prognostic biomarkers of preterm birth.

A person skilled in the art will appreciate that a number of methods can be used to determine the amount of a biomarker, including mass spectrometry approaches, such as MS/MS, LC-MS/MS, multiple reaction monitoring (MRM) or SRM and product-ion monitoring (PIM) and also including antibody based methods such as immunoassays such as Western blots, enzyme-linked immunosorbant assay (ELISA), immunoprecipitation, immunohistochemistry, immunofluorescence, radioimmunoassay, dot blotting, and FACS. Accordingly, in some embodiments, determining the level of the at least one biomarker comprises using an immunoassay and/or mass spectrometric methods. In additional embodiments, the mass spectrometric methods are selected from MS, MS/MS, LC-MS/MS, SRM, PIM, and other such methods that are known in the art. In other embodiments, LC-MS/MS further comprises 1D LC-MS/MS, 2D LC-MS/MS or 3D LC-MS/MS. Immunoassay techniques and protocols are generally known to those skilled in the art (Price and Newman, *Principles and Practice of Immunoassay*, 2nd Edition, Grove's Dictionaries, 1997; and Gosling, *Immunoassays: A Practical Approach*, Oxford University Press, 2000.) A variety of immunoassay techniques, including competitive and non-competitive immunoassays, can be used (Self et al., *Curr. Opin. Biotechnol.*, 7:60-65 (1996).

In further embodiments, the immunoassay is selected from Western blot, ELISA, immunoprecipitation, immunohistochemistry, immunofluorescence, radioimmunoassay (MA), dot blotting, and FACS. In certain embodiments, the immunoassay is an ELISA. In yet a further embodiment, the ELISA is direct ELISA (enzyme-linked immunosorbent assay), indirect ELISA, sandwich ELISA, competitive ELISA, multiplex ELISA, ELISPOT technologies, and other similar techniques known in the art. Principles of these immunoassay methods are known in the art, for example John R. Crowther, *The ELISA Guidebook*, 1st ed., Humana Press 2000, ISBN 0896037282. Typically ELISAs are performed with antibodies but they can be performed with any capture agents that bind specifically to one or more biomarkers of the invention and that can be detected. Multiplex ELISA allows simultaneous detection of two or more analytes within a single compartment (e.g., microplate well) usually at a plurality of array addresses (Nielsen and Geierstanger 2004. *J Immunol Methods* 290: 107-20 (2004) and Ling et al. 2007. *Expert Rev Mol Diagn* 7: 87-98 (2007)).

In some embodiments, Radioimmunoassay (MA) can be used to detect one or more biomarkers in the methods of the invention. MA is a competition-based assay that is well known in the art and involves mixing known quantities of radioactively-labelled (e.g., $^{125}$I or $^{131}$I-labelled) target analyte with antibody specific for the analyte, then adding non-labeled analyte from a sample and measuring the amount of labeled analyte that is displaced (see, e.g., *An Introduction to Radioimmunoassay and Related Techniques*, by Chard T, ed., Elsevier Science 1995, ISBN 0444821198 for guidance).

A detectable label can be used in the assays described herein for direct or indirect detection of the biomarkers in the methods of the invention. A wide variety of detectable labels can be used, with the choice of label depending on the sensitivity required, ease of conjugation with the antibody, stability requirements, and available instrumentation and disposal provisions. Those skilled in the art are familiar with selection of a suitable detectable label based on the assay detection of the biomarkers in the methods of the invention. Suitable detectable labels include, but are not limited to, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), enzymes (e.g., luciferase, horseradish peroxidase, alkaline phosphatase, etc.), nanoparticles, biotin, digoxigenin, metals, and the like.

For mass-spectrometry based analysis, differential tagging with isotopic reagents, e.g., isotope-coded affinity tags (ICAT) or the more recent variation that uses isobaric tagging reagents, iTRAQ (Applied Biosystems, Foster City, Calif.), or tandem mass tags, TMT, (Thermo Scientific, Rockford, Ill.), followed by multidimensional liquid chromatography (LC) and tandem mass spectrometry (MS/MS) analysis can provide a further methodology in practicing the methods of the invention.

A chemiluminescence assay using a chemiluminescent antibody can be used for sensitive, non-radioactive detection of protein levels. An antibody labeled with fluorochrome also can be suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), beta-galactosidase, urease, and the like. Detection systems using suitable substrates for horseradish-peroxidase, alkaline phosphatase, and beta-galactosidase are well known in the art.

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, assays used to practice the invention can be automated or performed robotically, and the signal from multiple samples can be detected simultaneously.

In some embodiments, the methods described herein encompass quantification of the biomarkers using mass spectrometry (MS). In further embodiments, the mass spectrometry can be liquid chromatography-mass spectrometry (LC-MS), multiple reaction monitoring (MRM) or selected reaction monitoring (SRM). In additional embodiments, the MRM or SRM can further encompass scheduled MRM or scheduled SRM.

As described above, chromatography can also be used in practicing the methods of the invention. Chromatography encompasses methods for separating chemical substances and generally involves a process in which a mixture of analytes is carried by a moving stream of liquid or gas ("mobile phase") and separated into components as a result of differential distribution of the analytes as they flow around or over a stationary liquid or solid phase ("stationary phase"), between the mobile phase and said stationary phase. The stationary phase can be usually a finely divided solid, a sheet of filter material, or a thin film of a liquid on the surface of a solid, or the like. Chromatography is well understood by those skilled in the art as a technique applicable for the separation of chemical compounds of biological origin, such as, e.g., amino acids, proteins, fragments of proteins or peptides, etc.

Chromatography can be columnar (i.e., wherein the stationary phase is deposited or packed in a column), preferably liquid chromatography, and yet more preferably high-performance liquid chromatography (HPLC), or ultra high performance/pressure liquid chromatography (UHPLC). Particulars of chromatography are well known in the art (Bidlingmeyer, *Practical HPLC Methodology and Applications*, John Wiley & Sons Inc., 1993). Exemplary types of chromatography include, without limitation, high-performance liquid chromatography (HPLC), UHPLC, normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilized metal affinity chromatography, and the like. Chromatography, including single-, two- or more-dimensional chromatography, can be used as a peptide fractionation method in conjunction with a further peptide analysis method, such as for example, with a downstream mass spectrometry analysis as described elsewhere in this specification.

Further peptide or polypeptide separation, identification or quantification methods can be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In the context of the invention, the term "capture agent" refers to a compound that can specifically bind to a target, in particular a biomarker. The term includes antibodies, antibody fragments, nucleic acid-based protein binding reagents (e.g. aptamers, Slow Off-rate Modified Aptamers (SOMAmer™)), protein-capture agents, natural ligands (i.e. a hormone for its receptor or vice versa), small molecules or variants thereof.

Capture agents can be configured to specifically bind to a target, in particular a biomarker. Capture agents can include but are not limited to organic molecules, such as polypeptides, polynucleotides and other non polymeric molecules that are identifiable to a skilled person. In the embodiments disclosed herein, capture agents include any agent that can be used to detect, purify, isolate, or enrich a target, in particular a biomarker. Any art-known affinity capture technologies can be used to selectively isolate and enrich/concentrate biomarkers that are components of complex mixtures of biological media for use in the disclosed methods.

Antibody capture agents that specifically bind to a biomarker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986). Antibody capture agents can be any immunoglobulin or derivative thereof, whether natural or wholly or partially synthetically produced. All derivatives thereof which maintain specific binding ability are also included in the term. Antibody capture agents have a binding domain that is homologous or largely homologous to an immunoglobulin binding domain and can be derived from natural sources, or partly or wholly synthetically produced. Antibody capture agents can be monoclonal or polyclonal antibodies. In some embodiments, an antibody is a single chain antibody. Those of ordinary skill in the art will appreciate that antibodies can be provided in any of a variety of forms including, for example, humanized, partially humanized, chimeric, chimeric humanized, etc. Antibody capture agents can be antibody fragments including, but not limited to, Fab, Fab', F(ab')2, scFv, Fv, dsFv diabody, and Fd fragments. An antibody capture agent can be produced by any means. For example, an antibody capture agent can be enzymatically or chemically produced by fragmentation of an intact antibody and/or it can be recombinantly produced from a gene encoding the partial antibody sequence. An antibody capture agent can comprise a single chain antibody fragment. Alternatively or additionally, antibody capture agent can comprise multiple chains which are linked together, for example, by disulfide linkages; and, any functional fragments obtained from such molecules, wherein such fragments retain specific-binding properties of the parent antibody molecule. Because of their smaller size as functional components of the whole molecule, antibody fragments can offer advantages over intact antibodies for use in certain immunochemical techniques and experimental applications.

Suitable capture agents useful for practicing the invention also include aptamers. Aptamers are oligonucleotide sequences that can bind to their targets specifically via unique three dimensional (3-D) structures. An aptamer can include any suitable number of nucleotides and different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Use of an aptamer capture agent can include the use of two or more aptamers that specifically bind the same biomarker. An aptamer can include a tag. An aptamer can be identified using any known method, including the SELEX (systematic evolution of ligands by exponential enrichment), process. Once identified, an aptamer can be prepared or synthesized in accordance with any known method, including chemical synthetic methods and enzymatic synthetic methods and used in a variety of applications for biomarker detection. Liu et al., *Curr Med Chem.* 18(27):4117-25 (2011). Capture agents useful in practicing the methods of the invention also include SOMAmers (Slow Off-Rate Modified Aptamers) known in the art to have improved off-rate characteristics. Brody et al., *J Mol Biol.* 422(5):595-606 (2012). SOMAmers can be generated using any known method, including the SELEX method.

It is understood by those skilled in the art that biomarkers can be modified prior to analysis to improve their resolution or to determine their identity. For example, the biomarkers can be subject to proteolytic digestion before analysis. Any protease can be used. Proteases, such as trypsin, that are likely to cleave the biomarkers into a discrete number of fragments are particularly useful. The fragments that result from digestion function as a fingerprint for the biomarkers, thereby enabling their detection indirectly. This is particularly useful where there are biomarkers with similar molecular masses that might be confused for the biomarker in question. Also, proteolytic fragmentation is useful for high molecular weight biomarkers because smaller biomarkers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the biomarkers can be modified by the attachment of a tag of particular molecular weight that specifically binds to molecular biomarkers, further distinguishing them. Optionally, after detecting such modified biomarkers, the identity of the biomarkers can be further determined by matching the physical and chemical characteristics of the modified biomarkers in a protein database (e.g., SwissProt).

It is further appreciated in the art that biomarkers in a sample can be captured on a substrate for detection. Traditional substrates include antibody-coated 96-well plates or nitrocellulose membranes that are subsequently probed for the presence of the proteins. Alternatively, protein-binding molecules attached to microspheres, microparticles, microbeads, beads, or other particles can be used for capture and detection of biomarkers. The protein-binding molecules can be antibodies, peptides, peptoids, aptamers, small molecule ligands or other protein-binding capture agents attached to the surface of particles. Each protein-binding molecule can include unique detectable label that is coded such that it can be distinguished from other detectable labels attached to other protein-binding molecules to allow detection of biomarkers in multiplex assays. Examples include, but are not limited to, color-coded microspheres with known fluorescent light intensities (see e.g., microspheres with xMAP technology produced by Luminex (Austin, Tex.); microspheres containing quantum dot nanocrystals, for example, having different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, Calif.); chemiluminescent dyes, combinations of dye compounds; and beads of detectably different sizes.

In another aspect, biochips can be used for capture and detection of the biomarkers of the invention. Many protein biochips are known in the art. These include, for example, protein biochips produced by Packard BioScience Company (Meriden Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture agent bound there. The capture agent can be a biological molecule, such as a polypeptide or a nucleic acid, which captures other biomarkers in a specific manner. Alternatively, the capture agent can be a chromatographic material, such as an anion exchange material or a hydrophilic material. Examples of protein biochips are well known in the art.

The present disclosure also provides methods for predicting the probability of pre-term birth comprising measuring a change in reversal value of a biomarker pair. For example, a biological sample can be contacted with a panel comprising one or more polynucleotide binding agents. The expression of one or more of the biomarkers detected can then be evaluated according to the methods disclosed below, e.g., with or without the use of nucleic acid amplification methods. Skilled practitioners appreciate that in the methods described herein, a measurement of gene expression can be automated. For example, a system that can carry out multiplexed measurement of gene expression can be used, e.g., providing digital readouts of the relative abundance of hundreds of mRNA species simultaneously.

In some embodiments, nucleic acid amplification methods can be used to detect a polynucleotide biomarker. For example, the oligonucleotide primers and probes of the present invention can be used in amplification and detection methods that use nucleic acid substrates isolated by any of a variety of well-known and established methodologies (e.g., Sambrook et al., Molecular Cloning, A laboratory Manual, pp. 7.37-7.57 (2nd ed., 1989); Lin et al., in Diagnostic Molecular Microbiology, Principles and Applications, pp. 605-16 (Persing et al., eds. (1993); Ausubel et al., Current Protocols in Molecular Biology (2001 and subsequent updates)). Methods for amplifying nucleic acids include, but are not limited to, for example the polymerase chain reaction (PCR) and reverse transcription PCR (RT-PCR) (see e.g., U.S. Pat. Nos. 4,683,195; 4,683,202; 4,800,159; 4,965,188), ligase chain reaction (LCR) (see, e.g., Weiss, Science 254:1292-93 (1991)), strand displacement amplification (SDA) (see e.g., Walker et al., Proc. Natl. Acad. Sci. USA 89:392-396 (1992); U.S. Pat. Nos. 5,270,184 and 5,455,166), Thermophilic SDA (tSDA) (see e.g., European Pat. No. 0 684 315) and methods described in U.S. Pat. No. 5,130,238; Lizardi et al., BioTechnol. 6:1197-1202 (1988); Kwoh et al., Proc. Natl. Acad. Sci. USA 86:1173-77 (1989); Guatelli et al., Proc. Natl. Acad. Sci. USA 87:1874-78 (1990); U.S. Pat. Nos. 5,480,784; 5,399,491; US Publication No. 2006/46265.

In some embodiments, measuring mRNA in a biological sample can be used as a surrogate for detection of the level of the corresponding protein biomarker in a biological sample. Thus, any of the biomarkers, biomarker pairs or biomarker reversal panels described herein can also be detected by detecting the appropriate RNA. Levels of mRNA can measured by reverse transcription quantitative polymerase chain reaction (RT-PCR followed with qPCR). RT-PCR is used to create a cDNA from the mRNA. The cDNA can be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See *Gene Expression Profiling: Methods and Protocols*, Richard A. Shimkets, editor, Humana Press, 2004.

Some embodiments disclosed herein relate to diagnostic and prognostic methods of determining the probability for preterm birth in a pregnant female. The detection of the level of expression of one or more biomarkers and/or the determination of a ratio of biomarkers can be used to determine the probability for preterm birth in a pregnant female. Such detection methods can be used, for example, for early diagnosis of the condition, to determine whether a subject is predisposed to preterm birth, to monitor the progress of preterm birth or the progress of treatment protocols, to assess the severity of preterm birth, to forecast the outcome of preterm birth and/or prospects of recovery or birth at full term, or to aid in the determination of a suitable treatment for preterm birth.

The quantitation of biomarkers in a biological sample can be determined, without limitation, by the methods described above as well as any other method known in the art. The quantitative data thus obtained is then subjected to an analytic classification process. In such a process, the raw data is manipulated according to an algorithm, where the algorithm has been pre-defined by a training set of data, for example as described in the examples provided herein. An algorithm can utilize the training set of data provided herein, or can utilize the guidelines provided herein to generate an algorithm with a different set of data.

In some embodiments, analyzing a measurable feature to determine the probability for preterm birth in a pregnant female encompasses the use of a predictive model. In further embodiments, analyzing a measurable feature to determine the probability for preterm birth in a pregnant female encompasses comparing said measurable feature with a reference feature. As those skilled in the art can appreciate, such comparison can be a direct comparison to the reference feature or an indirect comparison where the reference feature has been incorporated into the predictive model. In further embodiments, analyzing a measurable feature to determine the probability for preterm birth in a pregnant female encompasses one or more of a linear discriminant analysis model, a support vector machine classification algorithm, a recursive feature elimination model, a prediction analysis of microarray model, a logistic regression model, a CART algorithm, a flex tree algorithm, a LART algorithm, a random forest algorithm, a MART algorithm, a machine learning algorithm, a penalized regression method, or a combination thereof. In particular embodiments, the analysis comprises logistic regression.

An analytic classification process can use any one of a variety of statistical analytic methods to manipulate the quantitative data and provide for classification of the sample. Examples of useful methods include linear discriminant analysis, recursive feature elimination, a prediction analysis of microarray, a logistic regression, a CART algorithm, a FlexTree algorithm, a LART algorithm, a random forest algorithm, a MART algorithm, machine learning algorithms; etc.

For creation of a random forest for prediction of GAB one skilled in the art can consider a set of k subjects (pregnant women) for whom the gestational age at birth (GAB) is known, and for whom N analytes (transitions) have been measured in a blood specimen taken several weeks prior to birth. A regression tree begins with a root node that contains all the subjects. The average GAB for all subjects can be calculated in the root node. The variance of the GAB within the root node will be high, because there is a mixture of women with different GAB's. The root node is then divided (partitioned) into two branches, so that each branch contains women with a similar GAB. The average GAB for subjects in each branch is again calculated. The variance of the GAB within each branch will be lower than in the root node, because the subset of women within each branch has relatively more similar GAB's than those in the root node. The two branches are created by selecting an analyte and a threshold value for the analyte that creates branches with similar GAB. The analyte and threshold value are chosen from among the set of all analytes and threshold values, usually with a random subset of the analytes at each node. The procedure continues recursively producing branches to create leaves (terminal nodes) in which the subjects have very similar GAB's. The predicted GAB in each terminal node is the average GAB for subjects in that terminal node. This procedure creates a single regression tree. A random forest can consist of several hundred or several thousand such trees.

Classification can be made according to predictive modeling methods that set a threshold for determining the probability that a sample belongs to a given class. The probability preferably is at least 50%, or at least 60%, or at least 70%, or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUROC (area under the ROC curve) or accuracy, of a particular value, or range of values. Area under the curve measures are useful for comparing the accuracy of a classifier across the complete data range. Classifiers with a greater AUC have a greater capacity to classify unknowns correctly between two groups of interest. In some embodiments, a desired quality threshold is a predictive model that will classify a sample with an accuracy of at least about 0.5, at least about 0.55, at least about 0.6, at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be adjusted to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about 0.7, at least about 0.75, at least about 0.8, at least about 0.85, at least about 0.9, or higher.

The raw data can be initially analyzed by measuring the values for each biomarker, usually in triplicate or in multiple triplicates. The data can be manipulated, for example, raw data can be transformed using standard curves, and the average of triplicate measurements used to calculate the average and standard deviation for each patient. These values can be transformed before being used in the models, e.g. log-transformed, Box-Cox transformed (Box and Cox, *Royal Stat. Soc.*, Series B, 26:211-246(1964). The data are then input into a predictive model, which will classify the sample according to the state. The resulting information can be communicated to a patient or health care provider.

To generate a predictive model for preterm birth, a robust data set, comprising known control samples and samples corresponding to the preterm birth classification of interest is used in a training set. A sample size can be selected using generally accepted criteria. As discussed above, different statistical methods can be used to obtain a highly accurate predictive model. Examples of such analysis are provided in Example 2.

In one embodiment, hierarchical clustering is performed in the derivation of a predictive model, where the Pearson correlation is employed as the clustering metric. One approach is to consider a preterm birth dataset as a "learning sample" in a problem of "supervised learning." CART is a standard in applications to medicine (Singer, *Recursive Partitioning in the Health Sciences*, Springer (1999)) and can be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

This approach led to what is termed FlexTree (Huang, *Proc. Nat. Acad. Sci. U.S.A* 101:10529-10534(2004)). FlexTree performs very well in simulations and when applied to multiple forms of data and is useful for practicing the claimed methods. Software automating FlexTree has been developed. Alternatively, LARTree or LART can be used (Turnbull (2005) *Classification Trees with Subset Analysis Selection by the Lasso*, Stanford University). The name reflects binary trees, as in CART and FlexTree; the lasso, as has been noted; and the implementation of the lasso through what is termed LARS by Efron et al. (2004) *Annals of Statistics* 32:407-451 (2004). See, also, Huang et al., *Proc. Natl. Acad. Sci. USA.* 101(29):10529-34 (2004). Other methods of analysis that can be used include logic regression. One method of logic regression Ruczinski, *Journal of Computational and Graphical Statistics* 12:475-512 (2003). Logic regression resembles CART in that its classifier can be displayed as a binary tree. It is different in that each node has Boolean statements about features that are more general than the simple "and" statements produced by CART.

Another approach is that of nearest shrunken centroids (Tibshirani, *Proc. Natl. Acad. Sci. U.S.A* 99:6567-72(2002)). The technology is k-means-like, but has the advantage that by shrinking cluster centers, one automatically selects features, as is the case in the lasso, to focus attention on small numbers of those that are informative. The approach is available as PAM software and is widely used. Two further sets of algorithms that can be used are random forests (Breiman, *Machine Learning* 45:5-32 (2001)) and MART (Hastie, *The Elements of Statistical Learning*, Springer (2001)). These two methods are known in the art as "committee methods," that involve predictors that "vote" on outcome.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (Tusher et al., *Proc. Natl. Acad. Sci. U.S.A* 98, 5116-21 (2001)). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles. Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pair wise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

In an alternative analytical approach, variables chosen in the cross-sectional analysis are separately employed as predictors in a time-to-event analysis (survival analysis), where the event is the occurrence of preterm birth, and subjects with no event are considered censored at the time of giving birth. Given the specific pregnancy outcome (preterm birth event or no event), the random lengths of time each patient will be observed, and selection of proteomic and other features, a parametric approach to analyzing survival can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and corresponding functions are available with this model.

In addition the Cox models can be used, especially since reductions of numbers of covariates to manageable size with the lasso will significantly simplify the analysis, allowing the possibility of a nonparametric or semi-parametric approach to prediction of time to preterm birth. These statistical tools are known in the art and applicable to all manner of proteomic data. A set of biomarker, clinical and genetic data that can be easily determined, and that is highly informative regarding the probability for preterm birth and predicted time to a preterm birth event in said pregnant female is provided. Also, algorithms provide information regarding the probability for preterm birth in the pregnant female.

Accordingly, one skilled in the art understands that the probability for preterm birth according to the invention can be determined using either a quantitative or a categorical variable. For example, in practicing the methods of the invention the measurable feature of each of N biomarkers can be subjected to categorical data analysis to determine the probability for preterm birth as a binary categorical outcome. Alternatively, the methods of the invention may analyze the measurable feature of each of N biomarkers by initially calculating quantitative variables, in particular, predicted gestational age at birth. The predicted gestational age at birth can subsequently be used as a basis to predict risk of preterm birth. By initially using a quantitative variable and subsequently converting the quantitative variable into a categorical variable the methods of the invention take into account the continuum of measurements detected for the measurable features. For example, by predicting the gestational age at birth rather than making a binary prediction of preterm birth versus term birth, it is possible to tailor the treatment for the pregnant female. For example, an earlier predicted gestational age at birth will result in more intensive prenatal intervention, i.e. monitoring and treatment, than a predicted gestational age that approaches full term.

Among women with a predicted GAB of j days plus or minus k days, p(PTB) can estimated as the proportion of women in the PAPR clinical trial (see Example 1) with a predicted GAB of j days plus or minus k days who actually deliver before 37 weeks gestational age. More generally, for women with a predicted GAB of j days plus or minus k days, the probability that the actual gestational age at birth will be less than a specified gestational age, p(actual GAB<specified GAB), was estimated as the proportion of women in the PAPR clinical trial with a predicted GAB of j days plus or minus k days who actually deliver before the specified gestational age.

In the development of a predictive model, it can be desirable to select a subset of markers, i.e. at least 3, at least 4, at least 5, at least 6, up to the complete set of markers. Usually a subset of markers will be chosen that provides for the needs of the quantitative sample analysis, e.g. availability of reagents, convenience of quantitation, etc., while maintaining a highly accurate predictive model. The selection of a number of informative markers for building classification models requires the definition of a performance metric and a user-defined threshold for producing a model with useful predictive ability based on this metric. For example, the performance metric can be the AUC, the sensitivity and/or specificity of the prediction as well as the overall accuracy of the prediction model.

As will be understood by those skilled in the art, an analytic classification process can use any one of a variety of statistical analytic methods to manipulate the quantitative data and provide for classification of the sample. Examples of useful methods include, without limitation, linear discriminant analysis, recursive feature elimination, a prediction analysis of microarray, a logistic regression, a CART algorithm, a FlexTree algorithm, a LART algorithm, a random forest algorithm, a MART algorithm, and machine learning algorithms. Various methods are used in a training model. The selection of a subset of markers can be for a forward selection or a backward selection of a marker subset. The number of markers can be selected that will optimize the performance of a model without the use of all the markers. One way to define the optimum number of terms is to choose the number of terms that produce a model with desired predictive ability (e.g. an AUC>0.75, or equivalent measures of sensitivity/specificity) that lies no more than one standard error from the maximum value obtained for this metric using any combination and number of terms used for the given algorithm.

In yet another aspect, the invention provides kits for determining probability of preterm birth. The kit can include one or more agents for detection of biomarkers, a container for holding a biological sample isolated from a pregnant female; and printed instructions for reacting agents with the biological sample or a portion of the biological sample to detect the presence or amount of the isolated biomarkers in the biological sample. The agents can be packaged in separate containers. The kit can further comprise one or more control reference samples and reagents for performing an immunoassay.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of determining probability of preterm birth.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1. Development of Sample Set for Discovery and Validation of Biomarkers for Preterm Birth A standard protocol was developed governing conduct of the Proteomic Assessment of Preterm Risk (PAPR) clinical study. Specimens were obtained from women at 11 Institutional Review Board (IRB) approved sites across the United States. After providing informed consent, serum and plasma samples were obtained, as well as pertinent information regarding the patient's demographic characteristics, past medical and pregnancy history, current pregnancy history and concurrent medications. Following delivery, data were collected relating to maternal and infant conditions and complications. Serum and plasma samples were processed according to a protocol that requires standardized refrigerated centrifugation, aliquoting of the samples into 2-D bar-coded cryovials and subsequent freezing at −80° C.

Following delivery, preterm birth cases were individually reviewed to determine their status as either a spontaneous preterm birth or a medically indicated preterm birth. Only spontaneous preterm birth cases were used for this analysis. For discovery of biomarkers of preterm birth, serum samples from 86 preterm cases and 172 controls were analyzed covering gestational ages at blood draw (GABD) of 17 weeks and 0 days (17.0) to 28 weeks and 6 days (28.6). A separate sample set was also analyzed for purposes of verification and was composed of serum from 50 preterm cases and 100 controls, across the same gestational age range. The two controls for each case were matched by GABD and selected from several randomly generated panels of controls that matched the distribution of births reported in the 2012 National Vital Statistics Report. A protocol was instituted to ensure that laboratory staff were blinded to gestation age at birth and case vs control status of subjects used for both sample sets. Informatics staff were also blinded to the verification sample set until analytical analysis of samples was complete.

Serum samples were depleted of high abundance proteins using the Human 14 Multiple Affinity Removal System (MARS 14), which removes 14 of the most abundant proteins that are treated as uninformative with regard to the identification for disease-relevant changes in the serum proteome. To this end, equal volumes (50 µl) of each clinical, pooled human serum sample (HGS) sample, or a human pooled pregnant women serum sample (pHGS) were diluted with 150 µl Agilent column buffer A and filtered on a Captiva filter plate to remove precipitates. Filtered samples were depleted using a MARS-14 column (4.6×100 mm, Cat. #5188-6558, Agilent Technologies), according to manufacturer's protocol. Samples were chilled to 4° C. in the autosampler, the depletion column was run at room temperature, and collected fractions were kept at 4° C. until further analysis. The unbound fractions were collected for further analysis.

Depleted serum samples were, reduced with dithiothreitol, alkylated using iodoacetamide, and then digested with 5.0 µg Trypsin Gold—Mass Spec Grade (Promega) at 37° C. for 17 hours (±1 hour). Following trypsin digestion, a mixture of 187 Stable Isotope Standard (SIS) peptides were added to the samples and half of each sample was desalted on an Empore C18 96-well Solid Phase Extraction Plate (3M Bioanalytical Technologies). The plate was conditioned according to the manufacture's protocol. Peptides were washed with 300 µl 1.5% trifluoroacetic acid, 2% acetonitrile, eluted with 250 µl 1.5% trifluoroacetic acid, 95% acetonitrile, frozen at −80° C. for 30 minutes, and then lyophilized to dryness. Lyophilized peptides were reconstituted with 2% acetonitrile/0.1% formic acid containing three non-human internal standard (IS) peptides. Peptides were separated with a 30 min acetonitrile gradient at 400 µl/min on an Agilent Poroshell 120 EC-C18 column (2.1×100 mm, 2.7 µm) at 40° C. and injected into an Agilent 6490 Triple Quadrapole mass spectrometer.

Depleted and trypsin digested samples were analyzed using a scheduled Multiple Reaction Monitoring method (sMRM). The sMRM assay monitored 898 transitions that measured 259 biological peptides and 190 IS peptides (187 SIS+3 IS), representing 148 proteins. Chromatographic peaks were integrated using Mass Hunter Quantitative Analysis software (Agilent Technologies).

Data Analysis

Analysis of discovery and verification sample data was performed in two phases. In the first phase robust biomarkers were identified by selection using the discovery samples and confirmation using the independent verification sample set. In the second phase the discovery and verification data were combined and used to identify best analytes and panels of analytes for classifier development.

Phase I: Blinded Analysis

Initial classifier development focused on gestational ages 17.0 to 25.6. Using discovery samples a set of peptides corresponding to 62 proteins were selected based on pre-analytic and analytic criteria. Analyte diagnostic performance was assessed in a series of narrow GABD windows that span three weeks with two weeks of overlap between adjacent windows. Based on consistency in diagnostic performance (up and down regulation in cases vs controls across GABD), a subset of 43 analytes was selected for further analysis.

For each narrow GABD window a set of reversals was formed using all the combinations of up and down regulated analytes within the narrow window. A reversal value is the ratio of the relative peak area of an up regulated analyte over the relative peak area of a down regulated analyte and serves to both normalize variability and amplify diagnostic signal. Out of all the possible reversals within a narrow window, a subset was selected based on their individual univariate performance (AUC>=0.6).

For each window reversal panels of varying sizes were formed (sizes of 2, 3, 4, 6, 8). For each panel size within a window, a Monte Carlo Cross Validation (MCCV) was performed by training and testing a logistic classifier iteratively 1,000 times on 70% and 30% of the samples, respectively. A panel size of 4, determined to be optimal by mean MCCV AUC, was subsequently used for identification of candidate reversals that perform well on panels. Candidate reversals were identified by frequency of occurrence on top performing logistic classifiers of panels of size 4 in MCCV analysis. For each window, three sets of reversal frequency tables were created using performance measures of either AUC, or partial AUC (pAUC) for sensitivity ranging from 0.7 to 1, or correlation of the classifier output score to time to birth value (TTB) (difference in days between GABD and gestational age at birth). From each of these reversal lists, the top 15 reversals were selected for further analysis.

For each GABD narrow window, reversal panels of size 2, 3, 4 were formed from each of the three lists (AUC, pAUC, and TTB) and based on the performance of a MCCV analysis, the top 15 panels for each panel size in each window were selected. Along with the top 15 reversals from each of the three lists (AUC, pAUC, and TTB) for each window, these top 15 panels of size 2, 3, 4, were used to train logistic classifiers on the discovery samples and the classification scores were generated for verification samples in a blinded fashion.

A third party statistician assessed the performance of all reversals and classifier panels and the AUC, pAUC for ROC curves and the TTB correlation of the classifier scores were reported.

Phase II: Unblinded Analysis

Figures 3A, 3B, 3C:
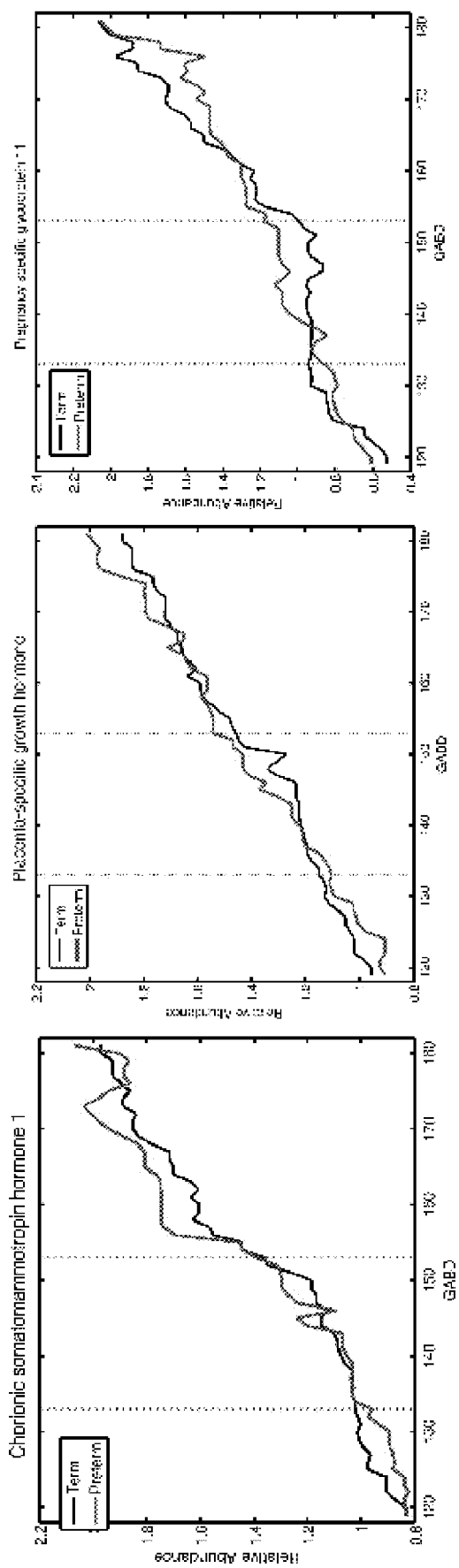
FIGS. 3A-3C. Protein expression during pregnancy. Various proteins can be analyzed based on known protein behavior and knowing proteins/pathways that are not affected by preterm birth.
Figure 4:
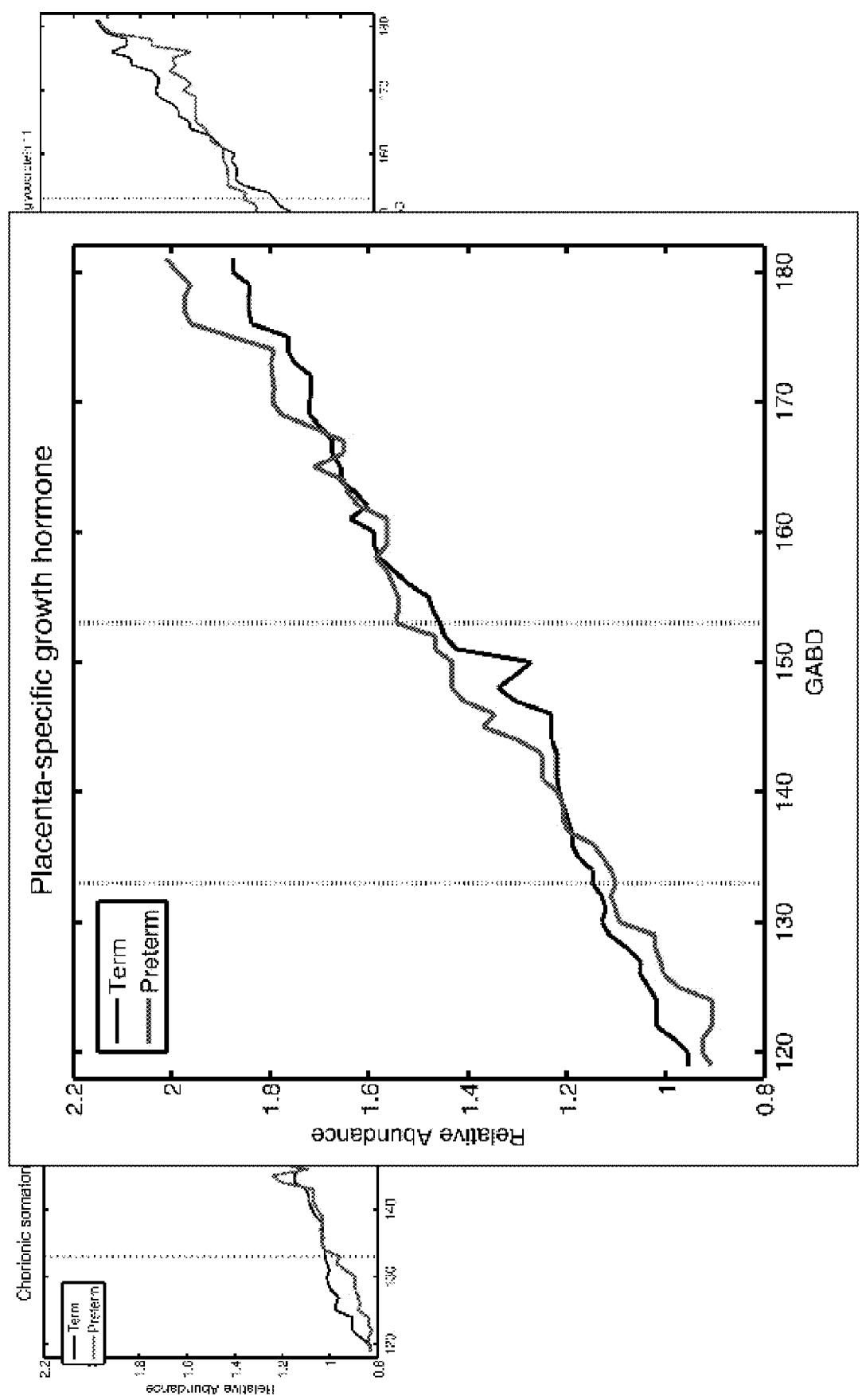
FIG. 4. Protein expression during pregnancy.
Figure 5B:
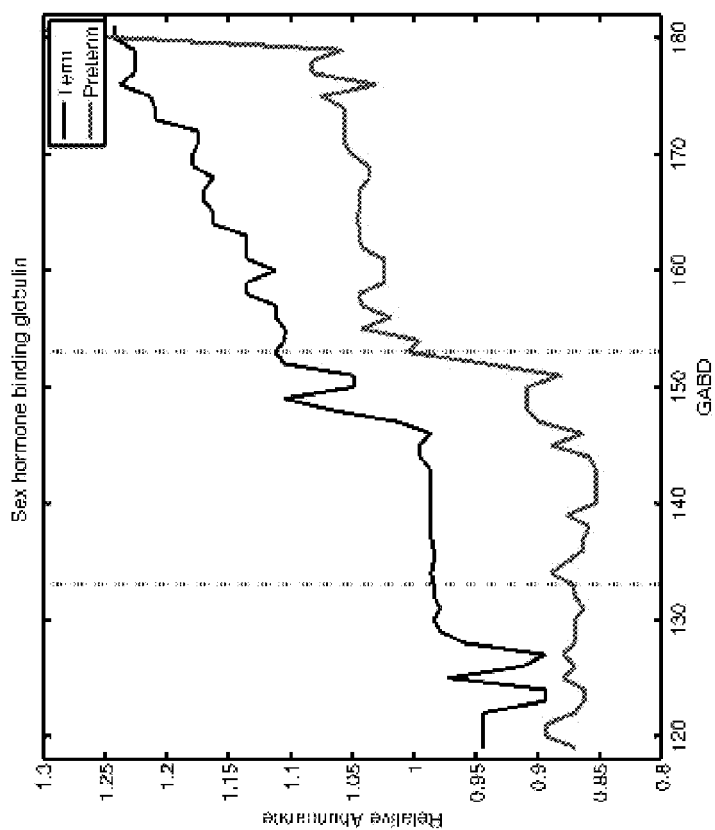
FIGS. 5A-5B. Protein pathology during pregnancy. Insulin-like growth factor binding protein 4 (IBP4) was over-expressed by at least 10% in blood draw window 19-21 weeks. Sex hormone binding globulin (SHBG) was under-expressed by at least 10% in blood draw window 19-21 weeks.
Figure 5A:
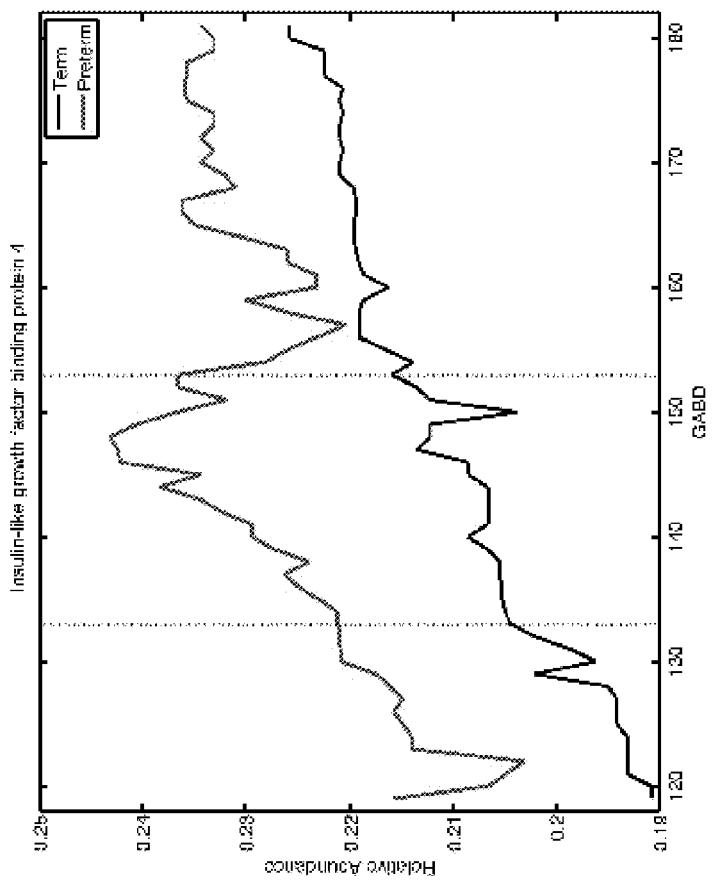
Figure 7:
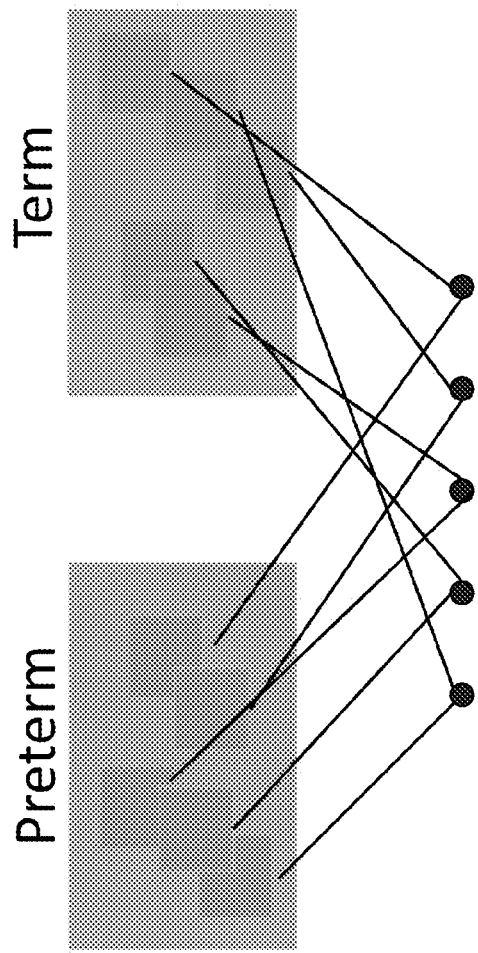
FIG. 7. Monte Carlo Cross Validation (MCVV). MCCV is a conservative method that estimates how well a classifier will perform on an independent set of samples drawn from the same population (e.g. PAPR).
Figure 8:
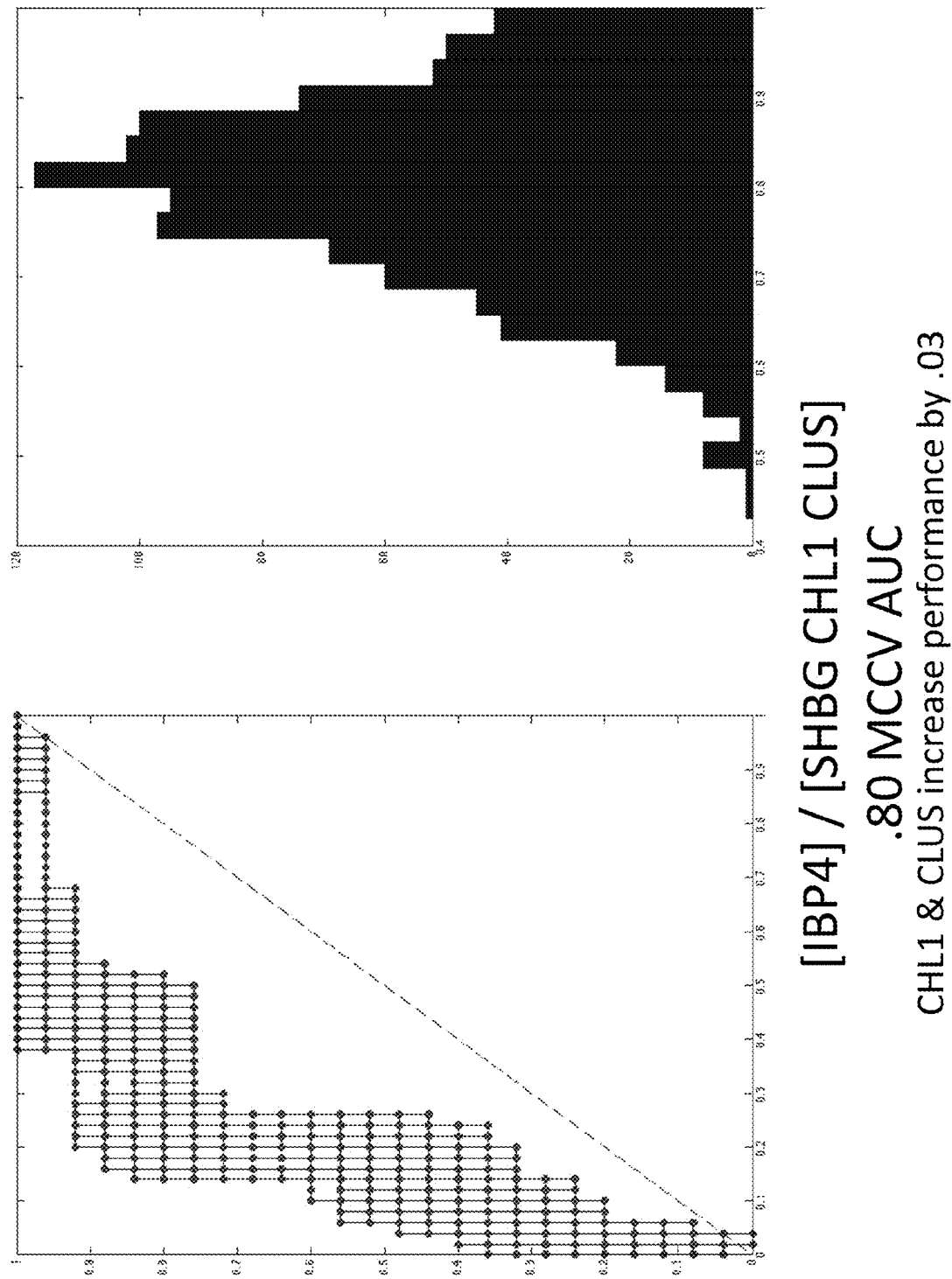
FIG. 8. Analysis of [IBP4]/[SHBG CHL1 CLUS]. CHL1 and CLUS increased performance by 0.03 relative to IBP4/SHBG only.
Figure 21:
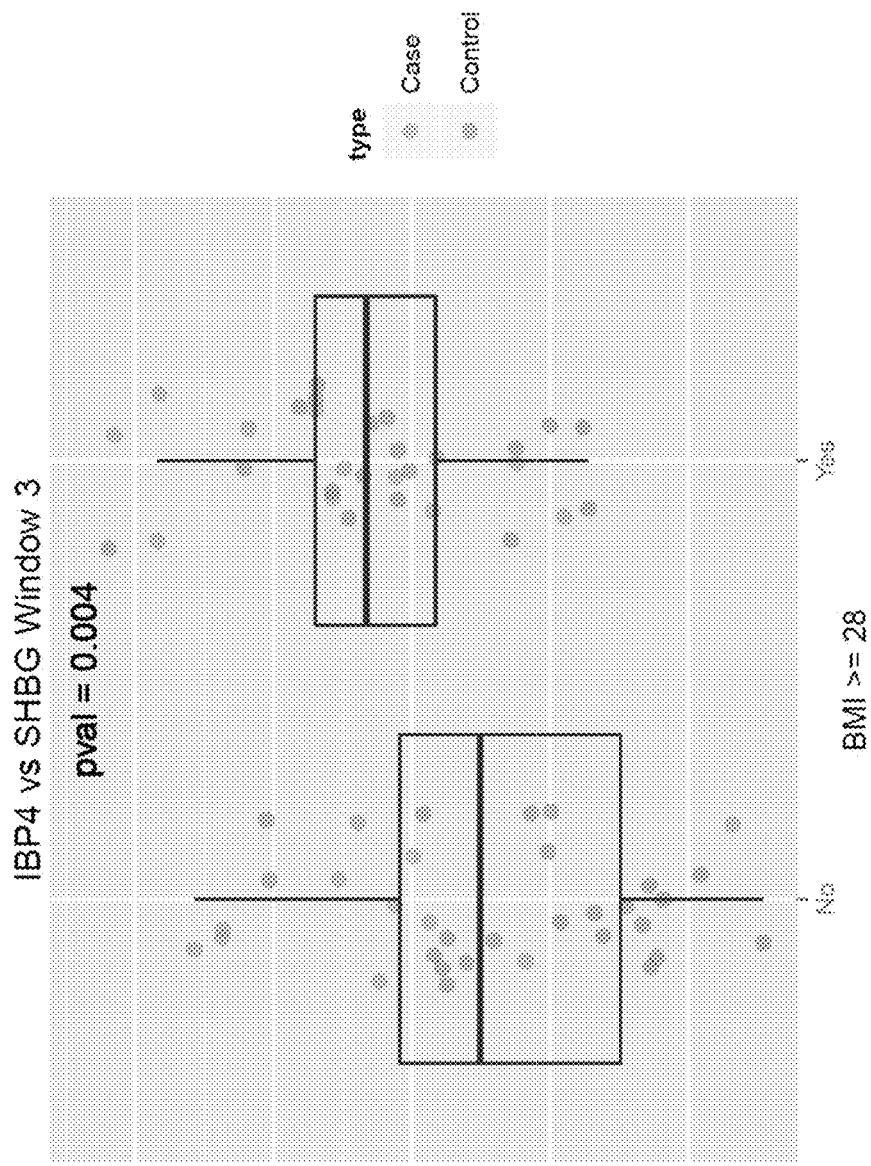
FIG. 21. PTB classification by IBP4/SHBG in discovery samples from 19-21 weeks GABD. Discovery samples for weeks 19-21 of gestation were divided by high and low BMI. IBP4/SHBG reversal values are higher in the high BMI category due to lower SHBG values. Separation of cases and controls is greater at lower BMI.
Figure 22:
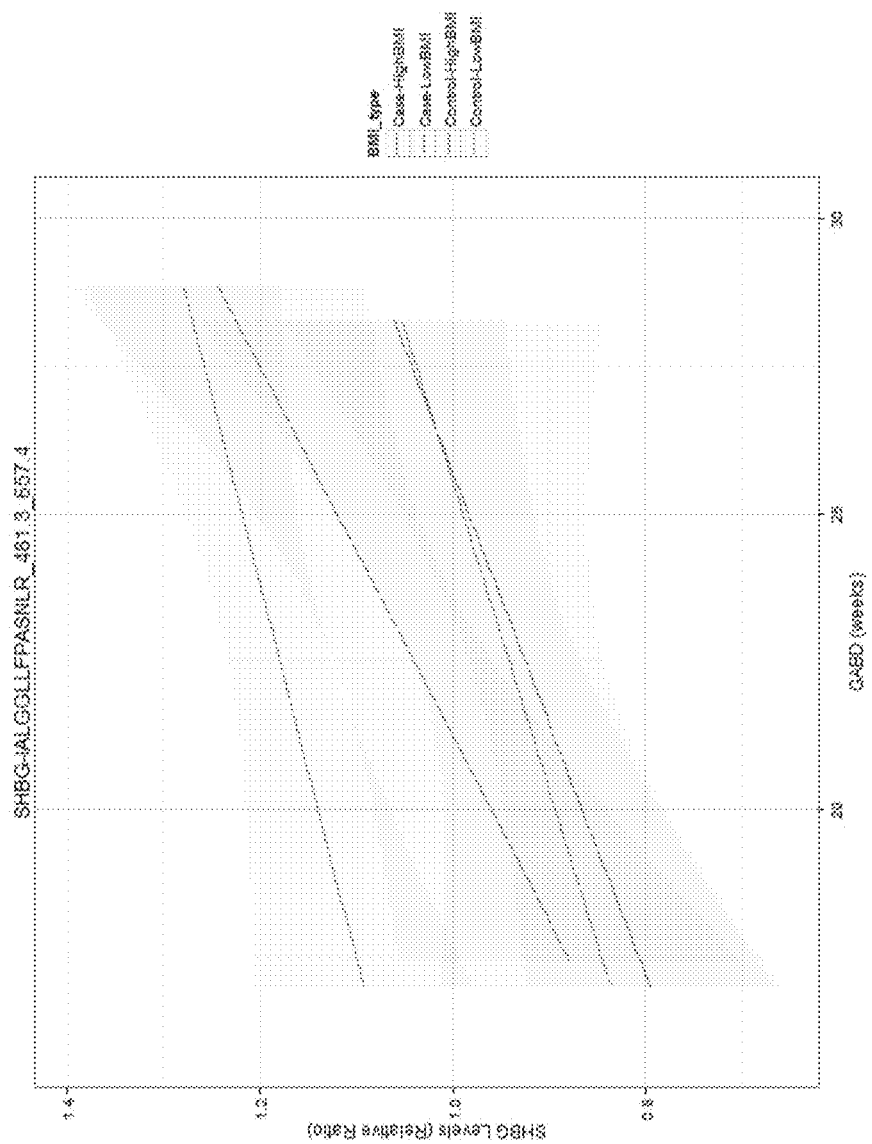
FIG. 22. Suppressed SHBG levels in PTB cases at low BMI. Linear fits of SHBG serum levels in PAPR subjects across GABD. SHBG levels are suppressed by high BMI. SHBG levels increase across gestation. PTB cases at low BMI have reduced SHBG levels that increase across gestation at an accelerated rate. Figure discloses SEQ ID NO:18.

Following unblinding, discovery and verification data sets were combined and reanalyzed. Because the expression of diagnostic proteins may change across pregnancy we examined the levels of proteins as a function of GABD. A median smoothing window of +/−10 days was applied to generate the kinetic plots. Relative levels of proteins were expressed as the ratio of the endogenous peptide peak area over its corresponding SIS standard (relative ratio). Examples of proteins with levels that increase in pregnancy but are not different in PTB cases and controls are shown in FIGS. 3, 4 and 10. Measurement of the levels of such proteins could be useful in accurate dating of pregnancy (e.g. a pregnancy "clock"). The pregnancy clock predicts gestational age from the relative abundance of one or more proteins (transitions). Alternatively, in this same analysis we identified proteins whose levels change across GABD but show differences between PTB cases and controls FIG. 5. These proteins are obvious diagnostic candidates for PTB classifier development. The impact of forming a reversal using the ratio of an overexpressed protein over that of an underexpressed protein was also exemplified (FIGS. 8 and 21). It is clear that this results in an increase in separation of PTB cases and controls. Previous analysis suggested that levels of some analytes may be influenced by pre-pregnancy body weight index (BMI). CLIN. CHEM. 37/5, 667-672 (1991); European Journal of Endocrinology (2004) 150 161-171. For this reason the impact of BMI on separation was explored by expressing the reversal value across gestation in only those patients whose BMI is less than 35 (FIG. 21). This results in a further improvement in separation.

Reversal selection and classifier development in the combined discovery and verification data set mirrored earlier studies. We focused on the 3rd overlapping GABD window (Days 133-153) to exemplify analysis. MCCV analysis was performed to identify candidate reversals. To assess performance of panels, reversal values were combined in a simple LogSum classifier. The LogSum classifier assigns a score to each sample based on the sum of the logs of each reversal's relative ratio value for that sample. The lack of coefficients in a classifier of this type helps to avoid problems of overfitting. Anyone skilled in the art can derive an equivalent logistic classifier using the same analytes with well-established techniques. Multivariate performance of a panel of three top reversals formed from four proteins is shown as a histogram of AUC values obtained by cross validation and in ROC curves in FIG. 8. Previous analysis suggested that levels of some analytes may be influenced by pre-pregnancy body weight index (BMI).

We determined proteins and/or reversals, exemplified here by using ITIH4/CSH, that are strong predictors of time to birth (TTB) (FIG. 10). TTB is defined as the difference between the GABD the gestational age at birth (GAB). This has potential to enable prediction, either individually or in mathematical combination of such analytes to clinically estimate TTB (or GAB).

Example 2. Validation of the IBP4/SHBG sPTB Predictor

This example demonstrates validation of the IBP4/SHBG sPTB predictor identified in a large maternal serum proteomics effort in asymptomatic women early in pregnancy.

Subjects

The Proteomic Assessment of Preterm Risk (PAPR) study was conducted under a standardized protocol at eleven Institutional Review Board (IRB)-approved sites across the U.S. (Clinicaltrials.gov identifier: NCT01371019). Subjects were enrolled between 17 0/7 and 28 6/7 weeks GA. Dating was established using a predefined protocol of menstrual dating confirmed by early ultrasound biometry, or ultrasound alone, to provide the best clinically estimated gestational age. Body mass index (BMI) was derived from height and pre-pregnancy self-reported weight. Pregnancies with multiple gestations and with known or suspected major fetal anomalies were excluded. Pertinent information regarding subject demographic characteristics, past medical and pregnancy history, current pregnancy history and concurrent medications was collected and entered into an electronic case report form. Following delivery, data were collected for maternal and infant outcomes and complications. All deliveries were adjudicated as term (≥37 0/7 weeks GA), spontaneous preterm (including preterm premature rupture of membranes) or medically indicated preterm births. As indicated, discrepancies were clarified with the Principal Investigator at the study site. Adjudication was completed and the data locked prior to validation studies.

Sample Collection

Maternal blood was collected and processed as follows: a 10 minute room temperature clotting period, followed by immediate refrigerated centrifugation or placement on an ice water bath at 4-8° C. until centrifugation. Blood was centrifuged within 2.5 hours of collection and 0.5 ml serum aliquots were stored at −80° C. until analyzed.

Predictor Development Principles

Development of the IBP4/SHBG predictor included independent and sequential discovery, verification and validation steps consistent with Institute of Medicine (IOM) guidelines for best practices in 'omics' research. IOM (Institute of Medicine). Evolution of Translation Omics: Lessons Learned and the Path Forward. (Micheel C M, Nass S J, Omenn G S, eds.). Washington, D.C.: The National Academies Press; 2012:1-355. Analytical validation preceded clinical validation sample analysis and included assessment of inter- and intra-batch precision, carryover and limit of detection.

The validation nested case/control analysis was performed on prespecified sPTB cases and control specimens independent of discovery and verification. sPTB cases included samples from nine sites in total, with two sites being unique to validation. Validation cases and controls underwent 100% on-site source document verification with each subject's medical record prior to mass spectrometry (MS) serum analysis. This process ensured that all subjects satisfied the inclusion and exclusion criteria, as well as confirmed medical/pregnancy complications and GA at birth assignments for all subjects at time of sample collection and delivery. Detailed analysis protocols, including the validation study design, analysis plan and a blinding protocol were pre-established. Personnel were blinded to subject case, control and GA at birth data assignments with the exception of the Director of Clinical Operations (DCO) and Clinical Data Manager. The data analysis plan included prespecified validation claims and a protocol for double independent external analyses. Predictor scores, calculated as described below, were determined for all subject samples by a blinded statistician. Case, control and GA data, linked to the predictor scores by the DCO, were subjected to independent external statistical analysis. Area under the receiver operating characteristic curve (AUROC) and significance testing results were then transferred back to the DCO. Transfer of data incorporated the use of the SUMPRODUCT function (Microsoft. Microsoft Excel. 2013) to ensure maintenance of data integrity. To provide an audit trail of data from each subject through to validation results, real-time digital time-stamping was applied to analytical data, plans and reports.

Validation Study Design

In the primary analysis, sPTB cases were defined as subjects with deliveries due to preterm premature rupture of the membranes (PPROM) or spontaneous onset of labor <37 0/7 weeks GA. Controls were subjects who delivered at ≥37 0/7 weeks GA. Prior discovery and verification analyses investigated 44 candidate biomarkers using serum samples collected across broad gestational age (17 0/7 through 25 6/7 weeks GA) (Supplementary Material). Discovery and verification identified an optimal narrow GA at blood draw interval (19 0/7 through 21 6/7 weeks) and two proteins, IBP4 and SHBG, used in a ratio (IBP4/SHBG) as the best predictor by AUROC for sPTB (Supplementary Material). In discovery and verification, subjects without extreme BMI values had improved classification performance by IBP4/SHBG (Supplementary Results). Following discovery and verification analyses, we proceeded to analytical and clinical validation.

Validation sPTB cases totaled 18 subjects collected between 19 0/7 through 21 6/7 weeks GA at blood draw (GABD), from a total available of 81 subjects across 17 0/7 through 28 6/7 weeks GA. Sets of controls, comprising two controls per sPTB case matched by GABD, were randomly selected using R Statistical program (R 3.0.2) (Team R C. R: a Language and Environment for Statistical Computing. Vienna, Austria; 2014. 2015; Matei A, Tillé Y. The R "sampling" package. European Conference on Quality in Survey Statistics. 2006) and compared to the term delivery distribution as outlined in the 2012 National Vital Statistics Report (Martin J A, Hamilton B E, Osterman M J, Curtin S C, Mathews T J. Births: Final Data for 2012. National Vital Statistics Reports. 2014; 63(09):1-86) using Chi-Square test. Randomly created control sets (in groups of 10) were examined for sets yielding a p-value approaching 1.0.

The primary objective was to validate the performance of the IBP4/SHBG ratio as a predictor for sPTB using AUROC (Team R C. R: a Language and Environment for Statistical Computing. Vienna, Austria; 2014. 2015; Sing T, Sander O, Beerenwinkel N, Lengauer T. ROCR: visualizing classifier performance in R. Bioinformatics. 2005; 21(20):7881). To control the overall multiple testing error rate ($\alpha$=0.05), the fixed sequence approach (Dmitrienko A, Tamhane A C, Bretz F, eds. Multiple Testing Problems in Pharmaceutical Statistics. Boca Raton, Fla.: CRC Press; 2009:1-320; Dmitrienko A, D'Agostino R B, Huque M F. Key multiplicity issues in clinical drug development. Stat Med. 2012; 32(7): 1079-111. doi:10.1002/sim.5642.) was applied to GABD increments within the optimal interval (19 0/7 through 21 6/7 weeks GA) identified in discovery and verification with and without the application of a BMI stratification (see Supplementary Material). Significance was assessed by the Wilcoxon-Mann-Whitney statistic that tests equivalence to AUROC=0.5 (random chance). (Bamber D. The area above the ordinal dominance graph and the area below the receiver operating characteristic graph. Journal of mathematical psychology. 1975; 12(4):387-415. doi:10.1016/0022-2496(75) 90001-2; Mason S J, Graham N E. Areas beneath the relative operating characteristics (ROC) and relative operating levels (ROL) curves: Statistical significance and interpretation. QJR Meteorol Soc. 2002; 128(584):2145-2166. doi: 10.1256/003590002320603584.) For determinations of classification performance at GA boundaries other than <37 0/7 vs. ≥37 0/7 weeks GA (e.g. <36 0/7 vs. ≥36 0/7, <35 0/7 vs. ≥35 0/7), cases and controls were redefined as all subjects below and equal to/above the specific boundary, respectively.

Laboratory Methods

A systems biology approach was employed to generate a highly multiplexed multiple reaction monitoring (MRM) MS assay (Supplementary Methods and Results). The validation assay quantified proteotypic peptides specific to predictor proteins IBP4 and SHBG and other controls. Samples were processed in batches of 32, which were comprised of clinical subjects (24), pooled serum standards from healthy non-pregnant donors (HGS)(3), pooled serum standards from healthy pregnant donors (pHGS)(3) and phosphate buffered saline that served as process controls (2). For all analyses, serum samples were first depleted of high abundance and non-diagnostic proteins using MARS-14 immuno-depletion columns (Agilent Technologies), reduced with dithiothreitol, alkylated with iodoacetamide, and digested with trypsin. Heavy-labeled stable isotope standard (SIS) peptides were then added to samples, which were subsequently desalted and analyzed by reversed-phase liquid chromatography (LC)/MRM-MS. SIS peptides were used for normalization by generating response ratios (RR), where the peak area of a peptide fragment ion (i.e. transition) measured in serum was divided by that of the corresponding SIS transition spiked into the same serum sample.

The IBP4/SHBG Predictor

The predictor score was defined as the natural log of the ratio of the IBP4 and SHBG peptide transition response ratios:

$$S = \ln\left(\frac{RR_{IBP4}}{RR_{SHBG}}\right),$$

where RR are the measured response ratios of the respective peptides.

Results

Figure 23:
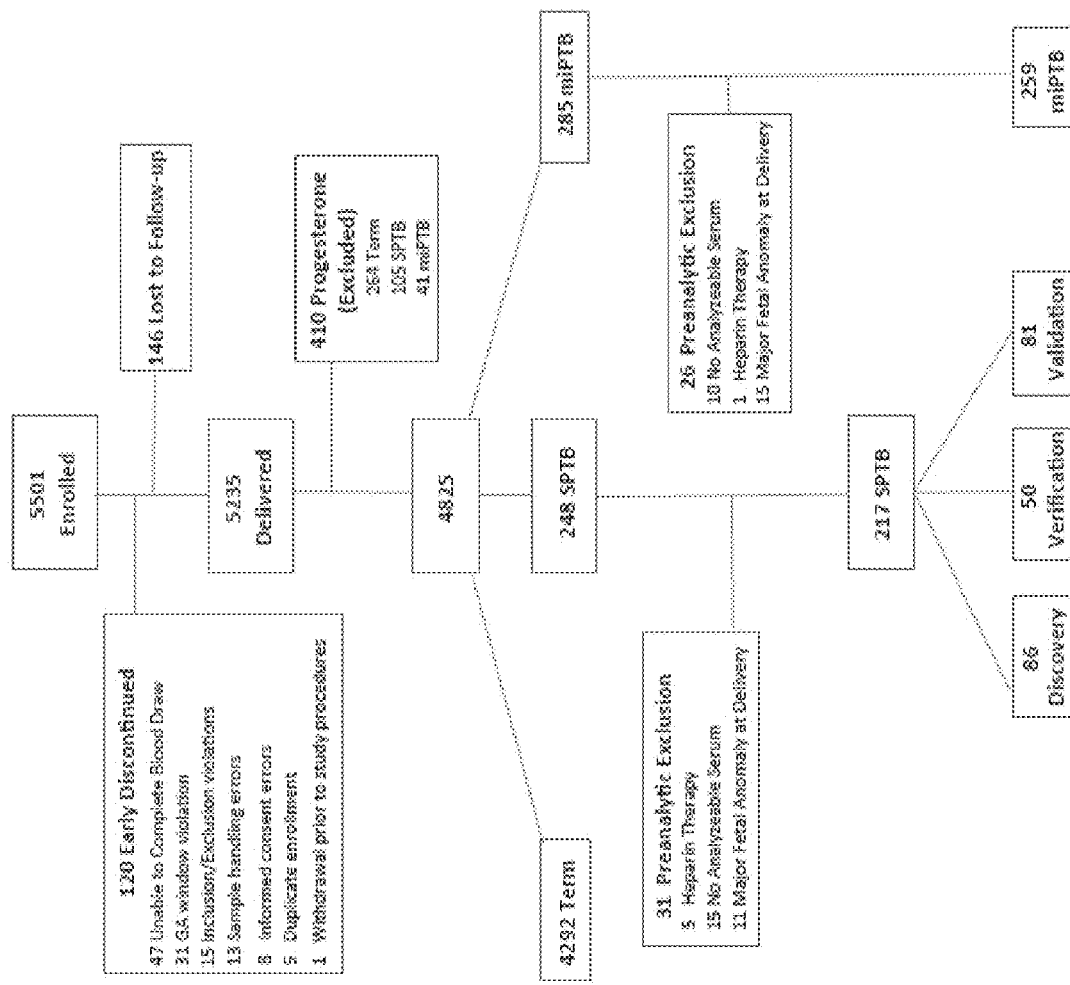
FIG. 23 summarizes the distribution of study subjects in PAPR.

FIG. 23 summarizes the distribution of study subjects in PAPR. Between March, 2011 and August, 2013, 5,501 subjects were enrolled. As predefined in the protocol, 410 (6.7%) subjects were excluded from analysis due to receiving progestogen therapy after the first trimester of pregnancy. An additional 120 (2.2%) subjects were excluded due to early discontinuation, and 146 (2.7%) were lost to follow-up. A total of 4,825 subjects were available for analysis. There were 533 PTBs; 248 (4.7%) spontaneous and 285 (5.9%) medically indicated. Compared to those who delivered at term, subjects with a sPTB were more likely to have had one or more prior PTBs and to have experienced bleeding after 12 weeks of gestation in the study pregnancy (Table 1). Characteristics of sPTB cases and term controls selected for validation were not significantly different from each other, with the exception that there were significantly more Hispanic controls (47.5% vs. 33.3% p=0.035). Similarly, subjects selected for validation were largely representative of the study cohort as a whole (Table 1), with the exception of ethnicity of term controls.

Validation Analysis

Figure 24:
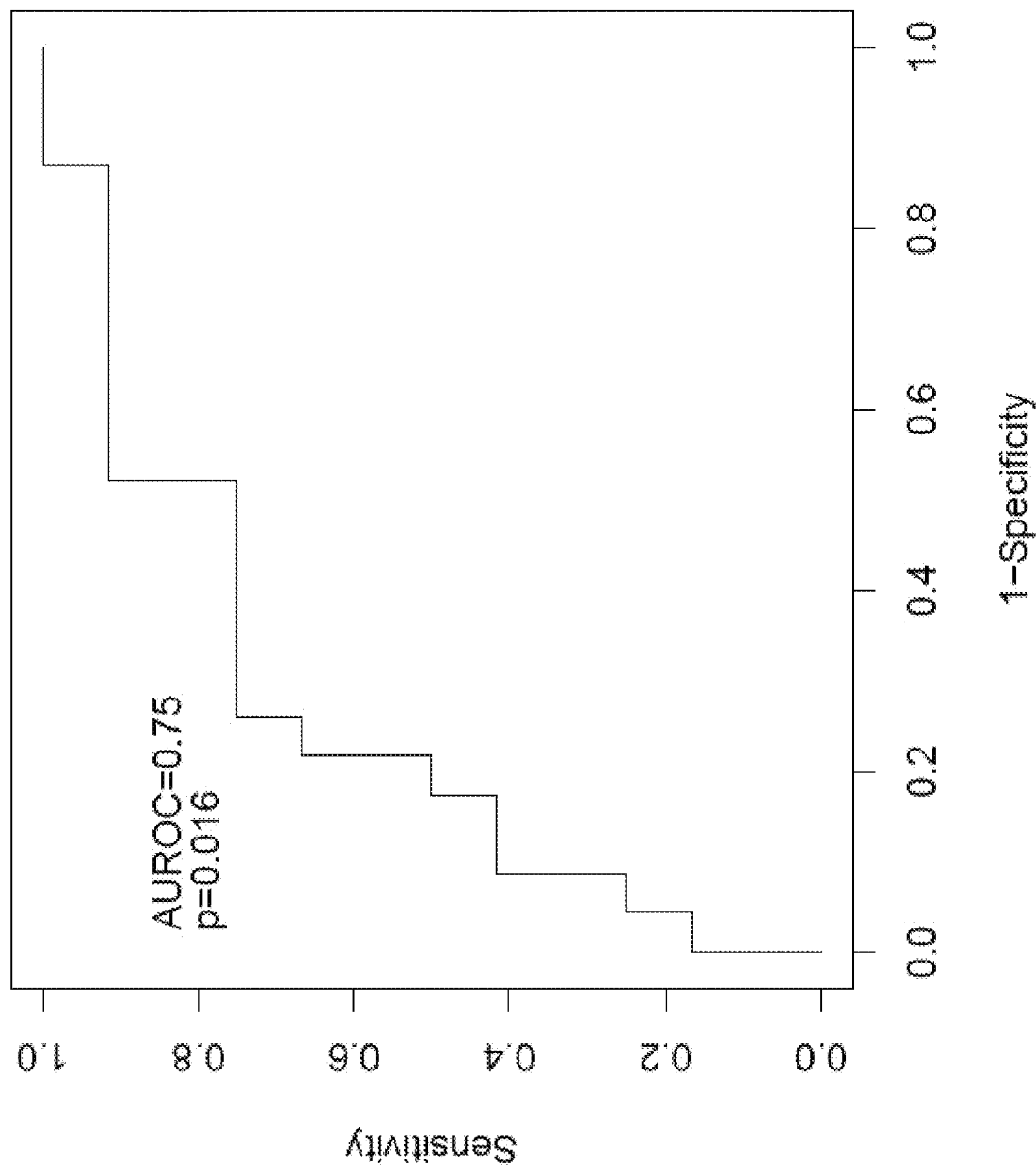
FIG. 24 shows the ROC curve and corresponding AUC value using the IBP4/SHBG predictor to classify the BMI stratified validation sample set.

In discovery and verification analyses the ratio of IBP4/ SHBG and the interval between 19 0/7 through 21 6/7 weeks GA was identified as the best performing sPTB predictor by AUROC and GA interval, respectively (Supplementary Results, below). For validation, a predefined fixed sequence approach validated the IBP4/SHBG predictor with and without BMI stratification, with optimal performance identified for the GA interval of 19 1/7 through 20 6/7 weeks. Without taking BMI into consideration, validated performance was AUROC=0.67 (p=0.02) (Supplementary Results). However, as expected, performance was improved with a BMI stratification of >22 and ≤37 kg/m² which corresponded to an AUROC of 0.75 (p=0.016, 95% CI 0.56-0.91) (FIG. 24). More detailed characterization of BMI stratification can be found in Supplementary Results. Performance measures of sensitivity, specificity, AUROC and odds ratios (ORs) were determined at varied case vs. control boundaries (Table 2). For sPTB vs. term birth (<37 0/7 vs. ≥37 0/7 weeks), the sensitivity and specificity was 0.75 and 0.74, respectively, with an odds ratio (OR) of 5.04 (95% CI 1.4-18). The results at other boundaries are summarized in Table 2. Accuracy of the test improved at lower GA boundaries.

Figure 26:
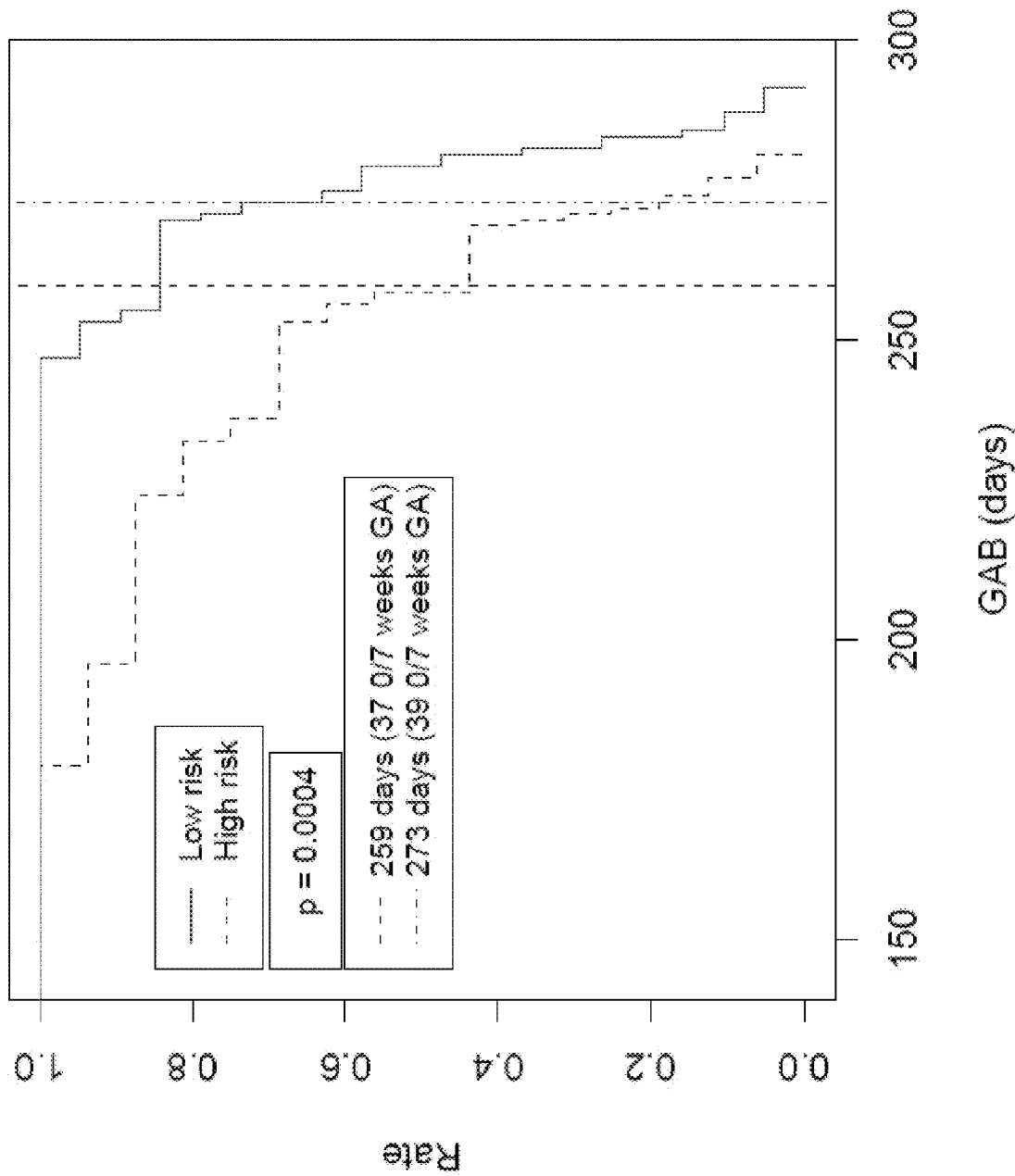
FIG. 26 displays rate of births for the high and low risk groups as events in a Kaplan Meier analysis. High and low risk was defined as above or below a relative risk of 2× the average population risk of sPTB (=14.6%) from data in FIG. 25.

The prevalence adjusted positive predictive value (PPV), a measure of clinical risk, is shown as a function of predictor score in FIG. 25. Stratification of subjects with increasing predictor score occurs as PPV increases from a background value (population sPTB rate of 7.3% for singleton births in the U.S.)(Martin et al., Births: final data for 2013. Natl Vital Stat Rep. 2015; 64(1):1-65 Martin J A, Hamilton B E, Osterman M J, Curtin S C, Matthews T J. Births: final data for 2013. Natl Vital Stat Rep. 2015; 64(1):1-65) to relative risks of 2× (14.6%) and 3× (21.9%) (dashed lines) and higher (FIG. 25). The distribution of IBP4/SHBG predictor score values for subjects color coded by GA at birth category are shown in box plots in FIG. 25. The earliest sPTB cases (<35 0/7 weeks GA) have higher predictor scores than late term controls (≥39 0/7 weeks GA) while the scores for late sPTB cases (≥35 0/7 through <37 0/7 weeks GA) overlap with early term controls (≥37 0/7 through <39 0/7 weeks GA) (FIG. 25). Validation subjects were identified as high or low risk according to a predictor score cut-off corresponding to 2× relative risk (PPV of 14.6%). The rate of births for the high and low risk groups were then displayed as events in a Kaplan Meier analysis (FIG. 26). From this analysis, those classified as high risk generally delivered earlier than those classified as low risk (p=0.0004).

Post Validation Analyses

Figure 27:
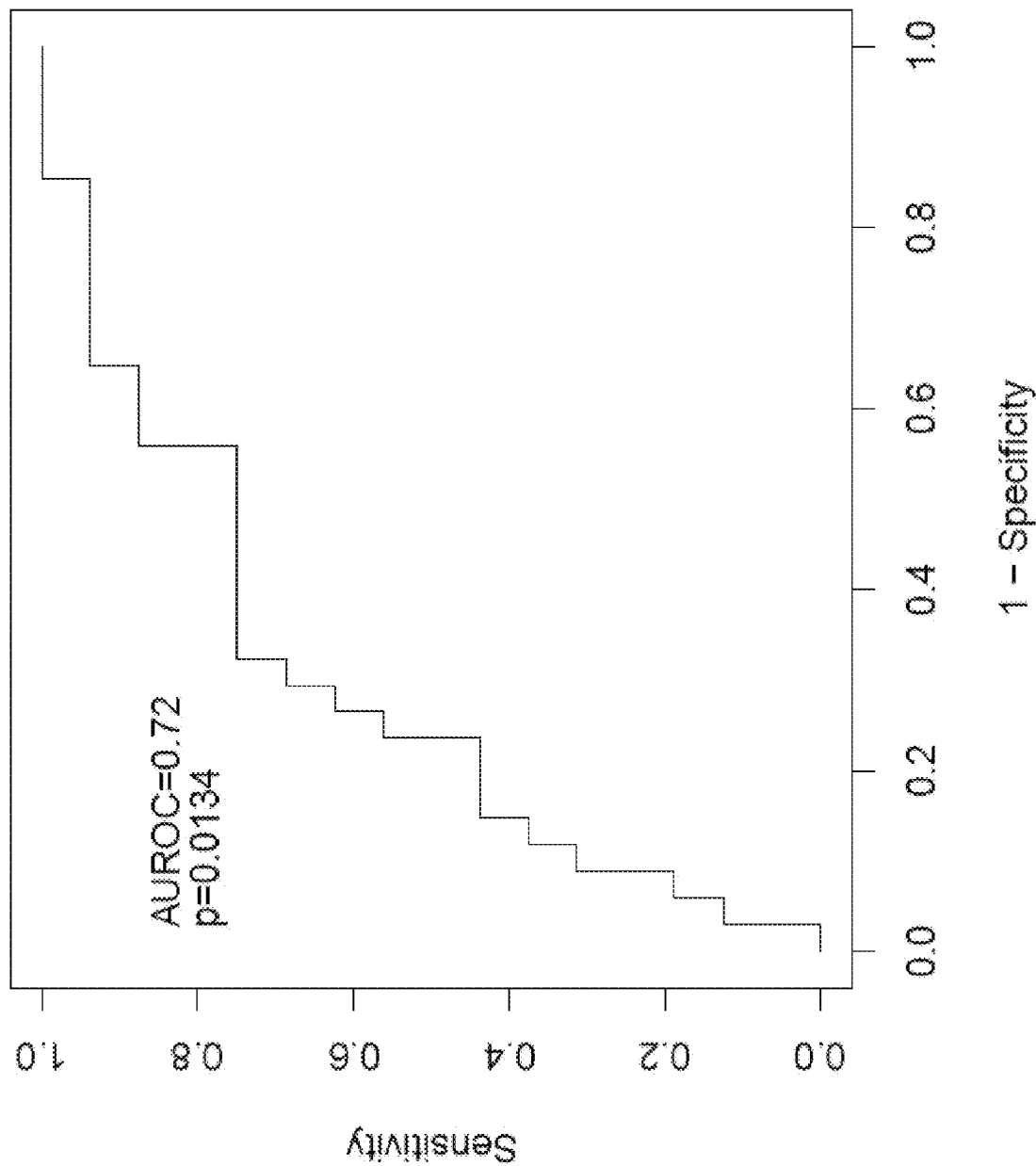
FIG. 27 shows an ROC curve corresponding to the predictor performance using a combination of subjects from the blinded verification and validation analyses within the optimal BMI and GA interval. The ROC curve for the combined sample corresponds to an AUROC of 0.72 (p=0.013)

Predictor performance was measured using a combination of subjects from the blinded verification (Supplementary data, below) and validation analyses within the optimal BMI and GA interval. The ROC curve for the combined sample set is shown and corresponds to an AUROC of 0.72 (p=0.013) (FIG. 27).

Using an 'omics approach we developed a maternal serum predictor comprised of the ratio of IBP4/SHBG levels at 19-20 weeks with a BMI interval of >22 and ≤37 kg/m2 that identified 75% of women destined for sPTB. Prior history of sPTB (Goldenberg et al., Epidemiology and causes of preterm birth. Lancet. 2008; 371(9606):75-84. doi:10.1016/50140-6736(08)60074-4, Petrini et al. Estimated effect of 17 alpha-hydroxyprogesterone caproate on preterm birth in the United States. Obstet Gynecol. 2005; 105(2):267-272) and cervical length measurements (Iams et al. The length of the cervix and the risk of spontaneous premature delivery. National Institute of Child Health and Human Development Maternal Fetal Medicine Unit Network. N Engl J Med. 1996; 334(9):567-72; Hassan et al. Vaginal progesterone reduces the rate of preterm birth in women with a sonographic short cervix: a multicenter, randomized, double-blind, placebo-controlled trial. Ultrasound Obstet Gynecol. 2011; 38(1):18-31) are considered the best measures of clinical risk to date; however, either individually or in combination they fail to predict the majority of sPTBs.

An ideal sPTB prediction tool would be minimally invasive, performed early in gestation coinciding with timing of routine obstetrical visits, and would accurately identify those at highest risk. Current 'omics studies suggest that perturbations in the physiological state of pregnancy can be detected in maternal serum analytes measured in sPTB subjects. 'Omics discovery studies in PTB have included proteomic (Gravett et al. Proteomic analysis of cervical-vaginal fluid: identification of novel biomarkers for detection of intra-amniotic infection. J Proteome Res. 2007; 6(1):89-96; Goldenberg et al. The preterm prediction study: the value of new vs standard risk factors in predicting early and all spontaneous preterm births. NICHD MFMU Network. Am J Public Health. 1998; 88(2):233-8; Gravett et al. Diagnosis of intra-amniotic infection by proteomic profiling and identification of novel biomarkers. JAMA. 2004; 292(4):462-469; Pereira et al. Insights into the multifactorial nature of preterm birth: proteomic profiling of the maternal serum glycoproteome and maternal serum peptidome among women in preterm labor. Am J Obstet Gynecol. 2010; 202(6):555.e1-10; 32. Pereira et al. Identification of novel protein biomarkers of preterm birth in human cervical-vaginal fluid. J Proteome Res. 2007; 6(4):1269-76; Dasari et al. Comprehensive proteomic analysis of human cervical-vaginal fluid. J Proteome Res. 2007; 6(4):1258-1268; Esplin et al. Proteomic identification of serum peptides predicting subsequent spontaneous preterm birth. Am J Obstet Gynecol. 2010; 204(5):391.e1-8.), transcriptomic (Weiner et al. Human effector/initiator gene sets that regulate myometrial contractility during term and preterm labor. Am J Obstet Gynecol. 2010; 202(5):474.e1-20; Chim et al. Systematic identification of spontaneous preterm birth-associated RNA transcripts in maternal plasma. PLoS ONE. 2012; 7(4): e34328. Enquobahrie et al. Early pregnancy peripheral blood gene expression and risk of preterm delivery: a nested case control study. BMC Pregnancy Childbirth. 2009; 9(1): 56), genomic (Bezold et al. The genomics of preterm birth: from animal models to human studies. Genome Med. 2013; 5(4):34; Romero et al. Identification of fetal and maternal single nucleotide polymorphisms in candidate genes that predispose to spontaneous preterm labor with intact membranes. Am J Obstet Gynecol. 2010; 202(5):431.e1-34; Swaggart et al. Genomics of preterm birth. Cold Spring Harb Perspect Med. 2015; 5(2):a023127; Haataja et al. Mapping a new spontaneous preterm birth susceptibility gene, IGF1R, using linkage, haplotype sharing, and association analysis. PLoS Genet. 2011; 7(2):e1001293; McElroy et al. Maternal coding variants in complement receptor 1 and spontaneous idiopathic preterm birth. Hum Genet. 2013; 132(8):935-42.), and metabolomic (Menon et al. Amniotic fluid metabolomic analysis in spontaneous preterm birth. Reprod Sci. 2014; 21(6):791-803) approaches. However, to date none of these approaches have produced validated testing methods to reliably predict the risk of sPTB in asymptomatic women.

The current invention is the result of a large prospective and contemporaneous clinical study that allowed independent discovery, verification and validation analyses, while adhering to IOM guidelines regarding omics' test development. It involved construction of a large and standardized multiplexed proteomic assay to probe biological pathways of relevance in pregnancy. The study size and relatively broad blood collection window (17 0/7 through 28 6/7 weeks GA) also enabled the identification of a GA interval where there were marked alterations in protein concentrations between sPTB cases and term controls. Use of a low complexity predictor model (i.e. the ratio of two proteins) limited the pitfalls of overfitting.

Application of the proteomic assay and model building led to the identification of a pair of critical proteins (IBP4 and SHBG) with consistently good predictive performance for sPTB. Despite the challenges of building a classifier for a condition attributed to multiple etiologies, the predictor demonstrated good performance at a cutoff of <37 0/7 vs. ≥37 0/7 weeks GA with an AUROC of 0.75. Importantly, accuracy of the predictor improves for earlier sPTBs (e.g. <35 0/7 weeks GA), enabling the detection of those sPTBs with the greatest potential for morbidity. Subjects determined to be at high risk for sPTB using the IBP4/SHBG predictor delivered significantly earlier than subjects identified as low risk. Our findings suggest that IBP4 and SHBG may perform important functions related to the etiologies of sPTB and/or act as convergence points in relevant biological pathways.

Universal transvaginal ultrasound (TVU) measurement of cervical length (CL) was not performed routinely at the majority of our study centers and was available for less than 1/3 of study subjects. It will be of interest to assess whether CL measurements improve upon the proteomic predictor in future studies or alternatively, if risk stratification by the IBP4/SHBG classifier identifies women that benefit most from serial CL measurements. Finally it will be intriguing to investigate the performance of the molecular predictor together with a BMI variable, or perhaps in combination with other medical/pregnancy history and sociodemographic characteristics.

In conclusion, a predefined predictive test for sPTB based on serum measurements of IBP4 and SHBG in asymptomatic parous and nulliparous women was validated in a completely independent set of subjects. Further functional studies on these proteins, their gene regulation and related pathways may help to elucidate the molecular and physiological underpinnings of sPTB. Application of this predictor should enable early and sensitive detection of women at risk of sPTB. This may improve pregnancy outcomes through increased clinical surveillance as well as to accelerate the development of clinical interventions for PTB prevention.

Supplementary Materials and Methods
Discovery and Verification Subjects

Discovery and verification subjects were derived from the PAPR study described above in this Example.

Discovery and Verification Principles sPTB cases were defined as described above in this Example. Discovery and verification of the predictor was conducted according to guidelines for best practices in 'omics' research. (IOM (Institute of Medicine). Evolution of Translation Omics: Lessons Learned and the Path Forward. (Micheel C M, Nass S J, Omenn G S, eds.). Washington, D.C.: The National Academies Press.; 2012:1-355). Nested case/control analyses used sample sets completely independent of each other. Cases and controls selected for discovery and verification underwent central review for within-subject data discrepancies; no source document verification (SDV) with the medical record was performed. All sPTB cases and controls for discovery and verification were individually adjudicated by the Chief Medical Officer and discrepancies were clarified with the PI at the clinical site. Detailed analysis protocols, including study designs, analysis plans and a verification blinding protocol were pre-established. Laboratory and data analysis personnel were blinded to verification subject's case, control and GA data assignments. Predictor scores, calculated as described below, were assigned to all subjects by an internal blinded statistician. Case, control and GA data, linked to the predictor scores by the DCO, were provided to an independent external statistician for analysis. AUROC results were then transferred back to the DCO. Transfer of data utilized a SUMPROD-UCT (Microsoft. Microsoft Excel. 2013) function in Excel to ensure maintenance of data integrity. To provide an audit trail of data from subjects through to verification results, digital timestamping was applied to analytical data, plans and reports.

Discovery and Verification Study Design

Discovery and verification sPTB cases totaled 86 and 50 subjects, respectively, collected across 17 0/7 through 28 6/7 weeks GA at blood draw (GABD). Subjects used in discovery and verification were completely independent of each other and independent from those used in validation. Matched controls were identified for sPTB cases in discovery and verification as described above in this Example.

Prevalence Analyses

Following discovery, verification and validation analyses, additional term controls, not used in prior studies, were selected from the PAPR database and processed in the laboratory using the MRM-MS assay applied in validation and described above in this Example. Using the Sampling package in R Statistical software (version 3.0.3) (Team R C. R: a Language and Environment for Statistical Computing. Vienna, Austria; 2014. 2015; Matei A, Tillé Y. The R "sampling" package. European Conference on Quality in Survey Statistics. 2006), sets of 187 subjects were randomly selected from the validated GA blood draw interval and compared via univariate statistical analyses (Chi-Square Test) against the gestational age at birth (GAB) data from the 2012 National Vital Statistics Report (NVSR). Martin et al.: Final Data for 2012. National Vital Statistics Reports. 2014; 63(09):1-86 Sets of controls most closely approximating the distribution of deliveries in the 2012 NVSR based on the best p value (approaching 1.0 with minimum acceptable value of 0.950) were then selected for comparison against the BMI distribution in the PAPR study as a whole. Using univariate statistical analyses (Chi-Square Test) against the BMI data from the PAPR study database, the sets of controls most closely approximating the distribution of BMI (approaching 1.0 with minimum acceptable value of 0.950) and the distribution of delivery timing in the NVSR were selected and compared to the GABD of the validated blood draw samples. The set that most closely approximated all three distributions was selected as the subject set for the Prevalence Study. Predictor score values for verification, validation and prevalence within the validation GABD interval and BMI restriction totaled 150 subjects. This composite dataset was used to obtain the best estimates of confidence intervals about the PPV curve in FIG. 25. Confidence intervals about the PPV were calculated with the normal approximation of the error for binomial proportions. Brown et al. Interval estimation for a binomial proportion. Statistical science. 2001; 16(2):101-133.

Laboratory Methods

A systems biology approach was employed to generate a highly multiplexed multiple reaction monitoring (MRM) mass spectrometry (MS) assay by iterative application of: literature curation, targeted and un-targeted proteomic discovery and small scale MRM-MS analyses of subject samples. The mature MRM-MS assay, measuring 147 proteins, was applied in discovery and verification studies. For all analyses, serum samples were processed in the laboratory as described above in this Example. Aliquots of pooled serum controls (pHGS) were used to calculate the inter-batch analytical coefficient of variation (CV) for IBP4 and SHBG.

General Predictor Development Strategy

A strategy was developed to avoid over-fitting and to overcome the dilution of biomarker performance expected across broad gestational age ranges due to the dynamic nature of protein expression during pregnancy. Ratios of up-regulated over down-regulated analyte intensities were employed in predictor development. Such "reversals" are similar to the top-scoring pair and 2-gene classifier strategies. (Geman et al. Classifying gene expression profiles from pair wise mRNA comparisons. Stat Appl Genet Mol Biol. 2004; 3(1):Article 19; Price et al. Highly accurate two-gene classifier for differentiating gastrointestinal stromal tumors and leiomyosarcomas. Proc Natl Acad Sci USA. 2007; 104(9):3414-9) This approach allowed amplification of the diagnostic signal and self-normalization as both proteins in a "reversal" underwent the same pre-analytical and analytical processing steps. As a strategy to normalize peptide intensity measures in complex proteomics workflows, reversals are also similar to a recently introduced approach termed "endogenous protein normalization (EPN)". (Li et al. An integrated quantification method to increase the precision, robustness, and resolution of protein measurement in human plasma samples. Clin Proteomics. 2015; 12(1):3; Li et al. A blood-based proteomic classifier for the molecular characterization of pulmonary nodules. Sci Transl Med. 2013; 5(207):207ra142) The number of candidate analytes used for model building was reduced by analytic criteria. Analytic filters included: cut-offs for analytical precision, intensity, evidence of interference, sample processing order dependence and pre-analytical stability. The total number of analytes in any one predictor was limited to a single reversal, thus avoiding complex mathematical models. Predictor scores were defined as the natural log of a single reversal value, where the reversal itself was a response ratio (defined above in this Example). Lastly, predictive performance was investigated in narrow overlapping 3-week intervals of gestation.

Receiver Operating Characteristic Curves

AUROC values and associated p-values were calculated for reversals as described above in this Example. The distribution and mean value for predictor AUROC in the combined discovery and verification set was calculated using a bootstrap sampling performed iteratively by selecting random sets of samples with replacement. Efron B, Tibshirani R J. An Introduction to the Bootstrap. Boca Raton, Fla.: Chapman and Hall/CRC Press; 1994. The total number of selected samples at each iteration corresponded to the total available in the starting pool.

Supplementary Results

Discovery, verification and validation subject characteristics are summarized in Table 3. The percentage of subjects with one or more prior sPTBs in discovery sPTB cases were higher than in verification or validation, and other characteristics were largely consistent across the studies.

Discovery and Verification Analyses

Figure 28:
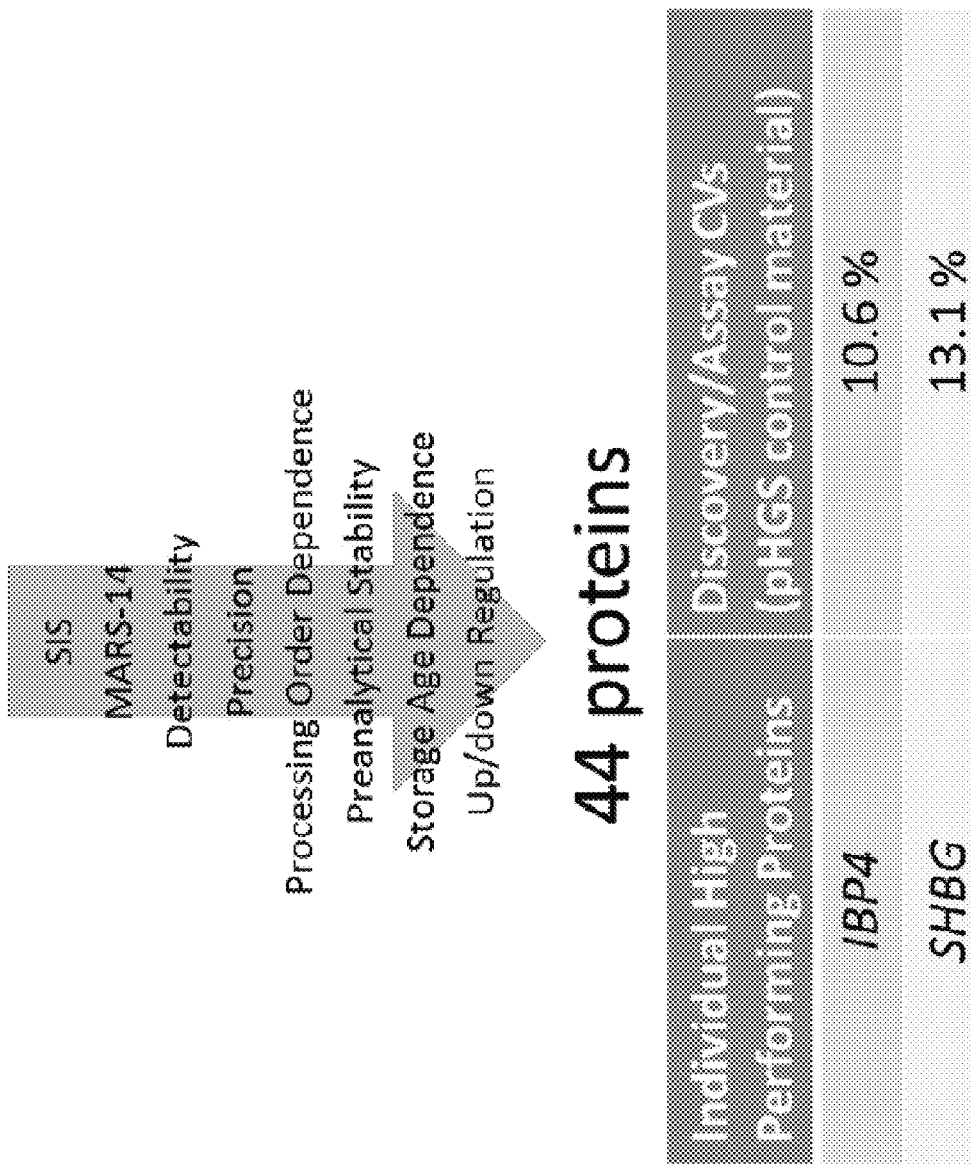
FIG. 28 shows 44 proteins were either up- or down-regulated in overlapping 3-week GA intervals and passed analytic filters.
Figure 29:
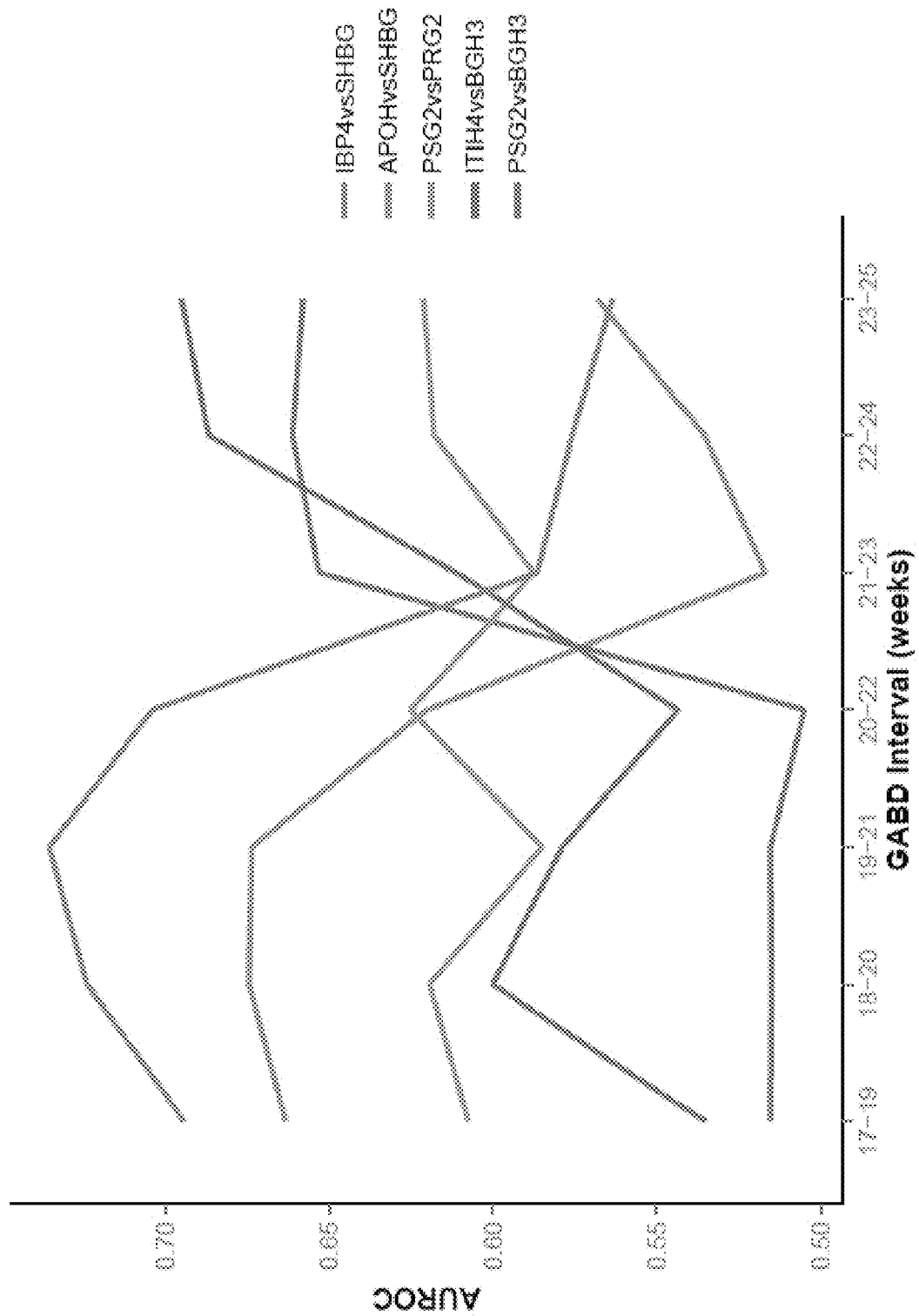
FIG. 29 shows the top performing reversal overall, IBP4/SHBG, had an AUROC=0.74 in the interval from 19 0/7 through 21 6/7.

Forty-four proteins were either up- or down-regulated in overlapping 3-week GA intervals and passed analytic filters (FIG. 28). Reversals were formed from the ratio of up-over down-regulated proteins and predictive performance tested in samples in each of the overlapping 3-week GA intervals. Performance for a subset of reversals displaying representative patterns is shown in FIG. 29. Waves of performance were evident: IBP4/SHBG and APOH/SHBG reversals possessed better AUROC values in early windows, while ITIH4/BGH3 and PSG2/BGH3 peaked later in gestation (FIG. 24). Some reversals had a consistent but moderate performance across the entire gestational age range (PSG2/PRG2) (FIG. 29). The top performing reversal overall, IBP4/SHBG, had an AUROC=0.74 in the interval from 19 0/7 through 21 6/7 (FIG. 29). AUROC performance of the IBP4/SHBG predictor increased to 0.79 when subjects were stratified by pre-pregnancy BMI <35 (kg/m2) (Table 4). Because of its consistently strong performance early in gestation (i.e. 17 0/7 through 22 6/7 weeks GA) (FIG. 29) and potentially desirable clinical utility the IBP4/SHBG predictor was selected for verification analysis.

Figure 30:
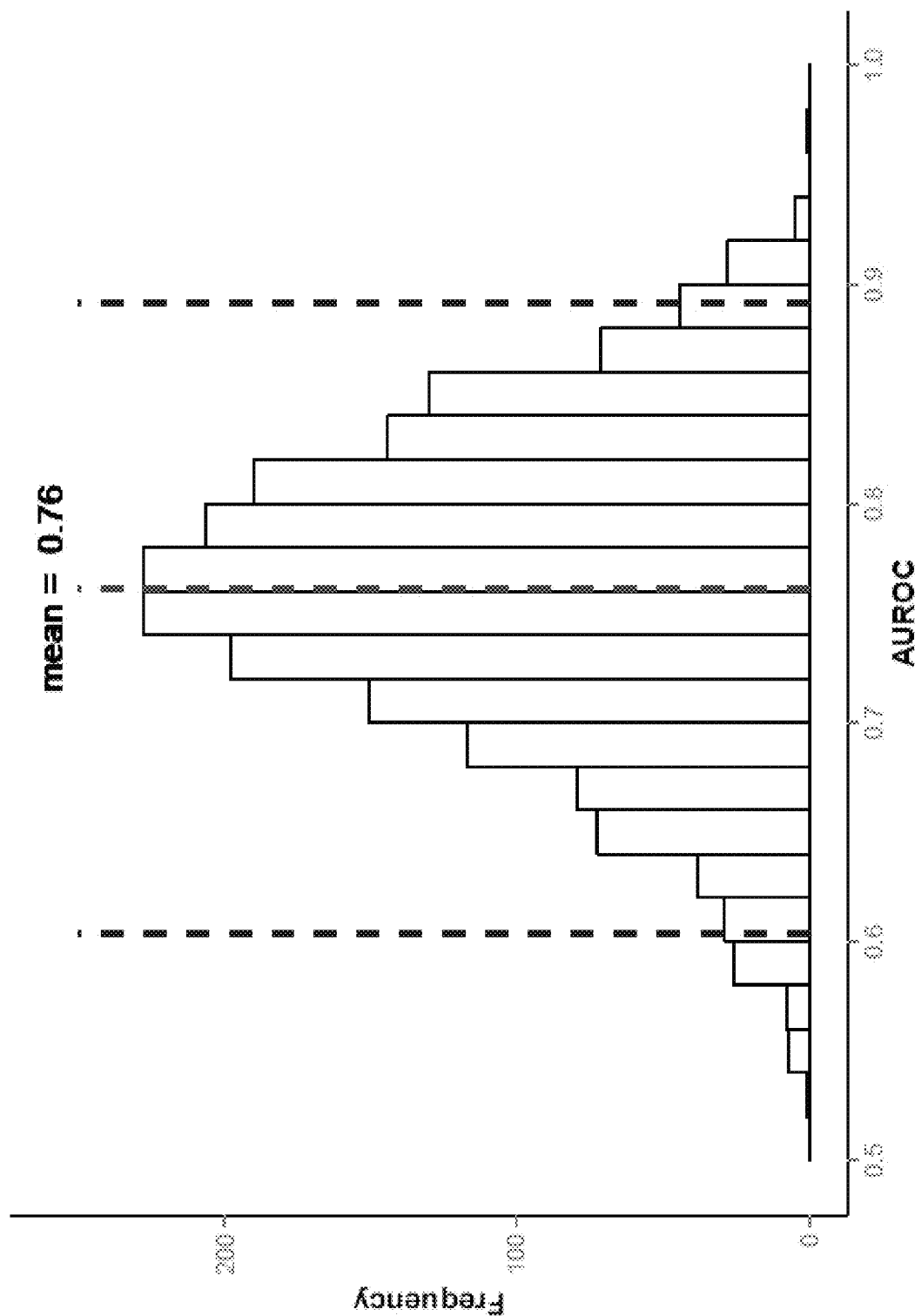
FIG. 30 shows the mean AUROC of 0.76 obtained from 2,000 bootstrap iterations. The blinded IBP4/SHBG AUROC performance on verification samples was 0.77 and 0.79 for all subjects and BMI stratified subjects, respectively, in good agreement with performance obtained in discovery. Following blinded verification, discovery and verification samples were combined for the bootstrap performance determination.

The blinded IBP4/SHBG AUROC performance on verification samples was 0.77 and 0.79 for all subjects and BMI stratified subjects, respectively, in good agreement with performance obtained in discovery (Table 5). Following blinded verification, discovery and verification samples were combined for a bootstrap performance determination. A mean AUROC of 0.76 was obtained from 2,000 bootstrap iterations (FIG. 30).

BMI Validation Analyses

The performance of the IBP4/SHBG predictor was evaluated at several cut-offs of BMI in the validation samples (Table 5). AUROC measured performance modestly improved by elimination of either very high (e.g. >37 kg/m2) or low BMI (e.g. ≤22 kg/m2). Stratification by a combination of those two cut-offs gave an AUROC of 0.75 (Table 5).

Example 3. Correlation of Mass Spectrometry and Immunoassay Data

This example demonstrates results of a Myriad RBM screen identifying IBP4 and other biomarkers individual biomarkers for sPTB in the early, middle, and late gestational age collection windows, (2) correlation of MS and immunoassay results for SHBG/IBP4, and (3) clinical data relating to SHBG as a biomarker for sPTB.

RBM Data

Briefly, RBM assayed 40 cases and 40 controls from PAPR (20/20 from Early Window), 10/10 from Middle Window, 10/10 from Late Window). RBM used the Human Discovery MAP 250+ v2.0 (Myriad RBM, Austin, Tex.). The objective of these analyses is to develop multivariate models to predict PTB using multiple analytes. We used four modeling methods: random forest (rf), boosting, lasso, and logistic (logit). We perform a first round of variable selection in which each method independently selects the 15 best variables for that method. From the 15, the best analytes were selected independently by each of the four modeling methods using backward stepwise selection and estimation of area under the ROC curve (AUC) using out-of-bag bootstrap samples. Table 6 shows the top hits from several multivariable models. Table 7 shows Early Window (GABD 17-22 wks) Analyte Ranking by Different Multivariate Models. Table 8 shows Middle Window (GABD 23-25 wks) Analyte Ranking by Different Multivariate Models. Table 9 shows Late Window (GABD 26-28 weeks) Analyte Ranking by Different Multivariate Model.

Identifying Commercial ELISA Kits that Correlate with Mass Spec Data

Briefly, ELISA versus MS comparisons involved multiple studies using PAPR samples and ranging in size from 30-40 subjects. Each ELISA was performed according to the manufacture's protocol. The predicted concentration of each analyte by ELISA was then compared to MS derived relative ratios from identical samples. A Person's r correlation value was then generated for comparison. ELISA versus MS comparisons involved multiple studies using PAPR samples and ranging in size from 30-40 subjects. Each ELISA was performed according to the manufacture's protocol. The predicted concentration of each analyte by ELISA was then compared to MS derived relative ratios from identical samples. A Person's r correlation value was then generated for comparison. Table 10 provides epitope and clonality information for kits tested for analytes IBP4 HUMAN and SHBG HUMAN. Table 11 shows that not all ELISA kits correlate with MS, even for proteins where correlation exists. See for example: IBP4, CHL1, ANGT, PAPP1.

Figure 31A:
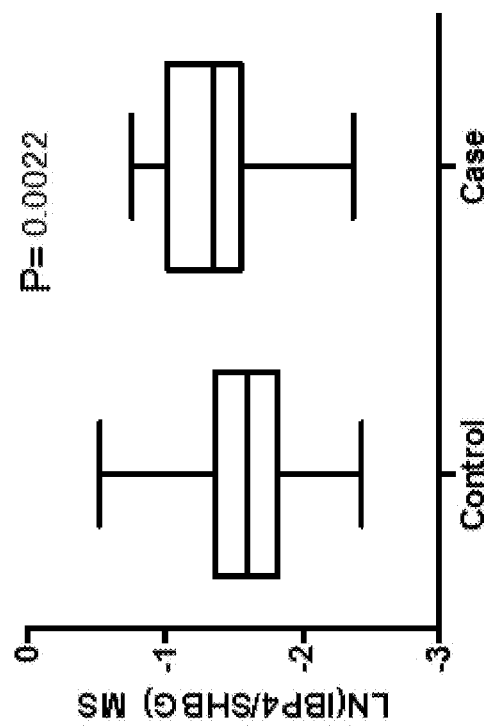
FIGS. 31A-31B show sPTB Case vs Control Separation Derived by MS vs ELISA Score Values
Figure 31B:
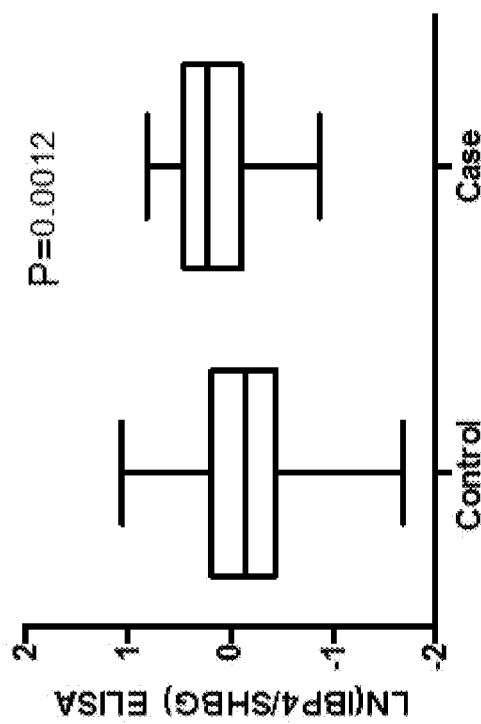

One hundred and twenty previously frozen serum samples with known outcomes from the PAPR study were selected for comparison between ELISA and MS assays. These samples have a Gestational Age at Blood Draw (GABD) between 119 and 180 days. Samples were not excluded due to maternal BMI. ELISA's were performed on commercially available kits for IBP4 (AL-126, ANSCH Labs Webster, Tex.), and SHBG (DSHBGOB, R&D Systems Minneapolis, Minn.). Assays were run according to the manufactures' protocols. Internal standards were used for plate-to-plate normalization. The score was calculated from the ELISA concentration values according to LN([IBP4]/[SHBG]), and by MS according to $LN(IBP4^{RR}/SHBG^{RR})$, where RR refers to the relative ratio of endogenous peptide to SIS peptide peak areas. Scores derived from the two approaches were compared in case versus control separation (p values derived from unpaired t-tests assuming equal standard deviations) (FIG. 31).

Figure 32B:
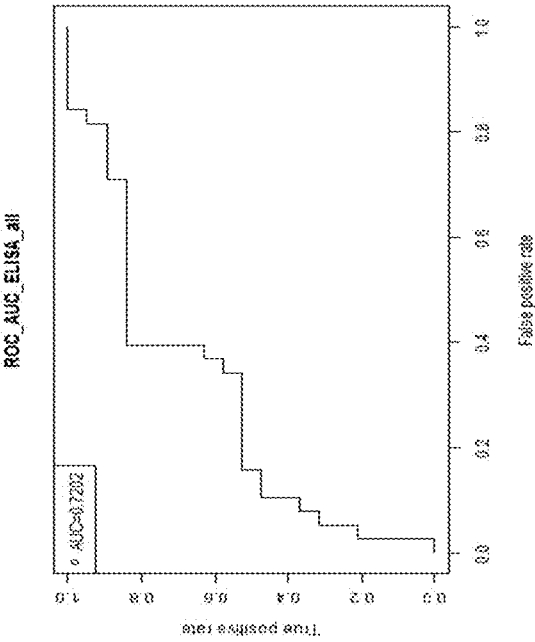
FIGS. 32A-32B show Immunoassay versus MS ROC Analyses without BMI restriction.
Figure 32A:
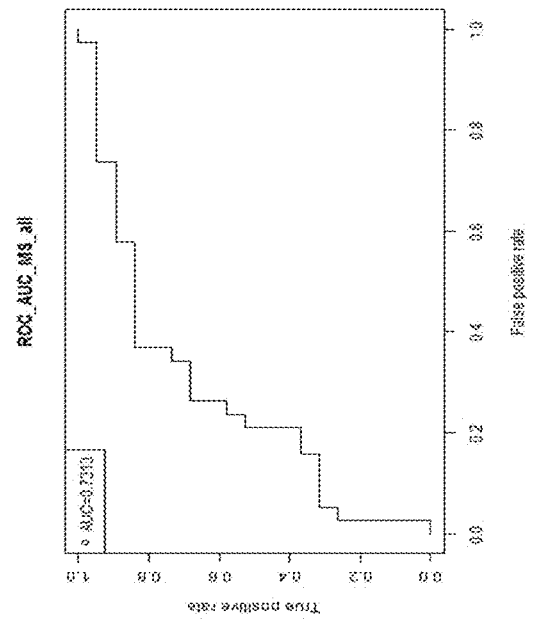
Figure 33B:
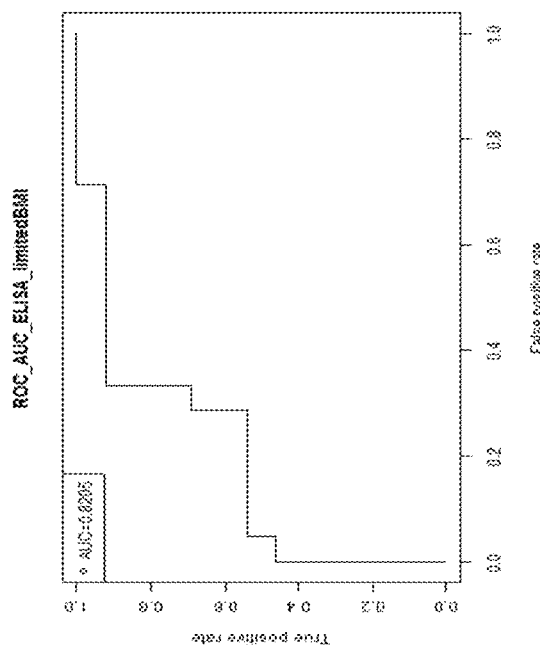
FIGS. 33A-33B show Immunoassay versus MS ROC Analyses for BMI higher than 22 and less or equal to 37.
Figure 33A:
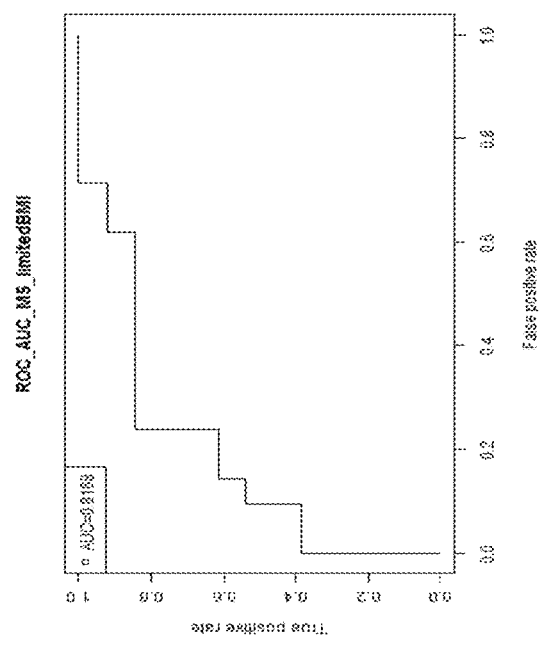

Fifty seven previously frozen serum samples (19 sPTB cases, 38 term controls) with known outcomes from the PAPR study were selected for comparison between ELISA and MS assays. These samples have a Gestational Age at Blood Draw (GABD) between 133 and 148 days. ELISA's were performed on commercially available kits for IBP4 (AL-126, ANSCH Labs Webster, Tex.), and SHBG (DSHB-GOB, R&D Systems Minneapolis, Minn.). Assays were run according to the manufactures' protocols. Samples run on different plates were normalized using internal standards. The score was calculated from the ELISA concentration values according to LN([IBP4]/[SHBG]), and by MS according to LN(IBP4$^{RR}$/SHBG$^{RR}$), where RR refers to the relative ratio of endogenous peptide to SIS peptide peak areas. Performance of the immunoassay by area under the receiver operating characteristic curve (AUC) was then determined and compared to the MS derived AUC on the same sample sets (FIG. 32). AUC values were also determined after applying a BMI stratification to the samples (BMI>22≤37) resulting in 34 total samples (13 sPTB cases, 21 term controls) (FIG. 33).

Figure 34B:
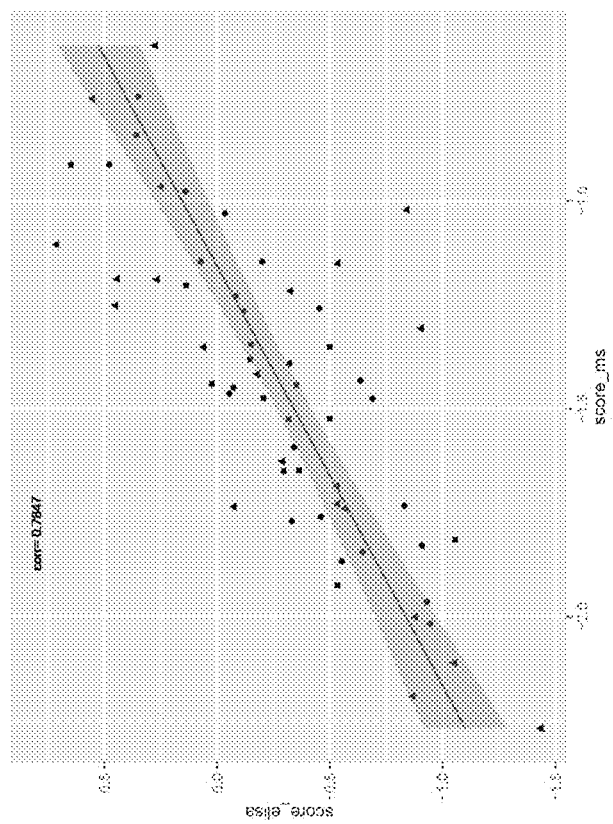
FIGS. 34A-34B show the correlation between MS and ELISA derived IBP4/SHBG score values within GABD 133-146, for BMI stratified subjects (left panel) and all subjects (right panel).
Figure 34A:
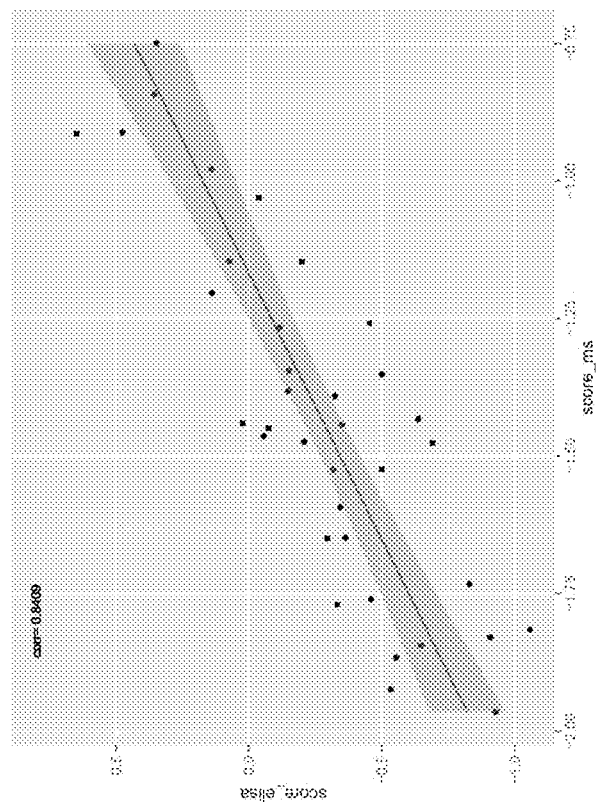
Figure 35B:
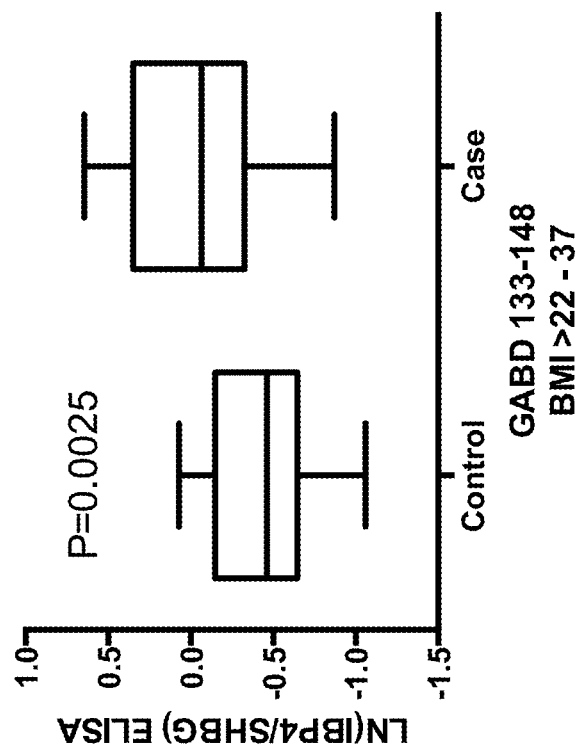
FIGS. 35A-35B show ELISA and MS Separation of Controls and Cases (BMI stratified)
Figure 35A:
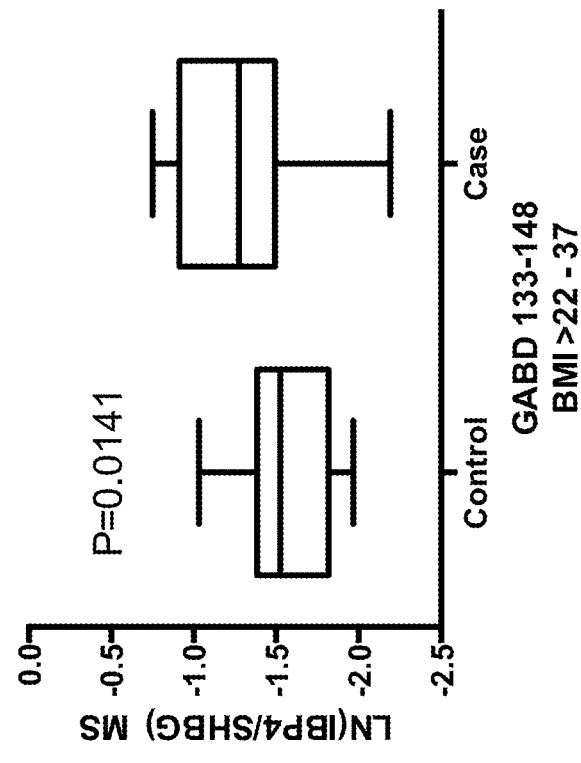
Figure 36B:
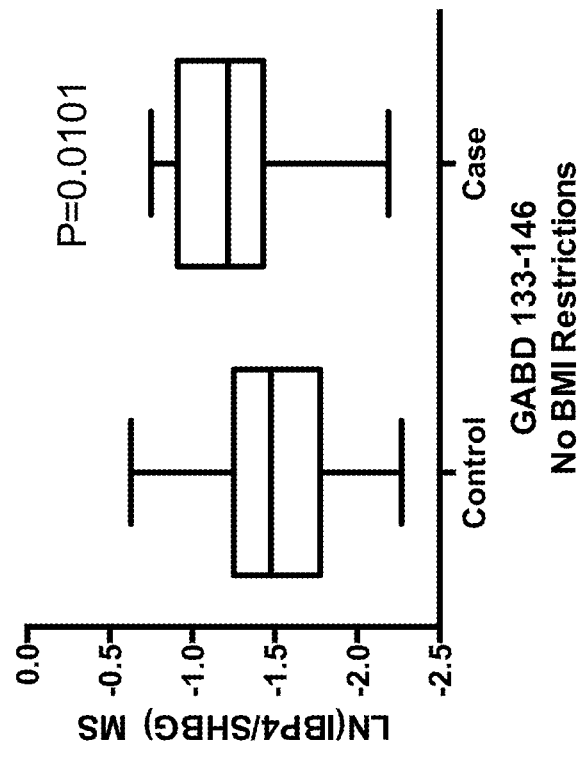
FIGS. 36A-36B show Elisa and MS Separation of Controls and Cases (All BMI)
Figure 36A:
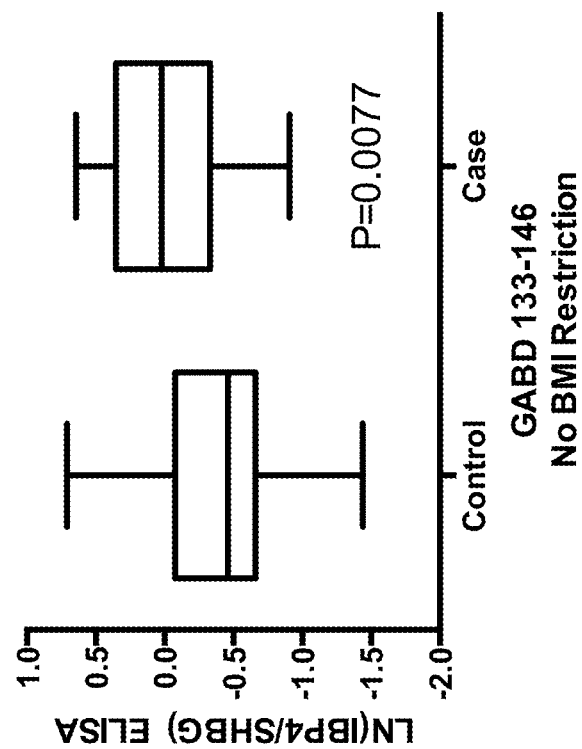

Sixty previously frozen serum samples with known outcomes from the PAPR study were analyzed by ELISA and MS assays. These samples have a predicted Gestational Age at Blood Draw (GABD) between 133 and 146 days. Correlation analyses were performed for samples at all BMI (FIG. 34, right panel) or for the subset of samples with a BMI >22 or ≤37 (FIG. 34, left panel). ELISA's were performed on commercially available kits for IBP4 (AL-126, ANSCH Labs Webster, Tex.), and SHBG (DSHBGOB, R&D Systems Minneapolis, Minn.). Assays were run according to the manufactures' protocols. Internal standards were used for plate-to-plate normalization. The score was calculated from the ELISA concentration values according to LN([IBP4]/[SHBG]), and by MS according to LN(IBP4$^{RR}$/SHBG$^{RR}$), where RR refers to the relative ratio of endogenous peptide to SIS peptide peak areas. Scores derived from the two approaches were compared by correlation and in case versus control separation (p values derived from unpaired t-tests assuming equal standard deviations). Table 12 shows IBP4 and SHBG ELISA Kits Demonstrating sPTB vs Control Separation (univariate).

Comparison of SHBG Measurements by Mass Spectrometry and Clinical Analyzers

Figure 37:
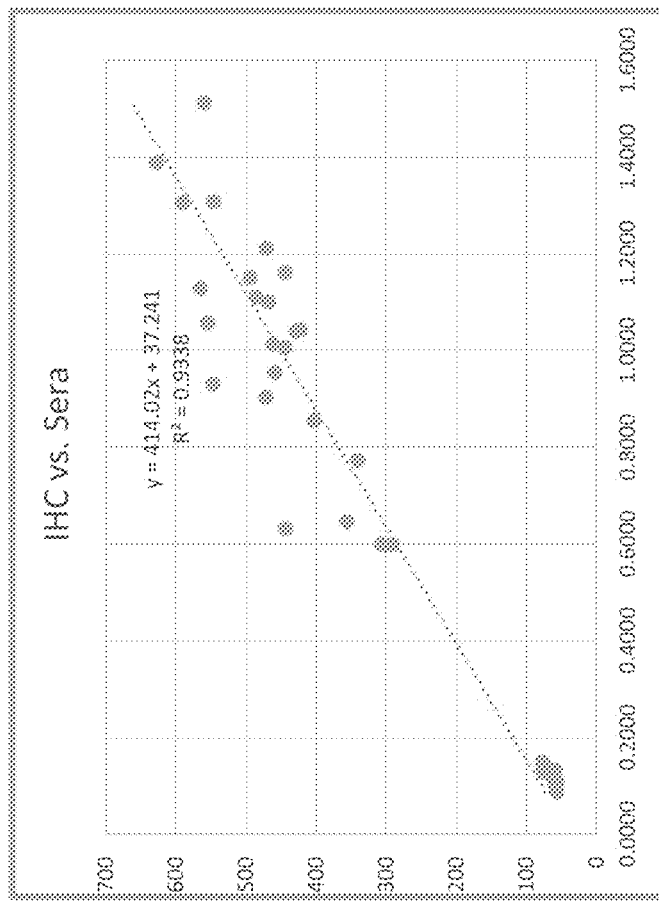
FIG. 37 shows comparison of SHBG measurements by Abbott Architect CMIA, semi-automated immunoassay instruments and Sera Prognostics' proteomic analysis method involving immuno-depletion of samples, enzymatic digestion and analysis on an Agilent 6490 Mass Spectrometer.
Figure 38:
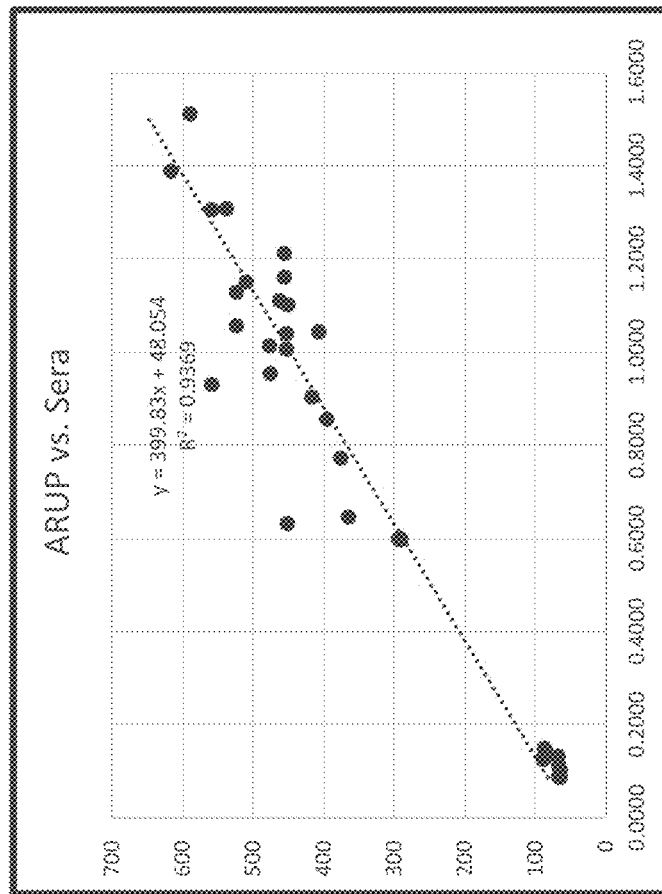
FIG. 38 shows comparison of SHBG measurements by Roche cobas e602 analyzer, semi-automated immunoassay instruments and Sera Prognostics' proteomic analysis method involving immuno-depletion of samples, enzymatic digestion and analysis on an Agilent 6490 Mass Spectrometer.
Figure 39:
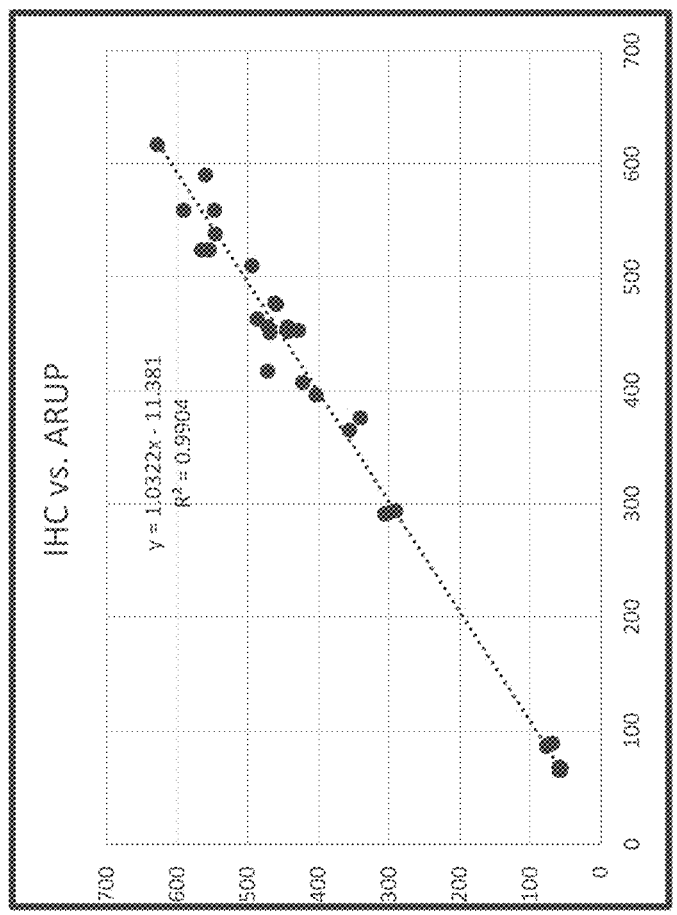
FIG. 39 shows comparison of SHBG measurements by Abbott Architect CMIA and Roche cobas e602 analyzer, both semi-automated immunoassay instruments.
Figure 40:
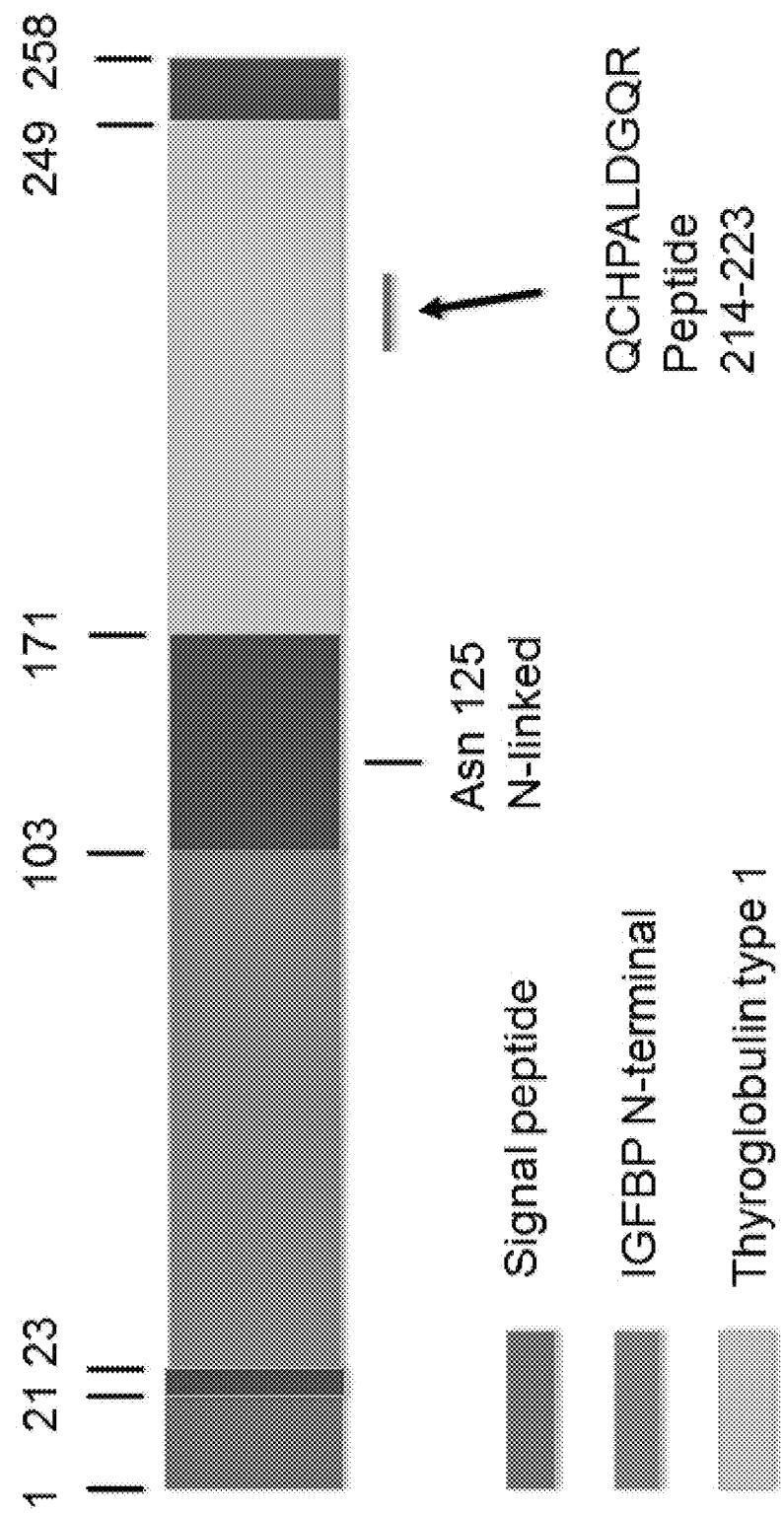
FIG. 40 shows the domain and structural characteristics of the longest isoform of the IBP4 protein (Uniprot: P22692). The IBP4 QCHPALDGQR (aa, 214-223) peptide (SEQ ID NO: 2) is located within the Thyroglobulin type 1 domain. IBP4 has a single N-linked glycosylation site at residue 125.
Figure 42:
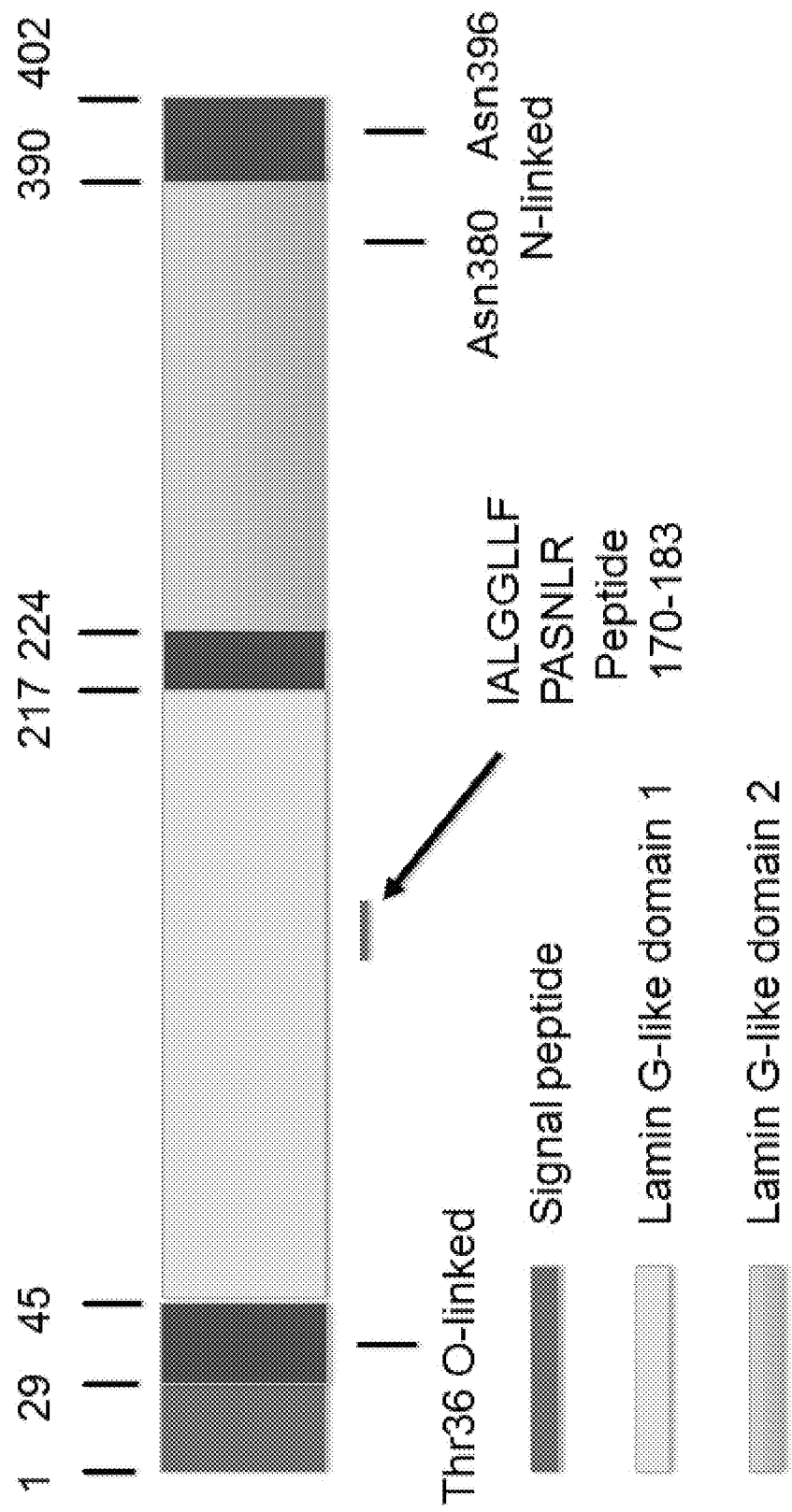
FIG. 42 shows the domain and structural characteristics of the longest isoform of the SHBG protein (Uniprot: P04278). The SHBG IALGGLLFPASNLR (aa, 170-183) peptide (SEQ ID NO: 18) is located in the first Lamin G-like domain. SHBG has three glycosylation sites; two N-linked sites at residue 380 and 396; one O-linked site at residue 36.

Thirty five samples from individual subjects and serum pools of pregnant and non-pregnant women were simultaneously analyzed at Sera Prognostics and two independent reference laboratories, ARUP Laboratories and Intermountain Laboratory Services. Aliquots were transported refrigerated to each laboratory and shipping was coordinated so testing would begin on the same date for all three laboratories. ARUP utilizes a Roche cobas e602 analyzer and Intermountain uses the Abbott Architect CMIA, both semi-automated immunoassay instruments. Sera Prognostics employs a unique proteomic analysis method involving immuno-depletion of samples, enzymatic digestion and analyzed on an Agilent 6490 Mass Spectrometer. Results from both ARUP and IHC were reported in nmol/L while Sera uses the Relative Ratio (RR) of heavy and light peptide surrogates. Data from ARUP and Intermountain were compared to each other to determine accuracy (FIG. 39). Linearity and precision matched well throughout the broad range of results with a linearity slope of 1.032 and $r^2$ value of 0.990. Each reference laboratory's data was then compared to Sera's RR and a linear regression plot (FIGS. 37 and 38). Data compared well to Sera results with ARUP having an $r^2$ value of 0.937 and Intermountain having an $r^2$ value of 0.934.

Example 4. SNPs, Insertions and Deletions and Structural Variants within the PreTRM IBP4 and SHBG Peptides This example shows the known SNPs, insertions and deletions (indels) and structural variants within the PreTRM IBP4 and SHBG peptides.

Table 13 and Table 14 detail the known SNPs, insertions and deletions (indels) and structural variants within the PreTRM IBP4 and SHBG peptides. The information is derived from the Single Nucleotide Polymorphism database (dbSNP) Build 146. A single missense variation (G>C) in SHBG, A179P (dbSNP id: r5115336700) has the highest overall allelic frequency of 0.0048. While this allelic frequency is low, several subpopulations studied in the 1000 genomes project had significantly higher frequencies. These populations (allele frequencies) are; Americans of African Ancestry in SW USA (0.0492); African Carribbeans in Barbados (0.0313); Yourba in Ibadan, Nigeria (0.0278); Luhya in Webuye, Kenya (0.0101); Esan in Nigeria (0.0101); Colombians from Medellin, Colombia (0.0053); Gambian in Western Divisions in The Gambia (0.0044). All other studied subpopulations had no variation in this nucleotide position. The table header includes the cluster id—(dbSNP rs number), Heterozygosity—average heterozygosity, Validation—validation method (or blank with no validation), MAF—Minor Allele Frequency, Function—functional characteristic of the polymorphism, dbSNP allele—identity of allelic nucleotide, Protein residue—residue resulting from allele, Codon pos—position in codon, NP_001031.2 Amino acid pos—amino acid position in reference sequence NP_001031.2, and NM_001040.2 mRNA pos—nucleotide position in a reference sequence NM_001040.2.

Example 5. IBP4/SHBG Reversal Amplifies Diagnostic Signal for sPTB and Reduces Analytical Variability This example demonstrates the amplification of diagnostic signal and reduction of variability obtained employing the IBP4/SHBG reversal strategy.

Figure 44:
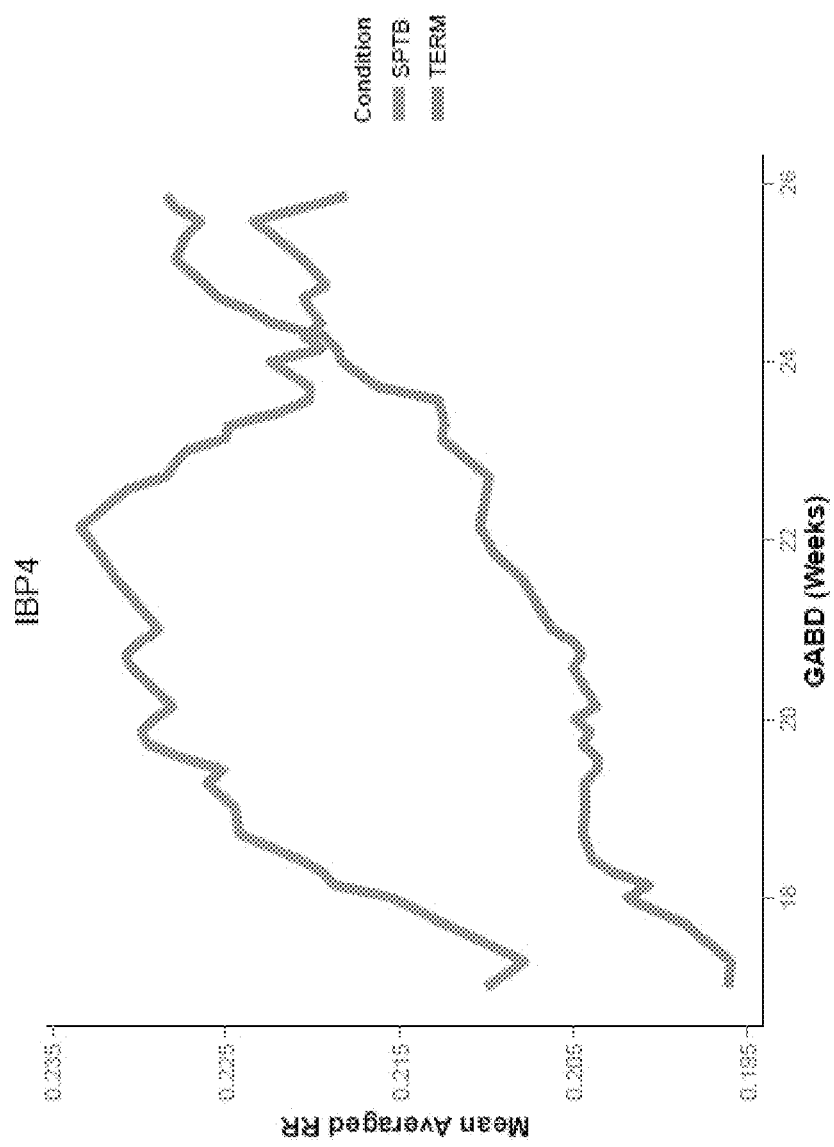
FIG. 44 shows the average response ratio for IBP4 levels separately for sPTB cases and term controls across gestational age at blood draw (GABD). Cross sectional discovery data was analyzed by smoothing using a sliding 10 day window. Case versus control signal corresponds to an approximate maximal 10% difference.
Figure 45:
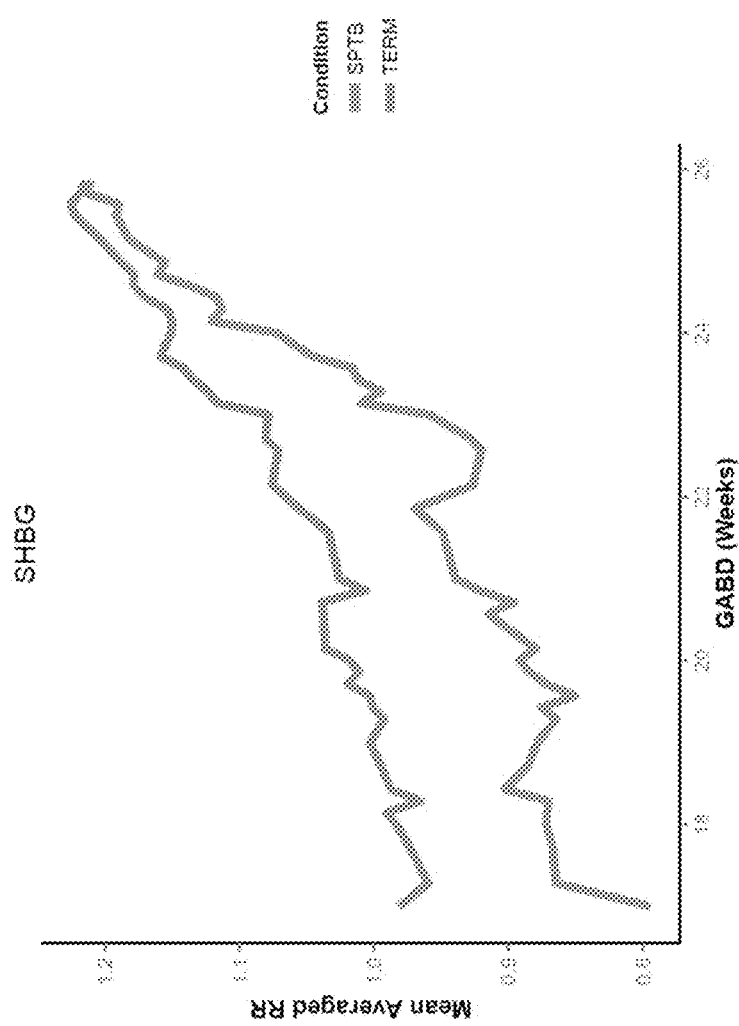
FIG. 45 shows the average response ratio for SHBG levels separately for sPTB cases and term controls across gestational age at blood draw (GABD). Cross sectional discovery data was analyzed by smoothing using a sliding 10 day window. Case versus control signal corresponds to an approximate maximal 10% difference.
Figure 46:
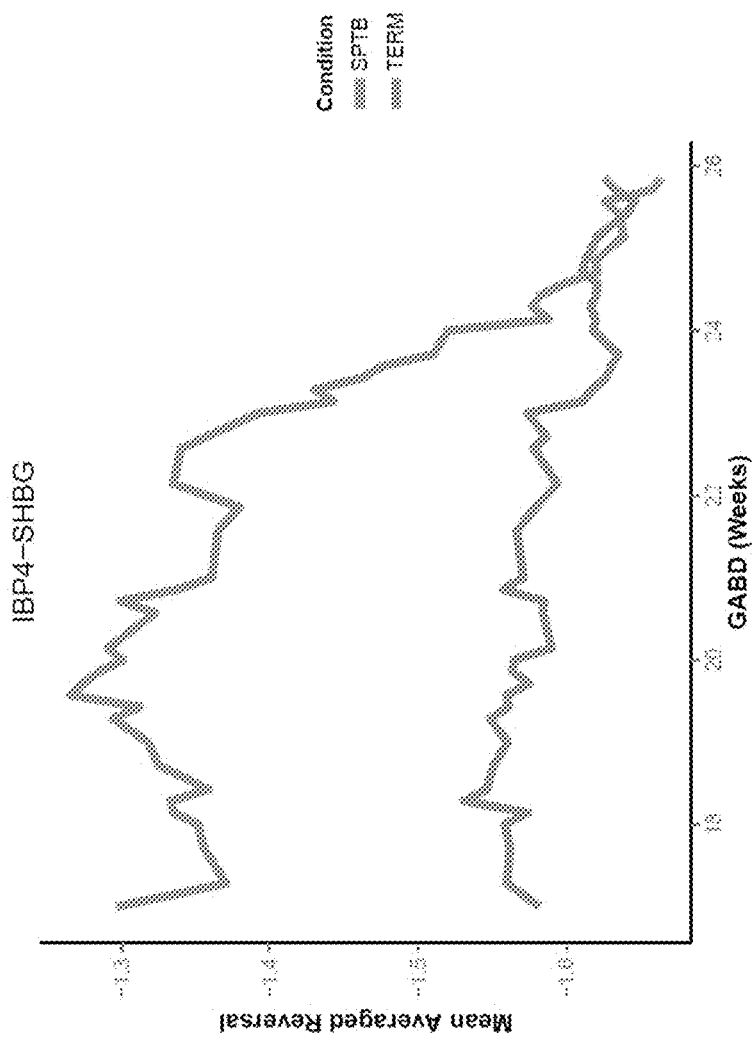
FIG. 46 shows the IBP4/SHBG predictor score separately for sPTB cases and term controls across gestational age at blood draw (GABD). Cross sectional discovery data was analyzed by smoothing using a sliding 10 day window. The maximal difference between the two curves corresponds to approximately a 20% difference, compared with the approximate 10% difference in signal for the individual analytes (FIGS. 45 and 46). These data demonstrate the amplification of diagnostic signal obtained by employing the IBP4/SHBG reversal strategy.

Shown are the levels of IBP4 and SHBG determined by MS across the indicated gestation age range for sPTB cases and term controls separately (FIG. 44 and FIG. 45). Curves were generated by a mean smoothing of the peptide relative ratios (endogenous peptide peak area over corresponding SIS peak area). Case versus control signal corresponds to an approximate maximal 10% difference for IBP4 and SHBG. When the score calculated as ln(IBP4RR/SHBGRR) is plotted an amplification of signal is evident (maximal difference of approximately 20%) (FIG. 46). These data demonstrate the amplification of diagnostic signal obtained employing the IBP4/SHBG reversal strategy.

Figure 48:
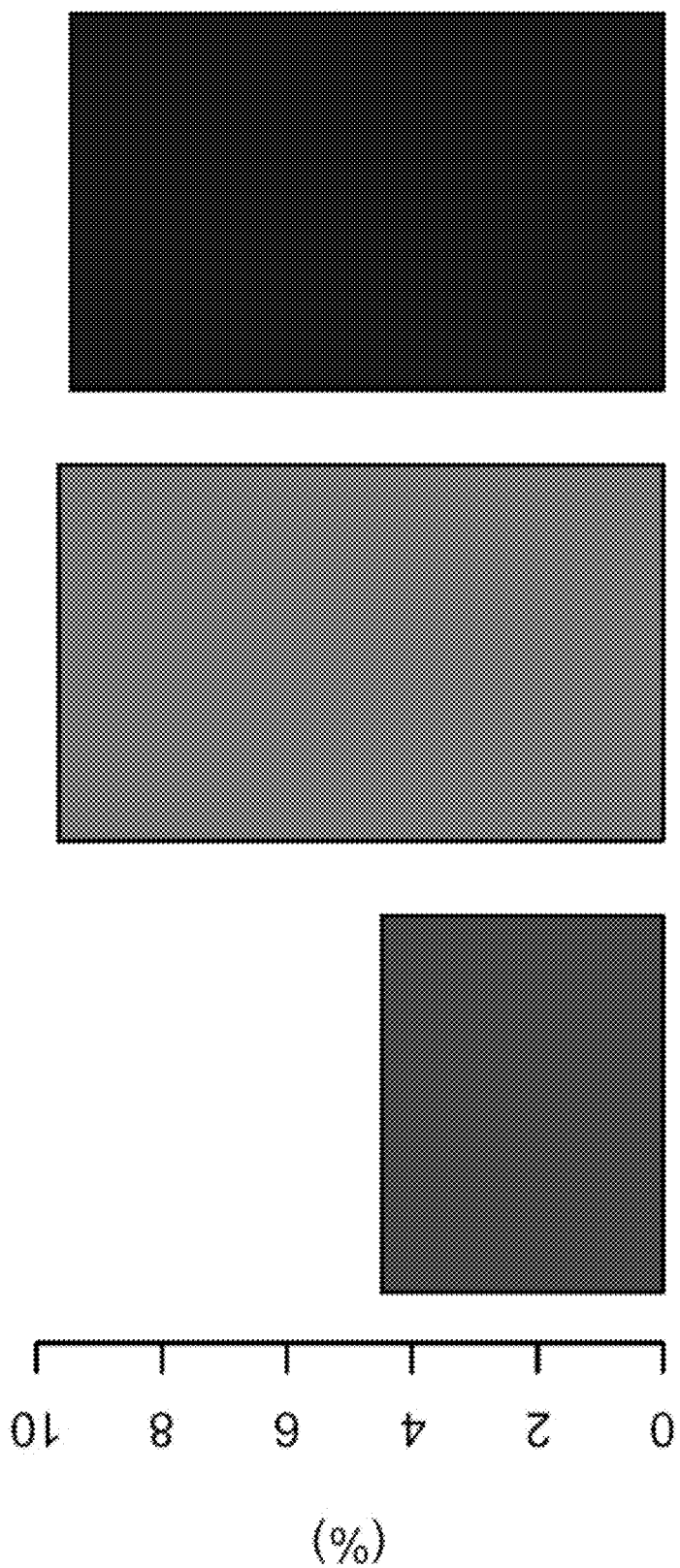
FIG. 48 shows the analytical coefficient of variation (CV) for the measure of individual IBP4 and SHBG response ratios and for the calculated corresponding reversal score. Pooled control serum samples from pregnant donors (pHGS) free of biological variability, were analyzed in multiple batches and across several days. Reversal variability is less than the variability associated with the individual proteins. These data indicate that formation of the reversal controls for analytical variability that occurs during the laboratory processing of samples. Analytical variability is not a biological phenomenon.

Forming the ratio of the levels of two proteins may reduce the variability because each protein experiences the same analytical and preanalytical processing steps. To examine the impact on variability the CVs were determined for the individual proteins (RR of IBP4 and SHBG) and for IBP4 RR/SHBG RR ratio in pooled control serum samples from pregnant donors (pHGS). Pooled control samples, free of biological variability, were analyzed in multiple batches and across several days. Reversal variability is less than the variability associated with the individual proteins. (FIG. 48)

Figure 47A:
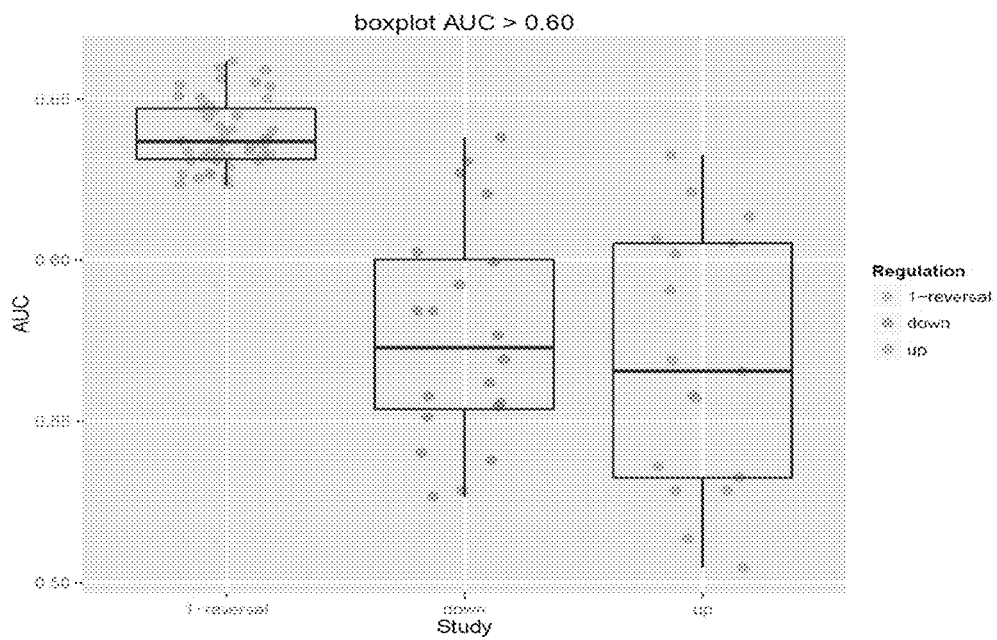
FIGS. 47A-47B show the amplification of diagnostic signal as a result of the formation of many different reversals. To investigate whether formation of reversals in general amplifies diagnostic signal we examined the diagnostic performance of reversals formed by many different proteins by ROC analysis. Shown in the top panel (FIG. 47A) is the range of AUC values (sPTB case vs term control) using datasets from samples collected between 19/0 weeks and 21/6 weeks gestation. The adjacent box plots show the range in ROC performance for the individual up-regulated and down-regulated proteins used to form the associated reversals. Similarly, the lower panel (FIG. 47B) shows the p-values derived from a Wilcoxon test (sPTB case vs. term controls) for reversals are more significant than those for the corresponding individual proteins.
Figure 47B:
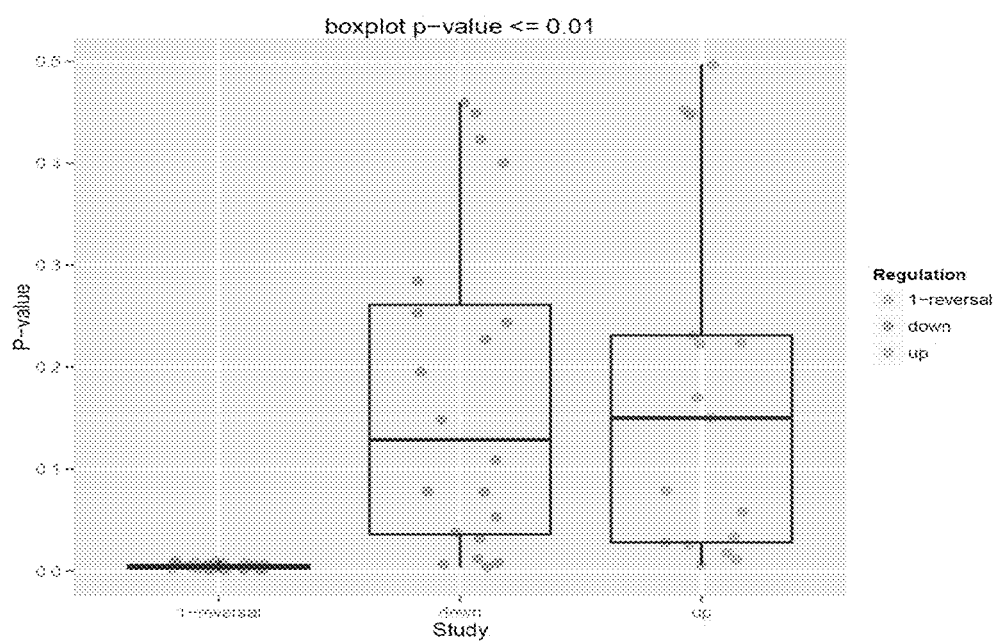

To investigate whether formation of reversals in general amplifies diagnostic signal we examined ROC performance (AUC) performance of high performing reversals (AUC>0.6) formed by the ratio of many proteins. Shown in the top panel of FIG. 47 is the range of AUC values (sPTB case vs term control) using datasets from samples collected between 19/0 weeks and 21/6 weeks gestation. The adjacent box plots show the range in ROC performance for the individual up-regulated and down-regulated proteins used to form the associated reversals. Similarly, p values derived from a Wilcoxon test (sPTB case vs. term controls) for reversals are more significant than those for the corresponding individual proteins (FIG. 47, bottom).

Figure 49:
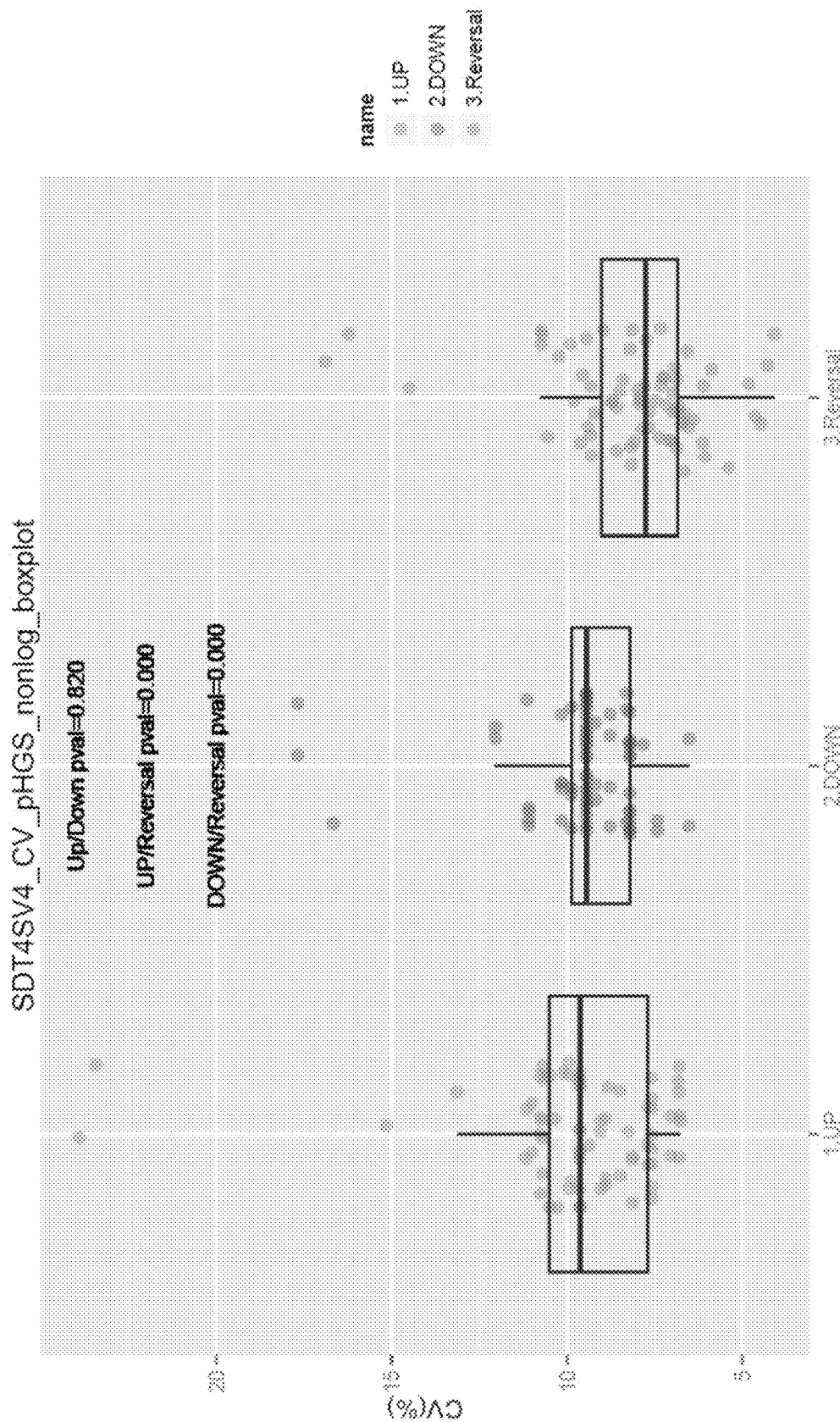
FIG. 49 shows the analytical CVs for many reversals and their individual up- and down-regulated proteins. To investigate whether formation of reversals in general amplifies diagnostic signal we examined ROC performance (AUC) of high performing reversals (AUC>0.6) formed by the ratio of many proteins. Shown in the top panel is the range of AUC values (sPTB case vs term control) using datasets from samples collected between 19/0 weeks and 21/6 weeks gestation. The adjacent box plots show the range in ROC performance for the individual up-regulated and down-regulated proteins used to form the associated reversals. Similarly, p values derived from a Wilcoxon test (sPTB case vs. term controls) for reversals are more significant than those for the corresponding individual proteins.

To investigate whether formation of reversals more generally reduces variability we examined the analytical variability for 72 different reversal values (i.e. ratio of relative peak areas versus the analytical variability of the individual proteins that comprise the reversals in pooled control serum samples from pregnant donors (pHGS). Pooled control samples, free of biological variability, were analyzed in multiple batches and across several days. Reversal variability is less than the variability associated with the individual proteins (FIG. 49).

Generalizability of the Reversal Strategy to Reduce Analytic Variability.

FIG. 48 reports the CVs calculated for pHGS specimens (pooled pregnant samples) analyzed in the lab in several batches, days and instruments. Because the CVs were calculated using pHGS specimens that are devoid of biological variability, they correspond to the measure of analytic variability introduced in the lab processing of samples. The analytic variability of associated with the ratioed value for 72 reversals is lower than the analytic variability of the relative peak areas of individual up-regulated and down-regulated proteins used to form the reversals FIG. 49.

Example 6. Medically Indicated PTB Analysis

This example confirms that the classifier is sensitive to a component of medically indicated PTB based on conditions such as preeclampsia or gestational diabetes.

Figure 50:
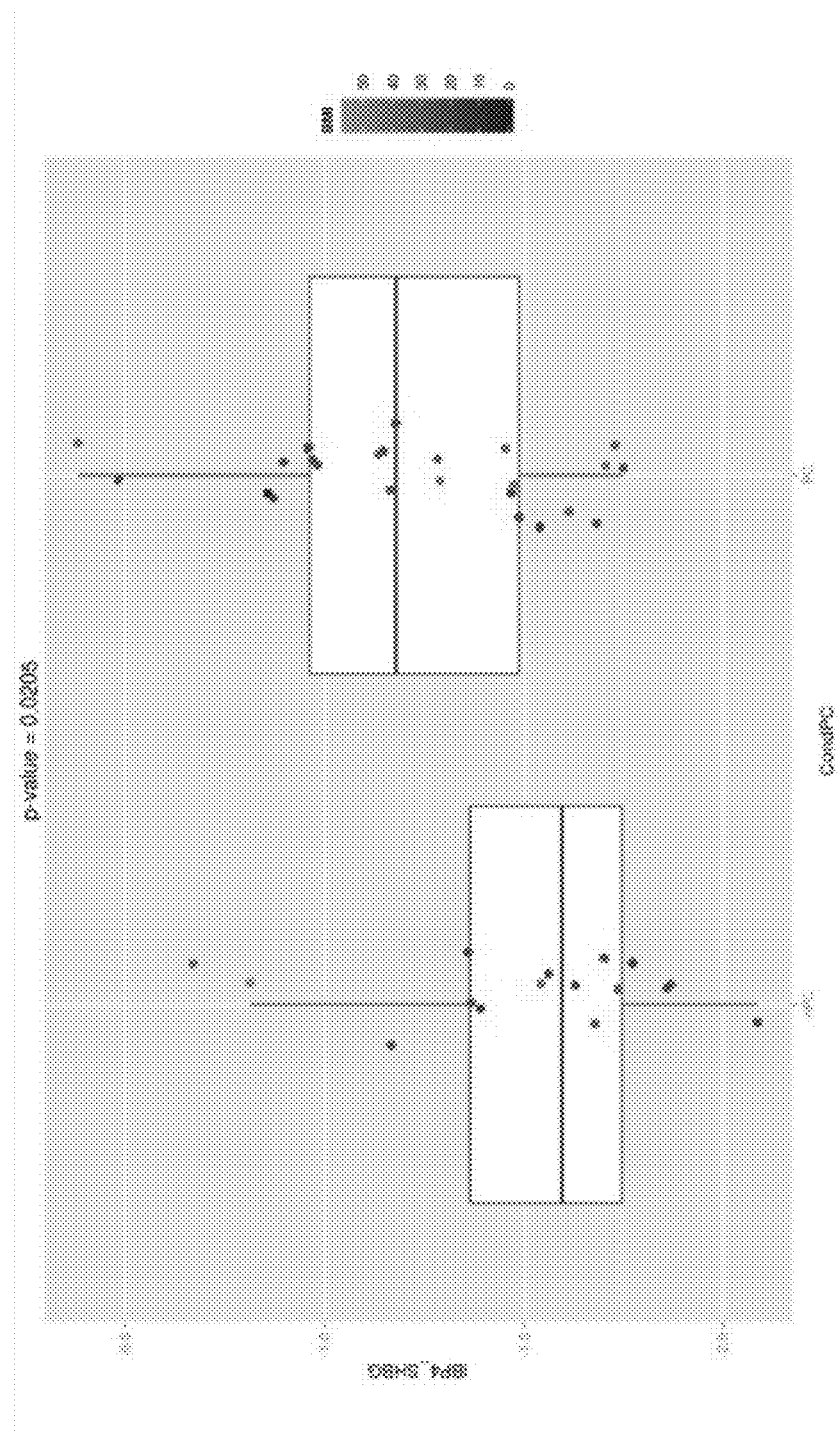
FIG. 50 shows PreTRM™ score comparison for subjects annotated as medically indicated for preeclampsia versus other indications.

PreTRM™ was developed and validated as a predictor for spontaneous PTB. About 75% of all PTB in the U.S. are spontaneous, the remaining are medically indicated due to some maternal or fetal complication (e.g. preeclampsia, intrauterine growth restriction, infection). 41 medically indicated PTB samples from the PAPR biobank were analyzed in the lab and PreTRM scores were calculated. The PreTRM™ scores were compared for those subjects annotated as medically indicated for preeclampsia versus other indications were compared. Subjects medically indicated for preterm delivery because of preeclampsia had significantly higher scores than others (FIG. 50).

Figure 52:
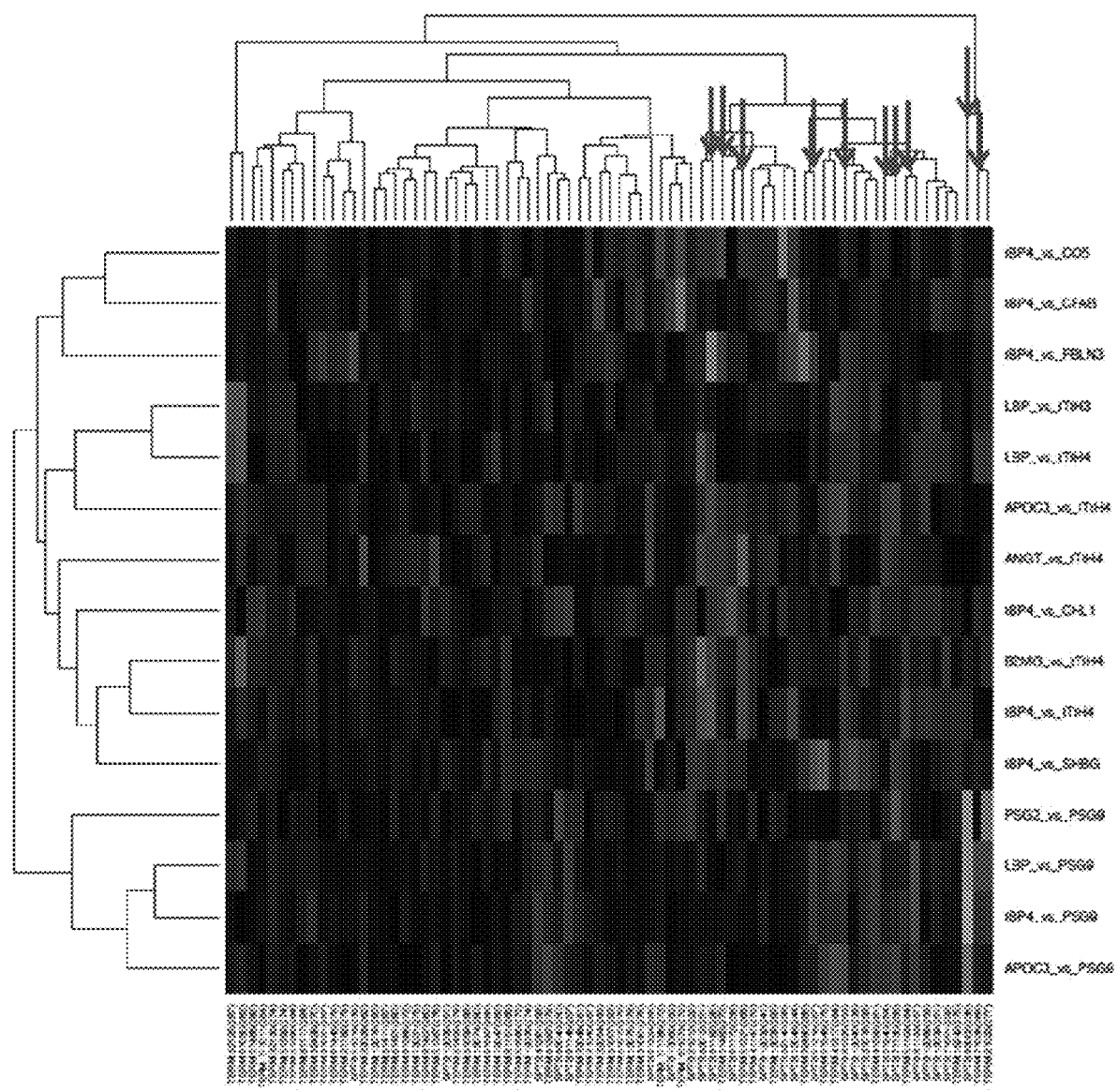
FIG. 52 shows a reversal intensity heatmap with diabetes annotation. The red arrows show diabetes cases. The samples are listed on the bottom with PTB cases on the right and term births on the left side of the screen. The diabetes patients are clustered on the right, showing that it is possible to build a diagnostic test from the biomarkers to predict gestational diabetes.

FIG. 52 shows a reversal intensity heatmap with diabetes annotation. The red arrows show diabetes subjects. The samples are listed on the bottom with PTB cases on the right and term births on the left side of the screen. The diabetes patients are clustered on the right, showing that reversals can be identified that stratify gestational diabetes and thus that it is possible to build a diagnostic test from the biomarkers to predict gestational diabetes.

Example 7. Other Transitions and Peptides

Table 16 shows comparative IBP4 peptide and transition MS data. Four different heavy labeled peptides (R*+10 daltons) exemplify various transitions and their relative intensities that could be monitored to quantify IBP4. Those skilled in the art could select potentially any of these peptides or transitions or others not exemplified to quantify IBP4.

Table 17 shows comparative IBP4 peptide and transition MS data. IBP4 tryptic peptides derived from recombinant protein was analyzed by MRM-MS to identify candidate surrogate peptide and their transitions. Those skilled in the art could select potentially any of these peptides or transitions or others not exemplified to quantify IBP4. IBP4 was identified in RBM (above), then the synthetic peptide was ordered to build the assay.

Table 18 shows Comparative SHBG peptide and transition MS data. SHBG tryptic peptides derived from recombinant protein or pooled pregnant serum was analyzed by MRM-MS to identify candidate surrogate peptide and their transitions. Those skilled in the art could select potentially any of these peptides or transitions or others not exemplified to quantify SHBG. Also shown are isoform specific peptides identified in serum.

Table 19 shows proteins with altered serum levels across 17-25 weeks GA in PTB samples. * Additional proteins limited to weeks 19-21 GA in PTB. LC-MS (MRM) assay of 148 proteins from multiple pathways and analyzed serum samples from gestational age (GA) weeks 17-25 from 312 women (104 sPTB cases, 208 term controls). MRM peak area data was analyzed by hierarchical clustering, t-tests, and relationship to GA. Following analytic filtering, 25 proteins exhibited significant differences ($p<0.05$) in sPTB vs term subjects (Table 1). Levels of 14 proteins were higher and 3 were lower in sPTB samples across the entire GA range. Other proteins were found to be dynamically regulated in sub-intervals of the GA period. For example, in GA weeks 19-21, an additional 7 proteins were elevated and 1 was lower in sPTB.

Table 20 lists 44 proteins meeting analytical filters that were up- or down-regulated in sPTB vs. term controls.

Example 8. Mechanistic Insights from Serum Proteomic Biomarkers Predictive of Spontaneous Preterm Birth This example demonstrates that, as specific protein expression changes dynamically throughout pregnancy, biomarker performance varies considerably across GA. Differentially expressed proteins have functions in steroid metabolism, placental development, immune tolerance, angiogenesis and maintenance of pregnancy. FIGS. 55, 57-59. These protein profile differences seen in sPTB reflect impaired developmental transitions within the fetal/placental compartment during the second trimester.

Briefly, the objective of the study described in this example was to gain insight into the physiological basis for biomarker association with spontaneous preterm birth (sPTB) prediction.

Study Design

Pathways such as inflammation, infection and bleeding have been implicated in the etiology of preterm birth. However, less is known about which proteins are measurable in blood and when in gestation they are disrupted. To answer these questions we created an LC-MS (MRM) assay of 148 proteins from multiple pathways and analyzed serum samples from gestational age (GA) weeks 17-25 from 312 women (104 sPTB cases, 208 term controls).

Briefly, serum samples were depleted of high abundance proteins, digested with trypsin and fortified with heavy-labeled stable isotope standard (SIS) peptides for nearly all of the proteins. SIS peptides were used for normalization by generating response ratios, where the peak area of a peptide fragment ion (i.e. transition) measured in serum was divided by that of the corresponding SIS transition. Response ratios of MRM peak area data were analyzed by hierarchical clustering, t-tests and relationship to GA.

Figure 53:
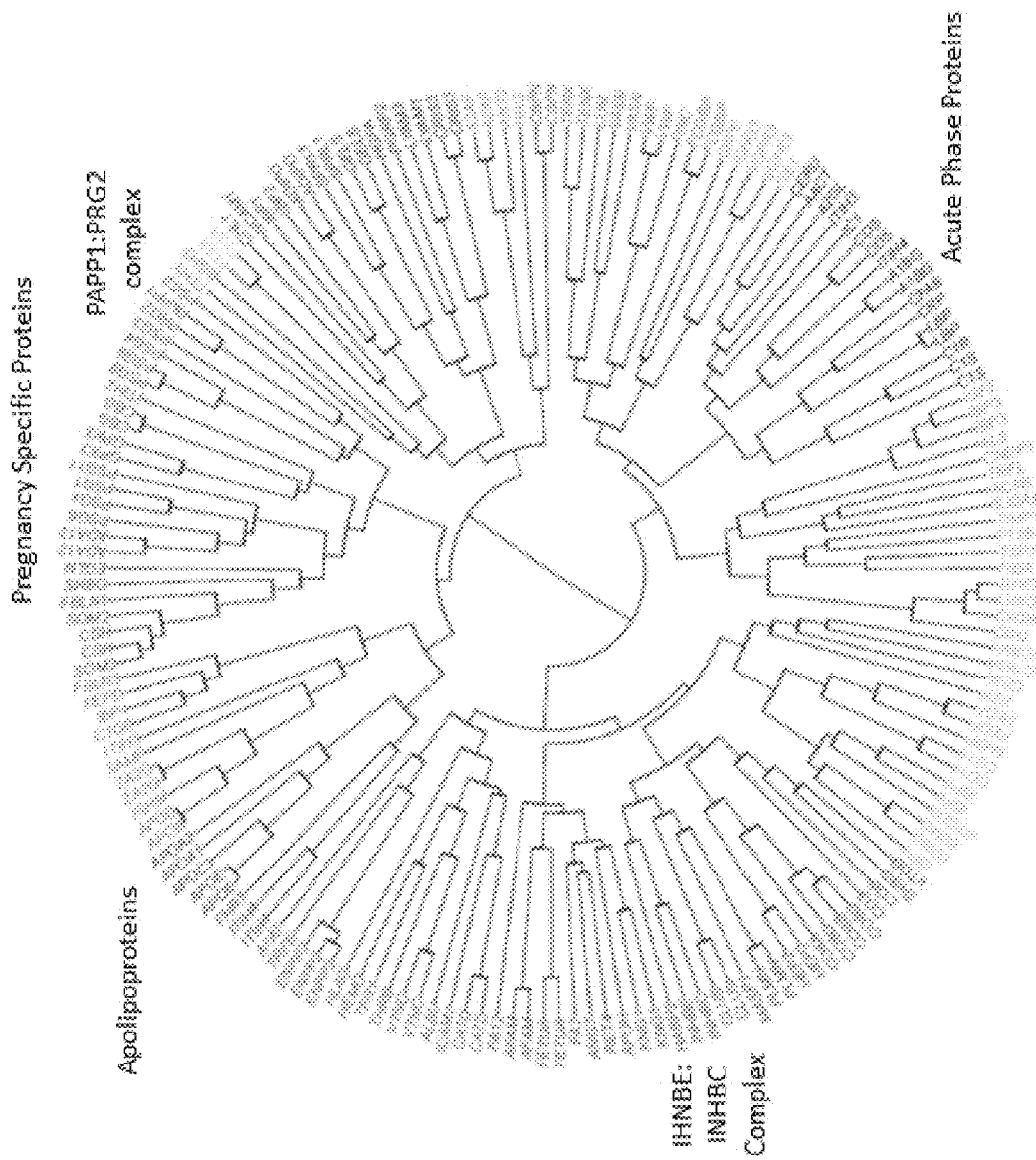
FIG. 53 shows hierarchical clustering of analyte response ratios.
Figure 55A:
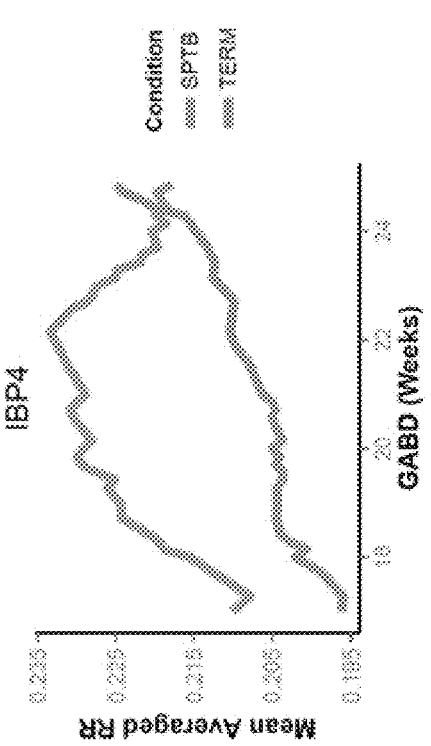
FIGS. 55A-55D show kinetic plots of differentially expressed proteins with functions in the IGF-2 pathway that show maximum separation at 18 weeks.
Figure 55B:
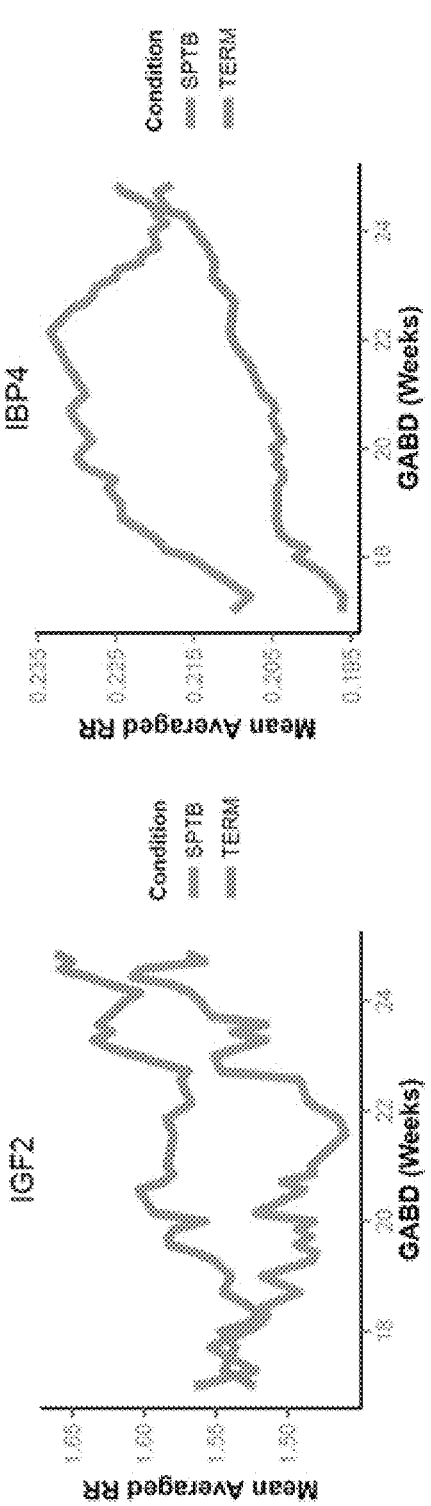
Figure 55C:
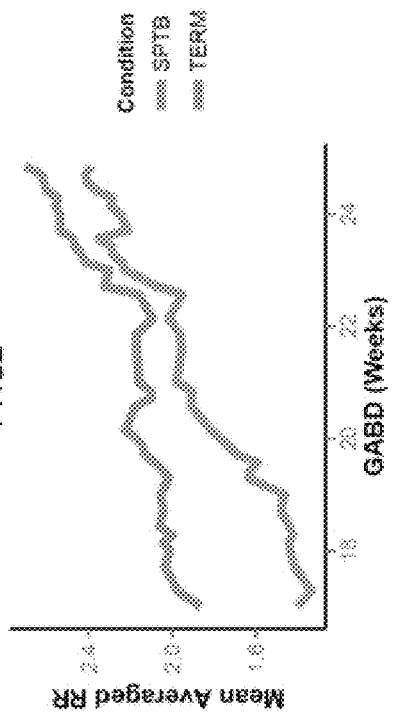
Figure 55D:
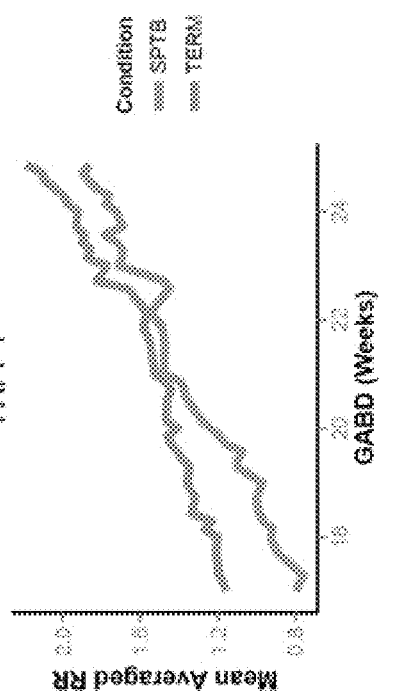

As shown in FIG. 53, multiple peptides to the same protein are well correlated. Discrete branches (grouped by color) correspond to identifiable functional categories such as: acute-phase proteins, apolipoproteins and known pregnancy specific proteins. Protein complexes important in reproductive biology such as: PAPP1:PRG2, INHBE:INHBC, and IGF2:IBP3:ALS are evident. These quality assessments and highlighted relationships validate the highly multiplexed MRM-MS assay described in this application for use in probing the biology of pregnancy and the discovery of analytes predictive of sPTB.

FIG. 54 shows differentially expressed proteins that function in extracellular matrix interactions. TENX activates latent TGF-b and is localized to fetal and maternal stroma at transition points of cytotrophoblast differentiation. Alcaraz, L., et al. 2014 J. Cell Biol. 205(3) 409-428; Damsky, C., et al. 1992 J. Clin. Invest. 89(1) 210-222. Reduced serum TENX levels in sPTB indicate blood vessel defects or reduced TGF-b activity in placenta. NCAM1(CD56) is highly expressed on neural cells and natural killer cells. NCAM1 is also expressed by endovascular trophoblasts, but is reduced or absent in PE placentas. Red-Horse, K., et al. 2004 J. Clin. Invest. 114:744-754. Inverted serum NCAM1 levels in sPTB cases can reflect poor spiral artery remodeling and/or defective immunoregulation. CHL1 is homologous to NCAM1 and directs integrin-mediated cell migration. BGH3(TGFBI), a cell adhesion molecule expressed in vascular endothelial cells, and inhibits angiogenesis via specific interactions with $\alpha v/\beta 3$ integrin. Son, H-N., et al. 2013 Biochimica et Biophysica Acta 1833(10) 2378-2388. Elevated TGFBI in sPTB cases may indicate reduced placental angiogenesis.

Figure 56B:
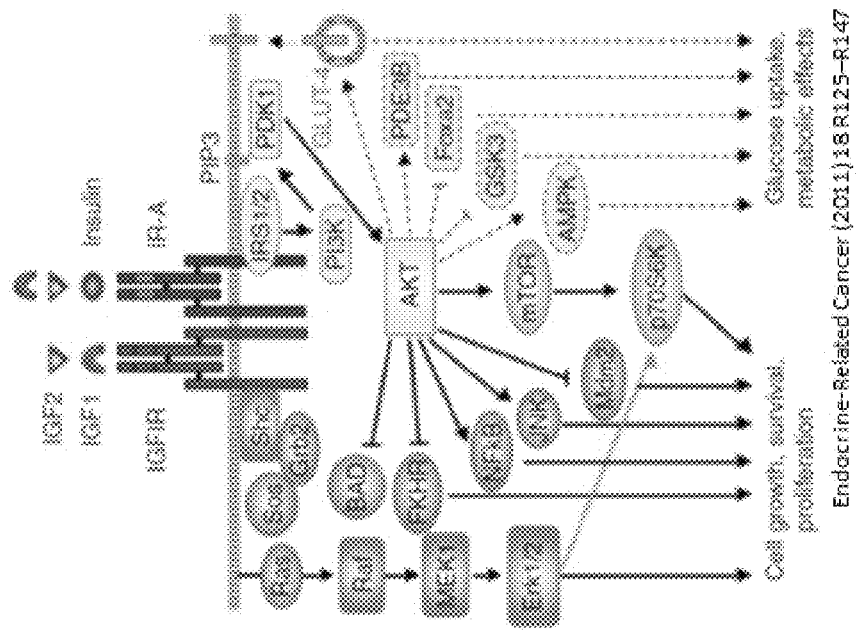
FIG. 56B shows a schematic of intracellular signals preferentially activated by insulin binding to the IR-B and by insulin and IGFs binding to either IR-A or IGF1R.
Figure 56A:
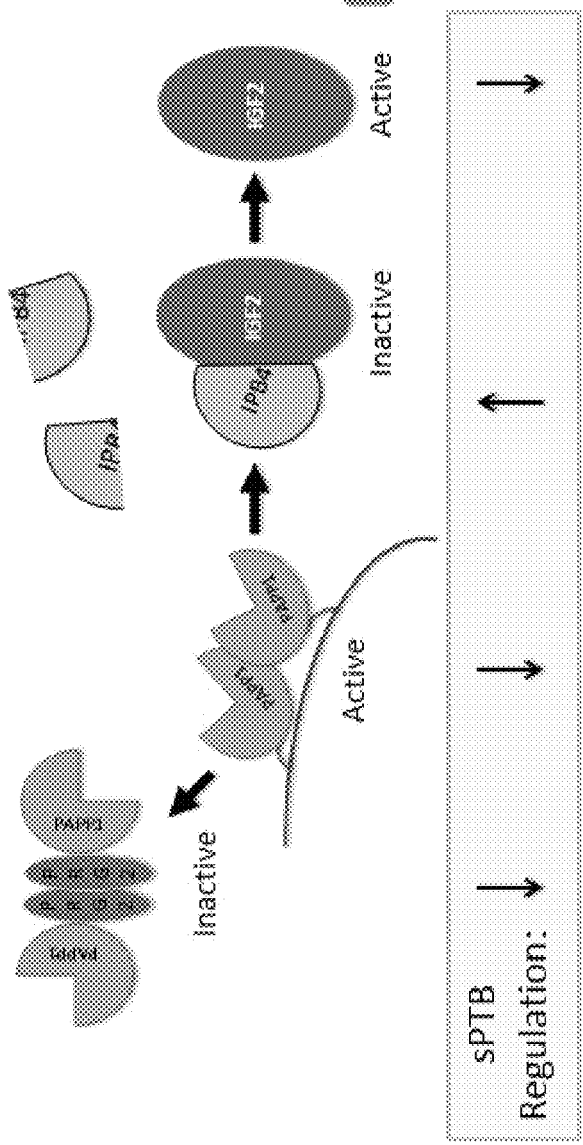
FIG. 56A shows a schematic of interactions between IGF-2, IBP4, PAPP1 and PRG2 proteins affecting bioavailability of these proteins in sPTB.

FIG. 55 shows kinetic plots of differentially expressed proteins with functions in the IGF-2 pathway that show maximum separation at 18 weeks. IGF2 stimulates proliferation, differentiation and endometrial invasion by extravillous trophoblasts in early pregnancy. IBP4 binds and modulates the bioavailability of IGF2 at maternal-fetal interface. Elevated IBP4 and reduced IGF2 during the 1st trimester are correlated with IUGR and SGA, respectively. Qiu, Q., et al. 2012 J. Clin. Endocrinol. Metab. 97(8):E1429-39; Demetriou, C., et al. 2014 PLOS 9(1): e85454. PAPP1 is a placental-specific protease that cleaves IBP4 and releases active IGF2. Low serum PAPP1 levels early in pregnancy are associated with IUGR, PE and PTB. Huynh, L., et al. 2014 Canadian Family Physician 60(10) 899-903.PRG2 (proMBP) is expressed in placenta and covalently binds and inactivates PAPP1. The PRG2:PAPP1 inactive complex circulates in maternal serum. Huynh, L., et al. 2014 Canadian Family Physician 60(10) 899-903. Perturbed pathway regulation is consistent with compromised IGF2 activity in sPTB cases that may result in abnormal placentation. FIG. 56 A shows a schematic of the dynamic regulation and bioavailability of the aforementioned proteins during sPTB.

FIG. 56 B shows a schematic of intracellular signals preferentially activated by insulin binding to the IR-B and by insulin and IGFs binding to either IR-A or IGF1R. Belfiore and Malaguarnera, Endocrine-Related Cancer (2011) 18 R125-R147. IR-A and IGF1R activation by insulin and IGFs leads to the predominance of growth and proliferative signals through the phosphorylation of IRS1/2 and Shc proteins. Shc activation leads to the recruitment of Grb2/Sos complex with subsequent activation of Ras/Raf/MEK1 and Erk1/2. This latter kinase translocates to the nucleus and induces the transcription of several genes involved in cell proliferation and survival. Phosphorylation of IRS1/2 induces the activation of the PI3K/PDK1/AKT pathway. Besides its role in metabolic effects, AKT leads to the activation of effectors involved in the control of apoptosis and survival (BAD, Mdm2, FKHR, NFkB, and JNK) and protein synthesis and cell growth (mTOR).

Figure 57A:
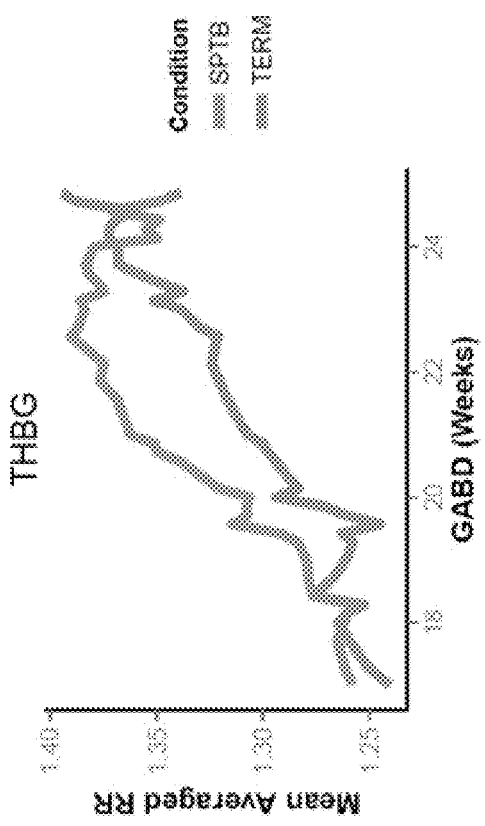
FIGS. 57A-57C show kinetic plots of differentially expressed proteins with functions in metabolic hormone balance.
Figure 57B:
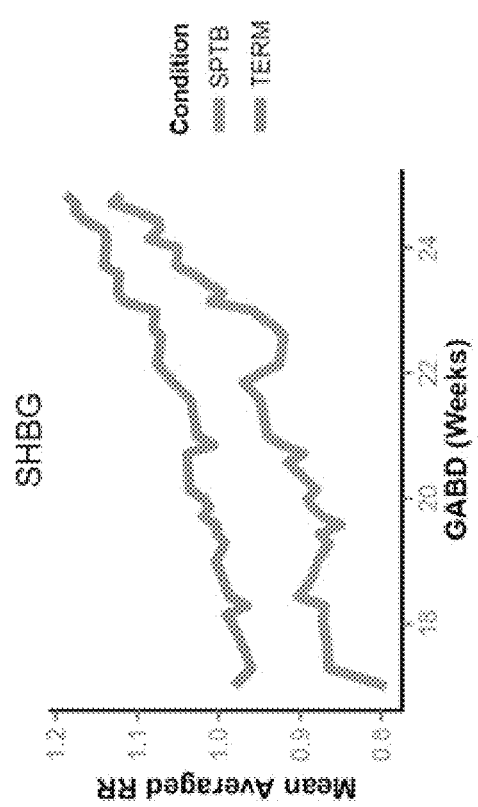
Figure 57C:
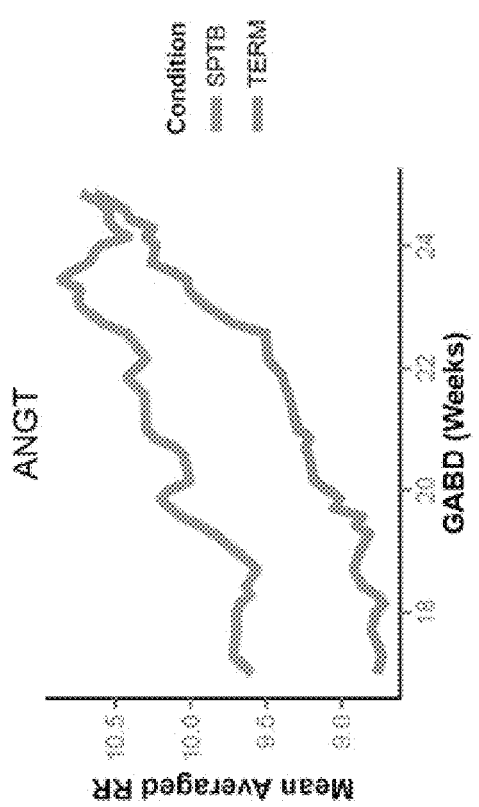
Figure 58A:
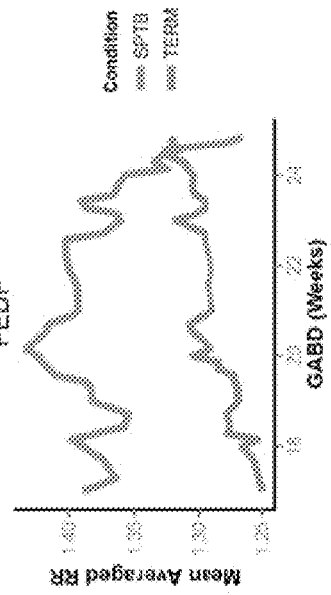
FIGS. 58A-58F show kinetic plots of differentially expressed proteins with functions in angiogenesis.
Figure 58B:
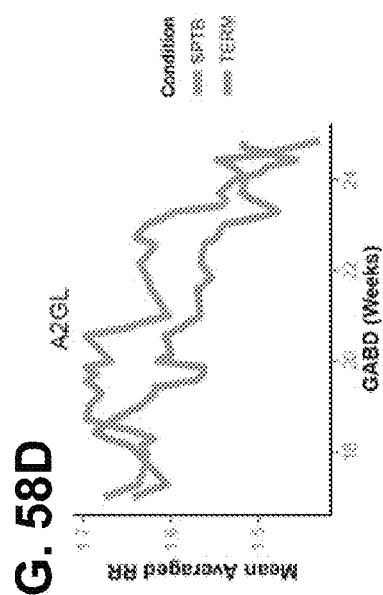
Figure 58C:
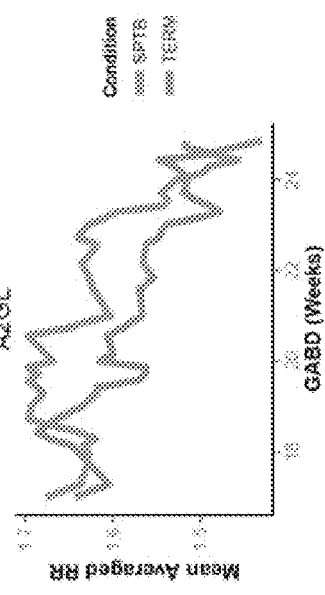
Figure 58D:
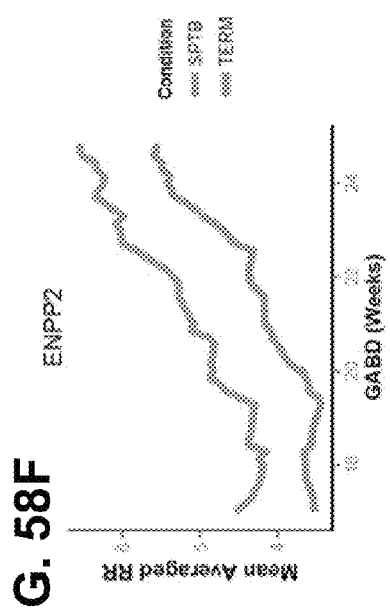
Figure 58E:
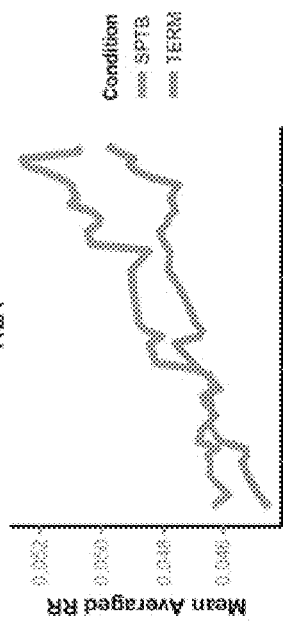
Figure 58F:
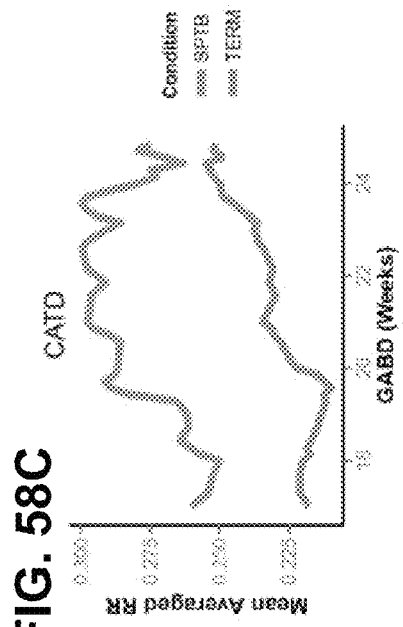
Figure 59A:
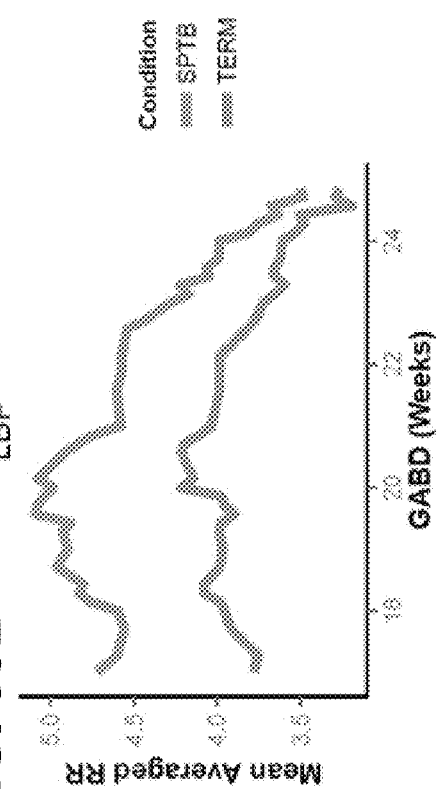
FIGS. 59A-59D show kinetic plots of differentially expressed proteins with functions in innate immunity.
Figure 59B:
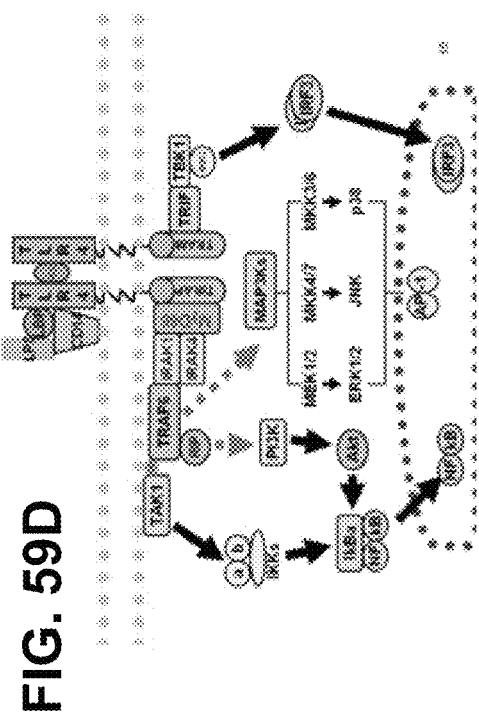
Figure 59C:
Figure 59D:
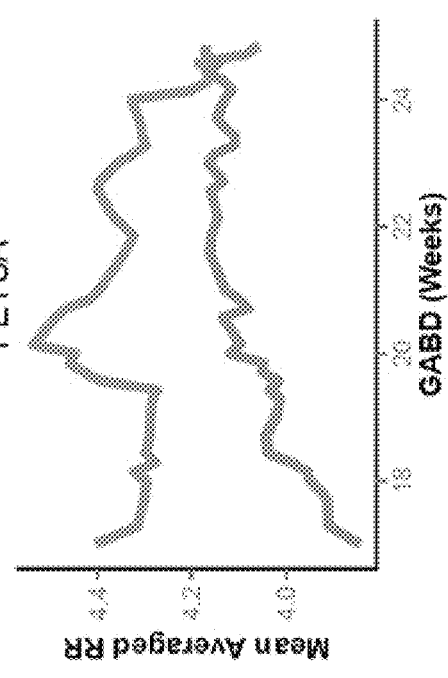
Figure 60A:
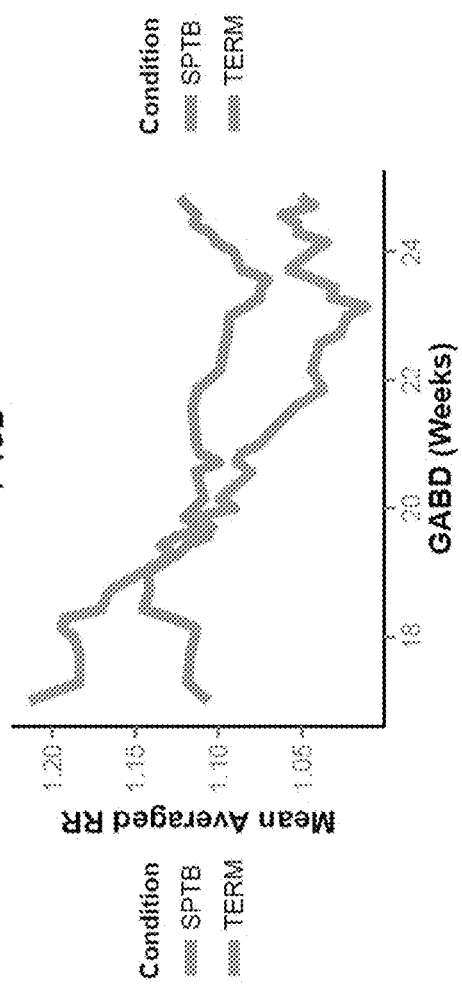
FIGS. 60A-60D show kinetic plots of differentially expressed proteins with functions in coagulation.
Figure 60B:
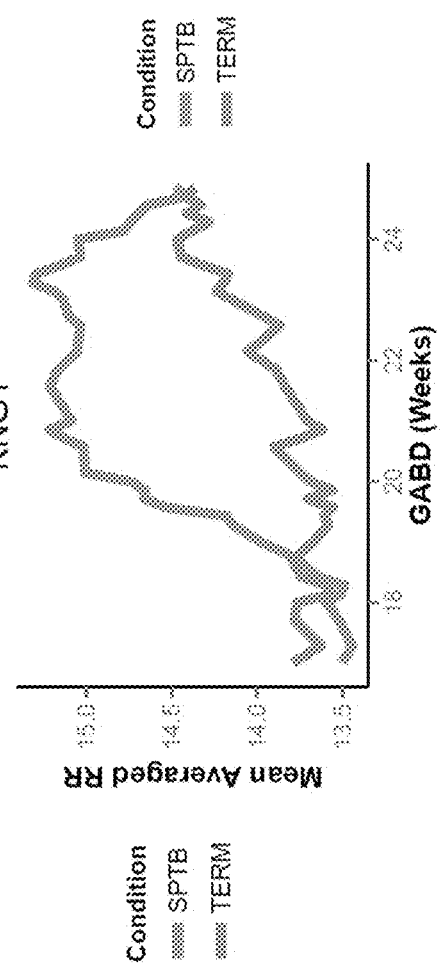
Figure 60C:
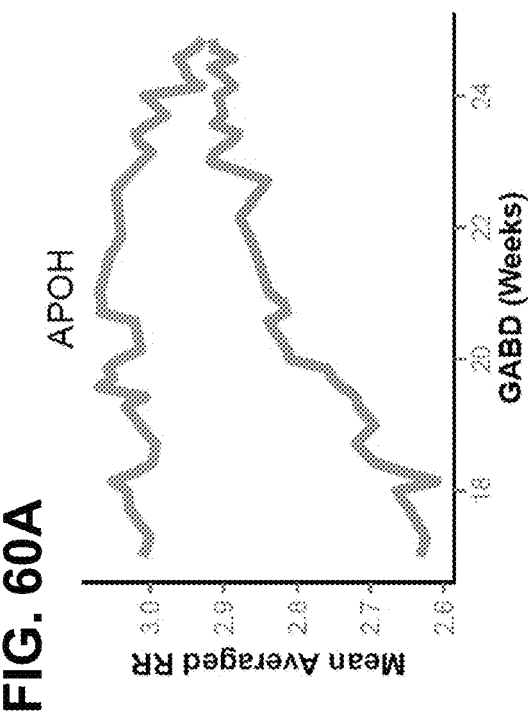
Figure 60D:
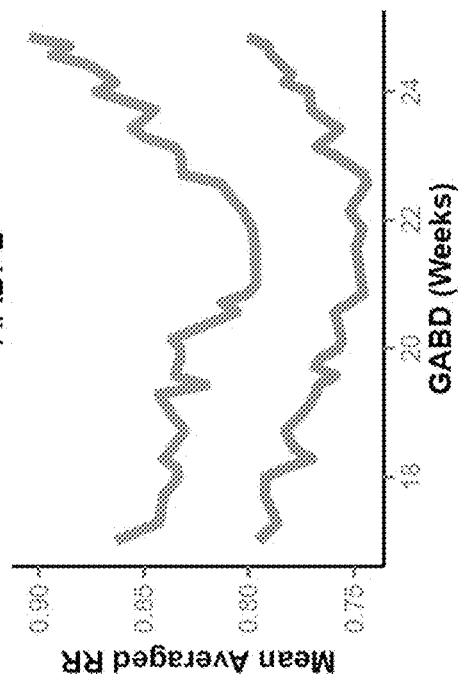
Figure 61A:
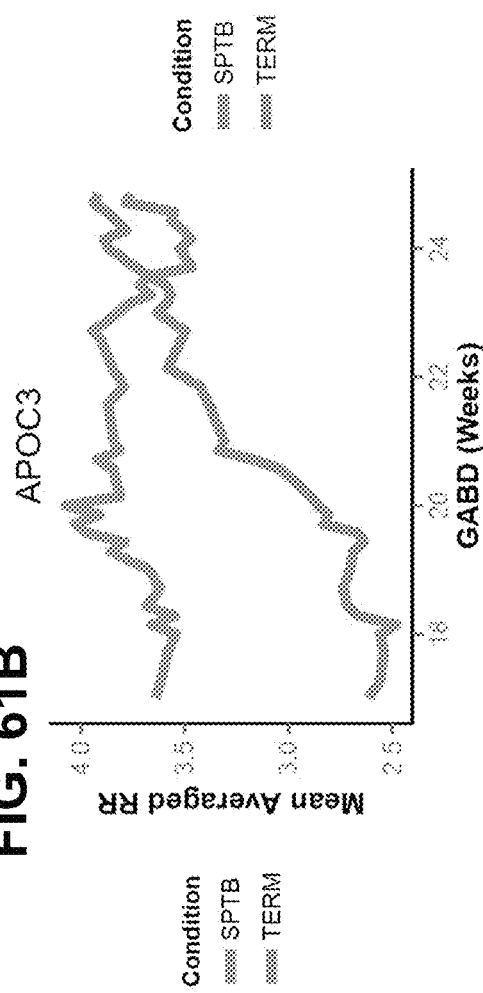
FIGS. 61A-61D show kinetic plots of differentially expressed serum/secreted proteins.
Figure 61B:
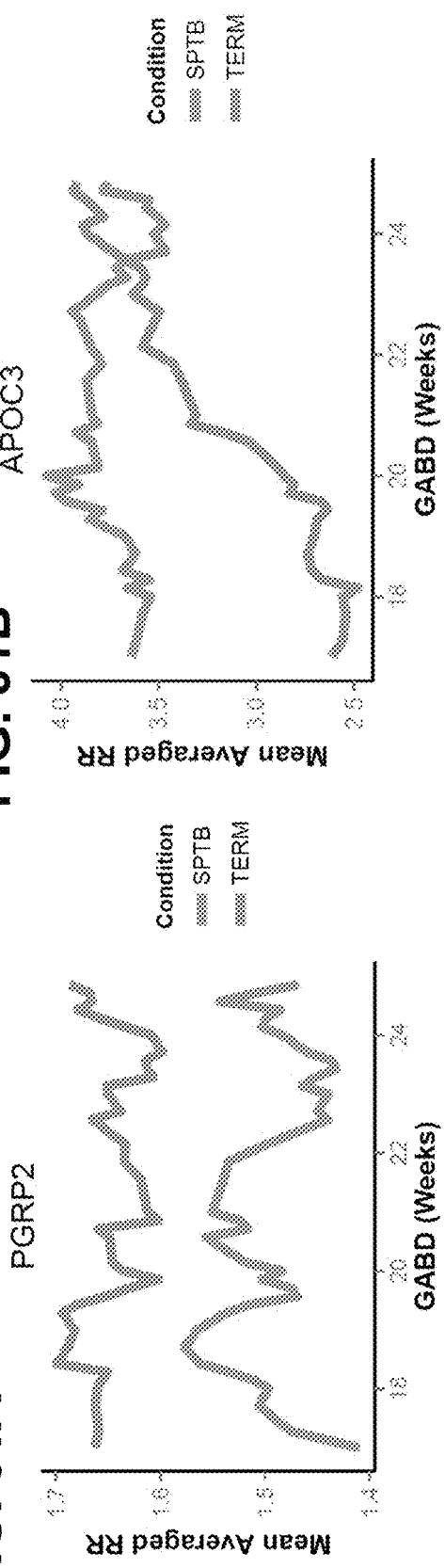
Figure 61C:
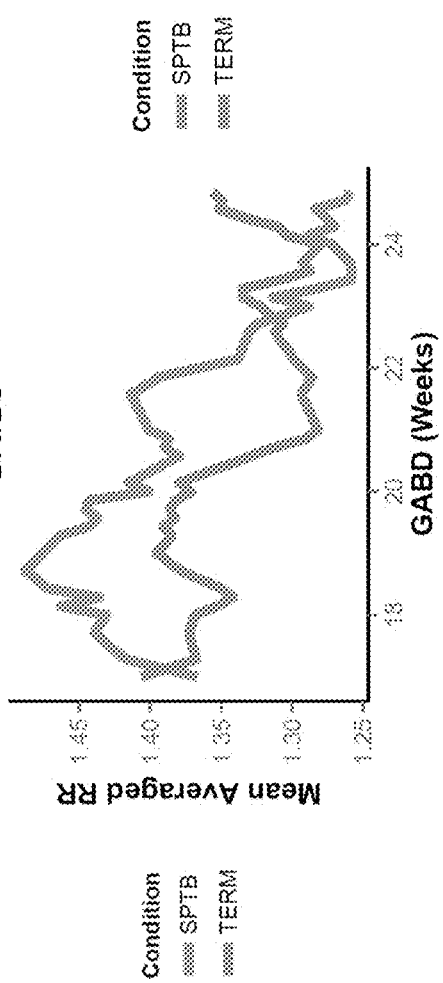
Figure 61D:
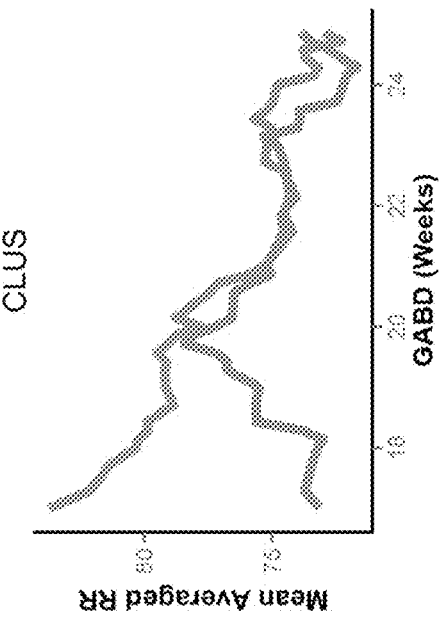
Figure 62A:
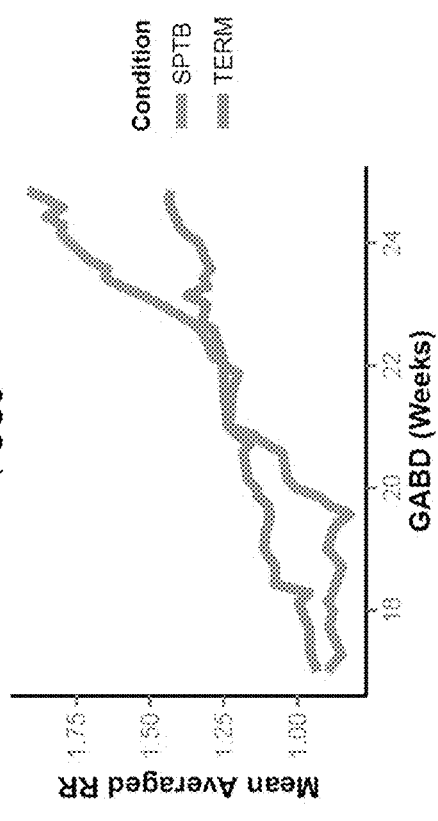
FIGS. 62A-62D show kinetic plots of differentially expressed PSGs/IBPs.
Figure 62B:
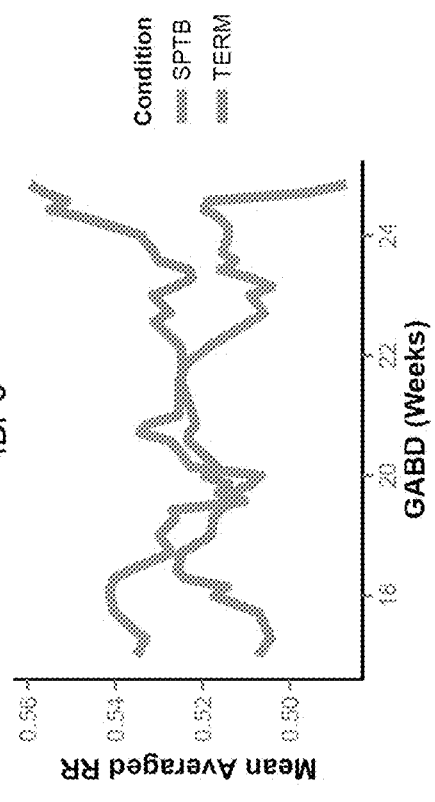
Figure 62C:
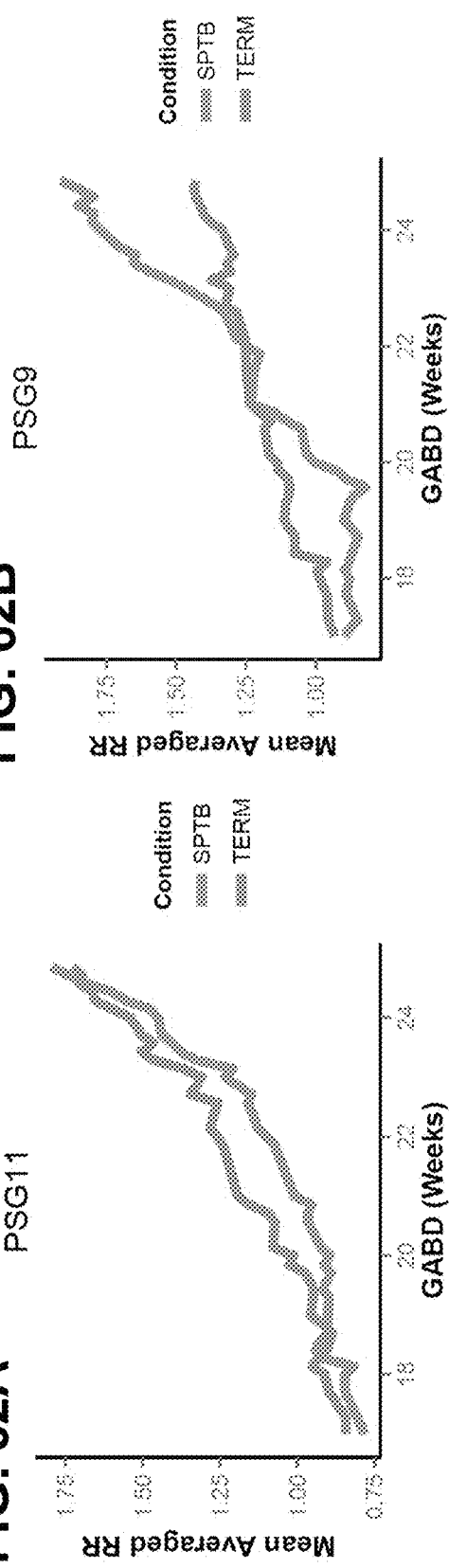
Figure 62D:
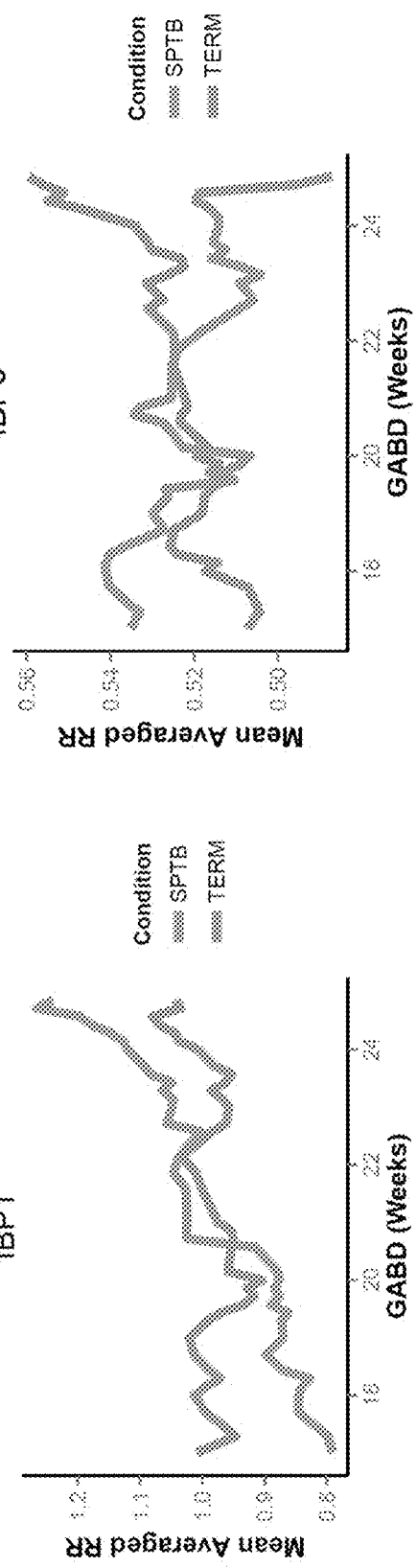
Figure 63A:
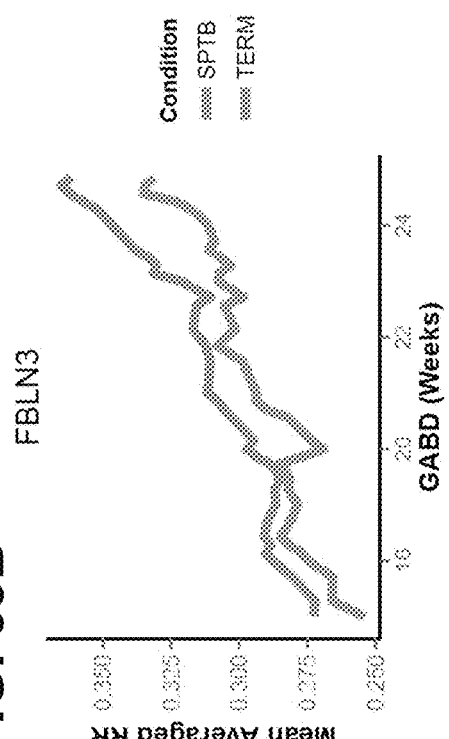
FIGS. 63A-63D show kinetic plots of differentially expressed ECM/cell surface proteins.
Figure 63B:
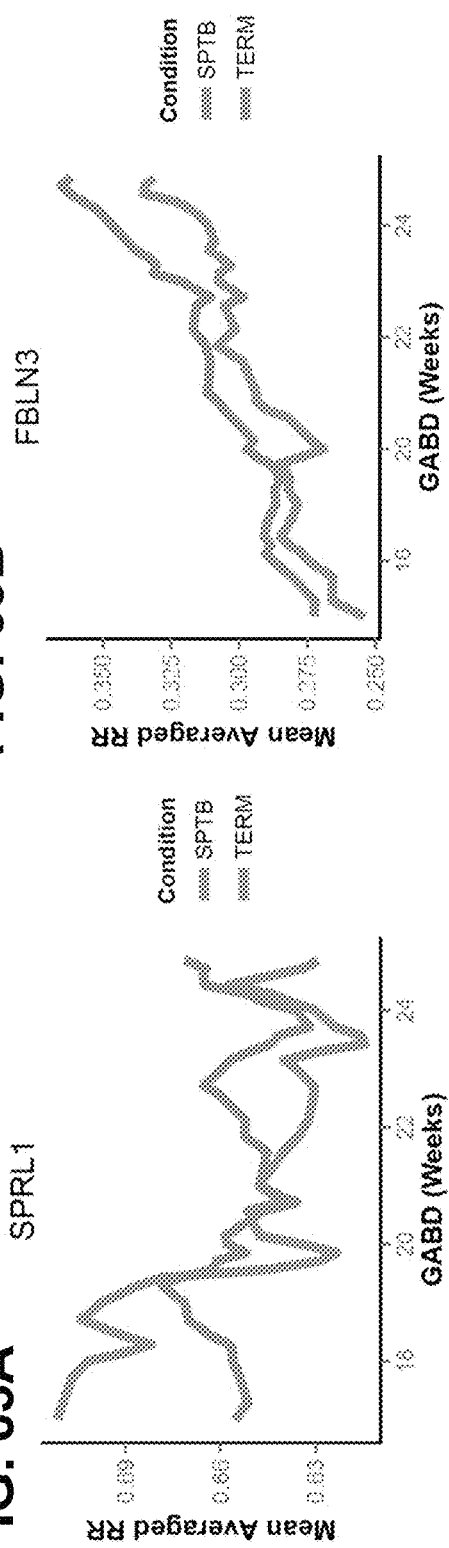
Figure 63C:
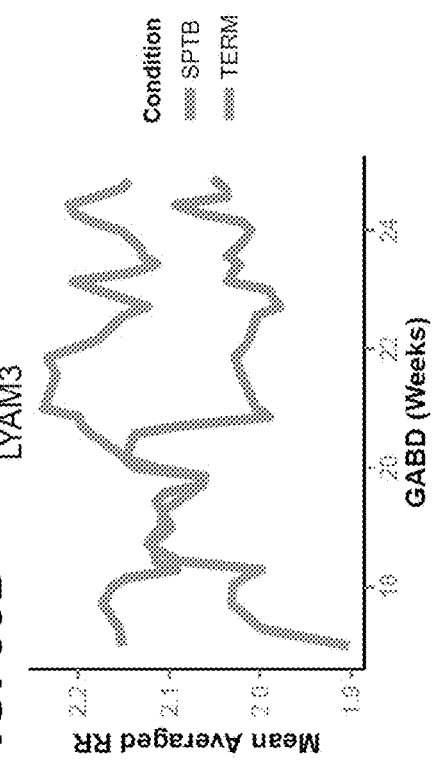
Figure 63D:
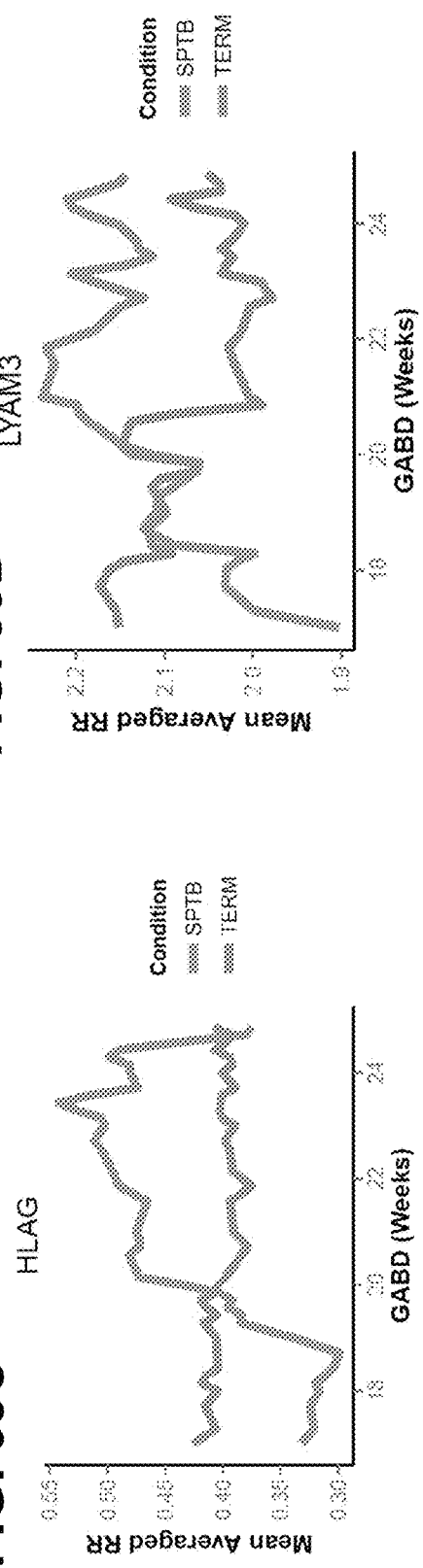
Figure 64A:
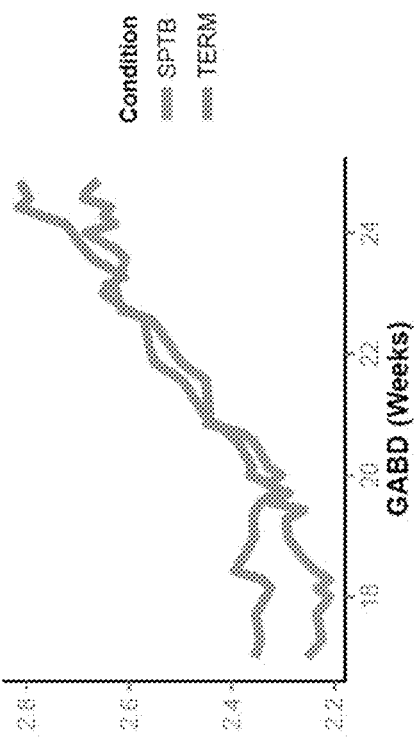
FIGS. 64A-64D show kinetic plots of differentially expressed complement/acute phase proteins-1.
Figure 64B:
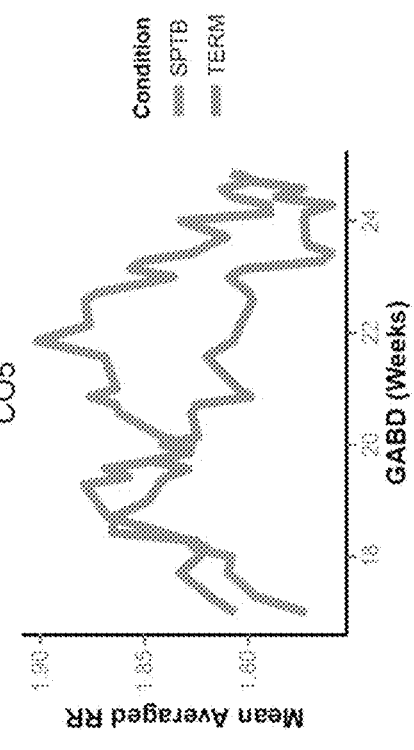
Figure 64C:
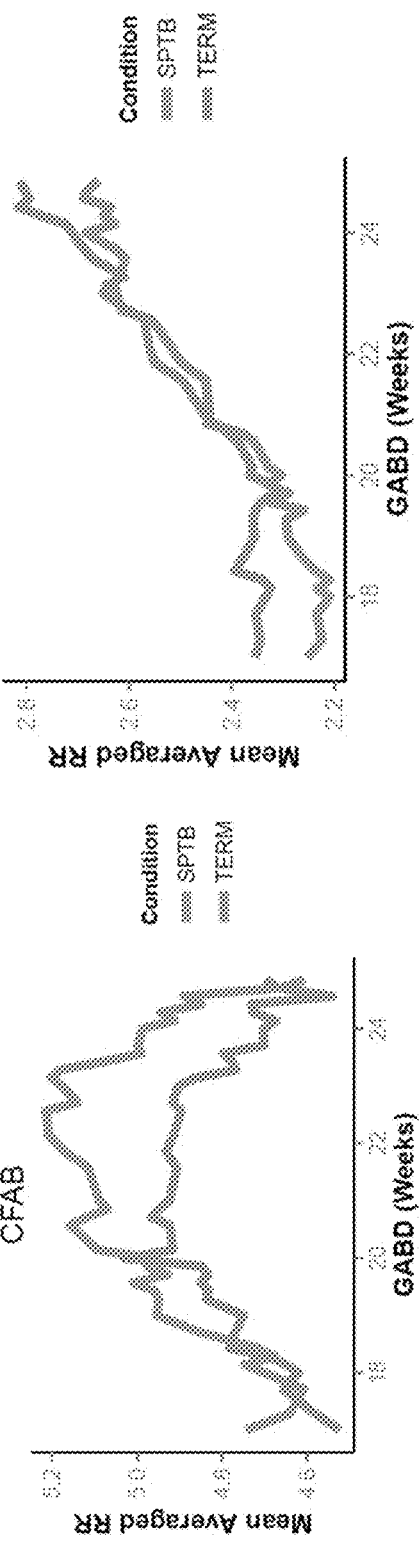
Figure 64D:
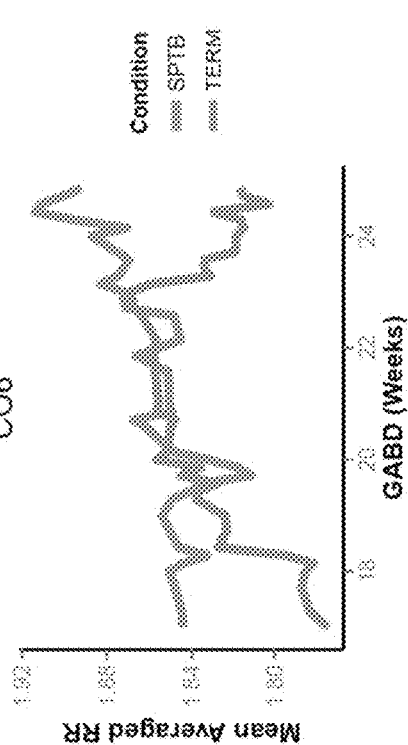
Figure 65A:
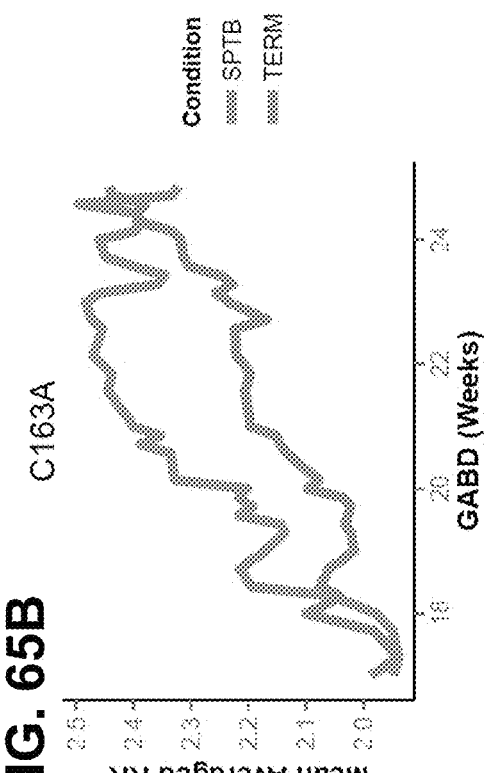
FIGS. 65A-65D show kinetic plots of differentially expressed shows kinetic plots of differentially expressed complement/acute phase proteins-2.
Figure 65B:
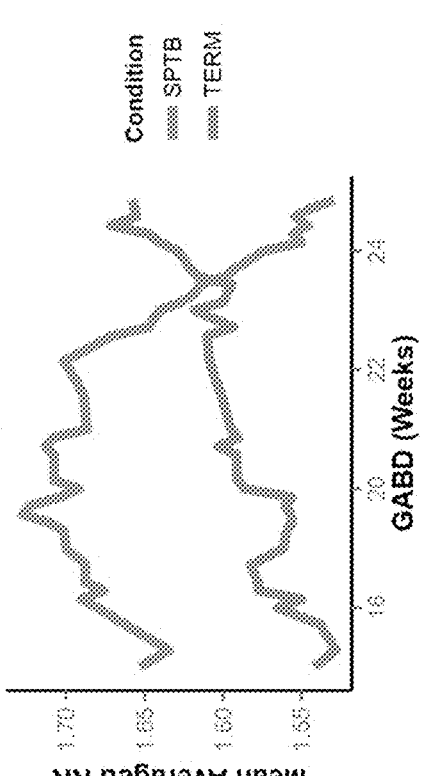
Figure 65C:
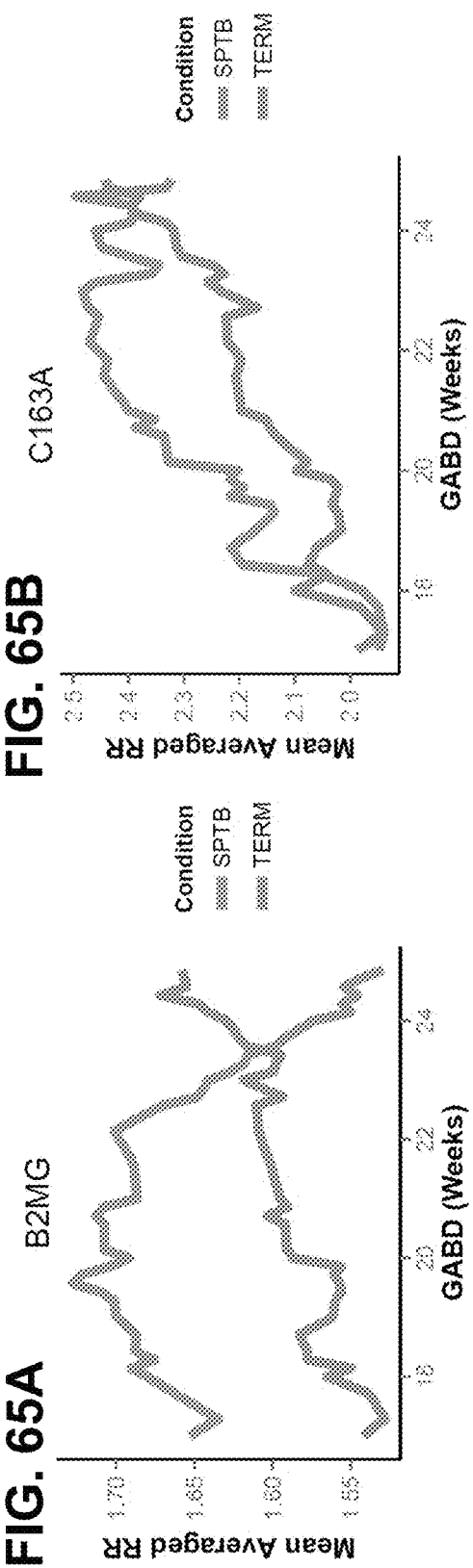
Figure 65D:
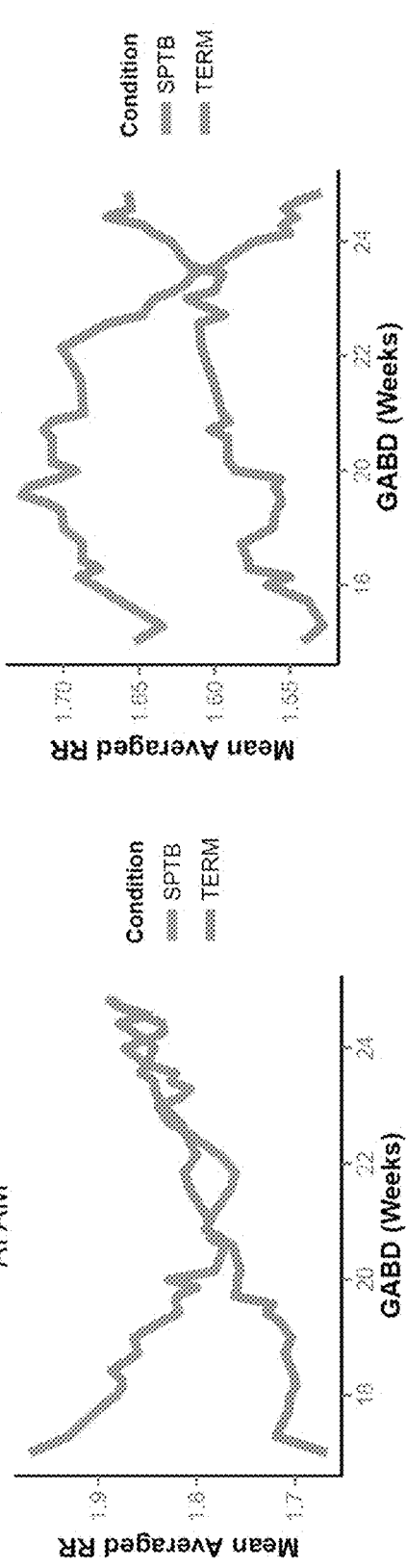
Figure 66B:
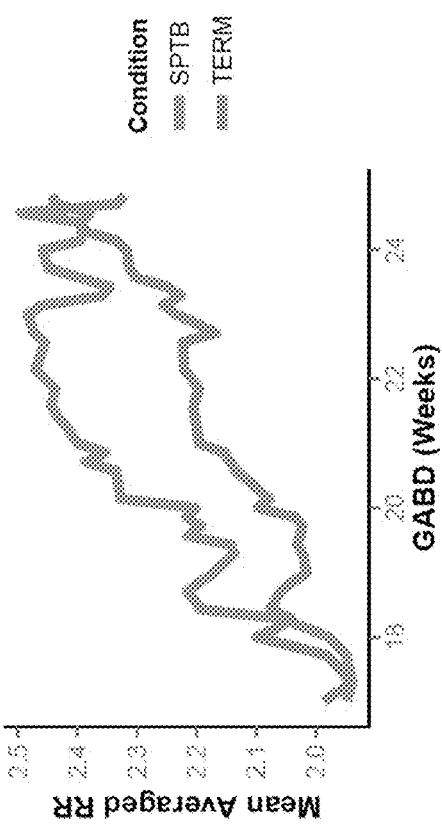
FIGS. 66A-66D show kinetic plots of differentially expressed complement/acute phase proteins-3.
Figure 66A:
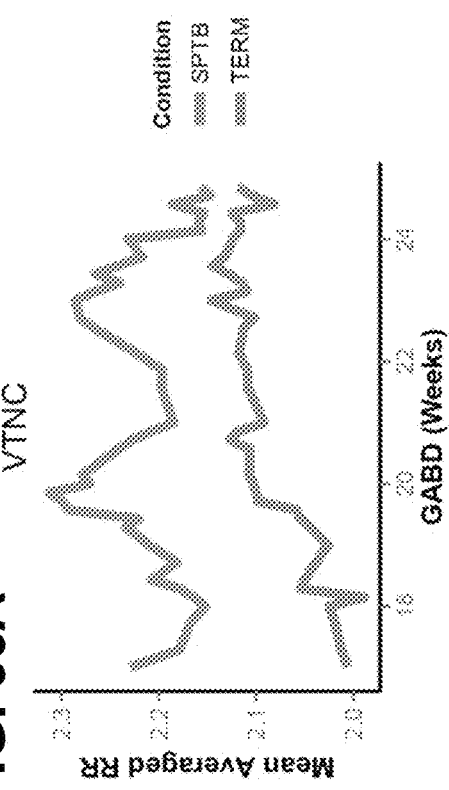
Figure 66D:
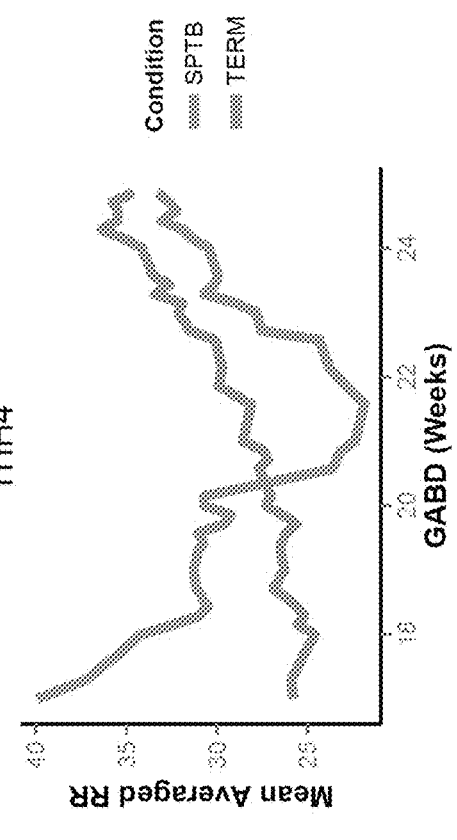
Figure 66C:
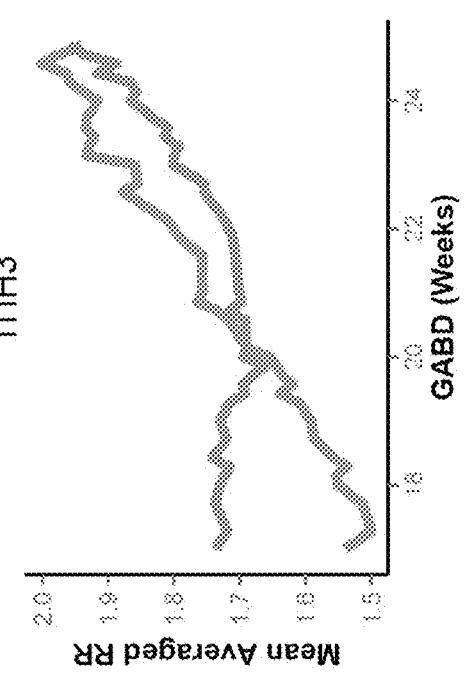
Figure 88A:
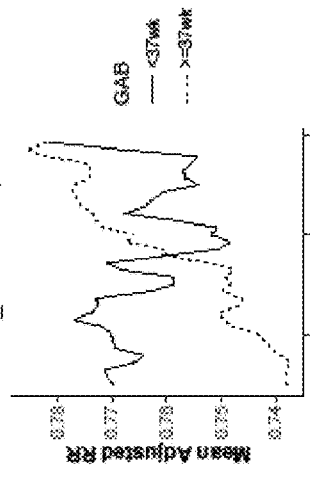
FIGS. 88A-88I show kinetic plots for peptide transitions specified in FIGS. 88A through 88I using gestational age at birth cutoff of <37 0/7 versus >=37 0/7 weeks. Figures disclose SEQ ID NOS:64, 66, 67, 68, 70, 71, 72, 74 and 76, respectively, in order of appearance.
Figure 88B:
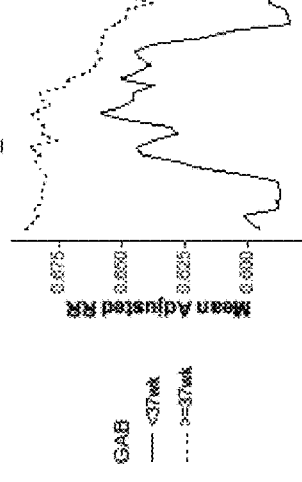
Figure 88C:
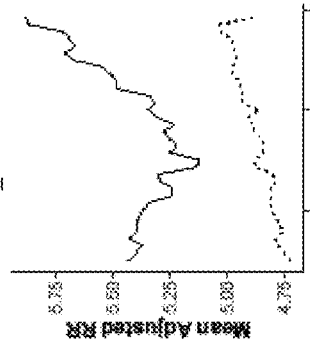
Figure 88D:
Figure 88E:
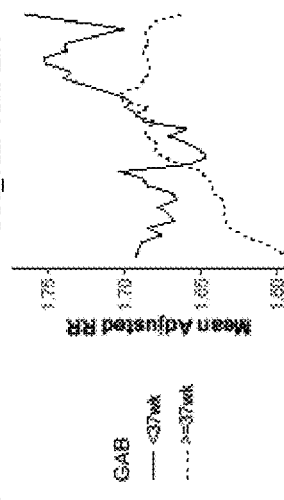
Figure 88F:
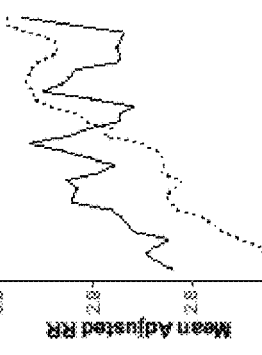
Figure 88G:
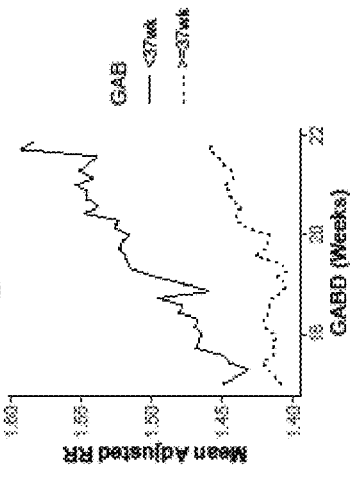
Figure 88H:
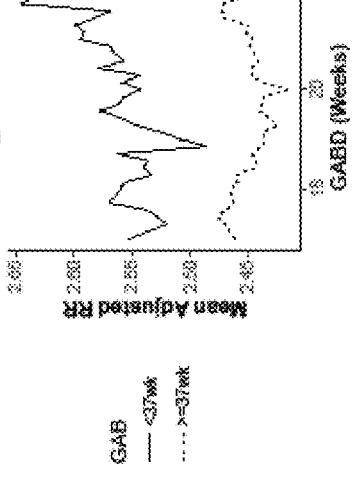
Figure 88I:
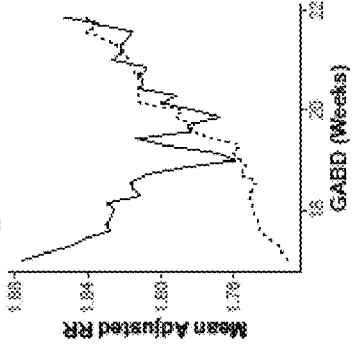
Figures 95A, 95B, 95C:
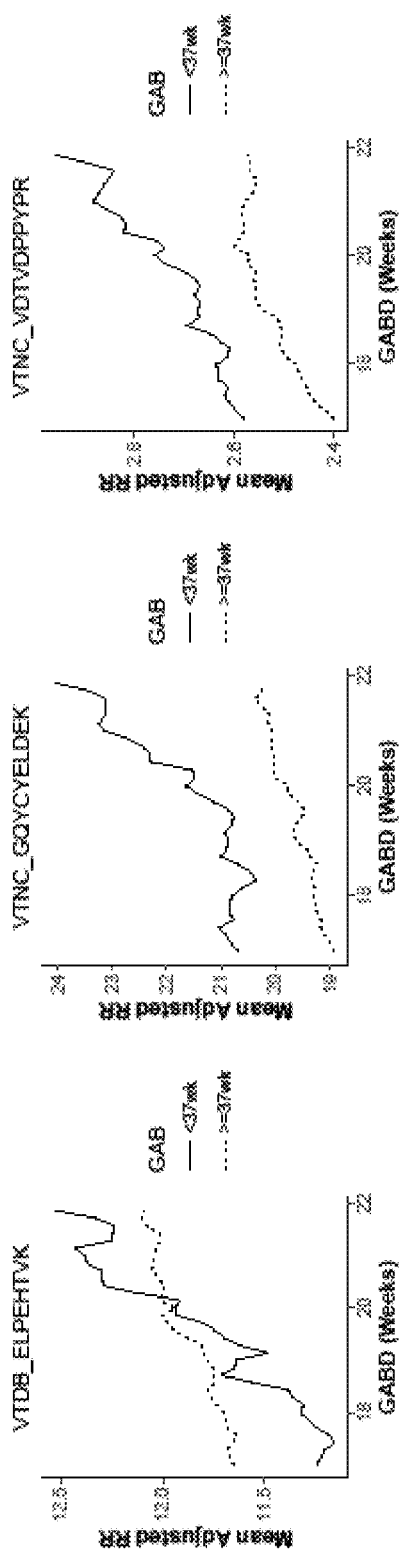
FIGS. 95A-95C show kinetic plots for peptide transitions specified in FIGS. 95A through 95C using gestational age at birth cutoff of <37 0/7 versus >=37 0/7 weeks. Figures disclose SEQ ID NOS:147, 149 and 150, respectively, in order of appearance.
Figures 105A, 105B, 105C:
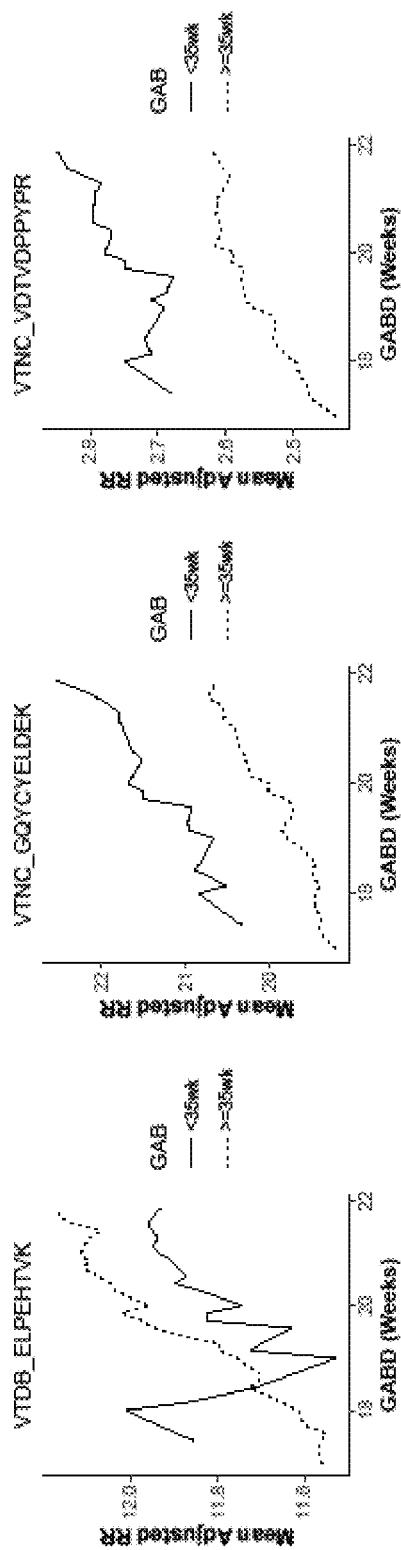
FIGS. 105A-105C show kinetic plots for peptide transitions specified in FIGS. 105A through 105C using gestational age at birth cutoff of <35 0/7 vs >=35 0/7 weeks. Figures disclose SEQ ID NOS:147, 149 and 150, respectively, in order of appearance.

FIG. 57 shows kinetic plots of differentially expressed proteins with functions in metabolic hormone balance. Sex hormone-binding globulin (SHBG), a placental protein, increases during pregnancy and determines bioavailability and metabolism of sex steroid hormones. Decreased SHBG levels result in higher free androgen and estrogen levels. Free androgens can be converted to estrogen by placental aromatase activity. Progesterone opposing activity of estrogens accelerate gestation/labor. Thyroxine-binding globulin (THBG) is induced by estrogen and increases ~2.5-fold by mid-pregnancy. The elevated serum THBG levels in sPTB cases may result in reduced free thyroid hormone. Hypothyroidism in pregnancy is associated with increased risk of miscarriage and preterm birth. Stagnaro-Green A. and Pearce E. 2012 Nat. Rev. Endocrinol. 8(11):650-8. Angiotensinogen is increased ~3-fold by estrogen by mid-pregnancy to stimulate the ~40% increase in plasma volume. Up-regulation of ANGT could lead to gestational hypertension, a condition associated with increased risk of sPTB.

FIG. 58 shows kinetic plots of differentially expressed proteins with functions in angiogenesis. TIE1, an inhibitory co-receptor of the TIE2 angiopoietin receptor, blocks the ability of Ang-2 to stimulate angiogenesis. Seegar, T., et al. 2010 Mol. Cell. 37(5): 643-655. Pigment epithelial derived factor (PEDF), an anti-angiogenesis factor expressed in placenta, stimulates cleavage and inactivation of VEGFR-1 by gamma-secretase.10 Cathepsin D (CATD) cleaves prolactin to generate vasoinhibins that inhibit angiogenesis. Elevated serum CATD and vasoinhibins are associated with preeclampsia. Nakajima, R., et al. 2015 Hypertension Research 38, 899-901. Leucine-rich alpha-2-glycoprotein (LRG1/A2GL) promotes TGF-$\beta$ signaling through binding co-receptor, endoglin. TGF-$\beta$ activates endothelial cell mitogenesis and angiogenesis by the Smad1/5/8 signaling pathway. Wang, X., et al. 2013 Nature 499(7458). PSG3 induces anti-inflammatory cytokines from monocytes and macrophages, and stimulates angiogenesis through binding TGF-$\beta$. Low levels of PSGs are associated with IUGR. Moore, T., and Dveksler, G. 2014 Int. J. Dev. Biol. 58: 273-280. ENPP2(autotaxin), an ectoenzyme with lysophospholipase D activity, produces lysophosphatidic acid (LPA). LPA acts on placental receptors to stimulate angiogenesis and chemotaxis of NK cells and monocytes. Levels of Autotaxin are reduced in cases of PIH and early onset PE. Chen, S-U., et al. 2010 Endocrinology 151(1):369-379.

FIG. 59 shows kinetic plots of differentially expressed proteins with functions in innate immunity. LBP presents bacterial LPS to the Toll-like receptor-4 via its co-receptor CD14 to induce the inflammatory response of the innate immunity pathway. Fetuin-A (alpha-2-HS-glycoprotein) is a carrier protein for fatty acids in blood and the FetA-FA complex can bind and activate TLR4 receptor. Pal, D., et al. 2012 Nature Med. 18(8):1279-85.

FIG. 60 shows kinetic plots of differentially expressed proteins with functions in coagulation.

FIG. 61 shows kinetic plots of differentially expressed serum/secreted proteins.

FIG. 62 shows kinetic plots of differentially expressed PSGs/IBPs.

FIG. 63 shows kinetic plots of differentially expressed ECM/cell surface proteins.

FIG. 64 shows kinetic plots of differentially expressed complement/acute phase proteins-1.

FIG. 65 shows kinetic plots of differentially expressed complement/acute phase proteins-2.

FIG. 66 shows kinetic plots of differentially expressed complement/acute phase proteins-3.

FIG. 67 shows kinetic plots of differentially expressed complement/acute phase proteins-4.

Example 9. SDT4/SV4 Kinetic Analysis

This example provides kinetic analysis for all analytes initially exemplified in Example 1, supra, with data from 17 weeks 0 days, through 28 weeks, 6 days.

For FIGS. 68-85, average relative ratios for each peptide transition are plotted using the R ggplot2 package against GABD using a mean average smoothing function (window=+/−10 days). Graphs feature separate plots for case vs. control using two different gestational age at birth cutoffs (<37 0/7 vs >=37 0/7 weeks and <35 0/7 vs >=35 0/7 weeks). Plot titles display a protein short name, underscore, and the peptide sequence. Analyte sequences may have been trimmed for titles to fit on the plots.

The kinetic analyses exemplified herein serve several purposes. These analyses demonstrate whether analyte levels are changing during pregnancy and in which direction, whether they change differently for cases and controls, and illustrate diagnostic differences as a function of gestational age. In some cases, the diagnostic signal is located in a narrow gestational age range, and increases or decreases across time. The shape of kinetic plots also provides visual guidance for selection of proteins that pair well in reversals.

Analytes that were discovered to show significant case versus control separation in an early window, e.g. sample collection between 18 and 20 weeks of gestational age, include, for example, AFAM, B2M, CATD, CAH1, C1QB, C1S, F13A, GELS, FETUA, HEMO, LBP, PEDF, PEPD, PLMN, PRG2, SHBG, TENX, THRB, and VCAM1. Analytes that were discovered to show significant case versus control separation in a later window, e.g. sample collection between 26 and 28 weeks of gestational age, include, for example, ITIH4, HEP2, IBP3, IGF2, KNG1, PSG11, PZP, VASN, and VTDB. Separation of cases versus controls improved using cutoff of less than 35 0/7 versus greater or equal to 35 0/7 weeks versus less than 37 0/7 versus greater or equal to 37 0/7 weeks, as seen for analytes including, for example, AFAM, APOH, CAH1, CATD, CD14, CLUS, CRIS3, F13B, IBP6, ITIH4, LYAM1, PGRP2, PRDX, PSG2, PTGDS, SHBG and SPRL1. It was discovered that many inflammatory and immuno-modulatory molecules show improved separation using the lower gestational at birth cutoff. One skilled in the art will appreciate that any of the analytes showing significant separation between cases and controls shown in the accompanying Figures for a given time window are candidates for use in a reversal pair of the present inventions, as a single biomarker or as part of a biomarker panel of analytes.

Lastly, kinetic plots for analytes that lack a case versus control difference, but demonstrate changes in analyte intensity across pregnancy, are useful in a pregnancy clock according to the methods of the invention. These analytes, also referred to herein as "clock proteins", can be used to date a pregnancy in the absence of or in conjunction with other dating methods (e.g. date of last menstrual period, ultrasound dating). Table 60 provides a list of clock proteins useful in a pregnancy clock of the invention.

Example 10. Discovery 2 Analysis of sPTB Cases

This example describes analysis of all previously analyzed sPTB cases as described in the preceding examples, their matched controls (2 per every case) and 2 new controls. This analysis described in this example expanded the commercial blood draw window beyond weeks 19 and 20, generated additional data with regards to prediction of sPTB <35 weeks based on larger number of samples from all previous examples, led to discovery of new analytes and reversals, defined molecular clock proteins, clarified risk thresholds and formed accurate validation claims for future clinical studies.

Sample Processing Methods

A standard protocol was developed governing conduct of the Proteomic Assessment of Preterm Risk (PAPR) clinical study. This protocol also specified that the samples and clinical information could be used to study other pregnancy complications. Specimens were obtained from women at 11 Internal Review Board (IRB) approved sites across the United States. After providing informed consent, serum and plasma samples were obtained, as well as pertinent information regarding the patient's demographic characteristics, past medical and pregnancy history, current pregnancy history and concurrent medications. Following delivery, data were collected relating to maternal and infant conditions and complications. Serum and plasma samples were processed according to a protocol that requires standardized refrigerated centrifugation, aliquoting of the samples into 0.5 ml 2-D bar-coded cryovials and subsequent freezing at −80° C.

Following delivery, preterm birth cases were individually reviewed to determine their status as either a spontaneous preterm birth or a medically indicated preterm birth. Only spontaneous preterm birth cases were used for this analysis. For discovery of biomarkers of preterm birth, LC-MS data was generated for 413 samples (82 sPTB cases, 331 term controls) spanning gestational ages 17 0/7-21 6/7 weeks, with each preterm sample matched to 4 term controls by gestational age at blood draw. Every gestational age day within 17 0/7-21 6/7 weeks included at least one sPTB case (and matched term controls), except for one day. 4 term controls were selected with blood draws from that day. One term control in the study that failed laboratory analysis was not reanalyzed.

The serum samples were subsequently depleted of high abundance proteins using the Human 14 Multiple Affinity Removal System (MARS-14), which removes 14 of the most abundant proteins. Equal volumes of each clinical sample or replicates of two quality control serum pools were diluted with column buffer and filtered to remove precipitates. Filtered samples were depleted using a MARS-14 column (4.6×100 mm, Agilent Technologies). Samples were chilled to 4° C. in the autosampler, the depletion column was run at room temperature, and collected fractions were kept at 4° C. until further analysis. The unbound fractions were collected for further analysis.

Depleted serum samples were reduced with dithiothreitol, alkylated using iodoacetamide, and then digested with trypsin. Following trypsin digestion, samples were fortified with a pool of stable isotope standards at concentrations that approximated the concentration of the surrogate peptide analyte. SIS fortified samples were mixed and split into two equal volumes. Each split was placed in −80° C. storage until ready to continue the work process. One frozen split from each sample was retrieved from −80° C. storage, allowed to thaw, and then desalted on a C18 solid phase extraction plate (Empore, 3M). Eluted peptides were lyophilized to dryness. The lyophilized samples were resolubilized in a reconstitution solution containing internal standards that monitor quality of the LC-MS step only (IS Recon).

Fully processed samples were analyzed using a dynamic Multiple Reaction Monitoring method (dMRM). The peptides were separated on a 2.1×100 mm Poroshell EC-C18, 2.7μ particle size column at a flow rate of 0.4 mL/min using an Agilent 1290 UPLC and eluted using an acetonitrile gradient into an Agilent 6490 triple quadrupole mass spectrometer with an electrospray source, operating in positive ion mode. The dMRM assay measured 442 transitions that correspond to 119 peptides and 77 proteins serving both diagnostic and quality roles. Chromatographic peaks were integrated using MassHunter Quantitative Analysis software (Agilent Technologies). Ratios of the chromatographic peak area of the surrogate peptide analyte to the corresponding SIS chromatographic peak area were reported.

A summary of the proteins, peptides and transitions for serum analytes, SIS transitions and IS Recon standards measured in the dMRM method is shown in Table 21. MARS-14 Depletion proteins identify analytes targeted by the MARS-14 immunodepletion column and are measured for quality control purposes. Quant transitions are used for relative response ratios and qual transitions serve quality control purposes. The asterisk (*) denotes name changes. CSH denotes that the peptide corresponds to both CSH1 and CSH2. HLAG now referred to as HLACI since the peptide is conserved in several class I HLA isotypes. LYAM3 now referred to as LYAM1 because, while the peptide sequence is present in each, it is only derived by trypsin cleavage from LYAM1. SOM2 now referred to as SOM2.CSH as the peptides are specific to both SOM2 and CSH.

Significant Protein and Reversal Selection

For each analyte, in each of the two week and three week overlapping window, with and without the BMI restriction, and with two SPTB definitions (37/37 and 35/35), the fold change value that denotes if the mean of the SPTB case samples was higher or lower than the mean of the TERM control samples, was calculated. Tables 22 and 23 show protein/transition AUROC for two week gestational age windows overlapping by one week (e.g. 119-132 refers to days 119-132 of pregnancy which equals gestational weeks 17 and 18). Performance in each two week window is reported for two different case vs control cut-offs (<37 0/7 vs >=37 0/7, <35 0/7 vs >=35 0/7) and with (rBMI) and without (aBMI) a BMI stratification. Tables 24 and 25 show protein/transition AUROC for three week gestational windows overlapping by two weeks (show in days, e.g. "119-139" refers to days 119-139 of pregnancy which equals gestational weeks 17, 18 and 19). Performance in each three week window is reported for two different case vs control cut-offs (<37 0/7 vs >=37 0/7, <35 0/7 vs >=35 0/7) and with (rBMI) and without (aBMI) a BMI stratification.

FIGS. 86 to 95 show kinetic plots of various peptide transitions for case vs. control using gestational age at birth cutoff of <37 0/7 vs >=37 0/7 weeks. FIGS. 96 to 105 show kinetic plots of various peptide transitions for case vs. control using gestational age at birth cutoff of <35 0/7 vs >=35 0/7 weeks. Briefly, average relative ratios for each peptide transition are plotted using the R ggplot2 package against GABD using a mean average smoothing function (window=+/−10 days). Graphs feature separate plots for case vs. control using two different gestational age at birth cutoffs (<37 0/7 vs >=37 0/7 weeks and <35 0/7 vs >=35 0/7 weeks). Plot titles display a protein short name, underscore, and the peptide sequence. Analyte sequences may have been trimmed for titles to fit on the plots.

Based on the fold change value, which denotes if the mean of the SPTB case samples was higher or lower than the mean of the TERM control samples, each analyte was marked as up or down regulated for each of the combinations (i.e. overlapping 2 or 3 week window, BMI restriction, and SPTB definition) and if an analyte had majority of the combinations marked as up regulated it was called an overall up regulated analyte and vice versa. This is shown in Table 26.

Based on these up and down regulation assignments (55 up regulated and 30 down regulated), reversals were created by dividing each of the up regulated analyte relative ratio value by that of a down regulated analyte and taking the natural logarithm of the result. This results in 1650 reversals (55×30=1650). For each reversal, an area under the ROC curve (AUCROC) denoting SPTB and TERM separation and a p-value denoting if the AUCROC value is significantly different from AUCROC=0.5 (i.e. no significant SPTB and TERM separation) was calculated. Performance of each reversal was tabulated for different conditions (e.g. gestational windows, with and without BMI restriction, and the two sPTB cut-offs), for those reversals with an AUCROC >0.6 and a p-value <0.05. Tables 27 to 42 show reversal classification performance for gestational weeks 17 and 18. Tables 47 to 58 show reversal classification performance for gestational weeks 17, 18 and 19. Tables 43 to 46 show reversal classification performance for gestational weeks 17 through 21. Additional reversals of potential significance are shown in Table 59.

Also demonstrated, was improved performance of predictors formed from more than one reversal (weeks 17-21). Briefly, reversals that gave strong predictive performance either early (e.g. weeks 17-19) or later (e.g. weeks 19-21) in this gestational age range were combined and performance was evaluated of predictors formed from combinations (SumLog) of multiple reversals for the entire blood draw range. This is shown in Table 61. Predictor score was derived from summing the Log values of the individual reversal (SumLog) but one skilled in the art could select other models (e.g. logistic regression). It is also contemplated to apply this multiple reversal approach to combinations of reversals specific to preterm premature rupture of membranes (PPROM) versus preterm labor in the absence of PPROM (PTL), fetal gender and gravidity. It is further contemplated that the predictor could contain an indicator variable that selects a subset of reversals to be used given knowledge of the blood draw period, fetal gender or gravidity.

Figure 110:
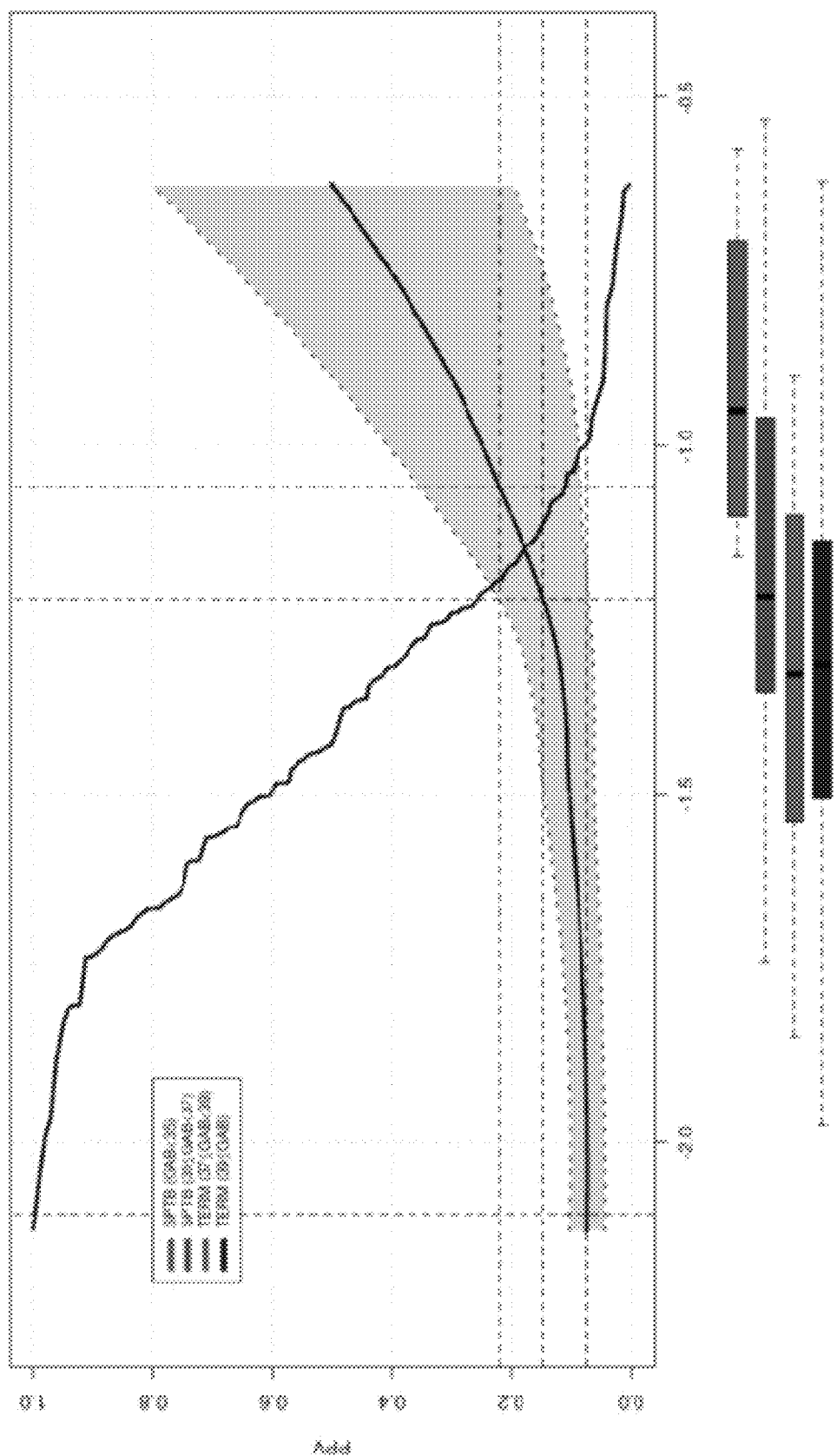
FIG. 110 is a risk curve showing relationships between the Predictor Score (ln IBP4/SHBG) and the prevalence adjusted relative risk of sPTB (Positive Predictive Value), using a cut-off of <37 0/7 weeks vs >=37 0/7 weeks gestation. Top (purple) line underneath risk curve graph corresponds to sPTB (GAB<35 weeks); second line (red) from top corresponds to sPTB (35≤GAB<37 weeks); third line (green) from corresponds to TERM (37≤GAB<39 weeks); fourth line (blue) from top corresponds to TERM (39 weeks≤GAB).

FIG. 110 shows the relationships between the Predictor Score (ln IBP4/SHBG) and the prevalence adjusted relative risk of sPTB (Positive Predictive Value), using a cut-off of <37 0/7 weeks vs >=37 0/7 weeks gestation. Samples were drawn between 19 1/7 weeks and 20 6/7 weeks with BMI >22<=37. The relative risk increases as predictor score increases from the background rate of 7.3% (average population risk of sPTB in singleton pregnancies) to approximately 50%. The screen positive rate curve for all score thresholds is superimposed. Confidence intervals (gray shade) were calculated assuming the binomially distributed observations and approximating the distribution of error with a normal distribution. Sample distribution by classifier score is shown by bar graph according to the color scheme in the figure legend.

FIG. 111 shows the relationships between the Predictor Score (ln IBP4/SHBG) and the prevalence adjusted relative risk of sPTB (Positive Predictive Value), using a cut-off of <35 0/7 weeks vs >=35 0/7 weeks gestation. Samples were drawn between 19 1/7 weeks and 20 6/7 weeks. The relative risk increases as predictor score increases from the background rate of 4.4% (average population risk of sPTB (<35) in singleton pregnancies) to approximately 50%. The screen positive rate curve for all score thresholds is superimposed. Confidence intervals (gray shade) were calculated assuming the binomially distributed observations and approximating the distribution of error with a normal distribution. Sample distribution by classifier score is shown by bar graph according to the color scheme in the figure legend.

Clinical Observations: sPTB, PPROM and PTL

Reversal performance (GABD weeks 17-21) was evaluated independently for two different phenotypes of sPTB, PPROM and PTL. PPROM more often occurs early and is associated with infection or inflammation. PTL can occur later and is generally considered a less severe phenotype. There were more significant reversals and with higher performance for PPROM and those reversals are populated with proteins known to be involved in inflammation and infection. Selection of reversals to build independent testing methods of PPROM and PTL, or to maximize performance overall with the combination of more than one reversal in a single predictor is contemplated. In the analysis shown in Tables 61 to 64, an AUC >0.65 and p<0.05 for either PPROM or PTL was required.

Table 61 shows reversal AUROC for gestational weeks 17 0/7 through 21 6/7 using a case vs control cut-off of <37 0/7 vs >37 0/7 weeks, without BMI stratification, separately for PPROM and PTL. Table 62 shows reversal AUROC for gestational weeks 17 0/7 through 21 6/7 using a case vs control cut-off of <37 0/7 vs >=37 0/7 weeks, with BMI stratification (>22<=37), separately for PPROM and PTL. Table 63 shows reversal AUROC for gestational weeks 17 0/7 through 21 6/7 using a case vs control cut-off of <35 0/7 vs >=35 0/7 weeks, without BMI stratification, separately for PPROM and PTL. Table 64 shows reversal AUROC for gestational weeks 17 0/7 through 21 6/7 using a case vs control cut-off of <35 0/7 vs >=35 0/7 weeks, with BMI stratification (>22<=37), separately for PPROM and PTL.

Figure 108A:
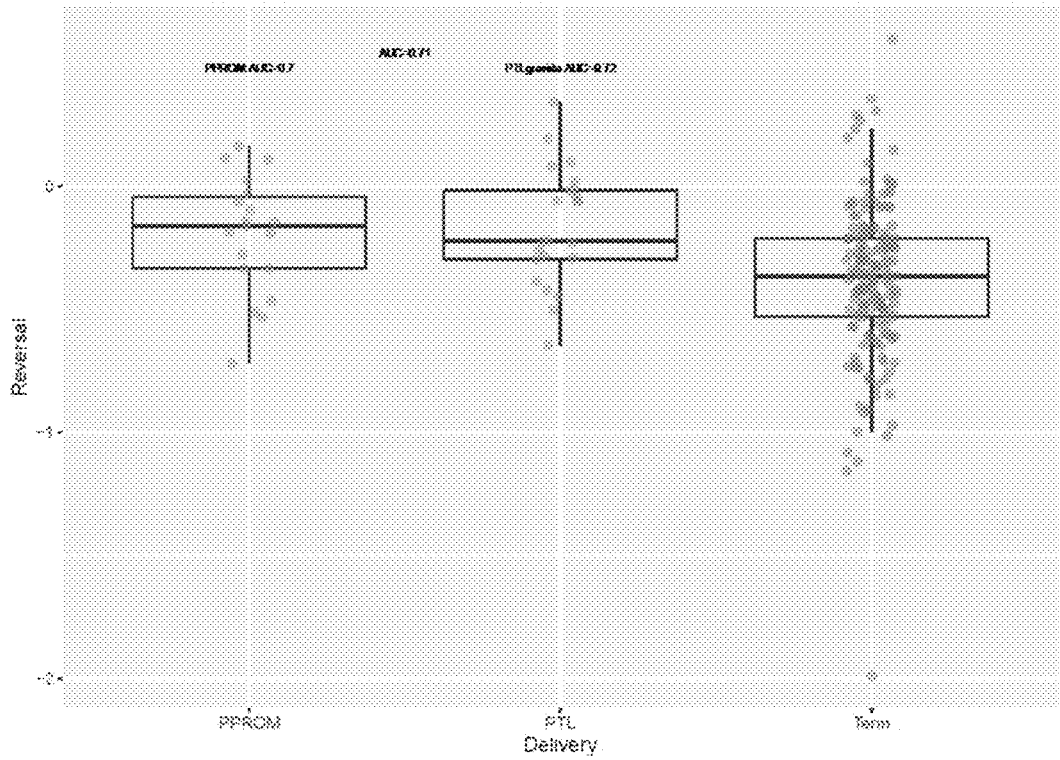
FIGS. 108A-108B provide box plots showing examples of reversals with good performance in weeks 19-20 in preterm labor in the absence of PPROM (PTL). Figures disclose SEQ ID NOS:2, 134, 2 and 103, respectively, in order of appearance.
Figure 108B:
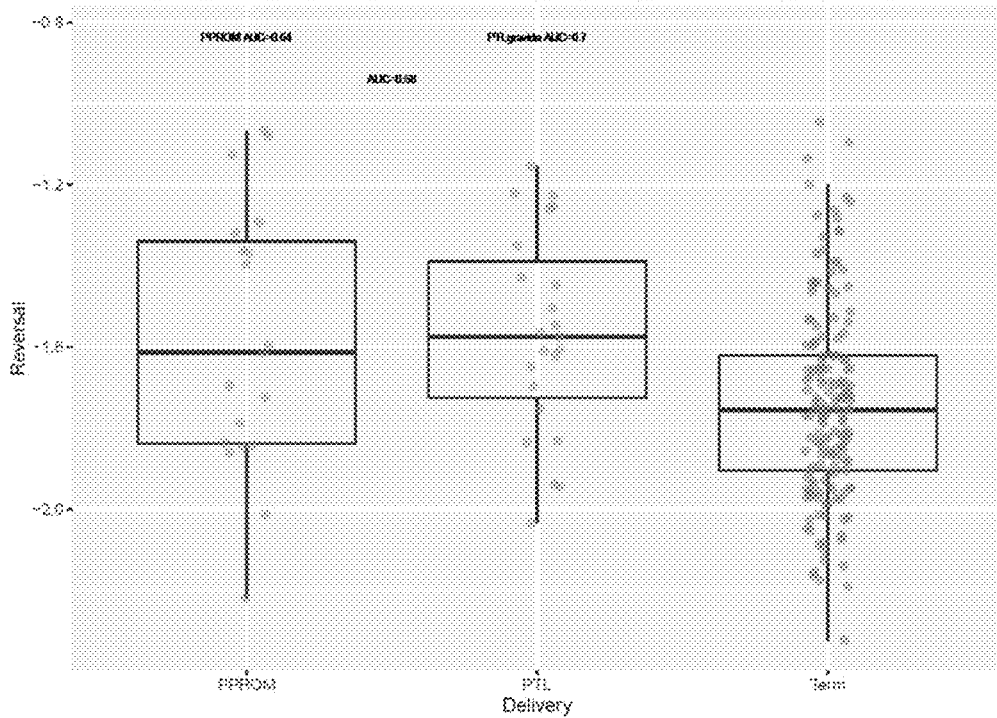
Figure 109A:
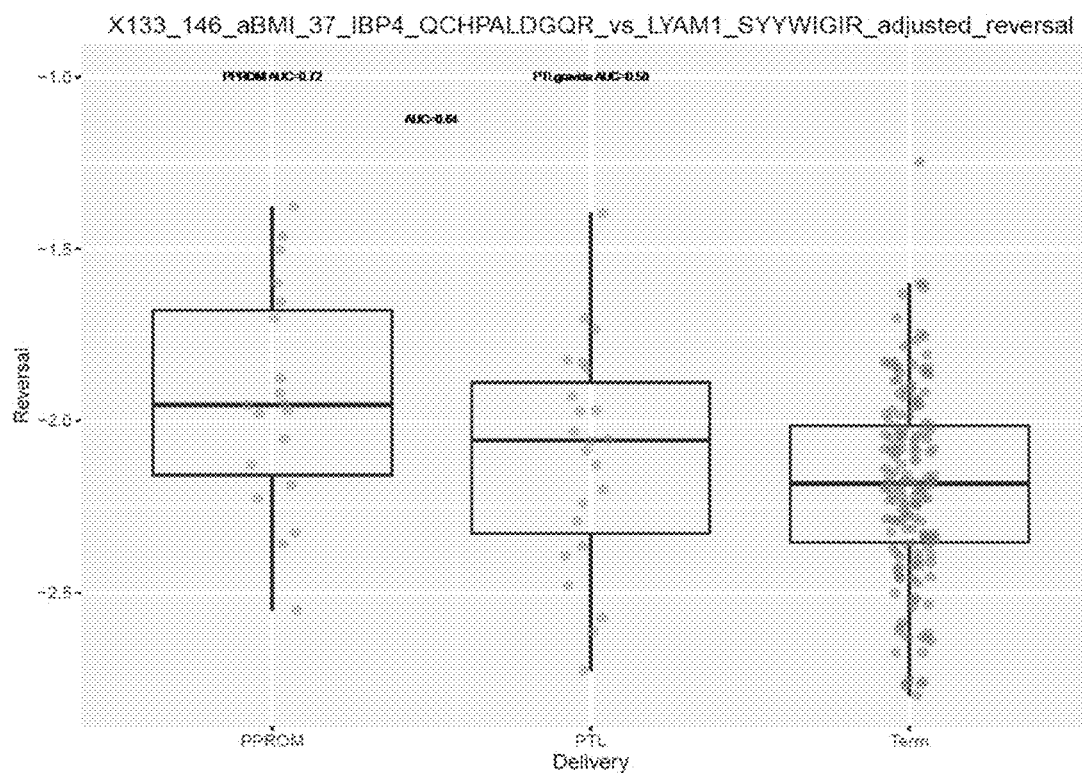
FIGS. 109A-109D provide box plots showing examples of reversals with good performance in weeks 19-20 in preterm premature rupture of membranes (PPROM). Figures disclose SEQ ID NOS:2, 120, 47, 120, 107, 18, 124 and 142, respectively, in order of appearance.
Figure 109B:
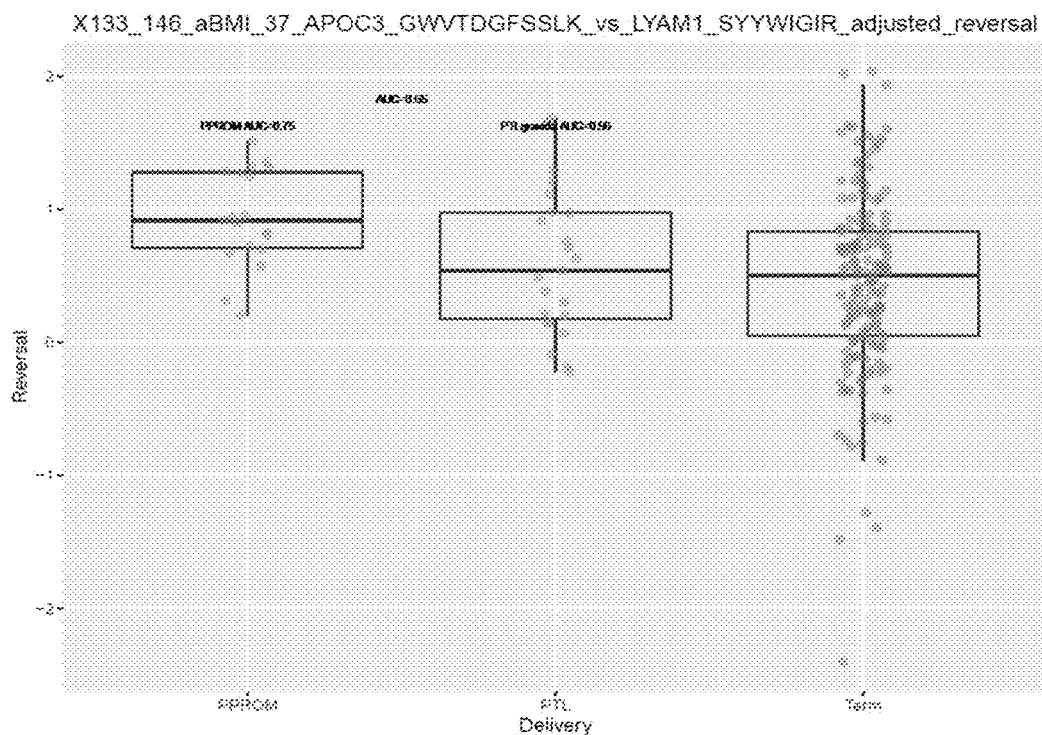
Figure 109C:
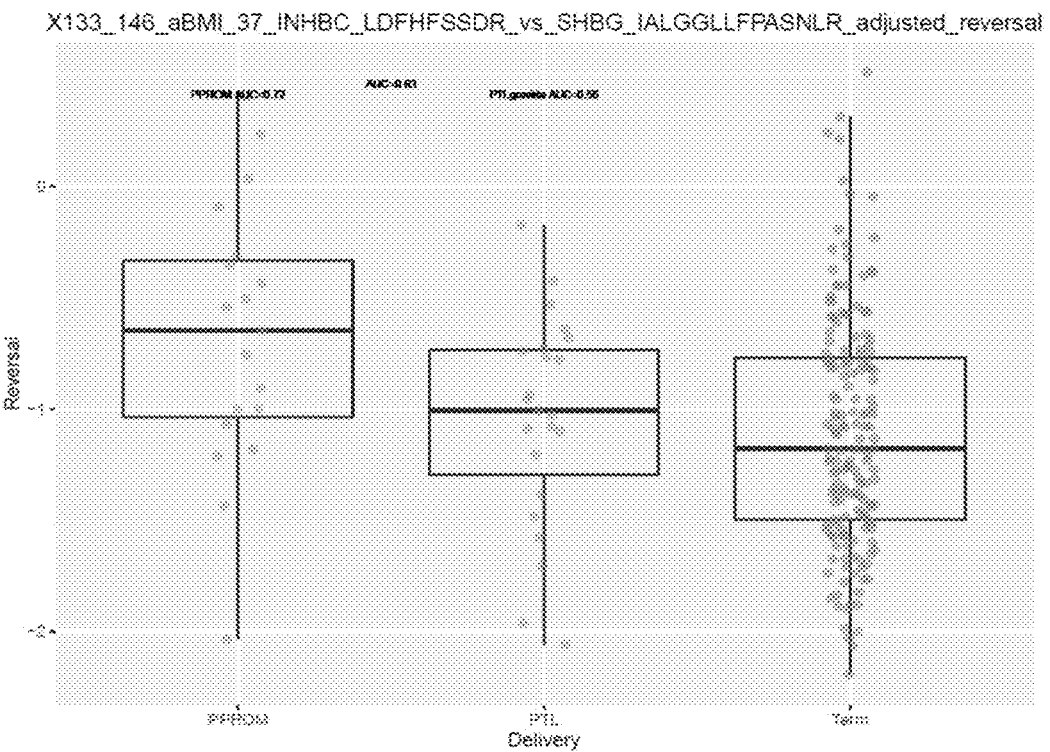
Figure 109D:
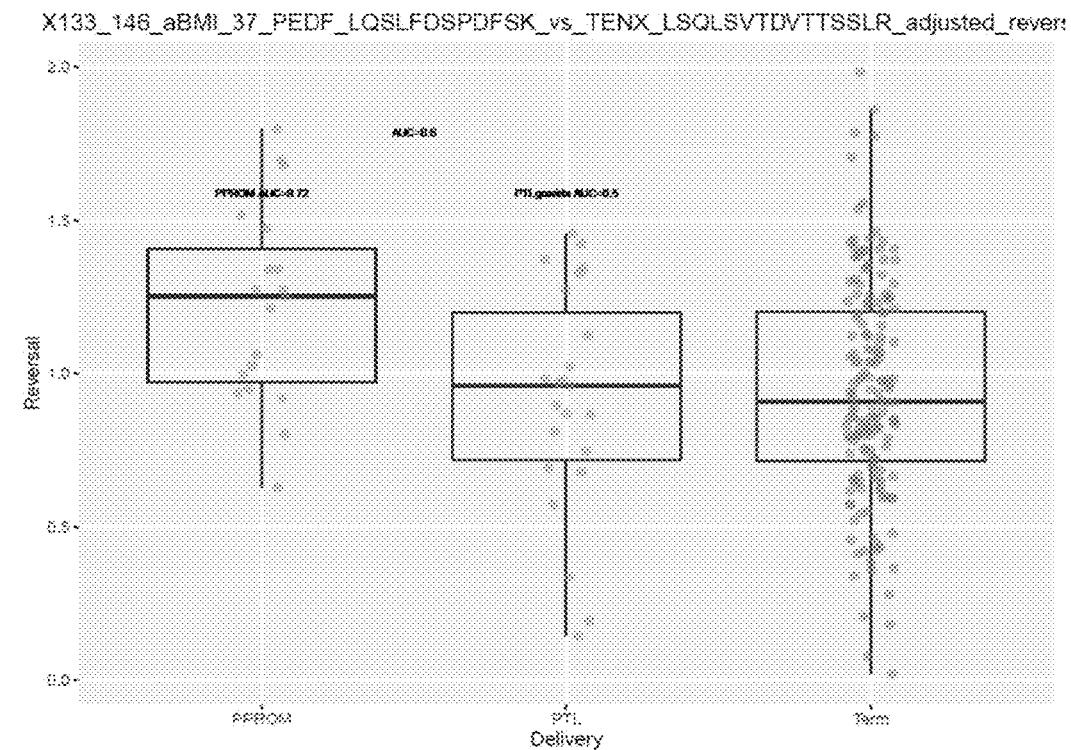

The best performing analytes for PTL and best performing analytes for PPROM for GABD weeks 19-20 were also determined and several reversals were constructed from the strongest performers. IBP4 is present as a good performer in both PTL and PPROM enabling its utility in general for sPTB. Table 76 lists transition AUROC for gestational weeks 19 1/7 through 20 6/7 using a case vs control cut-off of <37 0/7 vs >=37 0/7 weeks, without BMI stratification, for PTL. Table 77 lists transition AUROC for gestational weeks 19 1/7 through 20 6/7 using a case vs control cut-off of <37 0/7 vs >=37 0/7 weeks, without BMI stratification, for PPROM. FIG. 108 exemplifies reversals with good performance in weeks 19-20 in PTL. FIG. 109 exemplifies reversals with good performance in weeks 19-20 in PPROM.

Clinical Observations: Primigravida and Multigravida

Reversal performance (weeks 17-21) was further evaluated independently for two different phenotypes of sPTB, primigravida and multigravida. In Tables 65-68, the top performing reversals (weeks 17-21) are shown for primigravida (first time mothers) and multigravida subjects separately. First time mothers are most in need of a test to predict probability of PTB because they have no pregnancy history for physicians to determine/estimate risk. These results enable a test independent for these two groups, or to combine high performing reversals in a single classifier to predict risk for both. In the analysis shown in Tables 65-68, an AUC >0.65 and p<0.05 for either primigravida or multigravida was required.

Table 65 shows reversal AUROC for gestational weeks 17 0/7 through 21 6/7 using a case vs control cut-off of <37 0/7 vs >=37 0/7 weeks, without BMI stratification, separately for primigravida and multigravida. Table 66 shows reversal AUROC for gestational weeks 17 0/7 through 21 6/7 using a case vs control cut-off of <37 0/7 vs >=37 0/7 weeks, with BMI stratification (>22<=37), separately for primigravida and multigravida. Table 67 shows reversal AUROC for gestational weeks 17 0/7 through 21 6/7 using a case vs control cut-off of <35 0/7 vs >=35 0/7 weeks, without BMI stratification, separately for primigravida and multigravida. Table 68 shows reversal AUROC for gestational weeks 17 0/7 through 21 6/7 using a case vs control cut-off of <35 0/7 vs >=35 0/7 weeks, with BMI stratification (>22 <=37), separately for primigravida and multigravida.

Clinical Observations: Fetal Gender

Figures 106A, 106B, 106C:
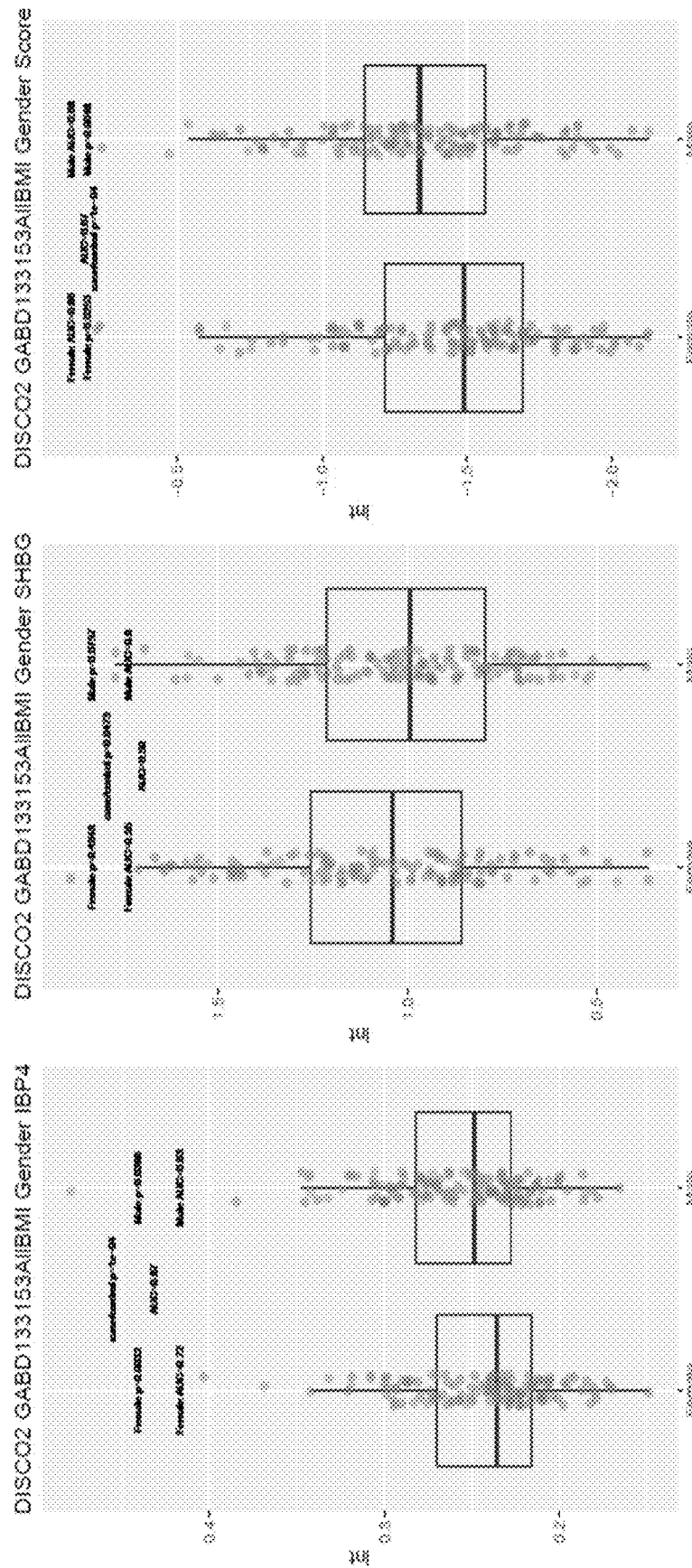
FIGS. 106A-106C show IBP4 and SHBG levels and IBP4/SHBG reversal values in sPTB cases and controls separately.

Reversal performance (weeks 17-21) was further evaluated independently for subjects pregnant with a male vs a female fetus. Some reversals were discovered to have fetal gender specific predictive performance. FIG. 106 demonstrates fetal gender specific IBP4 and SHBG analyte and score (IBP4/SHBG) differences. IBP4 is significant higher in subjects with male fetuses. Performance of the reversal remains comparable for gestational age weeks 19-21 without BMI stratification (FIG. 106). Additionally, in the PAPR clinical trial male fetuses were discovered to be at increased risk of sPTB with a p value of 0.0002 and an odds ratio of 1.6. Lastly, fetal gender can be incorporated into a predictor (e.g. a reversal value plus fetal gender). In the analysis shown in Tables 69-72, an AUC >0.65 and p<0.05 for either male or female fetuses was required.

Table 69 shows reversal AUROC for gestational weeks 17 0/7 through 21 6/7 using a case vs control cut-off of <37 0/7 vs >=37 0/7 weeks, without BMI stratification, separately by fetal gender. Table 70 shows reversal AUROC for gestational weeks 17 0/7 through 21 6/7 using a case vs control cut-off of <37 0/7 vs >=37 0/7 weeks, with BMI stratification (>22<=37), separately by fetal gender. Table 71 shows reversal AUROC for gestational weeks 17 0/7 through 21 6/7 using a case vs control cut-off of <35 0/7 vs >=35 0/7 weeks, without BMI stratification, separately by fetal gender. Table 72 shows reversal AUROC for gestational weeks 17 0/7 through 21 6/7 using a case vs control cut-off of <35 0/7 vs >=35 0/7 weeks, with BMI stratification (>22<=37), separately by fetal gender.

Example 11. Correlation of Mass Spectrometry and Immunoassay Data

This example demonstrates implementation of an immunoassays using an MSD platform (e.g. MSD data correlating with commercial ELISA data and MS data for IBP4 and SHBG).

Materials

The following antibodies were used: sex hormone binding globulin (Biospacific Catalog #s 6002-100051 and 6001-100050; R&D Systems Catalog #s MAB2656 and AF2656), IGFBP-4 (Ansh Catalog #s AB-308-A1039 and AB-308-A1042). SHBG proteins from Origene (Catalog

TP328307), Biospacific (Catalog 065200), NIBSC (code: 95/560), and R&D Systems (only available as part of the ELISA SHBG kit) were tested as calibrator. Recombinant Human IGFBP-4 (Ansh, Catalog #AG-308-A1050) was used as a calibrator.

Creating Individual U-PLEX-Coupled Antibody Solutions

Each biotinylated antibody was diluted to 10 µg/mL in Diluent 100 for a final volume of ≥200 µL. Biotinylated antibody was then added to 300 µL of assigned U-PLEX Linker. (A different linker was used for each biotinylated antibody). Samples were vortexed and incubated at room temperature for 30 minutes. Stop Solution (200 µl) was added to each tube. Tubes were vortexed and incubated at room temperature for 30 minutes.

Preparation of Multiplex Coating Solution

Each U-PLEX-coupled antibody (600 µL) solution was combined into a single tube and vortexed to mix. When combining fewer than 10 antibodies, the solution volume was brought to up to 6 mL with stop solution to result in a final 1× concentration. Note that in these experiments, there was only a single antibody per well.

Coating the U-PLEX Plate.

Multiplex Coating Solution (50 µL) was added to each well. Plates were sealed with adhesive plate seal and incubated at room temperature for 1 hour or at 2-8° C. for overnight, with shaking at around 700 rpm. After washing 3 times with at least 1504, of lx MSD wash buffer, plates were ready to use.

Sample Analysis

Aliquots, 50 µl, of sample or calibrator were added to each well. The plate was sealed and incubated at room temperature for 1 hour with shaking at around 700 rpm. The plate was then washed 3 times with at least 1504, of lx MSD wash buffer*. Detection antibody solution, 50 µL, was added to each well. After sealing, the plate was incubated at room temperature for 1 hour with shaking at around 700 rpm. The plate was washed 3 times with at least 1504, of lx MSD wash buffer. After addition of 1504, of 2× Read Buffer to each well, the plate was read immediately on an MSD instrument.

SHBG Antibody and Calibrator Screening

All antibodies were tested in both capture-detector orientations, all pair wise combinations. Capture antibodies were prepared at 10 µg/mL, coupled to U-PLEX linkers, and coated onto the U-PLEX plate. The SHBG R&D Systems calibrator was diluted in Diluent 43 to create a 7-point standard curve with assay diluent blank. Samples were diluted as follows in Diluent 43 and tested in the assays: Sera SHBG "high" and "low" samples: 100- and 500-fold dilutions, and the Sera Pregnant pool: 100-, 200-, 400-, 800-fold dilutions. Detection antibodies were tested at 1 µg/mL in Diluent 3. Standard curves and binding to native analyte in serum were evaluated. Top analyte pairs were then tested with the NIBSC and Biospacific calibrators, with dilutions made as above.

IGFBP-4 Antibody and Calibrator Screening.

The two antibodies were tested in both capture-detector orientations. Capture antibodies were prepared at 10 µg/mL, coupled to U-PLEX linkers, and coated onto the U-PLEX plate. IGFBP-4 calibrator was diluted in Diluent 12 and to create a 7-point standard curve with assay diluent blank. Samples were diluted as follows in Diluent 12 and tested in the assays: Sera IGFBP-4 "high" and "low" samples: 5-fold, Sera Pregnant pool: 2-fold dilutions from 2- to 64-fold, and 2 individual human serum samples (MSD samples): 2-, 4-, 8- and 16-fold. Detection antibodies were tested at 1 µg/mL in Diluent 12. Standard curves and binding to native analyte in serum were evaluated.

SHBG and IGFBP-4 Testing Using 60 Sera Samples.

Antibody pair 12 was selected to measure SHBG in 60 plasma samples in duplicate from Sera. For IGFBP-4, pair 2 was selected. Plasma samples were diluted 1:1000 and 1:20 for SHBG and IGFBP-4, respectively. Results from the MSD ELISA were compared to commercial ELISA kits and to MS-MRM data.

Results:

SHBG Antibody Screen

Only antibody pair 1 (R&D mono capture, poly detection), gave a strong signal with the Origene calibrator, suggesting that this calibrator may represent a subpopulation of the endogenous SHBG analyte. Thus, additional calibrators were tested in subsequent studies to identify a calibrator that works with all pairs. Nevertheless, all antibody pairs recognized native analyte in the Sera High, Low, and Pregnant pool samples. R&D poly AF2656 and Biospacific mono 6001-100050 gave similar performance. Pairs 2, 3, and 12 showed roughly linear titration with sample dilution (Table 73). The top four antibody pairs were then tested for performance with three additional calibrators. Good calibrator curves were achieved for the 4 top pairs across the 3 calibrators (Table 74). Differences in signal may be in part due to differences in assigned concentration.

The bottom panel shows that the NIBSC or Biospacific signals relative to the R&D calibrator varied depending on antibody pair. Pairs 3 and 10 (same antibodies with the capture-detection orientation flipped) had a similar profile. Pair 2 gave lower signals for NIBSC and Biospacific (compare with Pair 3, same capture). Pair 12 gave higher signals for Biospacific and more than 3-fold higher signals for the NIBSC standard.

IGFBP-4 Antibody Screen

The antibody pair 2 standard curve gave 4-6 fold higher specific calibrator signals and background compared to Pair 1 (Table 75). Serum sample signals fell in the linear range for most dilutions tested; the pregnant pool approached background at the 32 and 64-fold dilutions. Pair 2 gave ~12 fold higher signals for samples resulting in a 2-4 fold difference in quantification. Signal CVs were generally <5% for both pairs.

Measurement of SHBG and IGFBP-4 in 60 Serum Samples

For SHBG, with the 1000-fold dilution, samples fell between calibrator standards 1-3. The median measured concentration was 58.4 µg/mL. CVs of duplicate measurements were low with a median CV 2.4%. The median measured concentration for IGFBP-4 was 234 ng/ml and the median CV between duplicate samples was 2.2%. As shown in FIG. 107, good correlation was seen with both proteins in the MSD assay as compared to commercial ELISA kits and the MS-MRM assay.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

Lengthy table referenced here

US10961584-20210330-T00001

Please refer to the end of the specification for access instructions.

Lengthy table referenced here

US10961584-20210330-T00002

Please refer to the end of the specification for access instructions.

Lengthy table referenced here

US10961584-20210330-T00003

Please refer to the end of the specification for access instructions.

Lengthy table referenced here

US10961584-20210330-T00004

Please refer to the end of the specification for access instructions.

Lengthy table referenced here

US10961584-20210330-T00005

Please refer to the end of the specification for access instructions.

Lengthy table referenced here

US10961584-20210330-T00006

Please refer to the end of the specification for access instructions.

Lengthy table referenced here

US10961584-20210330-T00007

Please refer to the end of the specification for access instructions.

Lengthy table referenced here

US10961584-20210330-T00008

Please refer to the end of the specification for access instructions.

Lengthy table referenced here

US10961584-20210330-T00009

Please refer to the end of the specification for access instructions.

Lengthy table referenced here

US10961584-20210330-T00010

Please refer to the end of the specification for access instructions.

Lengthy table referenced here

US10961584-20210330-T00011

Please refer to the end of the specification for access instructions.

Lengthy table referenced here

US10961584-20210330-T00012

Please refer to the end of the specification for access instructions.

Lengthy table referenced here

US10961584-20210330-T00013

Please refer to the end of the specification for access instructions.

Lengthy table referenced here

US10961584-20210330-T00014

Please refer to the end of the specification for access instructions.

Lengthy table referenced here

US10961584-20210330-T00015

Please refer to the end of the specification for access instructions.

Lengthy table referenced here

US10961584-20210330-T00016

Please refer to the end of the specification for access instructions.

Lengthy table referenced here

US10961584-20210330-T00017

Please refer to the end of the specification for access instructions.

Lengthy table referenced here
US10961584-20210330-T00018
Please refer to the end of the specification for access instructions.

Lengthy table referenced here
US10961584-20210330-T00019
Please refer to the end of the specification for access instructions.

Lengthy table referenced here
US10961584-20210330-T00020
Please refer to the end of the specification for access instructions.

Lengthy table referenced here
US10961584-20210330-T00021
Please refer to the end of the specification for access instructions.

Lengthy table referenced here
US10961584-20210330-T00022
Please refer to the end of the specification for access instructions.

Lengthy table referenced here
US10961584-20210330-T00023
Please refer to the end of the specification for access instructions.

Lengthy table referenced here
US10961584-20210330-T00024
Please refer to the end of the specification for access instructions.

Lengthy table referenced here
US10961584-20210330-T00025
Please refer to the end of the specification for access instructions.

Lengthy table referenced here
US10961584-20210330-T00026
Please refer to the end of the specification for access instructions.

Lengthy table referenced here
US10961584-20210330-T00027
Please refer to the end of the specification for access instructions.

Lengthy table referenced here
US10961584-20210330-T00028
Please refer to the end of the specification for access instructions.

Lengthy table referenced here
US10961584-20210330-T00029
Please refer to the end of the specification for access instructions.

Lengthy table referenced here
US10961584-20210330-T00030
Please refer to the end of the specification for access instructions.

Lengthy table referenced here
US10961584-20210330-T00031
Please refer to the end of the specification for access instructions.

Lengthy table referenced here
US10961584-20210330-T00032
Please refer to the end of the specification for access instructions.

Lengthy table referenced here
US10961584-20210330-T00033
Please refer to the end of the specification for access instructions.

Lengthy table referenced here
US10961584-20210330-T00034
Please refer to the end of the specification for access instructions.

Lengthy table referenced here
US10961584-20210330-T00035
Please refer to the end of the specification for access instructions.

Lengthy table referenced here
US10961584-20210330-T00036
Please refer to the end of the specification for access instructions.

Lengthy table referenced here
US10961584-20210330-T00037
Please refer to the end of the specification for access instructions.

Lengthy table referenced here
US10961584-20210330-T00038
Please refer to the end of the specification for access instructions.

Lengthy table referenced here
US10961584-20210330-T00039
Please refer to the end of the specification for access instructions.

Lengthy table referenced here
US10961584-20210330-T00040
Please refer to the end of the specification for access instructions.

Lengthy table referenced here
US10961584-20210330-T00041
Please refer to the end of the specification for access instructions.

Lengthy table referenced here
US10961584-20210330-T00042
Please refer to the end of the specification for access instructions.

Lengthy table referenced here
US10961584-20210330-T00043
Please refer to the end of the specification for access instructions.

Lengthy table referenced here
US10961584-20210330-T00044
Please refer to the end of the specification for access instructions.

Lengthy table referenced here
US10961584-20210330-T00045
Please refer to the end of the specification for access instructions.

Lengthy table referenced here
US10961584-20210330-T00046
Please refer to the end of the specification for access instructions.

Lengthy table referenced here
US10961584-20210330-T00047
Please refer to the end of the specification for access instructions.

Lengthy table referenced here
US10961584-20210330-T00048
Please refer to the end of the specification for access instructions.

Lengthy table referenced here
US10961584-20210330-T00049
Please refer to the end of the specification for access instructions.

Lengthy table referenced here
US10961584-20210330-T00050
Please refer to the end of the specification for access instructions.

Lengthy table referenced here
US10961584-20210330-T00051
Please refer to the end of the specification for access instructions.

Lengthy table referenced here
US10961584-20210330-T00052
Please refer to the end of the specification for access instructions.

Lengthy table referenced here
US10961584-20210330-T00053
Please refer to the end of the specification for access instructions.

Lengthy table referenced here
US10961584-20210330-T00054
Please refer to the end of the specification for access instructions.

Lengthy table referenced here
US10961584-20210330-T00055
Please refer to the end of the specification for access instructions.

Lengthy table referenced here
US10961584-20210330-T00056
Please refer to the end of the specification for access instructions.

Lengthy table referenced here
US10961584-20210330-T00057
Please refer to the end of the specification for access instructions.

Lengthy table referenced here
US10961584-20210330-T00058
Please refer to the end of the specification for access instructions.

Lengthy table referenced here
US10961584-20210330-T00059
Please refer to the end of the specification for access instructions.

Lengthy table referenced here
US10961584-20210330-T00060
Please refer to the end of the specification for access instructions.

Lengthy table referenced here
US10961584-20210330-T00061
Please refer to the end of the specification for access instructions.

Lengthy table referenced here
US10961584-20210330-T00062
Please refer to the end of the specification for access instructions.

Lengthy table referenced here
US10961584-20210330-T00063
Please refer to the end of the specification for access instructions.

Lengthy table referenced here
US10961584-20210330-T00064
Please refer to the end of the specification for access instructions.

Lengthy table referenced here
US10961584-20210330-T00065
Please refer to the end of the specification for access instructions.

Lengthy table referenced here
US10961584-20210330-T00066
Please refer to the end of the specification for access instructions.

Lengthy table referenced here
US10961584-20210330-T00067
Please refer to the end of the specification for access instructions.

Lengthy table referenced here
US10961584-20210330-T00068
Please refer to the end of the specification for access instructions.

Lengthy table referenced here
US10961584-20210330-T00069
Please refer to the end of the specification for access instructions.

Lengthy table referenced here
US10961584-20210330-T00070
Please refer to the end of the specification for access instructions.

Lengthy table referenced here
US10961584-20210330-T00071
Please refer to the end of the specification for access instructions.

Lengthy table referenced here
US10961584-20210330-T00072

Please refer to the end of the specification for access instructions.

TABLE 73

SHBG Antibody Pair Screening

| | | Pair | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | | Capture | | | | | | | | | | | |
| | | MAB 2656 | MAB 2656 | MAB 2656 | AF2656 | AF2656 | AF2656 | 6001-100050 | 6001-100050 | 6001-100050 | 6002-100051 | 6002-100051 | 6002-100051 |
| | | Detection | | | | | | | | | | | |
| | | AF2656 | 6001-100050 | 6002-100051 | MAB 2656 | 6001-100050 | 6002-100051 | MAB 2656 | AF2656 | 6002-100051 | MAB 2656 | AF2656 | 6001-100050 |
| | Conc. (pg/mL) | | | | | | Avg. Signal | | | | | | |
| | 200,000 | 196,199 | 1,482 | 40 | 17,248 | 77 | 82 | 87 | 493 | 140 | 15 | 357 | 59 |
| | 50,000 | 45,345 | 230 | 68 | 6,424 | 81 | 72 | 77 | 323 | 134 | 74 | 286 | 62 |
| | 12,500 | 10,250 | 111 | 62 | 1,309 | 69 | 85 | 27 | 205 | 74 | 52 | 253 | 3 |
| | 3,125 | 2,218 | 5 | 31 | 310 | 45 | 66 | 83 | 240 | 137 | 29 | 194 | 60 |
| | 781 | 586 | 58 | 43 | 135 | 57 | 50 | 80 | 253 | 174 | 74 | 212 | 116 |
| | 195 | 285 | 112 | 69 | 85 | 68 | 58 | 73 | 281 | 156 | 95 | 236 | 32 |
| | 48.8 | 192 | 78 | 51 | 79 | 80 | 57 | 35 | 241 | 82 | 51 | 239 | 45 |
| | 0 | 134 | 57 | 36 | 65 | 31 | 81 | 70 | 222 | 145 | 61 | 207 | 50 |
| Sample | Dil. Factor | | | | | | Avg. Signal | | | | | | |
| Sera Ser SHBG High | 100 | 24,276 | 759,257 | 95,554 | 72,420 | 540,435 | 33,723 | 52,016 | 1,519,054 | 124,739 | 257,126 | 2,651,568 | 2,483,374 |
| Sera Ser SHBG High | 500 | 11,920 | 151,855 | 25,205 | 53,509 | 435,835 | 28,879 | 39,185 | 1,310,604 | 112,980 | 103,294 | 1,365,240 | 1,236,988 |
| Sera Ser SHBG Low | 100 | 4,968 | 466,625 | 60,954 | 81,666 | 488,908 | 30,966 | 54,664 | 1,409,717 | 113,560 | 211,022 | 2,093,523 | 1,854,111 |
| Sera Ser SHBG Low | 500 | 2,323 | 77,558 | 13,979 | 51,484 | 341,422 | 24,496 | 39,792 | 1,092,474 | 98,450 | 66,981 | 741,153 | 635,079 |
| Sera Pregnant Pool | 100 | 16,046 | 543,595 | 67,876 | 70,299 | 537,819 | 32,769 | 55,762 | 1,448,544 | 117,378 | 211,125 | 2,290,099 | 2,161,934 |
| Sera Pregnant Pool | 200 | 8,181 | 265,320 | 36,282 | 62,676 | 484,876 | 31,089 | 45,555 | 1,387,992 | 117,090 | 144,146 | 1,756,643 | 1,644,496 |
| Sera Pregnant Pool | 400 | 3,798 | 126,947 | 20,332 | 50,249 | 430,699 | 27,311 | 35,459 | 1,240,271 | 110,478 | 106,820 | 1,148,673 | 1,023,157 |
| Sera Pregnant Pool | 800 | 1,854 | 48,533 | 8,691 | 39,042 | 337,119 | 14,848 | 29,455 | 1,053,286 | 93,762 | 61,748 | 660,872 | 591,820 |

TABLE 74

Top Performing SHBG Antibody Pairs with Additional Calibrators

| | | Pair | | | | | | | | | | |
|---|---|---|---|---|---|---|---|---|---|---|---|---|
| | | 2 | | | 3 | | | 10 | | | 12 | | |
| | | Capture | | | | | | | | | | |
| | | MAB 2656 | MAB 2656 | MAB 2656 | MAB 2656 | MAB 2656 | MAB 2656 | 6001-100051 | 6001-100051 | 6001-100051 | 6001-100051 | 6001-100051 | 6001-100051 |
| | | Detection | | | | | | | | | | |
| | | 6001-10050 | 6001-10050 | 6001-10050 | 6002-100051 | 6002-100051 | 6002-100051 | MAB 2656 | MAB 2656 | MAB 2656 | 6001-10050 | 6001-10050 | 6001-10050 |
| | | Calibrator | | | | | | | | | | |
| | Conc. (pg/mL) | R&D Systems | Bios Pacific | NIBSC | R&D Systems | Bios Pacific | NIBSC | R&D Systems | Bios Pacific | NIBSC | R&D Systems | Bios Pacific | NIBSC |
| Std-01 | 200,000 | 238,290 | 249,922 | 412,613 | 186,867 | 196,012 | 426,503 | 596,225 | 293,312 | 554,954 | 1,898,159 | 1,779,244 | 3,175,127 |
| Std-02 | 50,000 | 88,340 | 76,077 | 107,001 | 77,374 | 88,009 | 134,934 | 158,181 | 150,021 | 237,546 | 554,319 | 882,130 | 1,538,720 |
| Std-03 | 12,500 | 22,003 | 14,194 | 18,988 | 20,160 | 20,899 | 33,358 | 35,226 | 32,464 | 54,024 | 129,885 | 227,721 | 452,461 |
| Std-04 | 3,125 | 5,261 | 3,137 | 3,960 | 5,215 | 5,151 | 8,048 | 8,701 | 7,791 | 12,118 | 32,771 | 57,949 | 117,096 |
| Std-05 | 781 | 1,650 | 813 | 1,126 | 1,351 | 1,211 | 2,121 | 2,165 | 1,781 | 2,842 | 9,383 | 14,943 | 33,614 |
| Std-06 | 195 | 534 | 247 | 323 | 474 | 371 | 554 | 751 | 482 | 766 | 2,869 | 3,630 | 8,559 |
| Std-07 | 48.8 | 193 | 107 | 108 | 173 | 151 | 145 | 260 | 198 | 265 | 832 | 1,045 | 2,337 |
| Std-08 | 0 | 87 | 68 | 42 | 83 | 60 | 58 | 93 | 127 | 100 | 171 | 232 | 210 |
| Hill Slope | | 0.96 | 1.09 | 1.07 | 0.99 | 1.04 | 1.05 | 1.00 | 1.13 | 1.08 | 0.96 | 1.04 | 0.99 |
| LLCD (pg/mL) | | 34 | 96 | 65 | 42 | 51 | 36 | 25 | 51 | 29 | 15 | 12 | 2.4 |
| Signals Norm. to R&D | Std-02 | 100% | 86% | 121% | 100% | 114% | 174% | 100% | 95% | 150% | 100% | 159% | 278% |
| | Std-03 | 100% | 65% | 86% | 100% | 104% | 165% | 100% | 92% | 153% | 100% | 175% | 348% |
| | Std-04 | 100% | 60% | 75% | 100% | 99% | 154% | 100% | 90% | 139% | 100% | 177% | 357% |
| | Std-05 | 100% | 49% | 68% | 100% | 90% | 157% | 100% | 82% | 131% | 100% | 159% | 358% |
| Average (STD02-05) | | 100% | 65% | 88% | 100% | 101% | 163% | 100% | 90% | 144% | 100% | 138% | 335% |

TABLE 75

IGFBP-4 Antibody Screen

| | Pair | 1 | 2 | |
|---|---|---|---|---|
| | Capture | Ansh AI039 | Ansh AI042 | |
| | Detection | Ansh AI042 | Ansh AI039 | |
| | Cond. (pg/mL) | Avg. Signal | | Ratio |
| STD01 | 200,000 | 425,323 | 1,804,559 | 4.2 |
| STD02 | 50,000 | 119,806 | 532,966 | 4.4 |
| STD03 | 12,500 | 24,178 | 117,219 | 4.8 |
| STD04 | 3,125 | 6,232 | 37,258 | 6.0 |
| STD05 | 781 | 2,816 | 17,032 | 6.0 |
| STD06 | 195 | 2,176 | 13,425 | 6.2 |
| STD07 | 48.8 | 2,019 | 11,901 | 5.9 |
| STD08 | 0 | 1,710 | 10,995 | 6.4 |
| Hill Slope | | 1.20 | 1.10 | |
| LLOD (pg/mL) | | 317 | 129 | |

| | Pair | 1 | 2 | |
|---|---|---|---|---|
| Sample | Dil. Factor | Avg. Signal | | Ratio |
| Sera Serum IGFBP-4 High | 5 | 80,262 | 923,638 | 11.5 |
| Sera Serum IGFBP-4 Low | 5 | 57,033 | 671,088 | 11.8 |
| Pregnant Pooled Serum 1 | 2 | 177,461 | 1,608,197 | 9.1 |
| Pregnant Pooled Serum 2 | 4 | 68,359 | 771,385 | 11.3 |
| Pregnant Pooled Serum 3 | 8 | 26,032 | 335,292 | 12.9 |
| Pregnant Pooled Serum 4 | 16 | 10,001 | 143,381 | 14.3 |
| Pregnant Pooled Serum 5 | 32 | 4,813 | 60,651 | 12.6 |
| Pregnant Pooled Serum 6 | 64 | 2,796 | 21,126 | 7.6 |
| MSD Serum 1 | 2 | 103,259 | 1,249,741 | 12.1 |
| MSD Serum 1 | 4 | 37,414 | 571,584 | 15.3 |
| MSD Serum 1 | 8 | 17,946 | 291,750 | 16.3 |
| MSD Serum 1 | 16 | 7,203 | 126,275 | 17.5 |
| MSD Serum 2 | 2 | 66,061 | 767,724 | 11.6 |
| MSD Serum 2 | 4 | 29,099 | 425,207 | 14.6 |

* Pregnant Pooled Serum 6 sample exhibited signals within 2X assay background

TABLE 76

Transition Classification Performance, weeks 19-20.
Transition AUROC for gestational weeks 19 1/7 through 20 6/7 using a case vs control cut-off of <37 0/7 vs >= 37 0/7 weeks, without BMI stratification, for PTL.

| Transition | SEQ ID NO: | 134_146_aBMI_37 PTL ROC_AUC |
|---|---|---|
| PSG3_VSAPSGTGHLPGLNPL | 134 | 0.66 |
| IGF2_GIVEECCFR | 103 | 0.66 |
| IBP4_QCHPALDGQR | 2 | 0.64 |
| IBP3_YGQPLPGYTTK | 100 | 0.64 |
| F13B_GDTYPAELYITGSILR | 84 | 0.61 |
| APOH_ATVVYQGER | 48 | 0.6 |
| IBP3_FLNVLSPR | 99 | 0.6 |

TABLE 77

Transition Classification Performance, weeks 19-20. Transition AUROC for gestational weeks 19 1/7 through 20 6/7 using a case vs control cut-off of <37 0/7 vs >=37 0/7 weeks, without BMI stratification, for PPROM.

| Analytes | SEQ ID NO: | 134_146_aBMI_37 ROC_AUC |
|---|---|---|
| APOC3_GWVTDGESSLK | 47 | 0.76 |
| PEDF_TVQAVLTVPK | 125 | 0.76 |
| INHBC_LDFHFSSDR | 107 | 0.76 |
| IBP4_QCHPALDGQR | 2 | 0.73 |
| PEDF_LQSLFDSPDFSK | 124 | 0.73 |
| A1AT_LSITGTYDLK | 33 | 0.73 |
| KNG1_QVVAGLNFR | 117 | 0.72 |
| CD14_LTVGAAQVPAQLLVGALR | 61 | 0.72 |
| VTNC_VDTVDPPYPR | 150 | 0.71 |
| KNG1_DIPTNSPELEETLTHTITK | 116 | 0.71 |
| CD14_SWLAELQQWLKPGLK | 62 | 0.71 |
| CO8A_SLLQPNK | 74 | 0.69 |
| CATD_VGFAEAAR | 57 | 0.69 |
| SHBG_IALGGLLFPASNLR | 18 | 0.69 |
| CO5_VFQFLEK | 71 | 0.69 |
| FETUA_FSVVYAK | 88 | 0.68 |
| HABP2_FLNWIK | 92 | 0.68 |
| VTNC_GQYCYELDEK | 149 | 0.68 |
| B2MG_VNHVTLSQPK | 51 | 0.68 |
| ENPP2_TYLHTYESEI | 83 | 0.67 |
| AFAM_HFQNLGK | 38 | 0.67 |
| APOH_ATVVYQGER | 48 | 0.66 |
| ITIH4_NPLVWVHASPEHVVVTR | 113 | 0.66 |
| CFAB_YGLVTYATYPK | 64 | 0.66 |
| CO8B_QALEEFQK | 76 | 0.65 |
| BGH3_LTLLAPLNSVFK | 52 | 0.65 |
| FETUA_HTLNQIDEVK | 89 | 0.65 |
| CO3_IHWESASLLR | 69 | 0.65 |
| ENPP2_TEFLSNYLTNVDDITLVPGTLGR | 82 | 0.65 |
| HEMO_NFPSPVDAAFR | 93 | 0.65 |
| LBP_ITLPDFTGDLR | 119 | 0.65 |
| CO5_TLLPVSKPEIR | 70 | 0.65 |
| FIBA_ESSSHHPGIAEFPSR | 90 | 0.64 |
| AFAM_DADPDTFFAK | 37 | 0.64 |
| ITIH3_ALDLSLK | 111 | 0.64 |
| LBP_ITGFLKPGK | 118 | 0.64 |
| CATD_VSTLPAITLK | 58 | 0.64 |
| PRDX2_GLFIIDGK | 128 | 0.63 |
| CO6_ALNHLPLEYNSALYSR | 72 | 0.63 |
| ANGT_DPTFIPAPIQAK | 42 | 0.62 |
| PRG2_WNFAYWAAHQPWSR | 129 | 0.62 |
| CBPN_NNANGVDLNR | 60 | 0.62 |
| IBP6_HLDSVLQQLQTEVYR | 102 | 0.62 |
| ITIH4_ILDDLSPR | 112 | 0.62 |
| IBP6_GAQTLYVPNCDHR | 101 | 0.62 |
| F13B_GDTYPAELYITGSILR | 84 | 0.61 |
| CLUS_LFDSDPITVTVPVEVSR | 68 | 0.61 |
| FBLN1_TGYYFDGISR | 86 | 0.61 |
| PAPP1_DIPHWLNPTR | 122 | 0.61 |
| TIE1_VSWSLPLVPGPLVGDGFLLR | 144 | 0.6 |
| CAH1_GGPFSDSYR | 56 | 0.6 |
| A2GL_DLLLPQPDLR | 34 | 0.6 |
| B2MG_VEHSDLSFSK | 50 | 0.6 |
| PSG2_IHPSYTNYR | 133 | 0.6 |

LENGTHY TABLES

The patent contains a lengthy table section. A copy of the table is available in electronic form from the USPTO web site (https://seqdata.uspto.gov/?pageRequest=docDetail&DocID=US10961584B2). An electronic copy of the table will also be available from the USPTO upon request and payment of the fee set forth in 37 CFR 1.19(b)(3).

What is claimed is:

1. A method of detecting a pair of biomarkers consisting of IBP4 and SHBG in a pregnant female, said method comprising:
   a. obtaining a biological sample from the pregnant female; and
   b. detecting whether said IBP4 and SHBG are present in the biological sample comprising subjecting the sample to a proteomics work-flow comprised of mass spectrometry quantification.

2. The method of claim 1, wherein the biological sample is selected from the group consisting of whole blood, plasma, and serum.

3. The method of claim 2, wherein the biological sample is serum.

4. The method of claim 2, wherein said sample is obtained between 19 and 21 weeks of gestational age.

5. The method of claim 1, wherein said proteomic work flow comprises quantification of stable isotope-labeled standard (SIS) peptides corresponding to said pair of biomarkers.

* * * * *

```
                      SEQUENCE LISTING

<160> NUMBER OF SEQ ID NOS: 239

<210> SEQ ID NO 1
<211> LENGTH: 8
<212> TYPE: PRT
<213> ORGANISM: Homo sapiens

<400> SEQUENCE: 1

Leu Pro Gly Gly Leu Glu Pro Lys
1               5

<210> SEQ ID NO 2
<211> LENGTH: 10
<212> TYPE: PRT
<213> ORGANISM: Homo sapiens

<400> SEQUENCE: 2

Gln Cys His Pro Ala Leu Asp Gly Gln Arg
1               5                   10
```

```
<210> SEQ ID NO 3
<211> LENGTH: 15
<212> TYPE: PRT
<213> ORGANISM: Homo sapiens

<400> SEQUENCE: 3

Thr His Glu Asp Leu Tyr Ile Ile Pro Ile Pro Asn Cys Asp Arg
1               5                   10                  15

<210> SEQ ID NO 4
<211> LENGTH: 17
<212> TYPE: PRT
<213> ORGANISM: Homo sapiens

<400> SEQUENCE: 4

Glu Asp Ala Arg Pro Val Pro Gln Gly Ser Cys Gln Ser Glu Leu His
1               5                   10                  15

Arg

<210> SEQ ID NO 5
<211> LENGTH: 12
<212> TYPE: PRT
<213> ORGANISM: Homo sapiens

<400> SEQUENCE: 5

Cys Arg Pro Pro Val Gly Cys Glu Glu Leu Val Arg
1               5                   10

<210> SEQ ID NO 6
<211> LENGTH: 6
<212> TYPE: PRT
<213> ORGANISM: Homo sapiens

<400> SEQUENCE: 6

Val Asn Gly Ala Pro Arg
1               5

<210> SEQ ID NO 7
<211> LENGTH: 7
<212> TYPE: PRT
<213> ORGANISM: Homo sapiens

<400> SEQUENCE: 7

Leu Ala Ala Ser Gln Ser Arg
1               5

<210> SEQ ID NO 8
<211> LENGTH: 7
<212> TYPE: PRT
<213> ORGANISM: Homo sapiens

<400> SEQUENCE: 8

Asn Gly Asn Phe His Pro Lys
1               5

<210> SEQ ID NO 9
<211> LENGTH: 6
<212> TYPE: PRT
<213> ORGANISM: Homo sapiens

<400> SEQUENCE: 9

Cys Trp Cys Val Asp Arg
1               5
```

```
<210> SEQ ID NO 10
<211> LENGTH: 13
<212> TYPE: PRT
<213> ORGANISM: Homo sapiens

<400> SEQUENCE: 10

Gly Glu Leu Asp Cys His Gln Leu Ala Asp Ser Phe Arg
1               5                   10

<210> SEQ ID NO 11
<211> LENGTH: 8
<212> TYPE: PRT
<213> ORGANISM: Homo sapiens

<400> SEQUENCE: 11

Thr Ser Ser Ser Phe Glu Val Arg
1               5

<210> SEQ ID NO 12
<211> LENGTH: 16
<212> TYPE: PRT
<213> ORGANISM: Homo sapiens

<400> SEQUENCE: 12

Thr Trp Asp Pro Glu Gly Val Ile Phe Tyr Gly Asp Thr Asn Pro Lys
1               5                   10                  15

<210> SEQ ID NO 13
<211> LENGTH: 9
<212> TYPE: PRT
<213> ORGANISM: Homo sapiens

<400> SEQUENCE: 13

Asp Asp Trp Phe Met Leu Gly Leu Arg
1               5

<210> SEQ ID NO 14
<211> LENGTH: 22
<212> TYPE: PRT
<213> ORGANISM: Homo sapiens

<400> SEQUENCE: 14

Asp Gly Arg Pro Glu Ile Gln Leu His Asn His Trp Ala Gln Leu Thr
1               5                   10                  15

Val Gly Ala Gly Pro Arg
            20

<210> SEQ ID NO 15
<211> LENGTH: 7
<212> TYPE: PRT
<213> ORGANISM: Homo sapiens

<400> SEQUENCE: 15

Trp His Gln Val Glu Val Lys
1               5

<210> SEQ ID NO 16
<211> LENGTH: 17
<212> TYPE: PRT
<213> ORGANISM: Homo sapiens

<400> SEQUENCE: 16

Met Glu Gly Asp Ser Val Leu Leu Glu Val Asp Gly Glu Glu Val Leu
1               5                   10                  15
```

Arg

<210> SEQ ID NO 17
<211> LENGTH: 9
<212> TYPE: PRT
<213> ORGANISM: Homo sapiens

<400> SEQUENCE: 17

Gln Val Ser Gly Pro Leu Thr Ser Lys
1               5

<210> SEQ ID NO 18
<211> LENGTH: 14
<212> TYPE: PRT
<213> ORGANISM: Homo sapiens

<400> SEQUENCE: 18

Ile Ala Leu Gly Gly Leu Leu Phe Pro Ala Ser Asn Leu Arg
1               5                   10

<210> SEQ ID NO 19
<211> LENGTH: 12
<212> TYPE: PRT
<213> ORGANISM: Homo sapiens

<400> SEQUENCE: 19

Leu Pro Leu Val Pro Ala Leu Asp Gly Cys Leu Arg
1               5                   10

<210> SEQ ID NO 20
<211> LENGTH: 6
<212> TYPE: PRT
<213> ORGANISM: Homo sapiens

<400> SEQUENCE: 20

Asp Ser Trp Leu Asp Lys
1               5

<210> SEQ ID NO 21
<211> LENGTH: 13
<212> TYPE: PRT
<213> ORGANISM: Homo sapiens

<400> SEQUENCE: 21

Gln Ala Glu Ile Ser Ala Ser Ala Pro Thr Ser Leu Arg
1               5                   10

<210> SEQ ID NO 22
<211> LENGTH: 23
<212> TYPE: PRT
<213> ORGANISM: Homo sapiens

<400> SEQUENCE: 22

Ser Cys Asp Val Glu Ser Asn Pro Gly Ile Phe Leu Pro Pro Gly Thr
1               5                   10                  15

Gln Ala Glu Phe Asn Leu Arg
            20

<210> SEQ ID NO 23
<211> LENGTH: 19
<212> TYPE: PRT
<213> ORGANISM: Homo sapiens

<400> SEQUENCE: 23

```
Asp Ile Pro Gln Pro His Ala Glu Pro Trp Ala Phe Ser Leu Asp Leu
1               5                   10                  15

Gly Leu Lys

<210> SEQ ID NO 24
<211> LENGTH: 24
<212> TYPE: PRT
<213> ORGANISM: Homo sapiens

<400> SEQUENCE: 24

Val Val Leu Ser Ser Gly Ser Gly Pro Gly Leu Asp Leu Pro Leu Val
1               5                   10                  15

Leu Gly Leu Pro Leu Gln Leu Lys
            20

<210> SEQ ID NO 25
<211> LENGTH: 8
<212> TYPE: PRT
<213> ORGANISM: Homo sapiens

<400> SEQUENCE: 25

Val Val Leu Ser Gln Gly Ser Lys
1               5

<210> SEQ ID NO 26
<211> LENGTH: 9
<212> TYPE: PRT
<213> ORGANISM: Homo sapiens

<400> SEQUENCE: 26

Leu Asp Val Asp Gln Ala Leu Asn Arg
1               5

<210> SEQ ID NO 27
<211> LENGTH: 22
<212> TYPE: PRT
<213> ORGANISM: Homo sapiens

<400> SEQUENCE: 27

Ala Leu Ala Leu Pro Pro Leu Gly Leu Ala Pro Leu Leu Asn Leu Trp
1               5                   10                  15

Ala Lys Pro Gln Gly Arg
            20

<210> SEQ ID NO 28
<211> LENGTH: 21
<212> TYPE: PRT
<213> ORGANISM: Homo sapiens

<400> SEQUENCE: 28

Ser His Glu Ile Trp Thr His Ser Cys Pro Gln Ser Pro Gly Asn Gly
1               5                   10                  15

Thr Asp Ala Ser His
            20

<210> SEQ ID NO 29
<211> LENGTH: 14
<212> TYPE: PRT
<213> ORGANISM: Homo sapiens

<400> SEQUENCE: 29

Leu Pro Ala Glu Ile Ser Ala Ser Ala Pro Thr Ser Leu Arg
1               5                   10
```

<210> SEQ ID NO 30
<211> LENGTH: 7
<212> TYPE: PRT
<213> ORGANISM: Homo sapiens

<400> SEQUENCE: 30

Thr Leu Pro Pro Leu Phe Ala
1               5

<210> SEQ ID NO 31
<211> LENGTH: 19
<212> TYPE: PRT
<213> ORGANISM: Homo sapiens

<400> SEQUENCE: 31

Gly Glu Asp Ser Ser Thr Ser Phe Cys Leu Asn Gly Leu Trp Ala Gln
1               5                   10                  15

Gly Gln Arg

<210> SEQ ID NO 32
<211> LENGTH: 15
<212> TYPE: PRT
<213> ORGANISM: Homo sapiens

<400> SEQUENCE: 32

Asn Trp Gly Leu Ser Val Tyr Ala Asp Lys Pro Glu Thr Thr Lys
1               5                   10                  15

<210> SEQ ID NO 33
<211> LENGTH: 10
<212> TYPE: PRT
<213> ORGANISM: Homo sapiens

<400> SEQUENCE: 33

Leu Ser Ile Thr Gly Thr Tyr Asp Leu Lys
1               5                   10

<210> SEQ ID NO 34
<211> LENGTH: 10
<212> TYPE: PRT
<213> ORGANISM: Homo sapiens

<400> SEQUENCE: 34

Asp Leu Leu Leu Pro Gln Pro Asp Leu Arg
1               5                   10

<210> SEQ ID NO 35
<211> LENGTH: 6
<212> TYPE: PRT
<213> ORGANISM: Homo sapiens

<400> SEQUENCE: 35

Leu Gln Val Leu Gly Lys
1               5

<210> SEQ ID NO 36
<211> LENGTH: 19
<212> TYPE: PRT
<213> ORGANISM: Homo sapiens

<400> SEQUENCE: 36

Leu His Thr Glu Ala Gln Ile Gln Glu Glu Gly Thr Val Val Glu Leu
1               5                   10                  15

Thr Gly Arg

<210> SEQ ID NO 37
<211> LENGTH: 10
<212> TYPE: PRT
<213> ORGANISM: Homo sapiens

<400> SEQUENCE: 37

Asp Ala Asp Pro Asp Thr Phe Phe Ala Lys
1               5                   10

<210> SEQ ID NO 38
<211> LENGTH: 7
<212> TYPE: PRT
<213> ORGANISM: Homo sapiens

<400> SEQUENCE: 38

His Phe Gln Asn Leu Gly Lys
1               5

<210> SEQ ID NO 39
<211> LENGTH: 7
<212> TYPE: PRT
<213> ORGANISM: Homo sapiens

<400> SEQUENCE: 39

Leu Val Thr Asp Leu Thr Lys
1               5

<210> SEQ ID NO 40
<211> LENGTH: 13
<212> TYPE: PRT
<213> ORGANISM: Homo sapiens

<400> SEQUENCE: 40

Ile Arg Pro His Thr Phe Thr Gly Leu Ser Gly Leu Arg
1               5                   10

<210> SEQ ID NO 41
<211> LENGTH: 8
<212> TYPE: PRT
<213> ORGANISM: Homo sapiens

<400> SEQUENCE: 41

Leu Glu Tyr Leu Leu Leu Ser Arg
1               5

<210> SEQ ID NO 42
<211> LENGTH: 12
<212> TYPE: PRT
<213> ORGANISM: Homo sapiens

<400> SEQUENCE: 42

Asp Pro Thr Phe Ile Pro Ala Pro Ile Gln Ala Lys
1               5                   10

<210> SEQ ID NO 43
<211> LENGTH: 13
<212> TYPE: PRT
<213> ORGANISM: Homo sapiens

<400> SEQUENCE: 43

Ser Leu Asp Phe Thr Glu Leu Asp Val Ala Ala Glu Lys
1               5                   10

```
<210> SEQ ID NO 44
<211> LENGTH: 9
<212> TYPE: PRT
<213> ORGANISM: Homo sapiens

<400> SEQUENCE: 44

Ala Lys Pro Ala Leu Glu Asp Leu Arg
1               5

<210> SEQ ID NO 45
<211> LENGTH: 9
<212> TYPE: PRT
<213> ORGANISM: Homo sapiens

<400> SEQUENCE: 45

Ser Pro Glu Leu Gln Ala Glu Ala Lys
1               5

<210> SEQ ID NO 46
<211> LENGTH: 7
<212> TYPE: PRT
<213> ORGANISM: Homo sapiens

<400> SEQUENCE: 46

Asp Tyr Trp Ser Thr Val Lys
1               5

<210> SEQ ID NO 47
<211> LENGTH: 11
<212> TYPE: PRT
<213> ORGANISM: Homo sapiens

<400> SEQUENCE: 47

Gly Trp Val Thr Asp Gly Phe Ser Ser Leu Lys
1               5                   10

<210> SEQ ID NO 48
<211> LENGTH: 9
<212> TYPE: PRT
<213> ORGANISM: Homo sapiens

<400> SEQUENCE: 48

Ala Thr Val Val Tyr Gln Gly Glu Arg
1               5

<210> SEQ ID NO 49
<211> LENGTH: 9
<212> TYPE: PRT
<213> ORGANISM: Homo sapiens

<400> SEQUENCE: 49

Glu His Ser Ser Leu Ala Phe Trp Lys
1               5

<210> SEQ ID NO 50
<211> LENGTH: 10
<212> TYPE: PRT
<213> ORGANISM: Homo sapiens

<400> SEQUENCE: 50

Val Glu His Ser Asp Leu Ser Phe Ser Lys
1               5                   10
```

```
<210> SEQ ID NO 51
<211> LENGTH: 10
<212> TYPE: PRT
<213> ORGANISM: Homo sapiens

<400> SEQUENCE: 51

Val Asn His Val Thr Leu Ser Gln Pro Lys
1               5                   10

<210> SEQ ID NO 52
<211> LENGTH: 12
<212> TYPE: PRT
<213> ORGANISM: Homo sapiens

<400> SEQUENCE: 52

Leu Thr Leu Leu Ala Pro Leu Asn Ser Val Phe Lys
1               5                   10

<210> SEQ ID NO 53
<211> LENGTH: 7
<212> TYPE: PRT
<213> ORGANISM: Homo sapiens

<400> SEQUENCE: 53

Val Leu Thr Asp Glu Leu Lys
1               5

<210> SEQ ID NO 54
<211> LENGTH: 8
<212> TYPE: PRT
<213> ORGANISM: Homo sapiens

<400> SEQUENCE: 54

Ile Asn Pro Ala Ser Leu Asp Lys
1               5

<210> SEQ ID NO 55
<211> LENGTH: 14
<212> TYPE: PRT
<213> ORGANISM: Homo sapiens

<400> SEQUENCE: 55

Val Pro Gly Leu Tyr Tyr Phe Thr Tyr His Ala Ser Ser Arg
1               5                   10

<210> SEQ ID NO 56
<211> LENGTH: 9
<212> TYPE: PRT
<213> ORGANISM: Homo sapiens

<400> SEQUENCE: 56

Gly Gly Pro Phe Ser Asp Ser Tyr Arg
1               5

<210> SEQ ID NO 57
<211> LENGTH: 8
<212> TYPE: PRT
<213> ORGANISM: Homo sapiens

<400> SEQUENCE: 57

Val Gly Phe Ala Glu Ala Ala Arg
1               5

<210> SEQ ID NO 58
<211> LENGTH: 10
```

```
<212> TYPE: PRT
<213> ORGANISM: Homo sapiens

<400> SEQUENCE: 58

Val Ser Thr Leu Pro Ala Ile Thr Leu Lys
1               5                   10

<210> SEQ ID NO 59
<211> LENGTH: 15
<212> TYPE: PRT
<213> ORGANISM: Homo sapiens

<400> SEQUENCE: 59

Glu Ala Leu Ile Gln Phe Leu Glu Gln Val His Gln Gly Ile Lys
1               5                   10                  15

<210> SEQ ID NO 60
<211> LENGTH: 10
<212> TYPE: PRT
<213> ORGANISM: Homo sapiens

<400> SEQUENCE: 60

Asn Asn Ala Asn Gly Val Asp Leu Asn Arg
1               5                   10

<210> SEQ ID NO 61
<211> LENGTH: 18
<212> TYPE: PRT
<213> ORGANISM: Homo sapiens

<400> SEQUENCE: 61

Leu Thr Val Gly Ala Ala Gln Val Pro Ala Gln Leu Leu Val Gly Ala
1               5                   10                  15

Leu Arg

<210> SEQ ID NO 62
<211> LENGTH: 15
<212> TYPE: PRT
<213> ORGANISM: Homo sapiens

<400> SEQUENCE: 62

Ser Trp Leu Ala Glu Leu Gln Gln Trp Leu Lys Pro Gly Leu Lys
1               5                   10                  15

<210> SEQ ID NO 63
<211> LENGTH: 14
<212> TYPE: PRT
<213> ORGANISM: Homo sapiens

<400> SEQUENCE: 63

Val Ser Glu Ala Asp Ser Ser Asn Ala Asp Trp Val Thr Lys
1               5                   10

<210> SEQ ID NO 64
<211> LENGTH: 11
<212> TYPE: PRT
<213> ORGANISM: Homo sapiens

<400> SEQUENCE: 64

Tyr Gly Leu Val Thr Tyr Ala Thr Tyr Pro Lys
1               5                   10

<210> SEQ ID NO 65
<211> LENGTH: 10
```

```
<212> TYPE: PRT
<213> ORGANISM: Homo sapiens

<400> SEQUENCE: 65

Thr Ala Val Thr Ala Asn Leu Asp Ile Arg
1               5                   10

<210> SEQ ID NO 66
<211> LENGTH: 9
<212> TYPE: PRT
<213> ORGANISM: Homo sapiens

<400> SEQUENCE: 66

Val Ile Ala Val Asn Glu Val Gly Arg
1               5

<210> SEQ ID NO 67
<211> LENGTH: 12
<212> TYPE: PRT
<213> ORGANISM: Homo sapiens

<400> SEQUENCE: 67

Ala Ser Ser Ile Ile Asp Glu Leu Phe Gln Asp Arg
1               5                   10

<210> SEQ ID NO 68
<211> LENGTH: 17
<212> TYPE: PRT
<213> ORGANISM: Homo sapiens

<400> SEQUENCE: 68

Leu Phe Asp Ser Asp Pro Ile Thr Val Thr Val Pro Val Glu Val Ser
1               5                   10                  15

Arg

<210> SEQ ID NO 69
<211> LENGTH: 10
<212> TYPE: PRT
<213> ORGANISM: Homo sapiens

<400> SEQUENCE: 69

Ile His Trp Glu Ser Ala Ser Leu Leu Arg
1               5                   10

<210> SEQ ID NO 70
<211> LENGTH: 11
<212> TYPE: PRT
<213> ORGANISM: Homo sapiens

<400> SEQUENCE: 70

Thr Leu Leu Pro Val Ser Lys Pro Glu Ile Arg
1               5                   10

<210> SEQ ID NO 71
<211> LENGTH: 7
<212> TYPE: PRT
<213> ORGANISM: Homo sapiens

<400> SEQUENCE: 71

Val Phe Gln Phe Leu Glu Lys
1               5

<210> SEQ ID NO 72
<211> LENGTH: 16
```

<212> TYPE: PRT
<213> ORGANISM: Homo sapiens

<400> SEQUENCE: 72

Ala Leu Asn His Leu Pro Leu Glu Tyr Asn Ser Ala Leu Tyr Ser Arg
1               5                   10                  15

<210> SEQ ID NO 73
<211> LENGTH: 11
<212> TYPE: PRT
<213> ORGANISM: Homo sapiens

<400> SEQUENCE: 73

Ser Glu Tyr Gly Ala Ala Leu Ala Trp Glu Lys
1               5                   10

<210> SEQ ID NO 74
<211> LENGTH: 7
<212> TYPE: PRT
<213> ORGANISM: Homo sapiens

<400> SEQUENCE: 74

Ser Leu Leu Gln Pro Asn Lys
1               5

<210> SEQ ID NO 75
<211> LENGTH: 25
<212> TYPE: PRT
<213> ORGANISM: Homo sapiens

<400> SEQUENCE: 75

Tyr His Phe Glu Ala Leu Ala Asp Thr Gly Ile Ser Ser Glu Phe Tyr
1               5                   10                  15

Asp Asn Ala Asn Asp Leu Leu Ser Lys
            20                  25

<210> SEQ ID NO 76
<211> LENGTH: 8
<212> TYPE: PRT
<213> ORGANISM: Homo sapiens

<400> SEQUENCE: 76

Gln Ala Leu Glu Glu Phe Gln Lys
1               5

<210> SEQ ID NO 77
<211> LENGTH: 8
<212> TYPE: PRT
<213> ORGANISM: Homo sapiens

<400> SEQUENCE: 77

Ser Gly Phe Ser Phe Gly Phe Lys
1               5

<210> SEQ ID NO 78
<211> LENGTH: 7
<212> TYPE: PRT
<213> ORGANISM: Homo sapiens

<400> SEQUENCE: 78

Ala Val Ser Pro Pro Ala Arg
1               5

<210> SEQ ID NO 79

```
<211> LENGTH: 9
<212> TYPE: PRT
<213> ORGANISM: Homo sapiens

<400> SEQUENCE: 79

Tyr Glu Asp Leu Tyr Ser Asn Cys Lys
1               5

<210> SEQ ID NO 80
<211> LENGTH: 19
<212> TYPE: PRT
<213> ORGANISM: Homo sapiens

<400> SEQUENCE: 80

Ala His Gln Leu Ala Ile Asp Thr Tyr Gln Glu Phe Glu Glu Thr Tyr
1               5                   10                  15

Ile Pro Lys

<210> SEQ ID NO 81
<211> LENGTH: 14
<212> TYPE: PRT
<213> ORGANISM: Homo sapiens

<400> SEQUENCE: 81

Ile Ser Leu Leu Leu Ile Glu Ser Trp Leu Glu Pro Val Arg
1               5                   10

<210> SEQ ID NO 82
<211> LENGTH: 23
<212> TYPE: PRT
<213> ORGANISM: Homo sapiens

<400> SEQUENCE: 82

Thr Glu Phe Leu Ser Asn Tyr Leu Thr Asn Val Asp Asp Ile Thr Leu
1               5                   10                  15

Val Pro Gly Thr Leu Gly Arg
            20

<210> SEQ ID NO 83
<211> LENGTH: 10
<212> TYPE: PRT
<213> ORGANISM: Homo sapiens

<400> SEQUENCE: 83

Thr Tyr Leu His Thr Tyr Glu Ser Glu Ile
1               5                   10

<210> SEQ ID NO 84
<211> LENGTH: 16
<212> TYPE: PRT
<213> ORGANISM: Homo sapiens

<400> SEQUENCE: 84

Gly Asp Thr Tyr Pro Ala Glu Leu Tyr Ile Thr Gly Ser Ile Leu Arg
1               5                   10                  15

<210> SEQ ID NO 85
<211> LENGTH: 9
<212> TYPE: PRT
<213> ORGANISM: Homo sapiens

<400> SEQUENCE: 85

Ile Ala Gln Tyr Tyr Tyr Thr Phe Lys
1               5
```

```
<210> SEQ ID NO 86
<211> LENGTH: 10
<212> TYPE: PRT
<213> ORGANISM: Homo sapiens

<400> SEQUENCE: 86

Thr Gly Tyr Tyr Phe Asp Gly Ile Ser Arg
1               5                   10

<210> SEQ ID NO 87
<211> LENGTH: 8
<212> TYPE: PRT
<213> ORGANISM: Homo sapiens

<400> SEQUENCE: 87

Ile Pro Ser Asn Pro Ser His Arg
1               5

<210> SEQ ID NO 88
<211> LENGTH: 7
<212> TYPE: PRT
<213> ORGANISM: Homo sapiens

<400> SEQUENCE: 88

Phe Ser Val Val Tyr Ala Lys
1               5

<210> SEQ ID NO 89
<211> LENGTH: 10
<212> TYPE: PRT
<213> ORGANISM: Homo sapiens

<400> SEQUENCE: 89

His Thr Leu Asn Gln Ile Asp Glu Val Lys
1               5                   10

<210> SEQ ID NO 90
<211> LENGTH: 15
<212> TYPE: PRT
<213> ORGANISM: Homo sapiens

<400> SEQUENCE: 90

Glu Ser Ser Ser His His Pro Gly Ile Ala Glu Phe Pro Ser Arg
1               5                   10                  15

<210> SEQ ID NO 91
<211> LENGTH: 13
<212> TYPE: PRT
<213> ORGANISM: Homo sapiens

<400> SEQUENCE: 91

Gln Gly Phe Gly Asn Val Ala Thr Asn Thr Asp Gly Lys
1               5                   10

<210> SEQ ID NO 92
<211> LENGTH: 6
<212> TYPE: PRT
<213> ORGANISM: Homo sapiens

<400> SEQUENCE: 92

Phe Leu Asn Trp Ile Lys
1               5
```

-continued

```
<210> SEQ ID NO 93
<211> LENGTH: 11
<212> TYPE: PRT
<213> ORGANISM: Homo sapiens

<400> SEQUENCE: 93

Asn Phe Pro Ser Pro Val Asp Ala Ala Phe Arg
1               5                   10

<210> SEQ ID NO 94
<211> LENGTH: 16
<212> TYPE: PRT
<213> ORGANISM: Homo sapiens

<400> SEQUENCE: 94

Ser Gly Ala Gln Ala Thr Trp Thr Glu Leu Pro Trp Pro His Glu Lys
1               5                   10                  15

<210> SEQ ID NO 95
<211> LENGTH: 13
<212> TYPE: PRT
<213> ORGANISM: Homo sapiens

<400> SEQUENCE: 95

Trp Ala Ala Val Val Pro Ser Gly Glu Glu Gln Arg
1               5                   10

<210> SEQ ID NO 96
<211> LENGTH: 13
<212> TYPE: PRT
<213> ORGANISM: Homo sapiens

<400> SEQUENCE: 96

Thr Glu Gly Asp Gly Val Tyr Thr Leu Asn Asn Glu Lys
1               5                   10

<210> SEQ ID NO 97
<211> LENGTH: 7
<212> TYPE: PRT
<213> ORGANISM: Homo sapiens

<400> SEQUENCE: 97

Val Val Glu Ser Leu Ala Lys
1               5

<210> SEQ ID NO 98
<211> LENGTH: 9
<212> TYPE: PRT
<213> ORGANISM: Homo sapiens

<400> SEQUENCE: 98

Leu Ile Gln Gly Ala Pro Thr Ile Arg
1               5

<210> SEQ ID NO 99
<211> LENGTH: 8
<212> TYPE: PRT
<213> ORGANISM: Homo sapiens

<400> SEQUENCE: 99

Phe Leu Asn Val Leu Ser Pro Arg
1               5

<210> SEQ ID NO 100
<211> LENGTH: 11
```

-continued

```
<212> TYPE: PRT
<213> ORGANISM: Homo sapiens

<400> SEQUENCE: 100

Tyr Gly Gln Pro Leu Pro Gly Tyr Thr Thr Lys
1               5                   10

<210> SEQ ID NO 101
<211> LENGTH: 13
<212> TYPE: PRT
<213> ORGANISM: Homo sapiens

<400> SEQUENCE: 101

Gly Ala Gln Thr Leu Tyr Val Pro Asn Cys Asp His Arg
1               5                   10

<210> SEQ ID NO 102
<211> LENGTH: 15
<212> TYPE: PRT
<213> ORGANISM: Homo sapiens

<400> SEQUENCE: 102

His Leu Asp Ser Val Leu Gln Gln Leu Gln Thr Glu Val Tyr Arg
1               5                   10                  15

<210> SEQ ID NO 103
<211> LENGTH: 9
<212> TYPE: PRT
<213> ORGANISM: Homo sapiens

<400> SEQUENCE: 103

Gly Ile Val Glu Glu Cys Cys Phe Arg
1               5

<210> SEQ ID NO 104
<211> LENGTH: 16
<212> TYPE: PRT
<213> ORGANISM: Homo sapiens

<400> SEQUENCE: 104

Ser Cys Asp Leu Ala Leu Leu Glu Thr Tyr Cys Ala Thr Pro Ala Lys
1               5                   10                  15

<210> SEQ ID NO 105
<211> LENGTH: 8
<212> TYPE: PRT
<213> ORGANISM: Homo sapiens

<400> SEQUENCE: 105

Ala Leu Pro Ala Pro Ile Glu Lys
1               5

<210> SEQ ID NO 106
<211> LENGTH: 7
<212> TYPE: PRT
<213> ORGANISM: Homo sapiens

<400> SEQUENCE: 106

Gly Phe Pro Ser Val Leu Arg
1               5

<210> SEQ ID NO 107
<211> LENGTH: 9
<212> TYPE: PRT
<213> ORGANISM: Homo sapiens
```

<400> SEQUENCE: 107

Leu Asp Phe His Phe Ser Ser Asp Arg
1               5

<210> SEQ ID NO 108
<211> LENGTH: 7
<212> TYPE: PRT
<213> ORGANISM: Homo sapiens

<400> SEQUENCE: 108

Ala Ser Ser Ile Leu Ala Thr
1               5

<210> SEQ ID NO 109
<211> LENGTH: 12
<212> TYPE: PRT
<213> ORGANISM: Homo sapiens

<400> SEQUENCE: 109

Glu Leu Trp Phe Ser Asp Asp Pro Asp Val Thr Lys
1               5                   10

<210> SEQ ID NO 110
<211> LENGTH: 11
<212> TYPE: PRT
<213> ORGANISM: Homo sapiens

<400> SEQUENCE: 110

Asn Val Asp Gln Ser Leu Leu Glu Leu His Lys
1               5                   10

<210> SEQ ID NO 111
<211> LENGTH: 7
<212> TYPE: PRT
<213> ORGANISM: Homo sapiens

<400> SEQUENCE: 111

Ala Leu Asp Leu Ser Leu Lys
1               5

<210> SEQ ID NO 112
<211> LENGTH: 8
<212> TYPE: PRT
<213> ORGANISM: Homo sapiens

<400> SEQUENCE: 112

Ile Leu Asp Asp Leu Ser Pro Arg
1               5

<210> SEQ ID NO 113
<211> LENGTH: 17
<212> TYPE: PRT
<213> ORGANISM: Homo sapiens

<400> SEQUENCE: 113

Asn Pro Leu Val Trp Val His Ala Ser Pro Glu His Val Val Thr
1               5                   10                  15

Arg

<210> SEQ ID NO 114
<211> LENGTH: 19
<212> TYPE: PRT
<213> ORGANISM: Homo sapiens

```
<400> SEQUENCE: 114

Gln Leu Gly Leu Pro Gly Pro Pro Asp Val Pro Asp His Ala Ala Tyr
1               5                   10                  15

His Pro Phe

<210> SEQ ID NO 115
<211> LENGTH: 8
<212> TYPE: PRT
<213> ORGANISM: Homo sapiens

<400> SEQUENCE: 115

Val Arg Pro Gln Gln Leu Val Lys
1               5

<210> SEQ ID NO 116
<211> LENGTH: 19
<212> TYPE: PRT
<213> ORGANISM: Homo sapiens

<400> SEQUENCE: 116

Asp Ile Pro Thr Asn Ser Pro Glu Leu Glu Glu Thr Leu Thr His Thr
1               5                   10                  15

Ile Thr Lys

<210> SEQ ID NO 117
<211> LENGTH: 9
<212> TYPE: PRT
<213> ORGANISM: Homo sapiens

<400> SEQUENCE: 117

Gln Val Val Ala Gly Leu Asn Phe Arg
1               5

<210> SEQ ID NO 118
<211> LENGTH: 9
<212> TYPE: PRT
<213> ORGANISM: Homo sapiens

<400> SEQUENCE: 118

Ile Thr Gly Phe Leu Lys Pro Gly Lys
1               5

<210> SEQ ID NO 119
<211> LENGTH: 11
<212> TYPE: PRT
<213> ORGANISM: Homo sapiens

<400> SEQUENCE: 119

Ile Thr Leu Pro Asp Phe Thr Gly Asp Leu Arg
1               5                   10

<210> SEQ ID NO 120
<211> LENGTH: 8
<212> TYPE: PRT
<213> ORGANISM: Homo sapiens

<400> SEQUENCE: 120

Ser Tyr Tyr Trp Ile Gly Ile Arg
1               5

<210> SEQ ID NO 121
<211> LENGTH: 12
```

<212> TYPE: PRT
<213> ORGANISM: Homo sapiens

<400> SEQUENCE: 121

Gly Leu Gly Glu Ile Ser Ala Ala Ser Glu Phe Lys
1               5                   10

<210> SEQ ID NO 122
<211> LENGTH: 10
<212> TYPE: PRT
<213> ORGANISM: Homo sapiens

<400> SEQUENCE: 122

Asp Ile Pro His Trp Leu Asn Pro Thr Arg
1               5                   10

<210> SEQ ID NO 123
<211> LENGTH: 13
<212> TYPE: PRT
<213> ORGANISM: Homo sapiens

<400> SEQUENCE: 123

Leu Asp Gly Ser Thr His Leu Asn Ile Phe Phe Ala Lys
1               5                   10

<210> SEQ ID NO 124
<211> LENGTH: 12
<212> TYPE: PRT
<213> ORGANISM: Homo sapiens

<400> SEQUENCE: 124

Leu Gln Ser Leu Phe Asp Ser Pro Asp Phe Ser Lys
1               5                   10

<210> SEQ ID NO 125
<211> LENGTH: 10
<212> TYPE: PRT
<213> ORGANISM: Homo sapiens

<400> SEQUENCE: 125

Thr Val Gln Ala Val Leu Thr Val Pro Lys
1               5                   10

<210> SEQ ID NO 126
<211> LENGTH: 14
<212> TYPE: PRT
<213> ORGANISM: Homo sapiens

<400> SEQUENCE: 126

Ala Gly Leu Leu Arg Pro Asp Tyr Ala Leu Leu Gly His Arg
1               5                   10

<210> SEQ ID NO 127
<211> LENGTH: 20
<212> TYPE: PRT
<213> ORGANISM: Homo sapiens

<400> SEQUENCE: 127

Asp Gly Ser Pro Asp Val Thr Thr Ala Asp Ile Gly Ala Asn Thr Pro
1               5                   10                  15

Asp Ala Thr Lys
            20

<210> SEQ ID NO 128

-continued

```
<211> LENGTH: 8
<212> TYPE: PRT
<213> ORGANISM: Homo sapiens

<400> SEQUENCE: 128

Gly Leu Phe Ile Ile Asp Gly Lys
1               5

<210> SEQ ID NO 129
<211> LENGTH: 14
<212> TYPE: PRT
<213> ORGANISM: Homo sapiens

<400> SEQUENCE: 129

Trp Asn Phe Ala Tyr Trp Ala Ala His Gln Pro Trp Ser Arg
1               5                   10

<210> SEQ ID NO 130
<211> LENGTH: 25
<212> TYPE: PRT
<213> ORGANISM: Homo sapiens

<400> SEQUENCE: 130

Asp Leu Tyr His Tyr Ile Thr Ser Tyr Val Val Asp Gly Glu Ile Ile
1               5                   10                  15

Ile Tyr Gly Pro Ala Tyr Ser Gly Arg
            20                  25

<210> SEQ ID NO 131
<211> LENGTH: 7
<212> TYPE: PRT
<213> ORGANISM: Homo sapiens

<400> SEQUENCE: 131

Phe Gln Leu Pro Gly Gln Lys
1               5

<210> SEQ ID NO 132
<211> LENGTH: 9
<212> TYPE: PRT
<213> ORGANISM: Homo sapiens

<400> SEQUENCE: 132

Leu Phe Ile Pro Gln Ile Thr Pro Lys
1               5

<210> SEQ ID NO 133
<211> LENGTH: 9
<212> TYPE: PRT
<213> ORGANISM: Homo sapiens

<400> SEQUENCE: 133

Ile His Pro Ser Tyr Thr Asn Tyr Arg
1               5

<210> SEQ ID NO 134
<211> LENGTH: 16
<212> TYPE: PRT
<213> ORGANISM: Homo sapiens

<400> SEQUENCE: 134

Val Ser Ala Pro Ser Gly Thr Gly His Leu Pro Gly Leu Asn Pro Leu
1               5                   10                  15
```

```
<210> SEQ ID NO 135
<211> LENGTH: 20
<212> TYPE: PRT
<213> ORGANISM: Homo sapiens

<400> SEQUENCE: 135

Asp Val Leu Leu Val His Asn Leu Pro Gln Asn Leu Pro Gly Tyr
1               5                   10                  15

Phe Trp Tyr Lys
            20

<210> SEQ ID NO 136
<211> LENGTH: 8
<212> TYPE: PRT
<213> ORGANISM: Homo sapiens

<400> SEQUENCE: 136

Leu Phe Ile Pro Gln Ile Thr Arg
1               5

<210> SEQ ID NO 137
<211> LENGTH: 7
<212> TYPE: PRT
<213> ORGANISM: Homo sapiens

<400> SEQUENCE: 137

Gly Pro Gly Glu Asp Phe Arg
1               5

<210> SEQ ID NO 138
<211> LENGTH: 9
<212> TYPE: PRT
<213> ORGANISM: Homo sapiens

<400> SEQUENCE: 138

Asn Tyr Gly Leu Leu Tyr Cys Phe Arg
1               5

<210> SEQ ID NO 139
<211> LENGTH: 8
<212> TYPE: PRT
<213> ORGANISM: Homo sapiens

<400> SEQUENCE: 139

Ser Val Glu Gly Ser Cys Gly Phe
1               5

<210> SEQ ID NO 140
<211> LENGTH: 11
<212> TYPE: PRT
<213> ORGANISM: Homo sapiens

<400> SEQUENCE: 140

Val Leu Thr His Ser Glu Leu Ala Pro Leu Arg
1               5                   10

<210> SEQ ID NO 141
<211> LENGTH: 16
<212> TYPE: PRT
<213> ORGANISM: Homo sapiens

<400> SEQUENCE: 141

Leu Asn Trp Glu Ala Pro Pro Gly Ala Phe Asp Ser Phe Leu Leu Arg
1               5                   10                  15
```

<210> SEQ ID NO 142
<211> LENGTH: 15
<212> TYPE: PRT
<213> ORGANISM: Homo sapiens

<400> SEQUENCE: 142

Leu Ser Gln Leu Ser Val Thr Asp Val Thr Thr Ser Ser Leu Arg
1               5                   10                  15

<210> SEQ ID NO 143
<211> LENGTH: 8
<212> TYPE: PRT
<213> ORGANISM: Homo sapiens

<400> SEQUENCE: 143

Ala Val Leu His Ile Gly Glu Lys
1               5

<210> SEQ ID NO 144
<211> LENGTH: 20
<212> TYPE: PRT
<213> ORGANISM: Homo sapiens

<400> SEQUENCE: 144

Val Ser Trp Ser Leu Pro Leu Val Pro Gly Pro Leu Val Gly Asp Gly
1               5                   10                  15

Phe Leu Leu Arg
            20

<210> SEQ ID NO 145
<211> LENGTH: 8
<212> TYPE: PRT
<213> ORGANISM: Homo sapiens

<400> SEQUENCE: 145

Tyr Leu Gly Glu Glu Tyr Val Lys
1               5

<210> SEQ ID NO 146
<211> LENGTH: 6
<212> TYPE: PRT
<213> ORGANISM: Homo sapiens

<400> SEQUENCE: 146

Val Glu Ile Asp Thr Lys
1               5

<210> SEQ ID NO 147
<211> LENGTH: 8
<212> TYPE: PRT
<213> ORGANISM: Homo sapiens

<400> SEQUENCE: 147

Glu Leu Pro Glu His Thr Val Lys
1               5

<210> SEQ ID NO 148
<211> LENGTH: 7
<212> TYPE: PRT
<213> ORGANISM: Homo sapiens

<400> SEQUENCE: 148

Val Leu Glu Pro Thr Leu Lys
1               5

<210> SEQ ID NO 149
<211> LENGTH: 10
<212> TYPE: PRT
<213> ORGANISM: Homo sapiens

<400> SEQUENCE: 149

Gly Gln Tyr Cys Tyr Glu Leu Asp Glu Lys
1               5                   10

<210> SEQ ID NO 150
<211> LENGTH: 10
<212> TYPE: PRT
<213> ORGANISM: Homo sapiens

<400> SEQUENCE: 150

Val Asp Thr Val Asp Pro Pro Tyr Pro Arg
1               5                   10

<210> SEQ ID NO 151
<211> LENGTH: 13
<212> TYPE: PRT
<213> ORGANISM: Homo sapiens

<400> SEQUENCE: 151

Phe Gly Phe Gly Gly Ser Thr Asp Ser Gly Pro Ile Arg
1               5                   10

<210> SEQ ID NO 152
<211> LENGTH: 10
<212> TYPE: PRT
<213> ORGANISM: Homo sapiens

<400> SEQUENCE: 152

Leu Ile Glu Ile Ala Asn His Val Asp Lys
1               5                   10

<210> SEQ ID NO 153
<211> LENGTH: 10
<212> TYPE: PRT
<213> ORGANISM: Homo sapiens

<400> SEQUENCE: 153

Leu Asn Ile Gly Tyr Ile Glu Asp Leu Lys
1               5                   10

<210> SEQ ID NO 154
<211> LENGTH: 16
<212> TYPE: PRT
<213> ORGANISM: Homo sapiens

<400> SEQUENCE: 154

Ser Asn Pro Val Thr Leu Asn Val Leu Tyr Gly Pro Asp Leu Pro Arg
1               5                   10                  15

<210> SEQ ID NO 155
<211> LENGTH: 11
<212> TYPE: PRT
<213> ORGANISM: Homo sapiens

<400> SEQUENCE: 155

Ser Gly Val Asp Leu Ala Asp Ser Asn Gln Lys
1               5                   10

```
<210> SEQ ID NO 156
<211> LENGTH: 10
<212> TYPE: PRT
<213> ORGANISM: Homo sapiens

<400> SEQUENCE: 156

His Ala Thr Leu Ser Leu Ser Ile Pro Arg
1               5                   10

<210> SEQ ID NO 157
<211> LENGTH: 7
<212> TYPE: PRT
<213> ORGANISM: Homo sapiens

<400> SEQUENCE: 157

Asn Gly Val Asp Leu Asn Arg
1               5

<210> SEQ ID NO 158
<211> LENGTH: 258
<212> TYPE: PRT
<213> ORGANISM: Homo sapiens

<400> SEQUENCE: 158

Met Leu Pro Leu Cys Leu Val Ala Ala Leu Leu Ala Ala Gly Pro
1               5                   10                  15

Gly Pro Ser Leu Gly Asp Glu Ala Ile His Cys Pro Pro Cys Ser Glu
                20                  25                  30

Glu Lys Leu Ala Arg Cys Arg Pro Val Gly Cys Glu Glu Leu Val
            35                  40                  45

Arg Glu Pro Gly Cys Gly Cys Cys Ala Thr Cys Ala Leu Gly Leu Gly
    50                  55                  60

Met Pro Cys Gly Val Tyr Thr Pro Arg Cys Gly Ser Gly Leu Arg Cys
65                  70                  75                  80

Tyr Pro Pro Arg Gly Val Glu Lys Pro Leu His Thr Leu Met His Gly
                85                  90                  95

Gln Gly Val Cys Met Glu Leu Ala Glu Ile Glu Ala Ile Gln Glu Ser
            100                 105                 110

Leu Gln Pro Ser Asp Lys Asp Glu Gly Asp His Pro Asn Asn Ser Phe
        115                 120                 125

Ser Pro Cys Ser Ala His Asp Arg Arg Cys Leu Gln Lys His Phe Ala
    130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
    210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe
                245                 250                 255

Arg Glu
```

<210> SEQ ID NO 159
<211> LENGTH: 158
<212> TYPE: PRT
<213> ORGANISM: Homo sapiens

<400> SEQUENCE: 159

```
Met Glu Leu Ala Glu Ile Glu Ala Ile Gln Glu Ser Leu Gln Pro Ser
1               5                   10                  15
Asp Lys Asp Glu Gly Asp His Pro Asn Asn Ser Phe Ser Pro Cys Ser
            20                  25                  30
Ala His Asp Arg Arg Cys Leu Gln Lys His Phe Ala Lys Ile Arg Asp
        35                  40                  45
Arg Ser Thr Ser Gly Gly Lys Met Lys Val Asn Gly Ala Pro Arg Glu
    50                  55                  60
Asp Ala Arg Pro Val Pro Gln Gly Ser Cys Gln Ser Glu Leu His Arg
65                  70                  75                  80
Ala Leu Glu Arg Leu Ala Ala Ser Gln Ser Arg Thr His Glu Asp Leu
                85                  90                  95
Tyr Ile Ile Pro Ile Pro Asn Cys Asp Arg Asn Gly Asn Phe His Pro
            100                 105                 110
Lys Gln Cys His Pro Ala Leu Asp Gly Gln Arg Gly Lys Cys Trp Cys
        115                 120                 125
Val Asp Arg Lys Thr Gly Val Lys Leu Pro Gly Gly Leu Glu Pro Lys
    130                 135                 140
Gly Glu Leu Asp Cys His Gln Leu Ala Asp Ser Phe Arg Glu
145                 150                 155
```

<210> SEQ ID NO 160
<211> LENGTH: 54
<212> TYPE: PRT
<213> ORGANISM: Homo sapiens

<400> SEQUENCE: 160

```
Val Glu Val Lys Met Glu Gly Asp Ser Val Leu Leu Glu Val Asp Gly
1               5                   10                  15
Glu Glu Val Leu Arg Leu Arg Gln Val Ser Gly Pro Leu Thr Ser Lys
            20                  25                  30
Arg His Pro Ile Met Arg Ile Ala Leu Gly Gly Leu Leu Phe Pro Ala
        35                  40                  45
Ser Asn Leu Arg Leu Pro
    50
```

<210> SEQ ID NO 161
<211> LENGTH: 36
<212> TYPE: PRT
<213> ORGANISM: Homo sapiens

<400> SEQUENCE: 161

```
Val Leu Arg Leu Arg Gln Val Ser Gly Pro Leu Thr Ser Lys Arg His
1               5                   10                  15
Pro Ile Met Arg Ile Ala Leu Gly Gly Leu Leu Phe Pro Ala Ser Asn
            20                  25                  30
Leu Arg Leu Pro
        35
```

<210> SEQ ID NO 162
<211> LENGTH: 11
<212> TYPE: PRT

```
<213> ORGANISM: Homo sapiens

<400> SEQUENCE: 162

Ala Thr Trp Ser Gly Ala Val Leu Ala Gly Arg
1               5                   10

<210> SEQ ID NO 163
<211> LENGTH: 8
<212> TYPE: PRT
<213> ORGANISM: Homo sapiens

<400> SEQUENCE: 163

Leu Leu Glu Leu Thr Gly Pro Lys
1               5

<210> SEQ ID NO 164
<211> LENGTH: 13
<212> TYPE: PRT
<213> ORGANISM: Homo sapiens

<400> SEQUENCE: 164

Leu Gly Asn Gln Glu Pro Gly Gly Gln Thr Ala Leu Lys
1               5                   10

<210> SEQ ID NO 165
<211> LENGTH: 17
<212> TYPE: PRT
<213> ORGANISM: Homo sapiens

<400> SEQUENCE: 165

Trp Phe Leu Leu Glu Gln Pro Glu Ile Gln Val Ala His Phe Pro Phe
1               5                   10                  15

Lys

<210> SEQ ID NO 166
<211> LENGTH: 9
<212> TYPE: PRT
<213> ORGANISM: Homo sapiens

<400> SEQUENCE: 166

Glu Ile Gly Glu Leu Tyr Leu Pro Lys
1               5

<210> SEQ ID NO 167
<211> LENGTH: 18
<212> TYPE: PRT
<213> ORGANISM: Homo sapiens

<400> SEQUENCE: 167

Val Ala Pro Glu Glu His Pro Val Leu Leu Thr Glu Ala Pro Leu Asn
1               5                   10                  15

Pro Lys

<210> SEQ ID NO 168
<211> LENGTH: 15
<212> TYPE: PRT
<213> ORGANISM: Homo sapiens

<400> SEQUENCE: 168

Gly Asp Ile Gly Glu Thr Gly Val Pro Gly Ala Glu Gly Pro Arg
1               5                   10                  15

<210> SEQ ID NO 169
```

```
<211> LENGTH: 15
<212> TYPE: PRT
<213> ORGANISM: Homo sapiens

<400> SEQUENCE: 169

Ile Phe Tyr Asn Gln Gln Asn His Tyr Asp Gly Ser Thr Gly Lys
1               5                   10                  15

<210> SEQ ID NO 170
<211> LENGTH: 8
<212> TYPE: PRT
<213> ORGANISM: Homo sapiens

<400> SEQUENCE: 170

Glu Thr Leu Leu Gln Asp Phe Arg
1               5

<210> SEQ ID NO 171
<211> LENGTH: 11
<212> TYPE: PRT
<213> ORGANISM: Homo sapiens

<400> SEQUENCE: 171

Thr Ser Asp Gln Ile His Phe Phe Phe Ala Lys
1               5                   10

<210> SEQ ID NO 172
<211> LENGTH: 15
<212> TYPE: PRT
<213> ORGANISM: Homo sapiens

<400> SEQUENCE: 172

Ile Glu Gly Asn Leu Ile Phe Asp Pro Asn Asn Tyr Leu Pro Lys
1               5                   10                  15

<210> SEQ ID NO 173
<211> LENGTH: 13
<212> TYPE: PRT
<213> ORGANISM: Homo sapiens

<400> SEQUENCE: 173

Ser Val Ser Leu Pro Ser Leu Asp Pro Ala Ser Ala Lys
1               5                   10

<210> SEQ ID NO 174
<211> LENGTH: 15
<212> TYPE: PRT
<213> ORGANISM: Homo sapiens

<400> SEQUENCE: 174

Ala Ala Thr Val Gly Ser Leu Ala Gly Gln Pro Leu Gln Glu Arg
1               5                   10                  15

<210> SEQ ID NO 175
<211> LENGTH: 9
<212> TYPE: PRT
<213> ORGANISM: Homo sapiens

<400> SEQUENCE: 175

Leu Gly Pro Leu Val Glu Gln Gly Arg
1               5

<210> SEQ ID NO 176
<211> LENGTH: 12
<212> TYPE: PRT
```

<213> ORGANISM: Homo sapiens

<400> SEQUENCE: 176

Trp Ile Leu Thr Ala Ala His Thr Leu Tyr Pro Lys
1               5                   10

<210> SEQ ID NO 177
<211> LENGTH: 15
<212> TYPE: PRT
<213> ORGANISM: Homo sapiens

<400> SEQUENCE: 177

Gly Asp Ser Gly Gly Ala Phe Ala Val Gln Asp Pro Asn Asp Lys
1               5                   10                  15

<210> SEQ ID NO 178
<211> LENGTH: 8
<212> TYPE: PRT
<213> ORGANISM: Homo sapiens

<400> SEQUENCE: 178

Leu Leu Glu Val Pro Glu Gly Arg
1               5

<210> SEQ ID NO 179
<211> LENGTH: 14
<212> TYPE: PRT
<213> ORGANISM: Homo sapiens

<400> SEQUENCE: 179

Glu Ser Ile Ser Val Ser Ser Glu Gln Leu Ala Gln Phe Arg
1               5                   10

<210> SEQ ID NO 180
<211> LENGTH: 8
<212> TYPE: PRT
<213> ORGANISM: Homo sapiens

<400> SEQUENCE: 180

Ile Thr Gln Asp Ala Gln Leu Lys
1               5

<210> SEQ ID NO 181
<211> LENGTH: 11
<212> TYPE: PRT
<213> ORGANISM: Homo sapiens

<400> SEQUENCE: 181

Ala Leu Glu Gln Asp Leu Pro Val Asn Ile Lys
1               5                   10

<210> SEQ ID NO 182
<211> LENGTH: 15
<212> TYPE: PRT
<213> ORGANISM: Homo sapiens

<400> SEQUENCE: 182

Ser Leu Pro Val Ser Asp Ser Val Leu Ser Gly Phe Glu Gln Arg
1               5                   10                  15

<210> SEQ ID NO 183
<211> LENGTH: 16
<212> TYPE: PRT
<213> ORGANISM: Homo sapiens

```
<400> SEQUENCE: 183

Val Gln Glu Ala His Leu Thr Glu Asp Gln Ile Phe Tyr Phe Pro Lys
1               5                   10                  15

<210> SEQ ID NO 184
<211> LENGTH: 10
<212> TYPE: PRT
<213> ORGANISM: Homo sapiens

<400> SEQUENCE: 184

Glu Ser Asp Thr Ser Tyr Val Ser Leu Lys
1               5                   10

<210> SEQ ID NO 185
<211> LENGTH: 18
<212> TYPE: PRT
<213> ORGANISM: Homo sapiens

<400> SEQUENCE: 185

Thr Glu Phe Leu Ser Asn Tyr Leu Thr Asn Val Asp Asp Ile Thr Leu
1               5                   10                  15

Val Pro

<210> SEQ ID NO 186
<211> LENGTH: 13
<212> TYPE: PRT
<213> ORGANISM: Homo sapiens

<400> SEQUENCE: 186

Trp Trp Gly Gly Gln Pro Leu Trp Ile Thr Ala Thr Lys
1               5                   10

<210> SEQ ID NO 187
<211> LENGTH: 17
<212> TYPE: PRT
<213> ORGANISM: Homo sapiens

<400> SEQUENCE: 187

Gly Val Asn Leu Gln Glu Phe Leu Asn Val Thr Ser Val His Leu Phe
1               5                   10                  15

Lys

<210> SEQ ID NO 188
<211> LENGTH: 12
<212> TYPE: PRT
<213> ORGANISM: Homo sapiens

<400> SEQUENCE: 188

Ser Thr Val Leu Thr Ile Pro Glu Ile Ile Ile Lys
1               5                   10

<210> SEQ ID NO 189
<211> LENGTH: 9
<212> TYPE: PRT
<213> ORGANISM: Homo sapiens

<400> SEQUENCE: 189

Val Val Gly Gly Leu Val Ala Leu Arg
1               5

<210> SEQ ID NO 190
<211> LENGTH: 10
<212> TYPE: PRT
```

<213> ORGANISM: Homo sapiens

<400> SEQUENCE: 190

Ser Glu Pro Arg Pro Gly Val Leu Leu Arg
1               5                   10

<210> SEQ ID NO 191
<211> LENGTH: 12
<212> TYPE: PRT
<213> ORGANISM: Homo sapiens

<400> SEQUENCE: 191

Ala Gly Cys Val Ala Glu Ser Thr Ala Val Cys Arg
1               5                   10

<210> SEQ ID NO 192
<211> LENGTH: 16
<212> TYPE: PRT
<213> ORGANISM: Homo sapiens

<400> SEQUENCE: 192

Val Asn Gly Val Leu Thr Ala Leu Pro Val Ser Val Ala Asp Gly Arg
1               5                   10                  15

<210> SEQ ID NO 193
<211> LENGTH: 19
<212> TYPE: PRT
<213> ORGANISM: Homo sapiens

<400> SEQUENCE: 193

Ser Thr Asp Thr Ser Cys Val Asn Pro Pro Thr Val Gln Asn Ala His
1               5                   10                  15

Ile Leu Ser

<210> SEQ ID NO 194
<211> LENGTH: 10
<212> TYPE: PRT
<213> ORGANISM: Homo sapiens

<400> SEQUENCE: 194

Thr Gly Glu Ser Ala Glu Phe Val Cys Lys
1               5                   10

<210> SEQ ID NO 195
<211> LENGTH: 14
<212> TYPE: PRT
<213> ORGANISM: Homo sapiens

<400> SEQUENCE: 195

Ser Tyr Thr Ile Thr Gly Leu Gln Pro Gly Thr Asp Tyr Lys
1               5                   10

<210> SEQ ID NO 196
<211> LENGTH: 10
<212> TYPE: PRT
<213> ORGANISM: Homo sapiens

<400> SEQUENCE: 196

Leu Leu Asp Phe Glu Phe Ser Ser Gly Arg
1               5                   10

<210> SEQ ID NO 197
<211> LENGTH: 19
<212> TYPE: PRT

<213> ORGANISM: Homo sapiens

<400> SEQUENCE: 197

Ala Gln Pro Val Gln Val Ala Glu Gly Ser Glu Pro Asp Gly Phe Trp
1               5                   10                  15
Glu Ala Leu

<210> SEQ ID NO 198
<211> LENGTH: 8
<212> TYPE: PRT
<213> ORGANISM: Homo sapiens

<400> SEQUENCE: 198

Thr Ala Ser Asp Phe Ile Thr Lys
1               5

<210> SEQ ID NO 199
<211> LENGTH: 14
<212> TYPE: PRT
<213> ORGANISM: Homo sapiens

<400> SEQUENCE: 199

Gln Glu Pro Gly Glu Asn Ser Glu Ile Leu Pro Thr Leu Lys
1               5                   10

<210> SEQ ID NO 200
<211> LENGTH: 17
<212> TYPE: PRT
<213> ORGANISM: Homo sapiens

<400> SEQUENCE: 200

Tyr Val Arg Pro Gly Gly Gly Phe Val Pro Asn Phe Gln Leu Phe Glu
1               5                   10                  15
Lys

<210> SEQ ID NO 201
<211> LENGTH: 7
<212> TYPE: PRT
<213> ORGANISM: Homo sapiens

<400> SEQUENCE: 201

Ile Ala Ile Asp Leu Phe Lys
1               5

<210> SEQ ID NO 202
<211> LENGTH: 9
<212> TYPE: PRT
<213> ORGANISM: Homo sapiens

<400> SEQUENCE: 202

Thr Leu Glu Ala Gln Leu Thr Pro Arg
1               5

<210> SEQ ID NO 203
<211> LENGTH: 9
<212> TYPE: PRT
<213> ORGANISM: Homo sapiens

<400> SEQUENCE: 203

Leu His Lys Pro Gly Val Tyr Thr Arg
1               5

<210> SEQ ID NO 204

<211> LENGTH: 16
<212> TYPE: PRT
<213> ORGANISM: Homo sapiens

<400> SEQUENCE: 204

Ala Asp Leu Phe Tyr Asp Val Glu Ala Leu Asp Leu Glu Ser Pro Lys
1               5                   10                  15

<210> SEQ ID NO 205
<211> LENGTH: 11
<212> TYPE: PRT
<213> ORGANISM: Homo sapiens

<400> SEQUENCE: 205

Thr Asn Leu Glu Ser Ile Leu Ser Tyr Pro Lys
1               5                   10

<210> SEQ ID NO 206
<211> LENGTH: 14
<212> TYPE: PRT
<213> ORGANISM: Homo sapiens

<400> SEQUENCE: 206

Val Glu Leu Ala Pro Leu Pro Ser Trp Gln Pro Val Gly Lys
1               5                   10

<210> SEQ ID NO 207
<211> LENGTH: 8
<212> TYPE: PRT
<213> ORGANISM: Homo sapiens

<400> SEQUENCE: 207

Ala Leu Val Leu Glu Leu Ala Lys
1               5

<210> SEQ ID NO 208
<211> LENGTH: 11
<212> TYPE: PRT
<213> ORGANISM: Homo sapiens

<400> SEQUENCE: 208

Leu Ser Asn Glu Asn His Gly Ile Ala Gln Arg
1               5                   10

<210> SEQ ID NO 209
<211> LENGTH: 18
<212> TYPE: PRT
<213> ORGANISM: Homo sapiens

<400> SEQUENCE: 209

Leu Ile Gln Asp Ala Val Thr Gly Leu Thr Val Asn Gly Gln Ile Thr
1               5                   10                  15

Gly Asp

<210> SEQ ID NO 210
<211> LENGTH: 18
<212> TYPE: PRT
<213> ORGANISM: Homo sapiens

<400> SEQUENCE: 210

Gln Leu Gly Leu Pro Gly Pro Pro Asp Val Pro Asp His Ala Ala Tyr
1               5                   10                  15

His Pro

<210> SEQ ID NO 211
<211> LENGTH: 11
<212> TYPE: PRT
<213> ORGANISM: Homo sapiens

<400> SEQUENCE: 211

Ser Leu Glu Asp Leu Gln Leu Thr His Asn Lys
1               5                   10

<210> SEQ ID NO 212
<211> LENGTH: 8
<212> TYPE: PRT
<213> ORGANISM: Homo sapiens

<400> SEQUENCE: 212

Ala Glu Ile Glu Tyr Leu Glu Lys
1               5

<210> SEQ ID NO 213
<211> LENGTH: 15
<212> TYPE: PRT
<213> ORGANISM: Homo sapiens

<400> SEQUENCE: 213

Thr Gly Val Ile Thr Ser Pro Asp Phe Pro Asn Pro Tyr Pro Lys
1               5                   10                  15

<210> SEQ ID NO 214
<211> LENGTH: 10
<212> TYPE: PRT
<213> ORGANISM: Homo sapiens

<400> SEQUENCE: 214

Val Pro Leu Ala Leu Phe Ala Leu Asn Arg
1               5                   10

<210> SEQ ID NO 215
<211> LENGTH: 10
<212> TYPE: PRT
<213> ORGANISM: Homo sapiens

<400> SEQUENCE: 215

Glu Ala Gln Leu Pro Val Ile Glu Asn Lys
1               5                   10

<210> SEQ ID NO 216
<211> LENGTH: 10
<212> TYPE: PRT
<213> ORGANISM: Homo sapiens

<400> SEQUENCE: 216

Leu Ser Ser Pro Ala Val Ile Thr Asp Lys
1               5                   10

<210> SEQ ID NO 217
<211> LENGTH: 9
<212> TYPE: PRT
<213> ORGANISM: Homo sapiens

<400> SEQUENCE: 217

Thr Leu Phe Ile Phe Gly Val Thr Lys
1               5

<210> SEQ ID NO 218

```
<211> LENGTH: 19
<212> TYPE: PRT
<213> ORGANISM: Homo sapiens

<400> SEQUENCE: 218

Asp Val Leu Leu Val His Asn Leu Pro Gln Asn Leu Pro Gly Tyr
1               5                   10                  15

Phe Trp Tyr

<210> SEQ ID NO 219
<211> LENGTH: 9
<212> TYPE: PRT
<213> ORGANISM: Homo sapiens

<400> SEQUENCE: 219

Ile Leu Ile Leu Pro Ser Val Thr Arg
1               5

<210> SEQ ID NO 220
<211> LENGTH: 11
<212> TYPE: PRT
<213> ORGANISM: Homo sapiens

<400> SEQUENCE: 220

Ala Val Gly Tyr Leu Ile Thr Gly Tyr Gln Arg
1               5                   10

<210> SEQ ID NO 221
<211> LENGTH: 10
<212> TYPE: PRT
<213> ORGANISM: Homo sapiens

<400> SEQUENCE: 221

Tyr Trp Gly Val Ala Ser Phe Leu Gln Lys
1               5                   10

<210> SEQ ID NO 222
<211> LENGTH: 11
<212> TYPE: PRT
<213> ORGANISM: Homo sapiens

<400> SEQUENCE: 222

Ala Leu Asn Ser Ile Ile Asp Val Tyr His Lys
1               5                   10

<210> SEQ ID NO 223
<211> LENGTH: 11
<212> TYPE: PRT
<213> ORGANISM: Homo sapiens

<400> SEQUENCE: 223

Gly Tyr Val Ile Ile Lys Pro Leu Val Trp Val
1               5                   10

<210> SEQ ID NO 224
<211> LENGTH: 16
<212> TYPE: PRT
<213> ORGANISM: Homo sapiens

<400> SEQUENCE: 224

Ser Ile Pro Thr Cys Thr Asp Phe Glu Val Ile Gln Phe Pro Leu Arg
1               5                   10                  15

<210> SEQ ID NO 225
```

```
<211> LENGTH: 10
<212> TYPE: PRT
<213> ORGANISM: Homo sapiens

<400> SEQUENCE: 225

Tyr Asn Ser Gln Leu Leu Ser Phe Val Arg
1               5                   10

<210> SEQ ID NO 226
<211> LENGTH: 9
<212> TYPE: PRT
<213> ORGANISM: Homo sapiens

<400> SEQUENCE: 226

Val Gly Glu Phe Ser Gly Ala Asn Lys
1               5

<210> SEQ ID NO 227
<211> LENGTH: 10
<212> TYPE: PRT
<213> ORGANISM: Homo sapiens

<400> SEQUENCE: 227

Glu Leu Leu Glu Ser Tyr Ile Asp Gly Arg
1               5                   10

<210> SEQ ID NO 228
<211> LENGTH: 19
<212> TYPE: PRT
<213> ORGANISM: Homo sapiens

<400> SEQUENCE: 228

Val Ser Trp Ser Leu Pro Leu Val Pro Gly Pro Leu Val Gly Asp Gly
1               5                   10                  15

Phe Leu Leu

<210> SEQ ID NO 229
<211> LENGTH: 12
<212> TYPE: PRT
<213> ORGANISM: Homo sapiens

<400> SEQUENCE: 229

Gly Phe Gln Ala Leu Gly Asp Ala Ala Asp Ile Arg
1               5                   10

<210> SEQ ID NO 230
<211> LENGTH: 9
<212> TYPE: PRT
<213> ORGANISM: Homo sapiens

<400> SEQUENCE: 230

Tyr Tyr Gly Tyr Thr Gly Ala Phe Arg
1               5

<210> SEQ ID NO 231
<211> LENGTH: 12
<212> TYPE: PRT
<213> ORGANISM: Homo sapiens

<400> SEQUENCE: 231

Phe Val Phe Gly Thr Thr Pro Glu Asp Ile Leu Arg
1               5                   10

<210> SEQ ID NO 232
```

```
<211> LENGTH: 16
<212> TYPE: PRT
<213> ORGANISM: Homo sapiens

<400> SEQUENCE: 232

Leu Ala Gly Leu Gly Leu Gln Gln Leu Asp Glu Gly Leu Phe Ser Arg
1               5                   10                  15

<210> SEQ ID NO 233
<211> LENGTH: 14
<212> TYPE: PRT
<213> ORGANISM: Homo sapiens

<400> SEQUENCE: 233

Asn Leu His Asp Leu Asp Val Ser Asp Asn Gln Leu Glu Arg
1               5                   10

<210> SEQ ID NO 234
<211> LENGTH: 10
<212> TYPE: PRT
<213> ORGANISM: Homo sapiens

<400> SEQUENCE: 234

Thr Gln Ile Asp Ser Pro Leu Ser Gly Lys
1               5                   10

<210> SEQ ID NO 235
<211> LENGTH: 18
<212> TYPE: PRT
<213> ORGANISM: Homo sapiens

<400> SEQUENCE: 235

Leu Gly Pro Gln Pro Leu Pro Ile His Val Gly Glu Leu Pro Thr Pro
1               5                   10                  15

Val Cys

<210> SEQ ID NO 236
<211> LENGTH: 9
<212> TYPE: PRT
<213> ORGANISM: Homo sapiens

<400> SEQUENCE: 236

Asp Gly Thr Val Thr Thr Asp Trp Lys
1               5

<210> SEQ ID NO 237
<211> LENGTH: 13
<212> TYPE: PRT
<213> ORGANISM: Homo sapiens

<400> SEQUENCE: 237

Ile Leu Ala Gly Pro Ala Gly Asp Ser Asn Val Val Lys
1               5                   10

<210> SEQ ID NO 238
<211> LENGTH: 16
<212> TYPE: PRT
<213> ORGANISM: Homo sapiens

<400> SEQUENCE: 238

Glu Ile Pro Ala Trp Val Pro Phe Asp Pro Ala Ala Gln Ile Thr Lys
1               5                   10                  15

<210> SEQ ID NO 239
```

```
<211> LENGTH: 12
<212> TYPE: PRT
<213> ORGANISM: Homo sapiens

<400> SEQUENCE: 239

Tyr Ser Leu Thr Tyr Ile Tyr Thr Gly Leu Ser Lys
1               5                   10
```